(12) United States Patent
Wagner et al.

(10) Patent No.: US 11,965,816 B2
(45) Date of Patent: Apr. 23, 2024

(54) USE OF VIBRATIONAL SPECTROSCOPY FOR MICROFLUIDIC LIQUID MEASUREMENT

(71) Applicant: 1087 Systems, Inc., Cambridge, MA (US)

(72) Inventors: Matthias Wagner, Cambridge, MA (US); John Heanue, Manchester, MA (US)

(73) Assignee: 1087 SYSTEMS, INC., Cambridge, MA (US)

( * ) Notice: Subject to any disclaimer, the term of this patent is extended or adjusted under 35 U.S.C. 154(b) by 505 days.

(21) Appl. No.: 17/164,710

(22) Filed: Feb. 1, 2021

(65) Prior Publication Data

US 2021/0215592 A1    Jul. 15, 2021

Related U.S. Application Data

(63) Continuation of application No. 16/282,903, filed on Feb. 22, 2019, now Pat. No. 10,908,066, which is a
(Continued)

(51) Int. Cl.
*G01N 15/14*    (2006.01)
*B01L 3/00*    (2006.01)
(Continued)

(52) U.S. Cl.
CPC ...... *G01N 15/147* (2013.01); *B01L 3/502761* (2013.01); *B07C 5/34* (2013.01);
(Continued)

(58) Field of Classification Search
CPC ............... G01N 15/14; G01N 15/1427; G01N 15/1436; G01N 15/1429; G01N 15/1434;
(Continued)

(56) References Cited

U.S. PATENT DOCUMENTS 3,390,449 A    7/1968 Fox
3,649,829 A    3/1972 Randolph
(Continued)

FOREIGN PATENT DOCUMENTS

CA    1341328 C    12/2001
CN    2125369 U    12/1992
(Continued)

OTHER PUBLICATIONS

Brazilian Office Action, Application No. BR112019004727-1, dated Mar. 20, 2023, 6 pages.
(Continued)

*Primary Examiner* — Paul M. West
(74) *Attorney, Agent, or Firm* — NGUYEN TARBET LLC

(57) ABSTRACT

This disclosure concerns a cytometry system including a handling system that enables presentation of single cells to at least one laser source. The laser source is configured to deliver light to a cell within the cells in order to induce bond vibrations in the cellular DNA. The system further includes a detection facility that detects the signature of the bond vibrations, wherein the bond vibration signature is used to determine the folding or packing of the DNA.

20 Claims, 61 Drawing Sheets

Related U.S. Application Data continuation of application No. 15/174,681, filed on Jun. 6, 2016, now Pat. No. 10,261,012, which is a continuation of application No. 13/894,831, filed on May 15, 2013, now Pat. No. 9,835,552, which is a continuation-in-part of application No. 13/447,647, filed on Apr. 16, 2012, now abandoned, and a continuation-in-part of application No. 13/298,148, filed on Nov. 16, 2011, now Pat. No. 8,941,062, said application No. 13/447,647 is a continuation-in-part of application No. 13/298,148, filed on Nov. 16, 2011, now Pat. No. 8,941,062.

(60) Provisional application No. 61/647,041, filed on May 15, 2012, provisional application No. 61/628,259, filed on Oct. 27, 2011, provisional application No. 61/575,799, filed on Aug. 29, 2011, provisional application No. 61/571,051, filed on Jun. 20, 2011, provisional application No. 61/519,567, filed on May 25, 2011, provisional application No. 61/516,623, filed on Apr. 5, 2011, provisional application No. 61/464,775, filed on Mar. 9, 2011, provisional application No. 61/456,997, filed on Nov. 16, 2010.

(51) Int. Cl.
  *B07C 5/34* (2006.01)
  *C12N 5/071* (2010.01)
  *G01N 15/00* (2006.01)
  *G01N 15/10* (2006.01)
  *G01N 15/1429* (2024.01)
  *G01N 15/1434* (2024.01)
  *G01N 21/17* (2006.01)
  *G01N 21/35* (2014.01)
  *G01N 21/3563* (2014.01)
  *G01N 21/65* (2006.01)
  *G01N 29/24* (2006.01)

(52) U.S. Cl.
  CPC ........... *C12N 5/0612* (2013.01); *G01N 15/14* (2013.01); *G01N 15/1427* (2013.01); *G01N 15/1429* (2013.01); *G01N 15/1434* (2013.01); *G01N 15/1436* (2013.01); *G01N 15/1459* (2013.01); *G01N 15/1475* (2013.01); *G01N 15/1484* (2013.01); *G01N 21/1702* (2013.01); *G01N 21/35* (2013.01); *G01N 21/3563* (2013.01); *G01N 21/65* (2013.01); *G01N 29/2418* (2013.01); *B01L 2200/0636* (2013.01); *B01L 2200/0652* (2013.01); *B01L 2300/0627* (2013.01); *B01L 2300/0864* (2013.01); *G01N 2015/0065* (2013.01); *G01N 2015/1006* (2013.01); *G01N 15/1463* (2013.01); *G01N 2015/1481* (2013.01); *G01N 2015/149* (2013.01); *G01N 2015/1493* (2013.01); *G01N 2015/1497* (2013.01); *G01N 2021/653* (2013.01); *G01N 2201/0612* (2013.01)

(58) Field of Classification Search
  CPC ........... G01N 15/1459; G01N 15/1484; G01N 15/1463; G01N 2015/0065; B01L 3/502761; B01L 2200/0652
  See application file for complete search history.

(56) References Cited

U.S. PATENT DOCUMENTS

| | | |
|---|---|---|
| 3,661,460 A | 5/1972 | Elking et al. |
| 3,710,933 A | 1/1973 | Fulwyler et al. |
| 3,764,901 A | 10/1973 | Kachel |
| 3,791,517 A | 2/1974 | Friedman |
| 4,175,662 A | 11/1979 | Zold |
| 4,325,706 A | 4/1982 | Gershman et al. |
| 4,395,397 A | 7/1983 | Shapiro |
| 4,409,106 A | 10/1983 | Furuta et al. |
| 4,424,132 A | 1/1984 | Iriguchi |
| 4,660,971 A | 4/1987 | Sage et al. |
| 4,667,830 A | 5/1987 | Nozaki, Jr. et al. |
| 4,765,737 A | 8/1988 | Harris et al. |
| 4,885,473 A | 12/1989 | Shofner et al. |
| 4,919,817 A | 4/1990 | Schoendorfer et al. |
| 4,983,038 A | 1/1991 | Ohki et al. |
| 5,007,732 A | 4/1991 | Ohki et al. |
| 5,030,002 A | 7/1991 | North, Jr. |
| 5,100,627 A | 3/1992 | Buican et al. |
| 5,125,749 A | 6/1992 | Leugers et al. |
| 5,135,759 A | 8/1992 | Johnson |
| 5,180,065 A | 1/1993 | Touge et al. |
| 5,194,909 A | 3/1993 | Tycko |
| 5,229,297 A | 7/1993 | Schnipelsky et al. |
| 5,483,469 A | 1/1996 | Van den Engh et al. |
| 5,491,550 A | 2/1996 | Dabbs |
| 5,620,857 A | 4/1997 | Weetall et al. |
| 5,674,743 A | 10/1997 | Ulmer |
| 5,689,109 A | 11/1997 | Schultze |
| 5,752,606 A | 5/1998 | Wilson et al. |
| 5,800,690 A | 9/1998 | Chow et al. |
| 5,837,115 A | 11/1998 | Austin et al. |
| 5,849,178 A | 12/1998 | Holm et al. |
| 5,858,187 A | 1/1999 | Ramsey et al. |
| 5,879,625 A | 3/1999 | Rosianiec et al. |
| 5,966,457 A | 10/1999 | Lemelson |
| 5,976,885 A | 11/1999 | Cohenford |
| 5,985,216 A | 11/1999 | Rens et al. |
| 6,008,010 A | 12/1999 | Greenberger et al. |
| 6,053,856 A | 4/2000 | Hlavinka |
| 6,071,442 A | 6/2000 | Dean et al. |
| 6,146,897 A | 11/2000 | Cohenford et al. |
| 6,159,739 A | 12/2000 | Weigl et al. |
| 6,159,749 A | 12/2000 | Yagang et al. |
| 6,171,865 B1 | 1/2001 | Weigl et al. |
| 6,185,664 B1 | 2/2001 | Jeddeloh |
| 6,213,151 B1 | 4/2001 | Jacobson et al. |
| H1960 H | 6/2001 | Conrad et al. |
| 6,368,871 B1 | 4/2002 | Christel et al. |
| 6,416,190 B1 | 7/2002 | Grier et al. |
| 6,416,959 B1 | 7/2002 | Giuliano et al. |
| 6,432,630 B1 | 8/2002 | Blankenstein |
| 6,451,264 B1 | 9/2002 | Bhullar et al. |
| 6,473,171 B1 | 10/2002 | Buttry et al. |
| 6,494,230 B2 | 12/2002 | Chow |
| 6,506,609 B1 | 1/2003 | Wada |
| 6,519,032 B1 | 2/2003 | Kuebler et al. |
| 6,519,954 B1 | 2/2003 | Prien et al. |
| 6,524,860 B1 | 2/2003 | Seidel et al. |
| 6,540,895 B1 | 4/2003 | Spence et al. |
| 6,549,275 B1 | 4/2003 | Cabuz et al. |
| 6,592,821 B1 | 7/2003 | Wada et al. |
| 6,637,463 B1 | 10/2003 | Lei et al. |
| 6,674,525 B2 | 1/2004 | Bardell et al. |
| 6,727,451 B1 | 4/2004 | Fuhr et al. |
| 6,808,075 B2 | 10/2004 | Böhm et al. |
| 6,833,542 B2 | 12/2004 | Wang et al. |
| 6,838,056 B2 | 1/2005 | Foster |
| 6,841,388 B2 | 1/2005 | Dukor et al. |
| 6,853,654 B2 | 2/2005 | Mcdonald et al. |
| 6,877,528 B2 | 4/2005 | Gilbert et al. |
| 6,944,324 B2 | 9/2005 | Tran et al. |
| 6,976,590 B2 | 12/2005 | Deshpande et al. |
| 7,029,430 B2 | 4/2006 | Hlavinka et al. |
| 7,069,943 B2 | 7/2006 | Gilbert et al. |
| 7,092,154 B2 | 8/2006 | Yasuda et al. |
| 7,104,405 B2 | 9/2006 | Böhm et al. |
| 7,208,265 B1 | 4/2007 | Schenk |
| 7,195,920 B2 | 5/2007 | Seidel et al. |
| 7,241,988 B2 | 7/2007 | Gruber et al. |
| 7,276,701 B2 | 10/2007 | Lendl |
| 7,298,478 B2 | 11/2007 | Gilbert et al. |

(56) References Cited

U.S. PATENT DOCUMENTS

| | | |
|---|---|---|
| 7,300,803 B2 | 11/2007 | Lin et al. |
| 7,311,476 B2 | 12/2007 | Gilbert et al. |
| 7,312,085 B2 | 12/2007 | Chou et al. |
| 7,355,696 B2 | 4/2008 | Mueth et al. |
| 7,355,699 B2 | 4/2008 | Gilbert et al. |
| 7,466,734 B1 | 12/2008 | Day et al. |
| 7,472,794 B2 | 1/2009 | Oakey et al. |
| 7,482,577 B2 | 1/2009 | Gruber et al. |
| 7,492,522 B2 | 2/2009 | Gilbert et al. |
| 7,524,681 B2 | 4/2009 | Wolf et al. |
| 7,569,788 B2 | 8/2009 | Deshpande et al. |
| 7,576,861 B2 | 8/2009 | Gilbert et al. |
| 7,584,857 B2 | 9/2009 | Böhm et al. |
| 7,611,309 B2 | 11/2009 | Gilbert et al. |
| 7,670,471 B2 | 3/2010 | Quake et al. |
| 7,697,576 B2 | 4/2010 | Maier et al. |
| 7,760,351 B2 | 7/2010 | Cox et al. |
| 7,820,425 B2 | 10/2010 | Schenk |
| 7,826,509 B2 | 11/2010 | Belkin et al. |
| 7,956,328 B2 | 6/2011 | Sundaram et al. |
| 7,963,399 B2 | 6/2011 | Böhm et al. |
| 7,997,831 B2 | 8/2011 | Gilbert et al. |
| 8,032,200 B2 | 10/2011 | Tearney et al. |
| 8,080,422 B2 | 12/2011 | Neas et al. |
| 8,123,044 B2 | 2/2012 | Johnson et al. |
| 8,149,402 B2 | 4/2012 | Rich |
| 8,158,122 B2 | 4/2012 | Hampson et al. |
| 8,173,001 B2 | 5/2012 | Quake et al. |
| 8,174,394 B2 | 5/2012 | Ridder et al. |
| 8,198,092 B2 | 6/2012 | Durack et al. |
| 8,206,987 B2 | 6/2012 | Durack et al. |
| 8,209,987 B2 | 7/2012 | Hautman et al. |
| 8,210,209 B2 | 7/2012 | Gilbert et al. |
| 8,277,764 B2 | 10/2012 | Gilbert et al. |
| 8,388,822 B2 | 3/2013 | Quake et al. |
| 8,408,399 B2 | 4/2013 | Böhm et al. |
| 8,502,148 B2 | 8/2013 | Wagner et al. |
| 8,529,161 B2 | 9/2013 | Gilbert et al. |
| 8,563,325 B1 | 10/2013 | Bartsch et al. |
| 8,567,608 B2 | 10/2013 | Deshpande et al. |
| 8,569,069 B2 | 10/2013 | Durack |
| 8,623,295 B2 | 1/2014 | Gilbert et al. |
| 8,727,131 B2 | 5/2014 | Deshpande et al. |
| 8,731,860 B2 | 5/2014 | Charles et al. |
| 8,863,962 B2 | 10/2014 | Johnson et al. |
| 8,941,062 B2 | 1/2015 | Wagner et al. |
| 8,961,904 B2 | 2/2015 | Xia et al. |
| 8,964,184 B2 | 2/2015 | Gilbert et al. |
| 8,981,298 B2 | 3/2015 | Wagner et al. |
| 9,000,357 B2 | 4/2015 | Mueth et al. |
| 9,003,869 B2 | 4/2015 | Wagner et al. |
| 9,011,797 B2 | 4/2015 | Gilbert et al. |
| 9,109,195 B2 | 8/2015 | Zimmermann et al. |
| 9,140,690 B2 | 9/2015 | Mueth et al. |
| 9,255,874 B2 | 2/2016 | Sharpe et al. |
| 9,260,693 B2 | 2/2016 | Johnson et al. |
| 9,335,247 B2 | 5/2016 | Sharpe et al. |
| 9,335,295 B2 | 5/2016 | Mueth et al. |
| 9,339,850 B2 | 5/2016 | Deshpande et al. |
| 9,365,822 B2 | 6/2016 | Seidel et al. |
| 9,377,400 B2 | 6/2016 | Wagner et al. |
| 9,446,912 B2 | 9/2016 | Gilbert et al. |
| 9,485,984 B2 | 11/2016 | Burbank et al. |
| 9,550,215 B2 | 1/2017 | Deshpande et al. |
| 9,588,100 B2 | 3/2017 | Appleyard et al. |
| 9,618,442 B2 | 4/2017 | Sharpe et al. |
| 9,683,922 B2 | 6/2017 | Wagner et al. |
| D791,338 S | 7/2017 | Morkos et al. |
| 9,752,976 B2 | 9/2017 | Gilbert et al. |
| 9,781,918 B2 | 10/2017 | Zimmermann et al. |
| 9,802,767 B2 | 10/2017 | Gilbert et al. |
| 9,823,252 B2 | 11/2017 | Gilbert et al. |
| 9,835,552 B2 | 12/2017 | Wagner |
| D815,754 S | 4/2018 | Morkos et al. |
| 9,943,847 B2 | 4/2018 | Gilbert et al. |
| 9,964,968 B2 | 5/2018 | Sharpe et al. |
| 10,025,322 B2 | 7/2018 | Lofstrom et al. |
| 10,029,283 B2 | 7/2018 | Deshpande et al. |
| 10,175,159 B2 | 1/2019 | Wagner et al. |
| 10,180,388 B2 | 1/2019 | Wagner |
| 10,315,194 B2 | 1/2019 | Akiyama et al. |
| 10,216,144 B2 | 2/2019 | Mueth et al. |
| 11,187,224 B2 | 11/2021 | Xia et al. |
| 1,119,387 A1 | 12/2021 | Wagner et al. |
| 11,243,494 B2 | 2/2022 | Mueth et al. |
| 2002/0027649 A1 | 3/2002 | Chudner |
| 2002/0042042 A1 | 4/2002 | Fahy |
| 2002/0058332 A1 | 5/2002 | Quake et al. |
| 2002/0106716 A1 | 8/2002 | Leboeuf et al. |
| 2002/0115208 A1 | 8/2002 | Mitchell et al. |
| 2002/0176069 A1 | 11/2002 | Hansen et al. |
| 2002/0198928 A1 | 12/2002 | Bukshpan et al. |
| 2003/0007894 A1 | 1/2003 | Wang et al. |
| 2003/0032204 A1 | 2/2003 | Walt et al. |
| 2003/0047676 A1 | 3/2003 | Grier et al. |
| 2003/0054365 A1 | 3/2003 | Xu et al. |
| 2003/0054558 A1 | 3/2003 | Kurabayashi et al. |
| 2003/0068646 A1 | 4/2003 | Singh et al. |
| 2003/0113709 A1 | 6/2003 | Alivisatos et al. |
| 2003/0175944 A1 | 9/2003 | Yang et al. |
| 2003/0175980 A1 | 9/2003 | Hayenga et al. |
| 2003/0186426 A1 | 10/2003 | Brewer et al. |
| 2004/0043506 A1 | 3/2004 | Haussecker et al. |
| 2004/0079893 A1 | 4/2004 | Dietz et al. |
| 2004/0089798 A1 | 5/2004 | Gruber et al. |
| 2004/0144648 A1 | 7/2004 | Jacobson et al. |
| 2004/0161772 A1 | 8/2004 | Bohm et al. |
| 2004/0166504 A1 | 8/2004 | Rossier et al. |
| 2004/0206399 A1 | 10/2004 | Heller et al. |
| 2004/0217297 A1 | 11/2004 | Moses et al. |
| 2004/0229349 A1 | 11/2004 | Daridon |
| 2004/0266022 A1 | 12/2004 | Sundararajan et al. |
| 2005/0037471 A1 | 2/2005 | Liu et al. |
| 2005/0061962 A1 | 3/2005 | Mueth et al. |
| 2005/0103690 A1 | 5/2005 | Kawano et al. |
| 2005/0112541 A1 | 5/2005 | Durack et al. |
| 2005/0121604 A1 | 6/2005 | Mueth et al. |
| 2005/0123450 A1 | 6/2005 | Gilbert |
| 2005/0124869 A1 | 6/2005 | Hefti et al. |
| 2005/0148085 A1 | 7/2005 | Larsen |
| 2005/0153354 A1 | 7/2005 | Gilmanshin |
| 2005/0190372 A1 | 9/2005 | Dogariu |
| 2005/0196876 A1 | 9/2005 | Chan et al. |
| 2005/0207940 A1 | 9/2005 | Butler et al. |
| 2005/0207943 A1 | 9/2005 | Puzey |
| 2006/0013270 A1 | 1/2006 | Yumoto et al. |
| 2006/0035273 A1 | 2/2006 | Quake et al. |
| 2006/0043301 A1 | 3/2006 | Mantele et al. |
| 2006/0058167 A1 | 3/2006 | Regusa et al. |
| 2006/0078888 A1 | 4/2006 | Griffiths |
| 2006/0105453 A1 | 5/2006 | Brenan et al. |
| 2006/0152707 A1 | 7/2006 | Kanda |
| 2006/0170912 A1 | 8/2006 | Mueth et al. |
| 2006/0252047 A1 | 11/2006 | Ekstrom et al. |
| 2006/0257089 A1 | 11/2006 | Mueth et al. |
| 2006/0263829 A1 | 11/2006 | Evans et al. |
| 2007/0009386 A1 | 1/2007 | Padmanabhan et al. |
| 2007/0078348 A1 | 4/2007 | Holman |
| 2007/0114172 A1 | 5/2007 | Mueth et al. |
| 2007/0128082 A1 | 6/2007 | Yang et al. |
| 2007/0207551 A1 | 9/2007 | Glensbjerg |
| 2007/0247620 A1 | 10/2007 | Koo |
| 2007/0248958 A1 | 10/2007 | Jovanovich et al. |
| 2007/0255362 A1 | 11/2007 | Levinson |
| 2008/0003685 A1 | 1/2008 | Goix et al. |
| 2008/0014574 A1 | 1/2008 | Viator et al. |
| 2008/0021674 A1* | 1/2008 | Puskas ............... G01N 21/6428 702/179 |
| 2008/0069733 A1 | 3/2008 | Maltezo et al. |
| 2008/0144037 A1 | 6/2008 | Mueth et al. |
| 2008/0166188 A1 | 7/2008 | Gilbert et al. |
| 2008/0195020 A1 | 8/2008 | Cabuz et al. |
| 2008/0213821 A1 | 9/2008 | Liu et al. |
| 2008/0248966 A1 | 10/2008 | Hansen et al. |

(56) References Cited

U.S. PATENT DOCUMENTS

| | | |
|---|---|---|
| 2008/0261295 A1 | 10/2008 | Butler et al. |
| 2008/0292555 A1 | 11/2008 | Ye et al. |
| 2008/0299013 A1 | 12/2008 | Trieu et al. |
| 2008/0309919 A1 | 12/2008 | Birmingham et al. |
| 2008/0311005 A1 | 12/2008 | Kim et al. |
| 2009/0004652 A1 | 1/2009 | Rubin et al. |
| 2009/0029870 A1 | 1/2009 | Ward et al. |
| 2009/0032449 A1 | 2/2009 | Mueth et al. |
| 2009/0042241 A1 | 2/2009 | Yu-Chong et al. |
| 2009/0051912 A1 | 2/2009 | Salazar et al. |
| 2009/0114285 A1 | 5/2009 | Hashimoto et al. |
| 2009/0125242 A1 | 5/2009 | Choi et al. |
| 2009/0141279 A1 | 6/2009 | Hillmer |
| 2009/0156932 A1* | 6/2009 | Zharov .......... A61B 5/412 600/437 |
| 2009/0170149 A1 | 7/2009 | Viator et al. |
| 2009/0176271 A1 | 7/2009 | Durack et al. |
| 2009/0201504 A1 | 8/2009 | Ho et al. |
| 2009/0225319 A1 | 9/2009 | Lee et al. |
| 2009/0281250 A1 | 11/2009 | DeSimone et al. |
| 2009/0290156 A1 | 11/2009 | Popescu et al. |
| 2010/0044570 A1 | 2/2010 | McGill et al. |
| 2010/0068723 A1 | 3/2010 | Jovanovich et al. |
| 2010/0079516 A1 | 4/2010 | Nakazawa |
| 2010/0171954 A1 | 7/2010 | Quake et al. |
| 2010/0216208 A1 | 8/2010 | Mueth et al. |
| 2010/0248362 A1 | 9/2010 | Durack et al. |
| 2010/0330693 A1 | 12/2010 | Chapin et al. |
| 2011/0001963 A1 | 1/2011 | Durack |
| 2011/0003303 A1 | 1/2011 | Pagano et al. |
| 2011/0003324 A1 | 1/2011 | Durack |
| 2011/0003325 A1 | 1/2011 | Durack |
| 2011/0003330 A1 | 1/2011 | Durack |
| 2011/0008764 A1 | 1/2011 | Silva et al. |
| 2011/0008767 A1 | 1/2011 | Durack |
| 2011/0008817 A1 | 1/2011 | Durack |
| 2011/0008818 A1 | 1/2011 | Durack |
| 2011/0075928 A1 | 3/2011 | Jeong et al. |
| 2011/0076712 A1 | 3/2011 | Gilligan et al. |
| 2011/0090500 A1 | 4/2011 | Hu et al. |
| 2011/0096327 A1 | 4/2011 | Papautsky et al. |
| 2011/0190146 A1 | 8/2011 | Boehm et al. |
| 2011/0223654 A1 | 9/2011 | Holman et al. |
| 2011/0256523 A1 | 10/2011 | Mendele et al. |
| 2011/0263747 A1 | 10/2011 | Doyle et al. |
| 2011/0294139 A1 | 12/2011 | Takeda |
| 2012/0009619 A1 | 1/2012 | Gilbert et al. |
| 2012/0028366 A1 | 2/2012 | Krager et al. |
| 2012/0033220 A1 | 2/2012 | Kotidis et al. |
| 2012/0033697 A1 | 2/2012 | Goyal et al. |
| 2012/0081709 A1 | 4/2012 | Durack |
| 2012/0082362 A1 | 4/2012 | Diem et al. |
| 2012/0107805 A1 | 5/2012 | Neas et al. |
| 2012/0122084 A1 | 5/2012 | Wagner et al. |
| 2012/0138152 A1 | 6/2012 | Villarruel et al. |
| 2012/0183947 A1 | 7/2012 | Mueth et al. |
| 2012/0196356 A1 | 8/2012 | Wagner et al. |
| 2012/0199741 A1 | 8/2012 | Wagner et al. |
| 2012/0199742 A1 | 8/2012 | Wagner et al. |
| 2012/0202237 A1 | 8/2012 | Sedoglavich et al. |
| 2012/0202277 A1 | 8/2012 | Wagner et al. |
| 2012/0202278 A1 | 8/2012 | Wagner et al. |
| 2012/0204628 A1 | 8/2012 | Wagner et al. |
| 2012/0225474 A1 | 9/2012 | Wagner et al. |
| 2012/0225475 A1 | 9/2012 | Wagner et al. |
| 2012/0273054 A1 | 11/2012 | Lou et al. |
| 2012/0287419 A1 | 11/2012 | Sharpe et al. |
| 2012/0295263 A1 | 11/2012 | Cantor et al. |
| 2012/0307244 A1 | 11/2012 | Lou et al. |
| 2013/0121877 A1 | 5/2013 | Ono |
| 2013/0164731 A1 | 6/2013 | Cimino et al. |
| 2013/0164773 A1 | 6/2013 | Bardell et al. |
| 2013/0200277 A1 | 8/2013 | Li et al. |
| 2013/0224843 A1 | 8/2013 | Evans et al. |
| 2013/0252237 A1 | 9/2013 | Wagner |
| 2013/0295602 A1 | 11/2013 | Fowler |
| 2013/0313170 A1 | 11/2013 | Bohm et al. |
| 2014/0033808 A1 | 2/2014 | Ding et al. |
| 2014/0050540 A1 | 2/2014 | Gilbert et al. |
| 2014/0091014 A1 | 4/2014 | Wagner et al. |
| 2014/0224710 A1 | 8/2014 | Di Carlo et al. |
| 2014/0273192 A1 | 9/2014 | Sharpe |
| 2014/0287243 A1 | 9/2014 | Weber et al. |
| 2014/0318645 A1 | 10/2014 | Koksal |
| 2014/0339446 A1 | 11/2014 | Yamamoto et al. |
| 2014/0361148 A1 | 12/2014 | Popescu et al. |
| 2015/0064694 A1 | 3/2015 | Sadri |
| 2015/0114093 A1 | 4/2015 | Appleyard et al. |
| 2015/0192511 A1 | 7/2015 | Wagner et al. |
| 2015/0198517 A1 | 7/2015 | Simpson et al. |
| 2015/0276588 A1 | 10/2015 | Marshall et al. |
| 2016/0004060 A1 | 1/2016 | Simpson et al. |
| 2016/0123858 A1 | 5/2016 | Kapur et al. |
| 2016/0199835 A1 | 7/2016 | Tachibana et al. |
| 2016/0303563 A1 | 10/2016 | Granier et al. |
| 2017/0016813 A1 | 1/2017 | Wagner et al. |
| 2017/0181425 A1 | 6/2017 | Burbank et al. |
| 2017/0307505 A1 | 10/2017 | Vrane et al. |
| 2017/0333902 A1 | 11/2017 | Masaeli et al. |
| 2018/0266937 A1 | 9/2018 | de Wagenaar et al. |
| 2019/0025212 A1 | 1/2019 | Evans |
| 2019/0040356 A1 | 2/2019 | Durack et al. |
| 2019/0071725 A1 | 3/2019 | Roti-Roti et al. |
| 2019/0187044 A1 | 6/2019 | Appleyard et al. |
| 2019/0382720 A1 | 12/2019 | Savage et al. |
| 2019/0390164 A1 | 12/2019 | Morjal et al. |
| 2020/0070152 A1 | 3/2020 | Kasai et al. |
| 2022/0025443 A1 | 1/2022 | Korani et al. |
| 2022/0026341 A1 | 1/2022 | Appleyard et al. |

FOREIGN PATENT DOCUMENTS

| | | |
|---|---|---|
| CN | 1482369 | 3/2004 |
| CN | 1886315 | 12/2006 |
| CN | 101189504 | 5/2008 |
| CN | 109221081 A | 1/2019 |
| CN | 109497040 | 3/2019 |
| CN | 109517787 | 3/2019 |
| EP | 0057907 | 8/1982 |
| EP | 0282994 | 9/1988 |
| EP | 0679325 | 7/1994 |
| EP | 0471758 A1 | 9/1996 |
| FR | 2798557 | 3/2001 |
| GB | 502971 | 5/1939 |
| GB | 2507959 | 5/2014 |
| JP | 57-131451 | 8/1982 |
| JP | 58090513 | 5/1983 |
| JP | S 64-26125 A | 1/1989 |
| JP | 64074451 | 3/1989 |
| JP | 02105041 | 4/1990 |
| JP | 03297385 | 12/1991 |
| JP | H0526799 | 2/1993 |
| JP | 06265452 | 9/1994 |
| JP | 06327494 | 11/1994 |
| JP | 07024309 | 1/1995 |
| JP | 07286953 | 10/1995 |
| JP | 2552582 | 11/1996 |
| JP | H10512952 | 12/1998 |
| JP | H11508182 | 7/1999 |
| JP | 2000146819 | 5/2000 |
| JP | 2000512541 | 9/2000 |
| JP | 2001504936 | 4/2001 |
| JP | 2002503334 | 1/2002 |
| JP | 2002153260 | 5/2002 |
| JP | 2003106980 | 4/2003 |
| JP | 2003515738 | 5/2003 |
| JP | 2004093553 | 3/2004 |
| JP | 2005502482 | 1/2005 |
| JP | 2005530986 | 10/2005 |
| JP | 2006524054 | 10/2006 |
| JP | 2007-514522 A | 6/2007 |
| JP | 2007148981 | 6/2007 |
| JP | 2007514522 | 6/2007 |
| JP | 2007515936 | 6/2007 |

(56) References Cited

FOREIGN PATENT DOCUMENTS

| | | |
|---|---|---|
| JP | 2008533440 | 8/2008 |
| JP | 2008261295 A1 | 10/2008 |
| JP | 2009085872 A | 4/2009 |
| JP | 2009115672 A | 5/2009 |
| JP | 2009162660 A | 7/2009 |
| JP | 2010117197 | 5/2010 |
| JP | 2010151777 | 7/2010 |
| JP | 2010190680 | 9/2010 |
| JP | 2011145185 | 7/2011 |
| JP | 2014503195 | 2/2014 |
| WO | WO9622521 | 7/1996 |
| WO | WO9700442 | 1/1997 |
| WO | WO-9730338 A1 * | 8/1997 ......... G01N 15/1459 |
| WO | WO9739338 | 10/1997 |
| WO | WO9747390 | 12/1997 |
| WO | WO9810267 | 3/1998 |
| WO | WO99/39223 | 8/1999 |
| WO | WO20000070080 A1 | 11/2000 |
| WO | WO0118400 | 3/2001 |
| WO | WO0131315 | 5/2001 |
| WO | WO2001040766 | 6/2001 |
| WO | WO0185913 | 11/2001 |
| WO | WO200241906 | 5/2002 |
| WO | WO2002081183 A1 | 10/2002 |
| WO | WO02087792 | 11/2002 |
| WO | WO03024163 | 3/2003 |
| WO | WO03062867 | 7/2003 |
| WO | WO03078065 A1 | 9/2003 |
| WO | WO2003078065 | 9/2003 |
| WO | WO2004012133 | 2/2004 |
| WO | WO2004029221 | 4/2004 |
| WO | WO2004043506 A1 | 5/2004 |
| WO | WO2004088283 | 10/2004 |
| WO | WO20040088283 A1 | 10/2004 |
| WO | WO2005023391 | 3/2005 |
| WO | WO2005075629 | 8/2005 |
| WO | WO20050075629 A1 | 8/2005 |
| WO | WO2006119806 | 11/2006 |
| WO | WO20060119806 A1 | 11/2006 |
| WO | WO2007008495 A2 | 1/2007 |
| WO | WO2007133710 A2 | 11/2007 |
| WO | WO2008114458 | 9/2008 |
| WO | WO2008126064 A2 | 10/2008 |
| WO | WO2008130977 A1 | 10/2008 |
| WO | WO2009032449 A1 | 3/2009 |
| WO | WO2009134395 | 11/2009 |
| WO | WO2010129441 | 11/2010 |
| WO | WO2012068287 A2 | 5/2012 |
| WO | WO2012112641 | 8/2012 |
| WO | WO20120112641 A1 | 8/2012 |
| WO | WO20130018273 A1 | 2/2013 |
| WO | WO2013173446 | 11/2013 |
| WO | WO2005037471 A1 | 9/2014 |
| WO | 2015038494 | 3/2015 |
| WO | WO2015063552 | 5/2015 |
| WO | WO2018047011 A2 | 3/2018 |
| WO | WO2018047011 A2 | 5/2018 |
| WO | WO2018151680 A1 | 8/2018 |
| WO | WO2020092321 A1 | 5/2020 |
| WO | WO2020182193 A1 | 9/2020 |

OTHER PUBLICATIONS

USPTO "Final Office Action," issued in connection with U.S. Appl. No. 16/852,303, dated May 1, 2023, 33 pages.

Jun et al. "Detecting and estimating contamination of human DNA samples in sequencing and array-based genotype data." The American Journal of Human Genetics 91.5 (2012): 839-848.

International Searching Authority, "International Search Report and Written Opinion," issued in connection with International Patent Application No. PCT/US21/56094, dated Mar. 16, 2022, 22 pages.

USPTO, "Notice of Allowance," issued in connection with U.S. Appl. No. 17/496,469, dated May 10, 2022, 54 pages.

China National Intellectual Property Administration, "Notice of Allowance," issued in connection with Chinese Patent Application No. 201480071952.0, dated Mar. 21, 2022, 3 pages.

China Patent Office, "The Fifth Office Action," issued in connection with China Patent Application No. 2014800719520, dated Oct. 20, 2021, 7 pages.

USPTO, "Non-Final Office Action," issued in connection with U.S. Appl. No. 17/458,947, dated Dec. 15, 2021, 9 pages.

USPTO, "Notice of Allowance," issued in connection with U.S. Appl. No. 16/864,514, dated Jan. 3, 2022, 24 pages.

USPTO, "Notice of Allowance," issued in connection with U.S. Appl. No. 16/419,756, dated Jan. 12, 2022, 16 pages.

USPTO, "Non-Final Office Action," issued in connection with U.S. Appl. No. 16/852,303, dated Jan. 6, 2022, 27 pages.

Intellectual Property India, "Examination Report," issued in connection with Indian Patent Application No. 202147003036, dated Jan. 4, 2022, 5 pages.

Di Carlo, "Inertial microfluidics." Lab on a Chip 9.21 (2009): 3038-3046.

Intellectual Property India, "Examination Report," issued in connection with Indian Patent Application No. 202017054203, dated Jan. 7, 2022, 5 pages.

Jokinen, Ville, et al. "Durable superhydrophobicity in embossed CYTOP fluoropolymer micro and nanostructures", Colloids and Surfaces A: Physicochemical and Engineering Aspects, vol. 434, 2013, pp. 207-212.

Forsberg, Pontus, Fredrik Nikolajeff, and Mikael Karlsson, "Cassie-Wenzel and Wenzel-Cassie transitions on immersed superhydrophobic surfaces under hydrostatic pressure", Soft Matter, vol. 7, No. 1, 2011, pp. 104-109.

Lu, Hang, Martin A. Schmidt, and Klavs F. Jensen, "Photochemical reactions and on-line UV detection in microfabricated reactors", Lab on a Chip, vol. 1, No. 1, 2001, pp. 22-28.

Ai-Holy et al., "The Use of Fourier Transform Infrared Spectroscopy to Differentiate *Escherichia coli* O157:H7 from Other Bacteria Inoculated Into Apple Juice," Food Microbiology, vol. 23, 2006, 162-168.

Alberts et al., "Molecular Biology of the Cell, 5th edition," New York: Garland Science, 2008, p. 1293.

Barcot et al., "Investigation of Spermatozoa and Seminal Plasma by Fourier Transform Infrared Spectroscopy," Applied Spectroscopy, vol. 61, No. 3, Mar. 2007, pp. 309-313.

Bassan et al; "Reflection Contributions to the Dispersion Artefact in FTIR Spectra of Single Biological Cells," Analyst, vol. 134, Apr. 9, 2009, pp. 1171-1175.

Bassan et al; "Resonant Mie Scattering in Infrared Spectrascopy of Biological Materials—Understanding the Dispersion Artefact," Analyst, vol. 134, 2009, pp. 1586-1593.

Bassan et al; "Resonant Mie Scattering {RMieS) Correction of Infrared Spectra From Highly Scattering Biological Samples," Analyst, vol. 135, No. 2, Feb. 2010, pp. 268-277.

Belkin et al.; "Intra-Cavity Absorption Spectroscopy with Narrow-Ridge Microfluidic Quantum Cascade Lasers," Applies Express, vol. 15, No. 18, Sep. 3, 2007, pp. 11262-11271.

Boustany et al.; "Microscopic Imaging and Spectroscopy with Scattered Light," Annual Review of Biomedical Engineering, vol. 12, 2010, pp. 285-314.

Chan et al.; "Nondestructive Identification of Individual Leukemia Cells by Laser Trapping Raman Spectroscopy," Analytical Chemistry, vol. 80, No. 6, Mar. 15, 2008, 8 pages.

Chan et al.; "Label-Free Biochemical Characterization of Stem Cells Using Vibrational Spectroscopy," Journal of Biophotonics vol. 2, No. 11, Aug. 5, 2009, pp. 656-668.

Chan et al.; "Label-Free Separation of Human Embryonic Stem Cells {hESCs) and their Cardiac Derivatives using Raman Spectroscopy," Lawrence Livermore Journal, LLNL-JRNL-406938, Sep. 11, 2008, 30 pages.

Chen et al,; "Synchrotron Infrared Measurements of Protein Phosphorylation in Living Single PC12 Cells during Neuronal Differentiation," Analytical Chemistry, vol. 84, 2012, pp. 4118-4125.

(56) References Cited

OTHER PUBLICATIONS

Cheng et al., "Laser-Scanning Coherent Anti-Strokes Raman Scattering Microscopy and Applications to Cell Biology," Biophysical Journal, vol. 83, Jul. 2002, pp. 502-509.
Cho et al., "Passively Driven Integrated Microfluidic System for Separation of Motile Sperm," Analytical Chemistry, vol. 75, Apr. 1, 2003, Abstract.
"Clinical Laboratory Instruments and In Vitro Diagnostic Reagents", Personnel Department of the State Food and Drug Administration, et al., pp. 17-21, China Medical Science and Technology Publishing House, Oct. 31, 2010).
Cho et al., A Microfluidic Device for Separating Motile Sperm From Nonmotile Sperm via Inter-Streamline.
Cleary et al., "Infrared Surface Plasmon Resonance Biosensor," OSA Biomed, Miami, Florida, Apr. 2010, 6 pages.
Dousseau et al., "On the Spectral Subtraction of Water from the FT-IR Spectra of Aqueous Solutions of Proteins," Applied Spectroscopy, vol. 43, No. 3, 1989, pp. 538-542.
Downes et al., "Optical Spectroscopy for Noninvasive Monitoring of Stem Cell Differentation," Journal of Biomedicine and Biotechnology, vol. 2010, Article ID 101864, 2010, 10 pages.
Ege, "Organic Chemistry: Structure and Reactivity," Fifth Edition, Boston, MA, Houghton Mifflin Company, 2004, pp. 453-457.
European Patent Office, "Extended European Search Report," issued in connection with European Patent Application No. 11841869.8, dated Feb. 15, 2018, 9 pages.
Fu et al., "A Microfabricated Fluorescence-Activated Cell Sorter," Nature Biotechnology, vol. 17, Nov. 1999, pp. 1109-1111.
Green et al., "Flow Cytometric Determination of Size and Complex Refractive Index for Marine Particles: Comparison with Independent and Bulk Estimates," Applied Optics, vol. 42, No. 3, Jan. 20, 2003, pp. 526-541.
Harvey et al., "Discrimination of Prostate Cancer Cells by Reflection Mode FTIR Photoacoustic Spectroscopy," The Analyst, vol. 132, 2007, pp. 292-295.
Herzenberg et al., "Fluorescence-activated Cell Sorting," Scientific American, vol. 234, Mar. 1976, pp. 108-117.
Holman et al., "Synchrotron-Based FTIR Spectromicroscopy: Cytotoxicity and Heating Considerations," Journal of Biological Physics, vol. 29, 2003, pp. 275-286.
Holman et al., "IR Spectroscopic Characteristics of Cell Cycle and Cell Death Probed by Synchrotron Radiation Based Fourier Transform IR Spectromicroscopy," Biopolymers (Biospectroscopy) vol. 57, 2000, pp. 329-335.
Holman et al., "Tracking Chemical Changes in a Live Cell: Biomedical Applications of SR-FTIR Spectromicroscopy," Lawrence Berkeley National Laboratory, http://escholarship.org/uc/item/9k185794, Berkeley, CA Jul. 25, 2002, 34 pages.
Huser et al., "Raman Spectroscopy of DNA Packaging in Individual Human Sperm Cells Distinguishes Normal From Abnormal Cells," Journal of Biophotonics, vol. 2, No. 5, 2009, pp. 322-332.
Intel, "Intel C-bank Tunable Laser, Performance and Design," White Paper, May 2003, 14 pages.
International Searching Authority, "International Search Report and Written Opinion," International Patent Application No. PCT/US2013/41123, dated Aug. 19, 2013, 12 pages.
International Search Authority, "International Preliminary Report on Patentability," International Patent Application No. PCT/US2011/061046, dated May 30, 2013, 7 pages.
International Searching Authority, "International Preliminary Report on Patentability," International Patent Application No. PCT/US2013/041123, dated Nov. 18, 2014, 7 pages.
Japan Patent Office, "Office Action," issued in connection with Japanese Patent Application No. 2013-539983, dated Jul. 8, 2015, 6 pages.
Japan Patent Office, "Office Action," issued in connection with Japanese Patent Application No. 2013-539983, dated Jul. 2, 2016, 6 pages.
Japan Patent Office, "Office Action," issued in connection with Japanese Patent Application No. 2016-198323, dated Oct. 2, 2017, 3 pages.
Japan Patent Office, "Office Action," issued in connection with Japanese Patent Application No. 2016-198323, dated Jul. 25, 2018, 9 pages.
Lee et al., "DFB Quantum Cascade Laser Arrays," IEEE Journal of Quantum Electronics, vol. 45, No. 5, May 9, pp. 554-565.
Ibbus et al., "Incidence of Chromosome Aberrations in Mammalian Sperm Stained with Hoechst 33342 and UV-aser Irradiated During Flow Sorting," Mutation Research, vol. 182, 1987, pp. 265-274.
Malone, Jr., "Infrared Microspectroscopy: A Study of the Single Isolated Bread Yeast Cell," Thesis, The Ohio State University, 2010, 162 pages.
Meister et al., "Confocal Raman Microspectroscopy as an Analytical Tool to Assess the Mitochondral Status in Human Spermatozoa," Analyst, vol. 135, 2010, pp. 1370-1374.
Miyamoto et al., "Label-free Detection and Classification of DNA by Surface Vibration Spectroscopy in Conjugation with Electrophoresis," Applied Physics Letters, vol. 86, No. 053902, 2005, 3 pages.
Mohlenhoff et al., "Mie-Type Scattering and Non-Beer-Lambert Absorption Behavior of Human Cells in Infared Microspectroscopy," Biophysical Journal, vol. 88, May 2005, pp. 3635-3640.
Montag et al., "Laser-induced Immobilization and Plasma Membrane Permeabilization in Human Spermatozoa," Human Reproduction, vol. 15, No. 4, 2000, pp. 846-852.
Mourant et al., "Methods for Measuring the Infrared Spectra of Biological Cells," Physics in Medicine and Biology, vol. 48, 2003, pp. 243-257.
Van Munster, "Interferometry in Flow to Sort Unstained X- and Y-Chromosome-Bearing Bull Spermatozoa," Cytometry, vol. 47, 2002, pp. 192-199.
Rajagopalan et al., "Aneuploidy and Cancer," Nature, vol. 432, Nov. 2004, pp. 338-341.
Ropcke et al., "Application of Mid-Infrared Tuneable Diode Laser Absorption Spectroscopy to Plasma Diagnostics: A Review," Plasma Sources Science and Technology, vol. 15, 2006, S148-S168.
Schaden et al., "Quantum Cascade Laser Modulation for Correction of Matrix-Induced Background Changes in Aqueous Samples," Applied Physics B, vol. 86, 2007, pp. 347-351.
Sandt et al., "Identification of Spectral Modifications Occurring during Reprogramming of Somatic Cells," PLoS One, vol. 7, Issue 4, e30743, Apr. 2012, 7 pages.
USPTO, "Final Office Action," issued in connection with U.S. Appl. No. 16/741,608, dated Oct. 19, 2022, 12 pages.
USPTO, "Non-Final Office Action," issued in connection with U.S. Appl. No. 17/851,319, dated Nov. 2, 2022, 12 pages.
USPTO, "Final Office Action," issued in connection with U.S. Appl. No. 16/279,430, dated Dec. 6, 2022, 18 pages.
Notice of Allowance issued in U.S. Appl. No. 17/692,876 dated Feb. 1, 2023, 24 pages.
European Patent Office, "European Search Report," issued in connection with European Patent Application No. 22190948.4, dated Jan. 23, 2023, 10 pages.
European Patent Office, "Intention to Grant Notice," issued in connection with patent application No. 20167363.9, dated Dec. 15, 2022, 8 pages.
Notice of Allowance issued in U.S. Appl. No. 16/741,608 dated Feb. 7, 2023, 22 pages.
New Zealand IP Office, "First Examination Report," issued in connection with New Zealand Patent Application No. 751869, dated Aug. 12, 2022, 3 pages.
Canadian Office Action, Application No. 3,034,007, dated Aug. 25, 2022, 3 pages.
USPTO, "Final Office Action," issued in connection with U.S. Appl. No. 16/741,608, dated Jun. 13, 2022, 11 pages.
USPTO, "Non-Final Office Action," issued in connection with U.S. Appl. No. 17/403,642, dated Jul. 13, 2022, 7 pages.
CNIPA, "First Office Action," issued in connection with Chinese Patent Application No. 202080028183.1, dated July 6, 2022, 21 pages.

(56) References Cited

OTHER PUBLICATIONS

USPTO, "Non-Final Office Action," issued in connection with U.S. Appl. No. 16/741,608, dated Mar. 18, 2022, 12 pages.
USPTO, "Notice of Allowance," issued in connection with U.S. Appl. No. 17/412,789, dated Mar. 21, 2022, 30 pages.
USPTO, "Notice of Allowance," issued in connection with U.S. Appl. No. 17/458,947, dated Mar. 31, 2022, 30 pages.
Altendorf et al., "Results Obtained Using a Prototype Microfluidics-Based Hematology Analyzer," in Proceedings of the microTAS 1998 Symposium, 73-76 (Oct. 1998).
Nieuwenhuis et al., "Particle-Shape Sensing-Elements for Integrated Flow Cytometer," in Proceedings of the microTAS 2001 Symposium, 357-358 (Oct. 21, 2001).
Nieuwenhuis et al. "Virtual Flow Channel: A Novel Micro-fluidics System with Orthogonal, Dynamic Control of Sample Flow Dimensions," in Proceedings of the microTAS 2002 Symposium, vol. 1, 103-105 (Nov. 3, 2002).
Nieuwenhuis, J., et al. "Integrated flow-cells for novel adjustable sheath flows." Lab Chip, 2003, 3, 56-61 (Mar. 2003).
Shoji, S., et al. "Design and fabrication of micromachined chemical/biochemical systems." Riken Rev., vol. 36, pp. 8-11, 2001.
Lin, C., et al. "A Novel Microflow Cytometer with 3-dimensional Focusing Utilizing Dielectrophoretic and Hydrodynamic Forces." The Sixteenth Annual International Conference on Micro Electro Mechanical Systems, 2003. MEMS-03 Kyoto. IEEE, Kyoto, Japan, 2003, pp. 439-442.
Miyake et al., "A Development of Micro Sheath Flow Chamber," in Proceedings of the IEEE Micro Electro Mechanical Systems Workshop 1991, 265-270 (Jan. 1991).
Tashiro et al., "Design and Simulation of Particles and Biomolecules Handling Micro Flow Cells with Three-Dimensional Sheath Flow," in Proceedings of the microTAS 2000 Symposium, 209-212 (May 14, 2000).
Weigl, B. et al. "Design and Rapid Prototyping of Thin-Film Laminate-Based Microfluidic Devices." Biomedical Microdevices, 3:4, pp. 267-274, 2001.
Blankenstein, G. et al. "Modular concept of a laboratory on a chip for chemical and biochemical analysis." Biosensors & Bioelectronics, vol. 13. No. 3-4, pp. 427-438, 1998.
Shapiro, Practical Flow Cytometry, 15-17, 133-135 (3rd ed. 1995).
Shapiro, Practical Flow Cytometry, 55-57, 166-169 (4th ed. 2003).
International Search Report for PCT Patent Application No. PCT/IB2014/001425 dated Apr. 28, 2015.
Herweijer, H. et al., "High Speed Photodamage Cell Selection Using Bromodeoxyuridine/Hoechst 33342 Photosensitized Cell Killing", Radiobiological Institute TNO, Rotterdam, The Netherlands, Jun. 1, 1987.
Johnson, L.A., et al., "Sex Preselection: High-Speed Flow Cytometric Sorting of X and Y Sperm for Maximum Efficiency" U.S. Dept. of Agriculture, Beltsville, MD, Sep. 23, 1999.
Bazyer H., et al., "Views and Reviews—Compact 151W Green Laser with U-Type Resonator for Prostate Surgery", Optics & Laser Technology, vol. 47, Apr. 27, 2013, 237-241.
Keij, J. et al, "High-Speed Photodamage Cell Sorting: An Evaluation of the ZAPPER Prototype", Methods in Cell Biology, 1994; pp. 371-386, vol. 42, Chapter 22, Academic Press, Inc.
International Search Report and Written Opinion dated Mar. 7, 2014 in connection with PCT/US2013/050669.
Kachel, V, et al., "Uniform Lateral Orientation, caused by Flow Forces, of Flat Particles in Flow-Through Systems", The Journal of Histochemistry and Cytochemistry, vol. 25, No. 7, pp. 774-780, 1977.
Notice of Allowance issued in U.S. Appl. No. 13/943,322 dated Sep. 12, 2014.
Fulwler, M., "Hydrodynamic Orientation of Cells", The Journal of Histochemistry and Cytochemistry, vol. 25, No. 7, pp. 781-783, 1977.
Khodjakov A., et al., "A Synergy of Technologies: Combining Laser Microsurgery with Green Fluorescent Protein Tagging", Cell Motility and the Cytoskeleton 38:311-317 (1997), Division of Molecular Medicine and Department of Biomedical Sciences, Albany, New York.
Canadian Office Action, Application No. 2,929,275, dated May 4, 2020, 8 pages.
Australian Office Action, Application No. 2019202882, dated Mar. 26, 2020, 3 pages.
Brazilian Office Action, Application No. BR122017012966-0, dated Jun. 2, 2020, 6 pages.
Japan Patent Office, "Reconsideration Report by Examiner before Appeal," issued in connection with Japanese Patent Application No. 2016-551082, dated Jul. 12, 2019, 17 pages. 20090114285.
Intellectual Property India, "Examination Report," issued in connection with Indian Patent Application No. 3425/DELNP/2015, dated Jan. 20, 2020, 6 pages.
European Patent Office, "Extended European Search Report," issued in connection with patent application No. 19182993.6, dated Oct. 21, 2019, 11 pages.
China National Intellectual Property Administration, "Second Office Action," issued in connection with Chinese Patent Application No. 201480071952.0, dated Nov. 26, 2018, 34 pages.
China National Intellectual Property Administration, "Decision of Rejection," issued in connection with Chinese Patent Application No. 201480071952.0, dated Mar. 4, 2019, 19 pages.
IP Australia, "Examination Report No. 1 for Standard Patent Application," issued in connection with Australian Patent Application No. 2014343391, dated Sep. 4, 2018, 3 pages.
International Preliminary Report on Patentability, issued in connection with application PCT/IB/001425, dated May 3, 2016, 11 pages.
Japan Patent Office, "Non Final Notice of Reasons for Rejection," issued in connection with Japanese Patent Application No. 2016-551082, dated Apr. 24, 2018, 5 pages.
New Zealand IP Office, "First Examination Report," issued in connection with New Zealand Patent Application No. 720575, dated Sep. 9, 2016, 5 pages.
New Zealand IP Office, "Further Examination Report," issued in connection with New Zealand Patent Application No. 720575, dated Apr. 28, 2017, 3 pages.
State Intellectual Property Office of People's Republic of China, "Notification of First Office Action," issued in connection with Chinese Patent Application No. 201480071952.0, dated Mar. 16, 2018, 31 pages.
New Zealand IP Office, "Further Examination Report," issued in connection with New Zealand Patent Application No. 735496, dated Aug. 31, 2018, 2 pages.
Drobnis et al., Cold Shock Damage is due to Lipid Phase Transitions in Cell Membranes: A Demonstration Using Sperm as a Model, The Journal of Experimental Zoology, 1993, 265:432-437.
Way et al., Comparison of four staining methods for evaluating acrosome status and viability of ejaculated and cauda epididymal bull spermatozoa, Theriogenology, 1995, 43(8): 1301-1316.
Marian et al., Hypo-osmotic Shock Induces an Osmolality-dependent Permeabilization and Structural Changes in the Membrane of Carp Sperm, 1993, 41(2):291-297.
Molecular Probes Inc., Product Information, Influx Pinocy1ic Cell-Loading Reagent (1-14402), Revised Feb. 1, 2001, 1-7.
Parks, Processing and Handling Bull Semen for Artificial Insemination—Don't Add Insult to Injury?, Department of Animal Sciences, Cornell University, 2001, retrieved on May 29, 2015, retrieved from the internet: http://www/ansci.cornell.edu/bullsemen.pdf.
Mammal (Online Datasheet), Wikipedia, 2003, retrieved on Aug. 13, 2018, retrieved from internet: http:/web.archive.org/web/20031230110838/hllps://en.wikipedia.org/wiki/Mammal.
International Searching Authority, "International Search Report and Written Opinion," issued in connection with International Patent Application No. PCT/IB2016/000295, dated Oct. 14, 2016, 19 pages.
International Bureau, "International Preliminary Report on Patentability," issued in connection with International Patent Application No. PCT/IB2016/000295, dated Aug. 31, 2017, 14 pages.
Japan Patent Office, "Office Action," issued in connection with Japanese Patent Application No. 2017-543990, dated Jul. 31, 2019, 23 pages.

(56) References Cited

OTHER PUBLICATIONS

Di Carlo et al. "Equilibrium Separation and Filtration of Particles Using Differential Inertial Focusing" Anal. Chem. 2008, 80, 2204-2211 (Year: 2008).
Hydraulic Diameter, Neutrium, Apr. 1, 2012, https://neutrium.net/fluid-flow/hydraulic-diameter/ (Year: 2012).
Gossett et al. "Particle Focusing Mechanisms in Curving Confined Flows" Anal. Chem. 2009, 81, 8459-8465 (Year: 2009).
Di Carlo et al. "Continuous inertial focusing, ordering, and separation of particles in microchannels" PNAS Nov. 27, 2007 vol. 104 No. 48 18893 (Year: 2007).
USPTO, "Non-Final Office Action," issued in connection with U.S. Appl. No. 17/496,614, dated Dec. 21, 2022, 9 pages.
UPSTO, "Non-Final Office Action," issued in connection with U.S. Appl. No. 16/852,303, dated Jan. 9, 2023, 30 pages.
European Patent Office, "European Search Report," issued in connection with European Patent Application No. 20792020.8, dated Dec. 23, 2022, 10 pages.
Brazilian Office Action, Application No. BR112020023607-1, dated Dec. 12, 2022, 5 pages.
Ron Bardell et al. "Microfluidic disposables for cellular and chemical detection: CFD model results and fluidic verification experiments," Proc. SPIE 4265, Biomedical Instrumentation Based on Micro- and Nanotechnology, May 21, 2001; doi: 10.1117/12.427961 Invited Paper: BiOS 2001 The International Symposium on Biomedical Optics, 2001, San Jose, CA, United States, 14 pages.
USPTO, "Final Office Action," issued in connection with U.S. Appl. No. 17/403,642, dated Mar. 4, 2022, 14 pages.
Australian Office Action, Application No. 2021200818, dated Mar. 4, 2022, 3 pages.
Sell, "Cellular Origin of Cancer: Dedifferentiation or Stem Cell Maturation Arrest?", Environmental Health Perspectives, vol. 101, Suppl. 5, 1993, p. 15-26.
Shapiro et al., "Pratical Flow Cytometry," Fourth Edition, New Jersey: John W. Wiley & Sons, 2003, 733 pages.
Sharpe et al.,"Advances in Flow Cytometry for Sperm Sexing," Theriogenology, vol. 71, 2009, pp. 4-10.
Short, "Raman Spectroscopy Detects Biochemical Changes Due to Proliferation in Mammalian Cell Cultures," Biophysical Journal, vol. 88, Jun. 2005, pp. 427 4-4288.
USPTO, "Non-Final Office Action," issued in connection with U.S. Appl. No. 15/226,899, dated Apr. 12, 2018, 14 pages.
USPTO, "Notice of Allowance," issued in connection with U.S. Appl. No. 15/226,899, dated Aug. 23, 2018, 5 pages.
USPTO, "Notice of Allowance," issued in connection with U.S. Appl. No. 15/226,899, dated Sep. 20, 2018, 6 pages.
USPTO, "Final Office Action," issued in connection with U.S. Appl. No. 15/174,681, dated Jan. 2, 2018, 15 pages.
USPTO, "Final Office Action," issued in connection with U.S. Appl. No. 15/174,681, dated Sep. 14, 2018, 17 pages.
USPTO, "Non-Final Office Action," issued in connection with U.S. Appl. No. 15/174,681, dated May 4, 2017, 13 pages.
USPTO, "Non-Final Office Action," issued in connection with U.S. Appl. No. 15/174,681, dated Apr. 5, 2018, 16 pages.
USPTO, "Notice of Allowance," issued in connection with U.S. Appl. No. 15/174,681, dated Nov. 27, 2018, 10 pages.
USPTO, "Final Office Action," issued in connection with U.S. Appl. No. 13/298,148, dated Oct. 18, 2013, 46 pages.
USPTO, "Non-Final Office Action," issued in connection with U.S. Appl. No. 13/298,148, dated Feb. 5, 2013, 66 pages.
USPTO, "Notice of Allowance," issued in connection with U.S. Appl. No. 13/298,148, dated Sep. 19, 2014, 9 pages.
USPTO, "Office Action," issued in connection with U.S. Appl. No. 13/298,148, dated Sep. 28, 2012, 5 pages.
USPTO, "Final Office Action," issued in connection with U.S. Appl. No. 13/894,831, dated Sep. 10, 2015, 11 pages.
USPTO, "Final Office Action," issued in connection with U.S. Appl. No. 13/894,831, dated Jun. 15, 2017, 19 pages.
USPTO, "Non-Final Office Action," issued in connection with U.S. Appl. No. 13/894,831, dated Dec. 23, 2014, 11 pages.
USPTO, "Non-Final Office Action," issued in connection with U.S. Appl. No. 13/894,831, dated Oct. 5, 2016, 17 pages.
USPTO, "Notice of Allowance," issued in connection with U.S. Appl. No. 13/894,831, dated Apr. 1, 2016, 8 pages.
USPTO, "Notice of Allowance," issued in connection with U.S. Appl. No. 13/894,831, dated Sep. 5, 2017, 9 pages.
Wang et al., Detection of endogenous biomolecules in Barrett's esophagus by Fourier transform infrared spectroscopy, PNAS, vol. 104, No. 40, Oct. 2, 2007, p. 15864-15869.
Webster, Merriam, "Definition of "successive," Merriam Webster's Online Dictionary, accessed at http://www.merriamwebster.com/dictionary/successive," Jun. 18, 2013, 1 page.
Weida et al., "Quantum Cascade Laser Based Replacement for FTIR Microscopy," http://www.daylightsolutions. :: om/assets/003/5308.pdf, accessed online Aug. 2, 2012, 7 pages.
International Bureau, "International Preliminary Report on Patentability," issued in connection with International Patent Application No. PCT/IB2017/001289, dated Mar. 21, 2019, 12 pages.
International Search Report and Written Opinion for Application Serial No. PCT/IP2017/001289, dated Apr. 3, 2018, 21 pages.
Mehrnoush Malek et al: flowDensity: reproducing manual gating of flow cytometry data by automated density-based cell population identification11, Bioinformatics., vol. 31, No. 4, Oct. 16, 2014 (Oct. 16, 2014), pp. 606-607.
International Search Report and Written Opinion for Application Serial No. PCT/IB2018/001641, dated Jun. 25, 2020 4 pages.
China Patent Office, "The Fourth Office Action," issued in connection with China Patent Application No. 201480071952.0, dated Jan. 3, 2021, 25 pages.
Japan Patent Office, "Notice of Reasons for Refusal," issued in connection with Japan Patent Application No. 2019-088655, dated Oct. 13, 2020, 5 pages.
Johnson LA et al., Flow sorting of X and Y chromosome-bearing spermatozoa into two populations, Gamete Research. Jan. 1987. 16(1):1-9. (Johnson 1987).
Paape et al., Flow Cytometry: A Versatile Tool for Studies on Cells From Domestic Animals, National Cytometry Symposium, Abstract Only, Dec. 14, 1997, https://www.ars.usda.gov/research/publications/publication/?seqNo115=86408.
Keij, J.F. et al., "High-Speed Photodamage Cell Selection Using a Frequency-Doubled Argon Ion Laser." Cytometry 19 (1995): 209-216. (Keij 1995).
Keij, J.F., "Introduction to High-Speed Flow Sorting." Flow and Image Cytometry. Series H: Cell Biology, 95 (1996): 213-227. (Keij 1996).
Johnson LA, Welch GR, Rens W. "The Beltsville sperm sexing technology: high-speed sperm sorting gives improved sperm output for in vitro fertilization and AI." J Anim Sci 1999. 77:213-220.
Counterclaim Defendants ABS Global Inc.'s and Genus PLC's Invalidity Contentions. *ABS Global, Inc.,* v. *Inguran, LLC D/B/A Sexing Technologies and. XY, LLC* v. *Genus PLC.* Case No. 14-cv-503 United States District Court for the Western District of Wisconsin; pp. 1, 43-114, and 168-177.
ABS Global, Inc. and Genus PLC's Renewed Motion for Judgment as a Matter of Law That the Asserted Claims of the '987 Patent Are Invalid for Lack of Enablement and, in the Alternative, for a New Trial. *ABS Global, Inc.* v. *Inguran, LLC & XY, LLC* v. *Genus PLC.* Case: 3:14-cv-00503-wmc. Filed on Jul. 3, 2020.
Brief in Support of ABS Global, Inc. and Genus PLC's Motion for Judgment as a Matter of Law That the Asserted Claims of the '987 Patent Are Not Enabled. *Inguran, LLC d/b/a Stgenetics, XY, LLC, and Cytonome/ST, LLC,* Plaintiffs/Counterclaim-Defendants, v.*ABS Global, Inc., Genus PLC, and Premium Genetics (UK) Ltd,* Defendants/Counterclaim-Plaintiffs. Case: 3:17-cv-00446-wmc. Filed Sep. 6, 2019.
ABS Global, Inc. and Genus Plc Renewed Motion for Judgment as a Matter of Law That the Asserted Claims of the 987 Patent Are Invalid for Lack of Enablement and, in the Alternative, for a New Trial. *Inguran, LLC d/b/a Stgenetics, XY, LLC, and Cytonome/ST, LLC,* Plaintiffs/Counterclaim-Defendants, v.*ABS Global, Inc., 3enus PLC, and Premium Genetics (UK) Ltd,* Defendants/Counterclaim-Plaintiffs. Case: 3:17-cv-00446-wmc. filed Jul. 3, 2020.

(56) References Cited

OTHER PUBLICATIONS

ABS Global, Inc. and Genus PLC's Reply in Support of Their Renewed Motion for Judgment as a Matter of Law That the Asserted Claims of the '987 Patent Are Invalid for Lack of Enablement and, in the Alternative, for a New Trial. *Inguran, LLC d/b/a Stgenetics, XY, LLC, and Cytonome/ST, LLC*, Plaintiffs/Counterclaim-Defendants, v. *ABS Global, Inc., Genus PLC, and Premium Genetics (UK) Ltd*, Defendants/Counterclaim-Plaintiffs. Case: :17-cv-00446-wmc. Filed Aug. 17, 2020.

ABS Global, Inc. and Genus PLC's Motion for Judgment as a Matter of Law That the Asserted Claims of the 987 and '092 Patents Are Invalid. *ABS Global, Inc.*, Plaintiff/Counterclaim Defendant, v. *Inguran, LLC d/b/a Sexing Technologies,* Defendant/Counterclaim Plaintiff, *and XY, LLC,* Intervenor-Defendant/Counterclaim Plaintiff, v. *Genus PLC,* Counterclaim Defendant. Case: 3:14-cv-00503-wmc. Filed Aug. 9, 2016.

ABS Global, Inc. and Genus PLC's Rule 50(8) Motion for Judgment as a Matter of Law and Rule 59 Motion for a New Trial. *ABS Global, Inc.,* Plaintiff/Counterclaim Defendant, v. *Inguran, LLC d/b/a Sexing Technologies,* Defendant/Counterclaim Plaintiff, *and XY, LLC,* Intervenor-Defendant/Counterclaim Plaintiff, v. *3enus PLC,* Counterclaim Defendant. Case: 3:14-cv-00503-wmc. Filed Sep. 2, 2016.

Opinion and Order of the United States District Court for the Western District of Wisconsin. Plaintiff/Counterclaim Defendant, v. *Inguran, LLC d/b/a Sexing Technologies,* Defendant/Counterclaim Plaintiff, *and XY, LLC,* Intervenor-Defendant/Counterclaim Plaintiff, v. *Genus PLC,* Counterclaim Defendant. Case: 3:14-cv-00503-wmc. riled Mar. 31, 2017.

Appeal from the United States District Court for the Western District of Wisconsin. No. 14-CV-503. *ABS Global, Nc.,* Plaintiff/Counterclaim Defendant-Appellant, *and Genus PLC,* Counterclaim Defendant-Appellant, v. *Inguran, LLC, doing business as Sexing Technologies,* Defendant/Counterclaim Plaintiff-Appellee, *and XY, LLC,* Intervening Defendant/Counterclaim Plaintiff-Appellee. Case: 3:14-cv-00503-wmc. Filed: Mar. 8, 2019.

Judge's Opinion & Order in Case No. 14-cv-503-wmc. Plaintiff/Counterclaim Defendant, v. *Inguran, LLC di b/a Sexing Technologies,* Defendant/Counterclaim Plaintiff, *and XY, LLC,* Intervenor-Defendant/Counterclaim Plaintiff, v. *Genus PLC,* Counterclaim Defendant. Case: 3:14-cv-00503-wmc. Filed Jul. 21, 2016.

ABS Global Inc. and Genus PLC's Reply in Support of Their Motion for Claim Construction and Partial Summary Judgment, *ABS Global, Inc.* v. *Inguran, LLC d/b/a Sexing Technologies,* Case No. 14-cv-503, United States District Court for the Western District of Wisconsin. Mar. 7, 2016.

USPTO, "Non-Final Office Action," issued in connection with U.S. Appl. No. 17/403,642, dated Nov. 29, 2021, 13 pages.

Intellectual Property India, "Examination Report," issued in connection with Indian Patent Application No. 201917009874, dated Nov. 25, 2021, 6 pages.

Australian Office Action, Application No. 2017323502, dated Oct. 22, 2021, 6 pages.

Japan Patent Office, "Office Action," issued in connection with Japanese Patent Application No. 2019-513891, dated Jun. 24, 2021, 11 pages.

Brazilian Office Action, Application No. BR112019004727-1, dated Jul. 6, 2021, 4 pages.

Australian Office Action, Application No. 2017323502, dated Jun. 28, 2021, 6 pages.

China Office Action, Application No. 201780056064.5, dated Apr. 26, 2021, 8 pages.

China Office Action, Application No. 201780056064.5, dated Nov. 4, 2020 11 pages.

Europe Office Action, Application No. 17808998.3, dated Jul. 21, 2020.

Pedreira Carlos E et al: "Overview of clinical flow cytometry data analysis: recent advances and future challenges", Trends in Biotechnology, Elsevier Publications, Cambridge, GB, vol. 31, No. 7, Jun. 5, 2013.

China Patent Office, "The Third Office Action," issued in connection with China Patent Application No. 201480071952.0, dated Jul. 23, 2020, 23 pages.

Intellectual Property India, "Examination Report," issued in connection with Indian Patent Application No. 3429/DELNP/2015, dated Mar. 26, 2018, 6 pages.

European Patent Office, "European Search Report," issued in connection with patent application No. 20167363.9, dated Jul. 21, 2020, 9 pages.

Japan Patent Office, "Notice of Reasons for Refusal," issued in connection with Japan Patent Application No. 2018-220397, dated Aug. 5, 2020, 3 pages.

European Patent Office, "Examination Report," issued in connection with European Patent Application No. 16723498.8, dated Oct. 12, 2020, 6 pages.

European Patent Office, "European Search Report," issued in connection with European Patent Application No. 14168200.5, dated Mar. 20, 2015, 12 pages.

European Patent Office, "European Search Report," issued in connection with European Patent Application No. 17172322.4, dated Aug. 24, 2017, 8 pages.

European Patent Office, "European Search Report," issued in connection with European Patent Application No. 15160613.4, dated Jul. 24, 2015, 14 pages.

European Patent Office, "Communication pursuant to Article 94(3) EPC," issued in connection with European Patent Application No. 17172322.4, dated Aug. 14, 2018, 5 pages.

European Patent Office, "Communication pursuant to Article 94(3) EPC," issued in connection with European Patent Application No. 11193936.9, dated Dec. 11, 2015, 3 pages.

European Patent Office, "Communication pursuant to Article 94(3) EPC," issued in connection with European Patent Application No. 15160613.4, dated Jul. 11, 2016, 4 pages.

Hori et al., "Cell fusion by optical trapping with laser-involves contacting different cells with each other then imparting high voltage pulse to cells," WPI/Thompson, Dec. 27, 1991, Abstract, 1 page.

Japan Patent Office, "Notification of Reasons for Refusal," issued in connection with Japanese Patent Application No. 2016-185743, dated Jul. 3, 2018, 7 pages.

Japan Patent Office, "Final Notification of Reasons for Rejection," issued in connection with Japanese Patent Application No. 2011-256171, dated Oct. 28, 2014, 5 pages.

Japan Patent Office, "Decision for Grant," issued in connection with Japanese Patent Application No. 2015-091320, dated May 6, 2017, 7 pages.

Japan Patent Office, "Final Notification of Reasons for Rejection," issued in connection with Japanese Patent Application No. 2015-091320, dated Mar. 22, 2016, 22 pages.

Japan Patent Office, "Notification of Reasons for Refusal," issued in connection with Japanese Patent Application No. 2016-185743, dated Jul. 26, 2017, 2 pages.

Smith et al., "Inexpensive Optical Tweezers for Undergraduate Laboratories," Am. J. Phys., vol. 67, No. 1, Jan. 1999, 10 pages.

Takayama et al., "Patterning Cells and Their Environments Using Multiple Laminar Fluid Flows in Capillary Networks," Proceedings of National Academy of Sciences, vol. 96, 1999, 4 pages.

Ts'O, Basic Principles in Nucleic Acid Chemistry, National Library of Medicine, 1974, pp. 311-387.

Japan Patent Office; "Notice of Reasons for Refusal," issued in connection with Japanese Patent Application No. 2019-088655, dated Feb. 18, 2020, 5 pages.

International Preliminary Report on Patentability corresponding to International Patent Application No. PCT/US2013/050669, dated Jan. 28, 2016, 15 pages.

Supplementary European Search Report for Application No. 13889551, dated May 22, 2017, 12 pages.

State Intellectual Property Office of People's Republic of China, "Second Office Action," issued in connection with Chinese Patent Application No. 201380079634.4, dated Jun. 4, 2018, 14 pages.

Japan Patent Office, "Notice of Reasons for Rejection," issued in connection with Japanese Patent Application No. 2017-168904, dated Jul. 6, 2018, 3 pages.

(56) References Cited

OTHER PUBLICATIONS

State Intellectual Property Office of People's Republic of China, "Third Office Action," issued in connection with Chinese Patent Application No. 201380079634.4, dated Nov. 1, 2018, 20 pages.
Japanese Office Action for Application No. 2016-527978 dated Mar. 28, 2017, 8 pages.
State Intellectual Property Office of People's Republic of China, "First Office Action," issued in connection with Chinese Patent Application No. 201380079634.4, dated Jul. 28, 2017, 18 pages.
Indian Patent Application No. 3425/DELNP/2015 Pre-Grant Opposition, mailed Dec. 4, 2020, 138 pages.
Indian Patent Application No. 3425/DELNP/2015 Pre-Grant Opposition, mailed Jul. 21, 2020, 59 pages.
Indian Patent Application No. 3425/DELNP/2015 Pre-Grant Opposition, mailed Jul. 21, 2020, 96 pages.
Indian Patent Application No. 3425/DELNP/2015 Pre-Grant Opposition, mailed Jul. 2, 2020, 137 pages.
Trial Transcript, Sep. 5, 2019 (a.m.); *ABS Global, Inc.* v. *Inguran, LLC d/b/a Sexing Technologies,* Case Nos. 17-cv-446 and 14-cv-503, United States District Court for the Western District of Wisconsin.
Brief in Support of ABS Global, Inc. and Genus PLC's Rule 50(8) Motion for Judgment as a Matter of Law and Rule 59 Motion for a New Trial, *ABS Global, Inc.* v. *Inguran, LLC d/b/a Sexing Technologies,* Case No. 14-cv-503, United States District Court for the Western District of Wisconsin. Filed Sep. 2, 2016.
Inguran, LLC and XY, LLC's Response to ABS Global, Inc. and Genus PLC's Rule 50(8) Motion Fof Judgment as a Matter of Law and Rule 59 Motion for New Trial, pp. 9-28, 33-36, 73-74. Filed Sep. 23, 2016.
ST's Response to ABS's Renewed Motion for Judgment as a Matter of Law That the Asserted Claims of the '987 Patent Are Invalid for Lack of Enablement and, in the Alternative, for a New Trial, *ABS Global, Inc.* v. *Inguran, LLC d/b/a Sexing Technologies,* Case No. 14-cv-503, United States District Court for the Western District of Wisconsin. Filed: Jul. 24, 2020.
Dicarlo "Continuous inertial focusing, ordering, and separation of particles in microchannels" BioMEMS Resource Center, Center for Engineering in Medicine and Surgical Services, Massachusetts General Hospital, Nov. 27, 2007, PNAS, 18892-18897, vol. 104, No. 48.
Dicarlo "Equilibrium Separation and Filtration of Particles Using Differential Inertial Focusing" BioMEMS Resource Center, Center for Engineering in Medicine and Surgical Services, Massachusetts General Hospital, Anal Chem 2008, 8, 2204-2211.
Dicarlo "Inertial Microfluidics: High-Throughput Focusing and Separation of Cells and Particles" BioMEMS Resource Center, Center for Engineering in Medicine, Massachusetts General Hospital, Twelfth International Conference on Miniaturized Systems for Chemistry and Life Sciences, Oct. 12-16, 2008, San Diego, California, USA.
USPTO, "Non-Final Office Action," issued in connection with U.S. Appl. No. 17/692,876, dated Sep. 19, 2022, 21 pages.
USPTO, "Notice of Allowance," issued in connection with U.S. Appl. No. 17/403,642, dated Sep. 29, 2022, 24 pages.
USPTO, "Final Office Action," issued in connection with U.S. Appl. No. 16/852,303, dated May 27, 2022, 48 pages.

USPTO, "Non-Final Office Action," issued in connection with U.S. Appl. No. 16/279,430, dated May 23, 2022, 14 pages.
European Patent Office, "Examination Report," issued in connection with patent application No. 20167363.9, dated Mar. 22, 2022, 4 pages.
European Patent Office, "Examination Report," issued in connection with patent application No. 19182993.6, dated May 10, 2022, 8 pages.
International Search Report and Written Opinion for Application Serial No. PCT/US2021/059148, dated May 4, 2022, 15 pages.
European Patent Office, "Communication under Rule 71(3) EPC," issued in connection with European Patent Application No. 16723498.8, dated May 18, 2022, 54 pages.
IP Australia, "Notice of Acceptance for Patent Application," issued in connection with Australian Patent Application No. 2021200818, dated Jun. 1, 2022, 3 pages.
China National Intellectual Property Administration, "Second Office Action," issued in connection with Chinese Patent Application No. 202080028183.1, dated Jan. 13, 2023, 23 pages.
Notice of Allowance issued in U.S. Appl. No. 17/851,319 dated Feb. 15, 2023, 52 pages.
Kang, et al. "Effect of an osmotic differential on the efficiency of gene transfer by electroporation of fish spermatozoa." Aquaculture 173.1-4 (1999): 297-307. (Year: 1999).
Rieth et al. "Electroporation of bovine spermatozoa to carry DNA containing highly repetitive sequences into oocytes and detection of homologous recombination events." Molecular Reproduction and Development: Incorporating Gamete Research 57.4 (2000): 338-345.
Chamberland et al. "The effect of heparin on motility parameters and protein phosphorylation during bovine sperm capacitation." Theriogenology 55.3 (2001): 823-835. (Year: 2001).
Chan, et al. "Luminescent quantum dots for multiplexed biological detection and imaging." Current opinion in biotechnology 13.1 (2002): 40-46. (Year: 2002).
USPTO, "Non-Final Office Action," issued in connection with U.S. Appl. No. 16/561,146, dated Jan. 21, 2022, 14 pages.
USPTO, "Non-Final Office Action," issued in connection with U.S. Appl. No. 17/496,469, dated Jan. 28, 2022, 13 pages.
National Institute of Industrial Property (INPI) Argentina, "Examination Report," issued in connection with Argentina Patent Application No. 20190101378, dated Apr. 19, 2023, 8 pages.
China National Intellectual Property Administration, "Decision of Rejection," issue in connection with Chinese Patent Application No. 202080028183.1, dated Jun. 7, 2023, 23 pages.
USPTO, "Notice of Allowance," issued in connection with U.S. Appl. No. 16/852,303, dated Sep. 20, 2023, 31 pages.
European Patent Office, "Communication pursuant to Article 94(3) EPC," issued in connection with European Patent Application No. 17808998.3, dated Sep. 15, 2023, 4 pages.
European Patent Office, "European Search Report," issued in connection with patent application No. 20913158.0, dated Sep. 20, 9 pages.
European Patent Office, "European Search Report," issued in connection with patent application No. 23169267.4 dated Jul. 14, 2023, 5 pages.
Brazilian Office Action, Application No. BR112021012000-9, dated Aug. 16, 2023, 4 pages.

\* cited by examiner

USE OF VIBRATIONAL SPECTROSCOPY FOR MICROFLUIDIC LIQUID MEASUREMENT

CROSS-REFERENCE TO RELATED APPLICATIONS

This application is a continuation of U.S. patent application Ser. No. 16/282,903 filed Feb. 22, 2019, which is a continuation of U.S. patent application Ser. No. 15/174,681 filed Jun. 6, 2016, now U.S. Pat. No. 10,261,012, which is a continuation of U.S. patent application Ser. No. 13/894,831 filed May 15, 2013, now U.S. Pat. No. 9,835,552, the specifications of each are incorporated herein by reference in their entirety.

U.S. patent application Ser. No. 13/894,831 claimed benefit of U.S. Provisional Application 61/647,041 filed May 15, 2012, the specifications of which are incorporated herein by reference in their entirety.

Also, U.S. patent application Ser. No. 13/894,831 is a continuation-in-part of U.S. patent application Ser. No. 13/447,647 filed Apr. 16, 2012, now abandoned. Also, U.S. patent application Ser. No. 13/894,831 is a continuation-in-part of U.S. patent application Ser. No. 13/298,148 filed Nov. 16, 2011, now U.S. Pat. No. 8,941,062, the specifications of which are incorporated herein by reference in their entirety.

U.S. patent application Ser. No. 13/447,647 claimed benefit of U.S. Provisional Application 61/628,259 filed Oct. 27, 2011, the specifications of which are incorporated herein by reference in their entirety. Also, U.S. patent application Ser. No. 13/447,647 is a continuation in part of U.S. patent application Ser. No. 13/298,148.

U.S. patent application Ser. No. 13/298,148 claimed benefit of U.S. Provisional Application 61/628,259 filed Oct. 27, 2011; and U.S. Provisional Application 61/575,799 filed Aug. 29, 2011; and U.S. Provisional Application 61/571,051 filed Jun. 20, 2011; and U.S. Provisional Application 61/519,567 filed May 25, 2011, and U.S. Provisional Application 61/516,623 filed Apr. 5, 2011; and U.S. Provisional Application 61/464,775 filed Mar. 9, 2011; and U.S. Provisional Application 61/456,997 filed Nov. 16, 2010, the specifications of which are incorporated herein by reference in their entirety.

BACKGROUND OF THE INVENTION

Field: This document relates generally to cellular measurements based on mid-infrared absorption measurements and particularly, but not by way of limitation, cellular measurements based on mid-infrared absorption measurements using quantum cascade lasers (QCLs)-based architecture for infrared activated cell sorting (IRACS).

Identification, classification and sorting of cells, in particular live cells, is a subject of considerable research and commercial interest. Most recently systems for sorting stem cells have been an area of particular focus. For example, methods for separating cancerous from non-cancerous cells have been demonstrated. For another example, there is an established market for cell sorting for gender offspring selection by identification and selection of X- or Y-bearing spermatozoa.

There is currently no safe and accurate method for cell sorting. The most advanced technology uses fluorescence-activated cell sorting (FACS), where living cells are incubated in a fluorescent DNA-attaching dye, exposed to a high-intensity, high-energy UV laser beam, and sorted according to observed fluorescence. There are two major disadvantages to this method applied to certain cells, including low accuracy and safety concerns. For example, in sperm cell sorting, the FACS process is able to achieve 88% X-enrichment and only 72% Y-enrichment, even at very low sort rates (20-30 per second output). High scattering at UV and visible wavelengths is a major factor. In sperm cell sorting, the FACS process has been shown to cause chromosomal damage in sperm cells as a result of the dyes used, and as a result of exposure to high intensity 355 nm laser light.

The use of optical methods to identify and classify cells has many potential advantages such as speed, selectivity/specificity, and their non-invasive nature. As a result, a number of methods have been demonstrated in which light is used to interrogate cells and determine critical information. One such method is the use of fluorescent markers, which are chemicals that bind to specific structures or compounds within the target cells and are introduced into the mixture of cells. The mixture is subsequently rinsed to remove excess fluorescent markers and the cells are exposed to intense UV or other short-wavelength radiation in order to "read out" relevant quantities and classify the cell. The chemical markers provide good specificity. However, these chemical markers may damage or later the function of the target cells, which is particularly disadvantageous for live cell sorting. In testing, dyes used as markers for DNA, for example, have resulted in chromosomal damage. Further, the intense UV or visible light used to read the level of marker in the cell may damage the cell, in particular, DNA damage results from exposure to high-energy UV or visible photons. Also, because of the wavelengths used in so called fluorescence activated cell sorting (FACS) systems, quantitative measurements (rather than yes/no measurements for a particular antibody) are made very difficult, because both the illuminating wavelength and the emitted fluorescence are scattered and absorbed by cellular components. This means that cell orientation becomes an important factor in accurate measurement, and can dramatically reduce the effectiveness of the system. For example, sperm cell sorts for X- and Y-carrying sperm, which measure the differential in DNA between cells, require very specific orientation (only 10% of cells typically meet the orientation criteria), and still provide accuracy only in the 70-90% range for humans.

Another method to interrogate cells and determine critical information is Raman spectroscopy. In Raman Spectroscopy, cells are exposed to intense visible or near infrared (NIR) light. This light is absorbed as a result of molecular bond vibrations within the cellular structure. Secondary emission of photons at slightly different wavelengths occurs, according to Stokes and anti-Stokes energy shifts. Measurement of these wavelengths allows the chemical composition of the cell to be measured. With Raman spectroscopy, the individual photon energy is generally lower than that used for fluorescent markers, however, the net energy absorbed can be very high and unsafe for live cells. Raman scattering is an extremely weak process: typically only 1 in $10^{10}$ incident photons give rise to a Raman-shifted photon, thus requiring long exposure times to generate sufficient shifted protons for accurate measurement. While Raman may not be suitable for high-volume live cell sorting, it can be used in conjunction with other methodologies described herein.

Higher sensitivity methods such as coherent anti-Stokes Raman scattering (CARS) are being developed which may enable high-throughput screening.

One significant drawback of mid-IR spectroscopy is the strong absorption by water over much of the "chemical fingerprint" range. This has strongly limited the application of Fourier Transform Infrared Spectroscopy (FTIR) techniques to applications involving liquid (and therefore most live cell applications) where long integration times are allowable-so sufficient light may be gathered to increase signal-to-noise ratio and therefore the accuracy of the measurement. The lack of availability of high-intensity, low etendue sources limit the combination of optical path lengths and short integration times that may be applied. In addition, because of the extended nature of the traditional sources used in FTIR, sampling small areas (on the order of the size of a single cell) using apertures further decimates the amount of optical power available to the system.

One approach to enabling liquid or solid-state measurements in the mid-IR is to use surface techniques. A popular method is the use of an attenuated total reflection (ATR) prism that is positioned directly in contact with the substance of interest (sometimes using high pressure in the case of solid samples). Mid-IR light penetrates from the prism up to several microns into the sample, and attenuates the internal reflection according to its wavelength-dependent absorption characteristics.

Another method which was more recently developed is the use of plasmonic surfaces which typically consist of conductive layers patterned to produce resonances at specific wavelengths; at these resonances, there is coupling into substances places on top of the layer, and again, absorption at a specific wavelength may be measured with good signal. Again, however, the coupling into the substance of interest is very shallow, typically restricted to microns.

Furthermore, one of the problems raised in mid-IR micro spectroscopy is that of scattering. Mie scattering is dominant when the particles in the path are on the order of the interrogating wavelength. The magnitude and angle of scattering is determined by size of particles and index of particles relative to the medium. Problems encountered center about the measurement of high-index cells using FTIR. Scattered light that is not captured by the instrument is misinterpreted as absorption, and results in artefacts in the Fourier-inverted spectrum. Some of the causes or promoters of this scattering loss include: 1) Measurement of cells in air, rather than in a water solution. This causes additional index mismatch between the medium and cells, dramatically raising scattering efficiency and angles; 2) Measurement of absorption peaks at high wavenumbers (short wavelengths) where scattering efficiency is higher; 3) Insufficient capture angle on the instrument. Typically the capture angle on these instruments is identical to the input angle, not allowing for light scattered outside of the delivered IR beam angle; and 4) Transflection or other surface-based measurements. These configurations may lead to additional artefacts in conjunction with Mie scattering effects.

SUMMARY OF THE INVENTION

In embodiments of the present invention, a system and method of cytometry may include presenting a single sperm cell to at least one laser source configured to deliver light to the sperm cell in order to induce bond vibrations in the sperm cell DNA, and detecting the signature of the bond vibrations. The bond vibration signature is used to calculate a DNA content carried by the sperm cell which is used to identify the sperm cell as carrying an X-chromosome or Y-chromosome. Another system and method may include flowing cells past at least one QCL source one-by-one using a fluid handling system, delivering QCL light to a single cell to induce resonant mid-IR absorption by one or more analytes of the cell, and detecting, using a mid-infrared detection facility, the transmitted mid-infrared wavelength light, wherein the transmitted mid-infrared wavelength light is used to identify a cell characteristic.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures:

FIG. 26a shows a configuration where DNA vs. cell count may be displayed in a histogram format. FIG. 26b shows a configuration where an additional parameter besides DNA may be used to classify cells.

FIG. 29a shows a chip that could be used in a measurement-only application.

FIG. 29b shows a similar chip, this one for use in sorting cells.

FIG. 30a shows a configuration where a diluting/sheath fluid may be used together with the sample in order to provide a centered flow in the measurement channels. FIG. 30b shows a configuration where cells may be switched, based on the vibrational spectroscopy measurement, using an electric field at the switch point 3032.

FIG. 45a shows the absorption of the particle (composed in part of the target molecule) and the medium in which it is measured, both as a function of optical frequency. FIG. 45b shows the derived real refractive index of the particle and the medium.

DETAILED DESCRIPTION OF THE PREFERRED EMBODIMENT(S)

Figure 1:
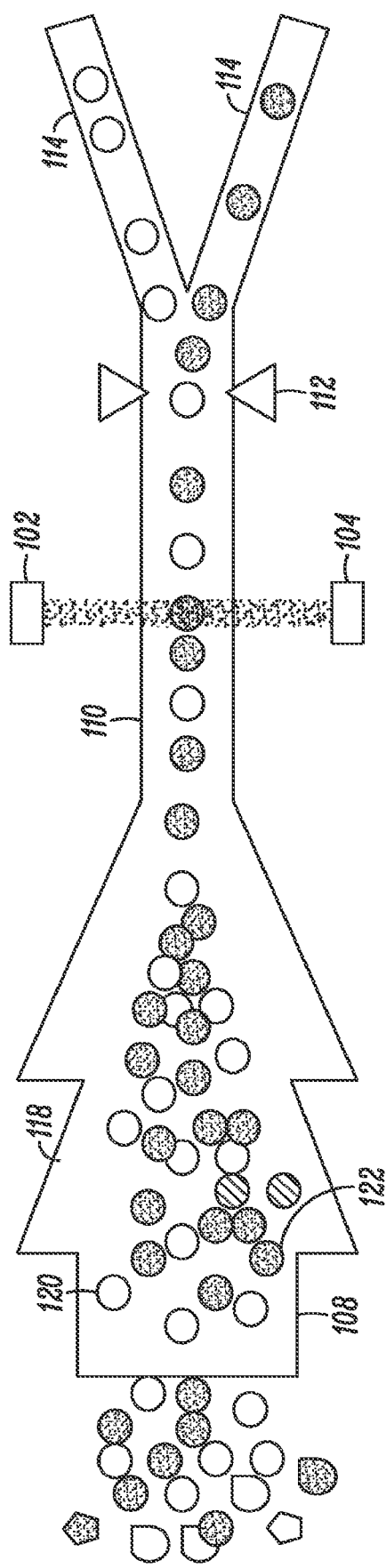
FIG. 1 illustrates the present invention built in a form similar to a flow cytometer.

The invention described herein presents a novel approach to cellular measurements based on mid-infrared absorption measurements. Mid-IR quantum cascade lasers (QCLs) have the potential to focus sufficient energy onto a single cell to make an accurate, high-speed measurement. QCLs have recently been commercialized by multiple vendors. They are built using the same processes and packaging as high-volume telecom lasers. QCLs offer several advantages over traditional mid-IR sources such as delivering very high spectral power density, delivering very high spatial or angular power density, among other advantages. This allows QCLs to put 10,000,000× more effective mid-IR power onto a single cell than traditional mid-IR sources. This disclosure seeks to describe certain applications enabled by QCLs, such as label-free detection without dyes or labels that can alter or damage cells, measurements using mid-IR illumination 25× less energetic than that used in FACS, eliminating photon damage, and high-throughput (>1000 cells/second) capability.

Embodiments of the present disclosure include an Infrared-Activated Cell Sorting (IRACS). The steps in an IRACS system may include prepare the cell sample (such as by centrifugation, etc.); for each cell flowing through: illuminating the cell with mid-IR laser(s), measuring the transmission of mid-IR wavelength(s), and sorting cells by transmission levels. The key "Input" parameters of the IRACS system model may be: cells per second entering the measurement volume; and spacing between cells ("duty cycle"). The input parameters may determine the measurement duration or integration time.

Most of the risks at the micro optical level may be addressed by careful design using existing techniques and materials. In this manner many of the mid-IR measurement issues may be avoided. The IRACS system may include a microfluidic channel architecture with one or more of the following features. One feature may be top and bottom mid-IR transmitting windows forming a channel. Potential materials include: Si, Ge, ZnSe, certain polymers. Si, ZnSe (or similar), polymers may be compatible with visible, NIR, or SWIR (500-1600 nm) optical interrogation or manipulation, if desired. ZnSe or similar may be used to permit visible light viewing, interrogation and possible manipulation (laser tweezers, laser-based cell disabling/destruction). Another feature may be antireflection coatings applied to both sides of each window, such as AR coatings designed for air externally, water internally. Another feature may be a channel depth tuned to be a gap that is out of resonance at the mid-IR wavelength(s). For example, a channel depth of approximately 20 microns may be used. Another feature may be tilting, or wedge-shaped windows to further reduce effects of reflections. Another feature may be a channel width that exceeds the spot size of the QCL may be so small shifts in the channel with respect to the beam to prevent creation of false signals.

Further, in the present disclosure, several aspects of particular measurements which greatly mitigate the effect of Mie scattering by the interrogated cell may be: 1) The cell is measured in a water medium (as opposed to a dried cell on a window, in air). This may significantly reduce the index contrast between the medium and cell. The estimated real cellular refractive index may be in the range of $n_{cell}$=1.27-1.30 vs $n_{H2O}$=1.25 at 1100 cm-1, for a cell/medium ratio of 1.02-1.04, and a nuclear refractive index higher than that; 2) DNA signatures are at the low-wavenumber (long wavelength) end of the vibrational fingerprint region. Scattering falls off with longer wavelength, so relatively less effect is experienced; and 3) Light is captured over a large angle using a high NA lens; this means even light scattered over moderate angles (10 degrees) may be captured and relayed to the detector.

Regarding the issue of cell orientation, scattering is estimated based on an equivalent spherical volume, and the computer scattering efficiency is multiplied by the actual cell cross-section that is dependent on cell presentation angle. This may ignore the fact that when cell cross-section is large, path length is relatively short, which would in turn reduce scattering effects (since scattering is a result of the phase shift and extinction on passage through the sample vs. surrounding medium). To further reduce the effect of cell orientation, the present invention may consider the following approaches: 1) Removing outliers from the distribution (which may be caused in large part by the orientation issues); 2) Using a measurement wavelength that may not be at the peak absorption level for DNA, or using a less strongly-absorbing DNA band. A high absorption coefficient results in both larger scattering, and also in more orientation/shape dependence in straight-through absorption. At low absorption, path length may better compensate for cross-section changes. At high absorption this may be less true; and 3) Using a shorter wavelength (possibly NIR) to more precisely determine cell cross-section/orientation, and compensating for or rejecting certain orientations.

Further, to reduce or compensate for the effects of scattering, the present disclosure may employ a plurality of solutions such as wavelength optimization, beam angle and capture angle optimization, scatter detection and compensation, scatter based measurement, and the like.

In an embodiment, the invention uses quantum cascade laser (QCL) components to directly measure absorption spectra of living cells for classification. Some areas where QCLs are used may include differentiating gender in sperm cells based on differences in X- and Y-chromosome mass, separation of stem cells from differentiated cells based on DNA/RNA mass change, differentiation of healthy and diseased cells, identification of cell phase of life, and the like.

In an embodiment of a DNA measurement system, the system utilizes optical absorption into molecular vibration modes specific to the DNA backbone to accurately measure DNA content of cells as they pass an optical illumination and readout system in a fluid stream. The system requires no staining or labels, or associated incubation process. The system may present a histogram showing cell count vs. DNA quantity per cell, and may optionally allow the user to sort out cells with certain quantities of DNA. The system may include reference measures to establish cell size (such as a Coulter-type electrical impedance measurement, or an optical scattering measurement), or other cellular components (such as protein content), which may further help distinguish cell types, and allow identification of cell agglomerates so as to remove them from the data or the sorted stream.

In various embodiments, one or more QCL may be used to measure transmission at one or more wavelengths through a living cell. An absorption by a cell of the one or more wavelengths may indicate concentrations or mass of constituent components within the cell. Further an absolute or relative level of absorption may be used to classify or identify the cell type or state. The absorption lines may correspond to vibrational modes of molecular bonds in target molecules.

QCLs may be able to directly emit coherent radiation in the mid-infrared range, covering at least the 3-15 micron wavelength range, such as 3-4 microns. The wavelength may coincide with the regions for infrared spectroscopy, and with the wavelengths used in many of the previous spectroscopic work on cells. The potential advantages of using mid-infrared light to interrogate cells for classification or sorting are numerous, however. They include very specific signatures, low photon energy, and direct measurement that potentially allow combinations of low optical power, fast measurement, and/or high precision measurement. Mid-infrared is an important range, since in this range, molecular vibrations may be measured directly through the use of absorption measurements. Essentially the same vibration signals that are measured using Raman spectroscopy are measured. Some major advantages of the mid-infrared range include that the absorption rate is much higher than in Raman, resulting in a significantly higher signal per input photon. Additionally, the photon energy used is extremely low compared to visible-light or even near-infrared measurements; this means no damage to cells or their components from ionization or two-photon absorption processes. Finally, molecular fingerprints in this range have been extensively characterized for decades using Fourier transform infrared (FTIR) spectroscopy. As opposed to FTIR, which typically uses a "globar" (glowing filament) source which provides very low spectral and areal power density, QCLs provide much more power on target and on wavelength, allowing much higher signal-to-noise (SNR) ratio and/or throughput.

QCLs may be manufactured in a number of varieties, including Fabry-Perot and Distributed Feedback (DFB) designs, as well as external cavity (EC) designs where wavelength may be set using external devices, and may be broadly tunable. Advantages of QCLs as a source for mid-infrared light for use in microspectroscopy of living cells may include ability to deliver a large amount of optical power in a narrow spectral band, ability to focus mid-infrared light onto a small spot, ability to produce significant power levels, ability to source QCLs in small packages, and the like.

In an embodiment, mid-infrared QCLs that may be used in the present invention generally target but are not restricted to the molecular "fingerprint region" of 6-12 microns. In some embodiments, the present invention may be applied to the problem of sorting living cells at high speed in a label-free manner, using relatively small amounts of optical power, and using very low-energy photons such as wavelengths around the 1000 cm"-1 range. In various other embodiments, multiple QCL wavelengths may be used to measure relative concentrations of one or more substances within cells, and establish a baseline measurement for the main measurement being performed. The QCL wavelengths may be supplemented by visible, near-infrared or other wavelength measurements to provide reference information such as cell location, shape, orientation, scattering, etc. In an embodiment, multiple QCL wavelengths may be generated through the use of multiple discrete components, single components generating multiple discrete wavelengths, broadband QCLs in addition to a filtering technique, tunable QCL components and the like. A mid-infrared source, such as the quantum cascade laser (QCL)—may be integrated with microfluidic systems for cell transport, presentation to the measurement system, and optionally, sorting into specific populations.

Microfluidic systems are in broad use in biomedical applications, including high-volume commercial applications. Their fabrication and use may be well-known. Microfluidics may be used to combine, measure, sort, and filter biochemical samples. In some embodiments, the combination of microfluidics with QCLs and mid-IR detectors to achieve accurate measurements of live cells may be described. Microfluidics may enable higher accuracy in such a system. Mid-IR light may be absorbed very strongly by water. Such a system with small path length (through liquid) may be highly desirable for systems requiring high throughput, low integration time, or very high signal-to-noise ratio. Furthermore, it makes a repeatable, constant path length desirable in order to eliminate fluctuations due to water stream diameter. Microfluidic devices or circuits, which are fabricated using semiconductor-like processes, may have the potential to provide such repeatability.

In addition, microfluidic devices enable closed-loop, compact systems that may be more appropriate for systems produced and used in high volume, which may be one goal of the present invention. Microfluidic components may be fabricated at low cost, and may therefore be disposable or recyclable and may offer a low-cost way of maintaining a clean system without run-to-run or patient-to-patient contamination.

In some embodiments, the combination of a label-free cell characterization system based on mid-IR QCLs may enable systems-on-a-chip with cell culturing, filtering, detecting, and sorting on a single chip, thereby minimizing inputs and outputs. The ability to use QCLs rather than fluorescent, magnetic or other labels (that must be attached to cells through specific, sometimes laborious procedures that may ultimately affect cell viability) multiplies the number of operations that may be performed on-chip for specific biomedical or even industrial biological applications.

Microfluidic systems of multiple configurations may be used as described below. Importantly, there is a wide range of prior art in microfluidics that can be used in conjunction with this system as a whole (QCLs+microfluidics+mid-IR detectors to measure individual cell properties). Most of these must be modified to be applicable to the present invention through the use of substrates (such as top and bottom caps or wafers that confine the fluid in the microfluidic structures) that transmit mid-IR light generated by the QCLs.

Multiple embodiments of QCL(s) in the system and mid-IR detectors are possible, and may depend on the application. In an example, one or more broadly-tunable QCLs may be used to cover a wide mid-IR spectrum corresponding to multiple molecular fingerprints for research applications. Beams may be combined by use of half-mirrors (with accompanying loss), thin film interference filters or diffraction gratings. Such a configuration may be used to gather a complete spectral signature for a cell, for instance, where a new QCL-based measurement is being developed. Once useful spectral features may have been identified, such a system based on tunable QCLs may be set up with each tunable QCL tuned to a peak, and then cells may be interrogated at higher speed, such as speed that may be used in a clinical system.

Narrowly tunable lasers may be used to interrogate a specific spectral feature, where derivative with wavelength information is important. For instance, rapid scanning over a small range corresponding to peak absorption of a cell constituent may significantly improve accuracy in some cases where absolute absorption is highly variable due to other factors.

Lower-cost, fixed QCL lasers such as distributed feedback, or DFB-QCLs may be used in systems where the sought-after spectral features are well known. In the simplest configuration, a single QCL and detector may be used to measure a chemical concentration within a cell. In the case where multiple constituents absorb at the signal wavelength, additional fixed QCLs may be added to the system to make reference measurements and "back out" the effect of those non-target constituents. For example, RNA and DNA share several absorption peaks, and to make an RNA concentration measurements in a cell, it is most likely necessary to measure two wavelengths and look at the relative absorption levels rather than measure a single absorption peak corresponding to RNA.

A number of configurations may be possible for the mid-IR detectors corresponding to the QCLs. In other embodiments, a plurality of detector types may be used, including mercury cadmium telluride (MCT) photovoltaic detectors, which may be liquid nitrogen cooled, thermoelectric cooler (TEC) cooled, or room temperature. Pyroelectric and other thermal detectors may also be used where cost is an issue. One or more detectors may be used in the system. For example, a system with two QCLs may use a single detector by using modulation on the QCLs which are often used in pulsed mode. The signals corresponding to the two QCLs, combined with the absorption of the sample, may be then measured by the detector, and may be separated electronically based on the modulation patterns of the QCLs. Alternatively, thin film interference filters may be used to separate the two wavelengths and send them to individual detectors. In any case, the detectors may have passband filters mounted in front of them to reject out-of-band mid-IR light blackbody radiation from the system components, or broadband signals relating to the heating or cooling of the cell as it passes through the QCL and possibly visible/Near Infra Red (NIR) beams.

In another embodiment, multiple QCLs may use completely distinct optical paths, either passing through the same sample volume at different angles, or using altogether separate measurement volumes where a cell passes through them sequentially. This simplifies the multiplexing of wavelengths from QCLs, but does not ensure the same measurement is being made.

Another detection method that may be used in an embodiment of the present invention is photoacoustic detection. Photoacoustic measurements may be used with mid-IR including QCL measurements of gas concentrations, even at very small concentrations. In this method, a mid-IR pulse may illuminate a sample. Owing to absorption by specific chemical species, there is some local heating and expansion. This expansion results in a shockwave which may be picked up by acoustic sensors. Because the present invention uses closed liquid channels, there is the potential to use "microphones" to pick up absorption signals as a cell is interrogated with one or more QCLs. Such microphones may be integrated into one of the wafers forming the top or bottom "cap" of the microfluidic device, or may be attached externally to the microfluidic structure.

Another potential detection method that may be implemented in embodiments of the present invention is one that may involve measurement of passive (blackbody) emissions from the cell components, as they are stimulated (heated) using a QCL. For example, the cell may be illuminated with one wavelength corresponding to the absorption peaks of several molecules, one of which is of interest, therefore a simple absorption measurement would not provide an accurate answer for the molecule of interest. Mid-IR radiation from the cell is then collected, and filtered using a narrow passband mid-IR filter around another absorption (emission) peak for the molecule of interest (or another molecule/bond vibration that is tightly coupled, but not directly addressed by the input QCL wavelength). The vibrations induced by the probe QCL wavelength may translate to an increase in temperature/vibrations, and these may be observed at this secondary mid-IR wavelength. This signal will of course be quite small, but may be electronically filtered with well-known lock-in techniques.

A number of architectures are presented which may be used in the present invention to minimize the effect of water absorption and provide accurate measurements of cellular biochemical components. This is not an exhaustive list, and the present invention will be applicable to other architecture as well. In an embodiment, the present invention consists of a flow cytometer in which one or more quantum cascade lasers may be used to measure vibrational absorption characteristics of single cells in the mid-infrared wavelength range.

Living cells may be interrogated at high speed using preparations such as traditional flow cytometer-type instruments retrofitted with QCL and mid-infrared transparent liquid handling microfluidics components built for cell classification and sorting that have been built with mid-infrared transparent components, substrates such as sheets, tapes or discs where live cells are distributed over a surface in a thin film and interrogated by scanning, and the like. In an embodiment, the present invention may be used in conjunction with certain chemical or other operations in advance of the measurement that accentuate differences between the cells to be sorted. For example, cells may be stimulated with temperature, light, fuel, or other stimulant to enhance biochemical concentrations that differentiate cells, for example, by differentially changing cell metabolism and therefore input or output products.

In an embodiment, the present invention may enable high-speed sperm sorting in a label-free manner, and without exposing cells to high-energy UV photons. For example, the separation of sperm by X- and Y-type is possible using the fact that the X chromosome has significantly more DNA content than the Y-chromosome, thereby enlarging the overall DNA mass of the sperm cell by 2% or more in mammalian species. At least one QCL may be used to probe at least one absorption band specific to DNA. In other embodiments, a plurality of QCL wavelengths may be used to measure other potentially interfering constituents. The measurements may be made from more than one orientation to normalize for the asymmetric shape of the sperm cell head. In various other embodiments, the measurement process may be supplemented using other lasers in the visible or near-infrared bands to measure cell orientation, size, position, density and the like, as well as additional mid-IR based lasers, such as alternately tuned QCL's. The amount of mid-infrared light transmitted in the DNA band, as normalized by the other measurements, may be used to compute total mass of DNA in the sperm cell. As the amount of DNA for X- or Y-bearing cells for a given species is very consistent, sperm cells may be sorted into X- and Y-bearing populations with one or more mechanisms known in the art such as flow cytometry-type equipment, microfluidics, methods where cells are spread onto larger substrates, cell cuvettes, and the like.

In an embodiment, the present invention may be a system consisting of fluidics for delivering live cells one by one to a measurement volume, laser sources which generate beam (s) that may preferentially act on DNA molecules within the cells, based on specific molecular vibration frequencies, detectors which measure the interaction of the sources with the DNA as the cell passes the measurement volume and signal processing equipment to capture these signals and process them in order to generate an estimate for DNA quantity in a single cell.

In an embodiment, the system may include an interface that displays a histogram of cell count vs. DNA quantity, a common plot used to analyze a sample of cells.

In an embodiment, the system may include other measurements made on the individual cells that may further characterize the cell. These may include, but are not limited to electrical impedance measurements in the fluid channel which may allow the system to estimate size or cross-section of the cell, and detect cell agglomerates which may produce false DNA readings, optical measurements in the visible or near infrared range of scattering or shape which may help determine cell type, and also measure agglomerates or vibrational optical measurements which may serve to quantify other biochemical constituents of the cell under inspection, including but not limited to measuring protein or lipid concentrations to determine the rough size and type of the cell, and detect cell agglomerates.

In an embodiment, the system may include a method of sorting the cells individually based on the DNA content calculated, as well as any reference signals including those described above. This sorting may be done in one of a number of ways well known to those skilled in the art of cytometry, fluorescence-activated cell sorting, and microfluidics, including but not limited to electrostatic diversion of droplets, fluid pressure diversion of a stream in microfluidics, mechanical actuation of measurement vs. output channels, and laser-based cell trapping/steering.

In an embodiment, the system may use a microfluidic chip on which at least a source reservoir, output reservoir and measurement channel have been patterned. The chip may be a consumable component that is used once per sample and then disposed or recycled. The core chip may be fabricated from a material that is both biocompatible and compatible optically with the wavelengths used for the optical vibrational DNA measurement. The core chip may be mounted in a plastic carrier with large reservoir capacity, the plastic carrier itself may be used with multiple core chips, where clogging occurs on the core chip and it is desirable to dispose of these chips instead of performing an automated unclogging procedure.

In an embodiment, the present invention may be used, and may be specialized for the purpose of measuring rate of cell division such as culture growth in a sample in accordance with the characteristic that DNA per cell doubles in the process of division. This disclosure may provide for separating X- from Y-bearing sperm cells in accordance with the characteristic that X-bearing sperm cells may carry more DNA than Y-bearing cells. This disclosure may provide for measuring occurrence of aneuploidy in a sample of cells, such as for the purpose of detecting cancerous cells or other cells indicative of a genetic disorder. This disclosure may provide for repeatedly measuring samples for the purpose of assessing effects of potential drugs on cells, such as cancer cells. This disclosure may provide for measuring the cell division rate simultaneously with assessing drug effect. This disclosure may provide for separating potential cancer cells based on an aneuploidy measurement from a larger cell culture, where these cells may be rare. This disclosure may provide for identifying and isolating cancer stem cells from tumor tissue for the purpose of characterizing the stem cells. Such characterization may enable further pharmacological study of the stem cells. This disclosure may provide for other applications where cellular DNA is a marker or potential marker for cell type, activity, or pathology.

Further, the present invention also describes a system for measuring the chemical composition/content of particles in the mid-IR using QCLs. In an embodiment, the present system describes optical system architectures to mitigate or harness scattering effects for the purpose of making these measurements. The optical system architectures minimize, compensate or harness these scattering effects with a minimum number of wavelengths, allowing high-speed measurements.

In an embodiment, the cell sorting system described in the present disclosure may use a QCL wavelength which corresponds to particular bond vibration frequencies. The QCL illuminates the particle/cell, and if that molecule is present, the cell and/or analytes within the cell may absorb light at that resonant frequency. The remaining light passing through the cell may be measured to determine the amount of light that was absorbed and therefore the concentration of analyte. For example, DNA quantity may be measured by illuminating the cell with one or more wavelengths, one or more of which are at/near resonant vibration frequencies for the DNA molecule. For sperm cells, measuring DNA may enable determining whether the sperm cell is carrying X or Y chromosomes because of the differential in DNA between X and Y (which is one of 23 chromosomes). The cell sorting system may comprise two or more QCLs. At least one QCL may correspond to the resonant absorption (signal wavelength) for a target analyte. At least one other QCL may correspond to a nearby wavelength to cancel out background noise from other analytes and system artifacts.

The other applications of the present invention may include, but not by the way of limitation, high-speed cell sorting in the separation of stem cells from other cells, including their differentiated derivatives, sorting live from dead cells, DNA content analysis for tumor biology, isolation of key cell populations in tumors, characterization of lymphoma cells, immune cell sorting, and the like.

A processor architecture may use the transmitted or scattered light detected by the detection facility to perform a calculation, such as to calculate a DNA content of a cell. The processor may implement software resident on an associated memory or server.

Throughout this Specification, UV light may be in the range of 10 nm to 400 nm, NIR light may be in the range of 0.75-1.7 µm, and visible light may be in the range of 390 to 750 nm.

Sorting of sperm cells according to the chromosomes they are carrying may enable a safe, accurate, label- and stain-free pre-fertilization gender selection method. Certain of the cytometry systems described below enable such a gender selection method.

In an embodiment, a minimally invasive cytometry system may use vibrational spectroscopy for gender selection. The cytometry system may include a handling system that enables presentation of single sperm cells to at least one laser source. The at least one laser source may be configured to deliver light to the sperm cell in order to induce bond vibrations in the sperm cell DNA. The at least one laser source emits at a wavelength corresponding to the resonant absorption for DNA and at least one laser source emits at a wavelength used to cancel out a background signal from other analytes and from system artifacts. The wavelength of the light delivered by the laser source may be greater than one third of the diameter of the sperm cell. A detection facility may detect the signature of the bond vibrations, which may be used by an associated or integrated processor to calculate a DNA content carried by the cell. The calculated DNA content may be used to identify the sperm cell as carrying an X-chromosome or Y-chromosome. This identification may be done by the associated or integrated processor. The minimally invasive cytometry system may also include a sort facility for sorting the sperm cell according to the identified chromosomes. The cytometry system may further include a second light source configured to deliver light to a sperm cell within the sperm cells in order to induce a scattering signature, wherein the scattering signature is used to identify a sperm cell characteristic and wherein the characteristic comprises one or more of size, cell type, cell density, and cell orientation. The second light source may be one or more of a VIS, UV, and NIR laser source and measurements made by the second light source may be used in gating the QCL-based vibrational measurements, in this embodiment and others described herein. The cytometry system may further include a cell destruction or immobilization facility, such as a laser emitting at 1.5 microns, that selectively destroys or immobilizes sperm cells based on the chromosome they are carrying. In this embodiment and others described herein, the second light source can be used to supplement the calculation of the content of the cell that is done primarily by the QCL signal (a second signal that can be used in a scatter plot).

In an embodiment, a cytometry method may include presenting a single sperm cell, using a handling system, to at least one laser source, the at least one laser source configured to deliver light to the sperm cell in order to induce bond vibrations in the sperm cell DNA, and detecting the signature of the bond vibrations, wherein the bond vibration signature is used to calculate a DNA content carried by the sperm cell, wherein the calculated DNA content is used to identify the sperm cell as carrying an X-chromosome or Y-chromosome.

In another embodiment of a minimally invasive cytometry system for gender selection, the cytometry system may include a handling system that presents single sperm cells to at least one quantum cascade laser (QCL) source, the at least one QCL laser source configured to deliver light to the single sperm cell in order to induce vibrational absorption by DNA molecules of the sperm cell. A detection facility may detect the transmitted mid-IR wavelength light, wherein the transmitted mid-IR wavelength light is used to calculate a DNA content carried by the sperm cell. The calculation may be done using an associated or integrated processor. In this embodiment as well as others described herein, the handling system may be a manifold/2D array. In this embodiment as well as others described herein, the handling system may include a carrier substrate upon which the cells are disposed and the carrier and/or the QCL laser source/detection facility translate with respect to one another. In this embodiment as well as others described herein, the handling system may be a microfluidic flow architecture. The microfluidic flow architecture may include multiple microfluidic channels such that multiple single cell flows may be measured simultaneously by the same light source(s). The calculated DNA content may be used to identify the sperm cell as carrying X-chromosomes or Y-chromosomes. The calculated DNA content may be used to identify an aneuploidy characteristic, such as an extra or missing chromosome or a low DNA count. The cytometry system may further include a second light source configured to deliver light to the sperm cell in order to induce a scattering signature, wherein the scattering signature is used to identify a sperm cell characteristic, and wherein the characteristic comprises one or more of size, cell type, cell density, and cell orientation. The second light source may be one or more of a VIS, UV, and NIR laser source and measurements made by the second light source may be used in gating the QCL-based vibrational measurements. The at least one QCL laser source emits at a wavelength corresponding to the resonant absorption for DNA and at least one QCL laser source emits at a wavelength used to cancel out a background signal from other analytes and from system artifacts. In this embodiment as well as others described herein, the cytometry system may further include a sort facility for sorting the sperm cell according to the identified chromosomes. In this embodiment as well as others described herein, when the system comprises more than one QCL laser source, the QCL laser sources may be pulsed such that they result in discrete measurements on the detector, such as alternately pulsed. Indeed, in any of the embodiments described herein, the at least one QCL laser source may be pulsed. In this embodiment as well as others described herein, a facility for electronically separating the transmitted light by wavelength may be included and/or a facility for optically separating the transmitted light by wavelength, such as with a dichroic filter and/or a grating. In any of the embodiments described herein, multiple detectors may be used to detect each wavelength. The cytometry system may further include a cell destruction or immobilization facility, such as a laser emitting at 1.5 microns, that selectively terminates or destroys sperm cells based on the chromosome they are carrying.

In an embodiment of a system using microfluidic architecture for gender selection, a microfluidic architecture may include a fluid handling system that enables a flow of sperm cells past at least one quantum cascade laser (QCL) source, wherein the fluid handling system comprises a facility to enable a single cell flow in a measurement volume of the microfluidic architecture. The at least one QCL laser source may be configured to deliver light to a sperm cell in the measurement volume of the fluid handling system in order to induce resonant absorption by DNA at one or more mid-IR wavelengths. A detection facility detects the transmitted mid-IR wavelength light, wherein the transmitted mid-IR wavelength light is used to calculate a DNA content of the sperm cells that identifies the sperm cell as carrying X-chromosomes or Y-chromosomes. At least one QCL laser source emits at a wavelength corresponding to the resonant absorption for a target analyte and at least one QCL laser source emits at a wavelength used to cancel out a background signal from other analytes and from system artifacts. The architecture may further include a sort facility for sorting the sperm cell according to the identified chromosomes. The architecture may further include a second light source configured to deliver light to a sperm cell within the sperm cells in order to induce a scattering signature, wherein the scattering signature is used to identify a sperm cell characteristic, wherein the characteristic comprises one or more of size, cell type, cell density, and cell orientation. The second light source may be one or more of a VIS, UV, and NR laser source. Gating the QCL-based vibrational measurements may be based on the second light source measurement. The architecture may further include a cell destruction or immobilization facility, such as a laser emitting at 1.5 microns, that selectively terminates or immobilizes sperm cells based on the chromosomes they are carrying.

In an embodiment, a cytometry method may include flowing cells past at least one quantum cascade laser (QCL) source using a fluid handling system, wherein the fluid handling system comprises a facility to enable a single cell flow in a measurement volume, delivering QCL light to the single cell in the measurement volume in order to induce resonant mid-infrared absorption by one or more analytes of the cell, and detecting, using a mid-infrared detection facility, the transmitted mid-infrared wavelength light, wherein the transmitted mid-infrared wavelength light is used to identify a cell characteristic.

In an embodiment, a label- and stain-free cytometry system for pre-fertilization gender selection may include a handling system that presents a single unlabeled and unstained sperm cell to at least one laser source, the at least one laser source configured to deliver light to the sperm cell in order to induce a resonant absorption by DNA within the sperm cell at one or mid-IR wavelengths. The wavelength of the light delivered by the laser source is greater than one third of the diameter of the sperm cell. A detection facility may detect the transmitted mid-IR wavelength light, wherein the transmitted mid-IR wavelength light is used to identify the sperm cell as carrying X-chromosomes or Y-chromosomes. The system may further include a sort facility for sorting the sperm cell according to the identified chromosomes. At least one laser source emits at a wavelength corresponding to the resonant absorption for a target analyte and at least one laser source emits at a wavelength used to cancel out a background signal from other analytes and from system artifacts. The system may further include a second light source configured to deliver light to the sperm cell in order to induce a scattering signature, wherein the scattering signature is used to identify a sperm cell characteristic, wherein the characteristic comprises one or more of size, cell type, cell density, and cell orientation. The second light source may be one or more of a VIS, UV, and NIR laser source. The system may further include a cell destruction or immobilization facility, such as a laser emitting at 1.5 microns, that selectively terminates or immobilizes sperm cells based on the chromosomes they are carrying.

In embodiments, cytometry systems for pre-fertilization gender selection may use substantially orientation-independent spectroscopy.

In an embodiment, a high yield cytometry system for pre-fertilization gender selection using mid-IR spectroscopy may include a handling system that presents a single sperm cell to at least one QCL laser source, the at least one QCL laser source configured to deliver light to the sperm cell in order to induce resonant absorption by the sperm cell DNA at one or more mid-IR wavelengths. A detection facility may detect the transmitted mid-infrared wavelength light, wherein the transmitted mid-infrared wavelength light is used to identify the sperm cell as carrying X-chromosomes or Y-chromosomes. A sort facility for sorting the sperm cell according to the identified chromosomes may achieve purities on the order of at least 75%, greater than 90%, or at least 99%. For example, the purity of Y-chromosome carrying sperm cells may be at least 75%. In another example, the purity of X-chromosome carrying sperm cells may be at least 90%. At least one QCL laser source emits at a wavelength corresponding to the resonant absorption for a target analyte and at least one QCL laser source emits at a wavelength used to cancel out a background signal from other analytes and from system artifacts. A second light source may be configured to deliver light to the sperm cell in order to induce a scattering signature, wherein the scattering signature is used to identify a sperm cell characteristic, wherein the characteristic comprises one or more of size, cell type, cell density, and cell orientation. The second light source may be one or more of a VIS, UV, and NIR laser source. Gating the QCL-based vibrational measurements may be based on the second light source measurement. The system may further include a cell destruction facility, such as a laser emitting at 1.5 microns, that selectively terminates sperm cells based on the chromosomes they are carrying.

In an embodiment, a low energy cytometry system for pre-fertilization gender selection with diminished risk of cell damage may include a handling system that presents a single sperm cell to at least one laser source, the at least one laser source configured to deliver photons with an energy of less than 1 eV to the sperm cell in order to induce a bond vibration in DNA of the sperm cell. A detection facility may detect the transmitted photon energy, wherein the transmitted photon energy is used to identify the sperm cell as carrying X-chromosomes or Y-chromosomes. The system may further include a sort facility for sorting the sperm cell according to the identified chromosomes. At least one laser source emits at a wavelength corresponding to the resonant absorption for DNA and at least one laser source emits at a wavelength used to cancel out a background signal from other analytes and from system artifacts.

Cytometry systems also described herein enable single cell study and inspection. Such systems may include light sources that induce resonant absorption in the mid-IR wavelength region, such as a QCL laser. However, these systems may also include other light sources and other technologies, such as fluorescence-activated spectroscopy systems and microfluidic architectures.

in an embodiment, a minimally invasive cytometry system with QCL inspection of single cells for cancer detection may include a handling system that presents a single cell to at least one QCL laser source, the at least one QCL laser source configured to deliver light to the cell in order to induce vibrational bond absorption in one or more analytes within the cell and a detection facility that detects the mid-infrared wavelength light transmitted by the cell and identifies the cell as either cancerous or non-cancerous. The system may further include a sort facility for sorting the cell according to its status. At least one QCL laser source emits at a wavelength corresponding to the resonant absorption for a target analyte and at least one QCL laser source emits at a wavelength used to cancel out a background signal from other analytes and from system artifacts. The system may further include a second light source configured to deliver light to the cell in order to induce a scattering signature, wherein the scattering signature is used to identify a cell characteristic, wherein the characteristic comprises one or more of size, cell type, cell density, and cell orientation. The second light source may be one or more of a VIS, UV, and NIR laser source and measurement with the second light source may be used in gating the QCL-based vibrational measurements. The system may further include a cell destruction or immobilization facility, such as a laser emitting at 1.5 microns, that selectively terminates or immobilizes cells based on the identification.

In an embodiment, a cytometry system with a QCL laser source, acoustic detection facility, and micro-fluidic cell handling system may be configured for inspection of individual cells. The cytometry system may include a microfluidic cell handling system that enables a flow of cells past at least one quantum cascade laser (QCL) source, wherein the handling system comprises a facility to enable a single cell flow in a measurement volume of the microfluidic architecture, the at least one QCL laser source configured to deliver light to a single cell in the measurement volume in order to induce resonant mid-IR vibrational absorption by one or more analytes, leading to local heating that results in thermal expansion and an associated shockwave. An acoustic detection facility detects the shockwave emitted by the single cell. The magnitude of the shockwave is indicative of a cell characteristic. The characteristic may be a quantity of a nucleic acid, a protein, a lipid, a nutrient, and a metabolic product. The micro-fluidic cell handling system further comprises a filter that excludes cells based on at least one of a shape, a size, and a membrane integrity. The cytometry system may further include a sort facility for sorting the single cell according to the identified characteristic. At least one QCL laser source emits at a wavelength corresponding to the resonant absorption for a target analyte and at least one QCL laser source emits at a wavelength used to cancel out a background signal from other analytes and from system artifacts.

In an embodiment, a minimally invasive inspection system may use mid-IR vibrational spectroscopy for high throughput, high accuracy cytometry. The system may include a handling system that enables high throughput presentation of single live cells to at least one light source, the at least one light source configured to deliver light to the live cell in order to induce vibrational bond absorption in one or more analytes within the cell at one or more mid-IR wavelengths. A mid-infrared detection facility may detect the transmitted mid-infrared wavelength light, wherein the transmitted mid-infrared wavelength light is used to determine a cell characteristic comprising one or more of chemical composition, size, shape, and density. The throughput of live cells may be at least 1 cell per second, at least 10 cells/sec, at least 100 cells/sec, at least 1,000 cells/sec, at least 4,000 cells/sec or at least 10,000 cells/sec. In this embodiment and in other embodiments described herein, at least one light source emits at a wavelength corresponding to the resonant absorption for a target analyte and at least one light source emits at a wavelength used to cancel out a background signal from other analytes and from system artifacts. In this embodiment and in other embodiments described herein, the system may further include a second light source configured to deliver light to the cell in order to induce a scattering signature, wherein the scattering signature is used to identify a cell characteristic, wherein the characteristic comprises one or more of size, cell type, cell density, and cell orientation. The second light source may be one or more of a VIS, UV, and NIR laser source. The wavelength of the light delivered by the light source may be greater than one third of the diameter of the cell. In this embodiment and in other embodiments described herein, the system may further include a cell destruction facility, such as a laser emitting at 1.5 microns, that selectively terminates cells based on the characteristic.

In an embodiment, a low energy cytometry system with diminished risk of cell damage may include a handling system that presents a cell to at least one laser source, the at least one laser source configured to deliver photons with an energy of less than 1 eV to the cell in order to induce a bond vibration in DNA of the cell. A detection facility may detect the transmitted photon energy, wherein the transmitted photon energy is used to identify a DNA characteristic of the cell.

In an embodiment, a minimally invasive cytometry system using QCL vibrational spectroscopy for differentiation of pluripotent stem cells from functionally differentiated cells based on inspection of single cells may include a handling system that presents a single cell to at least one QCL laser source, the at least one QCL laser source configured to deliver light to the single cell in order to induce vibrational bond absorption in one or more analytes within the cell. A detection facility may detect the transmitted mid-infrared wavelength light, wherein the transmitted mid-infrared wavelength light is used to identify the differentiation status of the cell as either pluripotent or functionally differentiated. The system may further include a sort facility for sorting the cell according to its differentiation status. At least one QCL laser source may emit at a wavelength corresponding to the resonant absorption for a target analyte and at least one QCL laser source emits at a wavelength used to cancel out a background signal from other analytes and from system artifacts. The system may further include a second light source configured to deliver light to the cell in order to induce a scattering signature, wherein the scattering signature is used to identify a cell characteristic, wherein the characteristic comprises one or more of size, cell type, cell density, and cell orientation. The second light source may be one or more of a VIS, UV, and NIR laser source. The system may further include gating the QCL-based vibrational measurements based on the second light source measurement. The system may further include a cell destruction or immobilization facility, such as a laser emitting at 1.5 microns, that selectively terminates or immobilizes cells based on the differentiation status.

In an embodiment, a cytometry system with a QCL source, mid-infrared detector, and micro-fluidic cell handling system configured for inspection of individual cells may include a fluid handling system that enables a flow of cells past at least one quantum cascade laser (QCL) source, wherein the fluid handling system comprises a facility to enable a single cell flow in a measurement volume. The at least one QCL laser source may be configured to deliver light to the single cell in the measurement volume in order to induce resonant mid-infrared absorption by one or more analytes of the cell. A mid-infrared detection facility may detect the transmitted mid-infrared wavelength light, wherein the transmitted mid-infrared wavelength light is used to identify a cell characteristic. The characteristic may be a quantity of at least one of a nucleic acid, a protein, a lipid, a metabolic product, a dissolved gas, and a nutrient. The fluid handling system may comprise a microfluidic architecture. At least one QCL laser source emits at a wavelength corresponding to the resonant absorption for a target analyte and at least one QCL laser source emits at a wavelength used to cancel out a background signal from other analytes and from system artifacts. The system may further include a sort facility for sorting the single cell according to the identified characteristic. The fluid handling system may further include a filter that excludes cells based on at least one of a shape, a size, and membrane integrity. The system further includes a cell destruction or immobilization facility, such as a laser emitting at 1.5 microns, that selectively terminates or immobilizes cells based on the identified characteristic. A second light source may be configured to deliver light to the cell in order to induce a scattering signature, wherein the scattering signature is used to identify a cell characteristic, wherein the characteristic comprises one or more of size, cell type, cell density, and cell orientation. The second light source may be one or more of a VIS, UV, and NIR laser source. The system may further include gating the QCL-based vibrational measurements based on the second light source measurement.

In an embodiment, a mid-IR spectroscopy cytometry system with selective cell destruction capability may include a handling system that presents a live cell to at least one laser source, the at least one laser source configured to deliver light to the live cell in order to induce resonant mid-infrared absorption by at least one analyte within the cell. A mid-infrared detection facility may detect the transmitted mid-infrared wavelength light, wherein the transmitted mid-infrared wavelength light is used to determine a cell characteristic. A cell destruction facility may selectively terminate cells based on the characteristic. The cell characteristic may include one or more of a nucleic acid quantity, a nucleic acid type, a chemical composition, a size, a shape, and a density. The cell destruction facility may be a laser emitting at 1.5 microns. At least one laser source emits at a wavelength corresponding to the resonant absorption for a target analyte and at least one laser source emits at a wavelength used to cancel out a background signal from other analytes and from system artifacts. The system may further include a second light source configured to deliver light to the live cell in order to induce a scattering signature, wherein the scattering signature is used to identify a live cell characteristic, wherein the characteristic comprises one or more of size, cell type, cell density, and cell orientation. The second light source may be one or more of a VIS, UV, and NIR laser source. The wavelength of the light delivered by the laser source may be greater than one third of the diameter of the sperm cell.

In an embodiment, a mid-IR spectroscopy system may include laser tweezers for moving cells into position for measurement with a light source that induces resonant absorption in an analyte within the cell.

In an embodiment, a mid-IR spectroscopy system with fluidic features that pre-filter cells to obtain cells of appropriate size may include a fluid handling system that enables a flow of cells past at least one laser source, wherein the fluid handling system comprises a filter that excludes cells from a measurement volume of the fluid handling system based on size and/or shape, the at least one laser source configured to deliver light to a single cell in the measurement volume in order to induce resonant absorption in at least one analyte within the cell. A mid-infrared detection facility may detect the transmitted mid-infrared wavelength light. At least one laser source emits at a wavelength corresponding to the resonant absorption for a target analyte and at least one laser source emits at a wavelength used to cancel out a background signal from other analytes and from system artifacts. The system may further include a second light source configured to deliver light to the cell in order to induce a scattering signature, wherein the scattering signature is used to identify a cell characteristic, wherein the characteristic comprises one or more of size, cell type, cell density, and cell orientation. The second light source may be one or more of a VIS, UV, and NIR laser source. The wavelength of the light delivered by the laser source may be greater than one third of the diameter of the sperm cell. The system may further include a cell destruction or immobilization facility, such as a laser emitting at 1.5 microns, that selectively terminates or immobilizes cells based on the transmitted mid-infrared wavelength light.

In an embodiment, a cellular DNA measurement system may include a handling system that presents a single cell to at least one laser source, the at least one laser source configured to deliver light to the cell in a measurement volume of the handling system in order to induce resonant absorption in the DNA within the cell. A mid-infrared detection facility may detect transmitted mid-infrared wavelength light, wherein the transmitted mid-infrared wavelength light is used to calculate the cellular DNA content. The DNA content may be used to identify cell cycle status in a plurality of cells and the cell cycle status for a plurality of cells is used to determine a growth rate of the cells. The DNA content may be used to determine aneuploidy, wherein the aneuploidy characteristic is identified by a low DNA count, an extra chromosome, and/or a missing chromosome. The system may further include a sort facility for sorting the cells according to the aneuploidy characteristic. The handling system may further include a filter that excludes cells based on a characteristic. At least one laser source emits at a wavelength corresponding to the resonant absorption for a target analyte and at least one laser source emits at a wavelength used to cancel out a background signal from other analytes and from system artifacts.

In an embodiment, a cellular DNA measurement system may include a handling system that presents a fluorescently labeled single cell to one or more of a visible or UV laser source and a handling system that presents the fluorescently labeled single cell to at least one QCL laser source. The at least one QCL laser source may be configured to deliver light to the cell in order to induce resonant absorption in the DNA within the cell. A mid-infrared detection facility may detect transmitted mid-infrared wavelength light, wherein the transmitted mid-infrared wavelength light is used to calculate cellular DNA content. A visible light detection facility may detect the fluorescing label.

Mid-IR based systems described herein enable single particle study and inspection. Such systems may include light sources that induce resonant absorption in the mid-IR wavelength region, such as a QCL laser. However, these systems may also include other light sources and other technologies, such as fluorescence-activated spectroscopy systems, microfluidic architectures, additional optics, scattering analysis, and the like.

In an embodiment, a single particle QCL-based mid-IR spectroscopy system with differential numerical aperture optics for emitted and scattered light may include a handling system that presents a single particle to at least one quantum cascade laser (QCL) source, the at least one QCL laser source configured to deliver light to the single particle in order to induce resonant mid-infrared absorption in one of the particle or at least one analyte within the particle. The system may also include an optic to capture mid-IR wavelength light transmitted through the cell, wherein the optic has a smaller numerical aperture than a focusing optic focusing the QCL laser emission on the cell. A mid-infrared detection facility may detect the transmitted mid-IR wavelength light and scattered mid-IR wavelength light. The particle may be a cell. The handling system may further include a filter that excludes particles based on at least one of a shape, a size, and a membrane integrity. The system may further include a sort facility for sorting the single particle according to one of the transmitted light and scattered light. At least one QCL laser source emits at a wavelength corresponding to the resonant absorption for a target analyte and at least one QCL laser source emits at a wavelength used to cancel out a background signal from other analytes and from system artifacts.

In an embodiment, a single particle QCL-based mid-IR spectroscopy system using resonant scattering for measurement may include a handling system that presents a single particle to at least one quantum cascade laser (QCL) source, the at least one QCL laser source configured to deliver light to the single particle in order to induce resonant optical scattering based on wavelength-specific refractive index shifts resulting from resonant bond vibration of one or more target analytes. A mid-infrared detection facility may detect the mid-infrared wavelength light scattered by the single particle. The particle may be a cell. The handling system may further include a filter that excludes particles based on at least one of a shape, a size, and a membrane integrity. The system may further include a sort facility for sorting the single particle according to the scattered light. At least one QCL laser source emits at a wavelength corresponding to the resonant absorption for a target analyte and at least one QCL laser source emits at a wavelength used to cancel out a background signal from other analytes and from system artifacts. The mid-infrared detection facility may include a plurality of mid-infrared detectors deployed at multiple angles that detect the mid-infrared wavelength light scattered by the single particle.

In an embodiment, a single particle QCL-based mid-IR spectroscopy system with in-droplet microfluidic system may include a handling system that suspends particles in or as a droplet within another liquid, wherein the handling system presents individual droplets to the at least one quantum cascade laser (QCL) source, the at least one QCL laser source configured to deliver light to a single droplet in the measurement volume of the microfluidic system in order to induce resonant mid-infrared absorption in at least one analyte within the droplet. A mid-infrared detection facility may detect the mid-infrared wavelength light transmitted by the droplet. The droplet and the another liquid may be immiscible. The particle may be a cell. When the particle is a cell, the mid-infrared wavelength light transmitted may be used to measure byproducts of cell metabolism in the fluid surrounding the cell. The particle may undergo a chemical reaction with the surrounding fluid in the droplet and the mid-infrared wavelength light transmitted may be used to measure the level of reactants or the products of this reaction. At least one QCL laser source emits at a wavelength corresponding to the resonant absorption for a target analyte and at least one QCL laser source emits at a wavelength used to cancel out a background signal from other analytes and from system artifacts.

In an embodiment, a single particle QCL-based mid-IR spectroscopy system with analysis of scattering includes a handling system that presents a single particle tagged with a mid-IR active tag to at least one quantum cascade laser (QCL) source, the at least one QCL laser source configured to deliver light to the single particle in order to induce resonant mid-infrared absorption in the particle or an analyte within the particle. A mid-infrared detection facility may detect the mid-infrared wavelength light scattered by the single particle. A wavelength and angle analysis of the scattered mid-IR wavelength light may be used to determine analyte-specific structural and concentration information. The particle may be a cell. The mid-IR active tag may be a quantum dot. The handling system may further include a filter that excludes particles based on at least one of a shape, a size, and a membrane integrity. The system may further include a sort facility for sorting the single particle according to one or more of a transmitted mid-IR wavelength light and the scattered mid-IR wavelength light. At least one QCL laser source emits at a wavelength corresponding to the resonant absorption for a target analyte and at least one QCL laser source emits at a wavelength used to cancel out a background signal from other analytes and from system artifacts. In embodiments, mid-IR active tags may be used in a direct transmission measurement as well, such as with any of the embodiments described herein.

In an embodiment, a handling system may present a single particle labeled with a mid-IR active label to at least one quantum cascade laser (QCL) source, the at least one QCL laser source configured to deliver light to the single particle in order to induce resonant mid-infrared absorption by the mid-IR active label of the particle. A mid-infrared detection facility may detect the transmitted mid-infrared wavelength light.

In embodiments of the present invention, the wavelength for inspection may include wavelengths in the mid-IR band, wavelength specific to peaks corresponding to DNA vibrational modes, and the like. Wavelength selection may be optimized such as to inhibit scattering, and the like.

In embodiments, optical architecture and system components for the present invention may include facilities associated with reducing optoelectronic noise, confirming and/or modifying cell angle or position in a measurement volume, controlling cell rate spacing, accounting for nuclear volume in analysis, and reducing and accounting for QCL supply noise. Laser sources may include tunable QCLs, multiple tunable lasers, broadband lasers, scanning lasers, THz QCLs, QCL-on-a-chip, Vernier-tuned QCLs, single pulsed QCL, multiple pulsed QCLs, parametric oscillators, and the like. The architecture may also enable measurements from various angles of capture and using beams from multiple angles. A phase scrambling device may be used to get rid of coherent artifacts. As described herein, differential aperture optics for input and output may be used to focus the emitted light and then capture transmitted light in a wider area.

Systems with QCL sources may have a facility for separating wavelengths electronically based on timing of pulses and relaying them to separate detection facilities. Filters, such as dichroic filters and gratings, may be used to optically filter wavelengths. A prism or beam splitter may be used to separate wavelengths. The output from multiple sources may be combined in one detector. An array of lasers may cross the channel at different points—these can be combined and directed to a single detector.

Reference detection facilities may also be located at an angle outside the main angle of capture to detect scattered light. Use of resonant scattering may be made to obtain shape and position information. Scattered light may serve a gating signal or calibration for the primary measurement, such as the QCL-based measurement. Use of mid-IR active tags and reagents with QCL interrogation may enable an analysis of scattering (e.g. for angle, wavelength). The architecture may enable polarization-based measurements of particles in flow.

In embodiments, form factors for the present invention may include a cassette, a chip, a 2D manifold, 2D array, microfluidic architecture, flow cuvette, flow cytometer, cell-on-tape/substrate and the like. Handling systems may include laser tweezers, micro-fluidic handling system (e.g. for circulating cells, micro-fluidic flow system components, charge applied to cell for selection), fluid flow components, with tracers, with additives, with anti-reflective coating, with labels (e.g. quantum dot labels), pre-sorting particles based on size, a scanner system where the source moves relative to the detected item rather than moving the item, a microfluidic manifold (cells move relative to each other) and the like. The scanner system may include formats such as Cell on tape, Cell on substrate, Cells on a 2D carrier that is read out by translating at least one of the (i) carrier or (ii) the source and the detector. Flow architecture may be a species of a microfluidic manifold. Multiple channels of flow and multiple detection points may be present in a single system Vibrational spectroscopy may include direct, indirect, Raman, coherent, anti-Stokes Raman, and the like. Functional benefits may include a minimally invasive system, with no labels, with no dyes, using no UV laser, with increased accuracy, increased throughput (e.g. orientation independent), low coefficient of variation, and the like. Two systems may be put end-to-end to sort for one thing in the a first system, then take the output and do a task, such as a measurement or a second sort.

In embodiments, the present invention may provide facilities associated with scattering, such as measuring scattering, mitigating the effects of scattering, correcting for scattering, utilizing resonant Mie scattering, and the like. The present invention may provide for cell destruction through the use of a laser.

In embodiments, the present invention may be applied to a variety of applications, including gender selection (e.g. sperm DNA assessment, such as with humans, horses, cattle, pets), motility detection (e.g. sorting for motility, integrated onto the chip), cancer detection, stem cell study and manipulation (e.g. for monitoring differentiation of pluripotent cells into functionally differentiated cells, in harvesting stem cells, in the purification of stem cells before transfer to patients), aneuploidy detection, in the measuring of cell growth rate in a sample, measuring RNA characteristics, measuring sugars characteristics, measuring protein characteristics, as a DNA statistics tool, in the measurement of other particles in liquids, in reaction monitoring, in measuring circulating tumor cells, for embryo scoring, in determining blood count, in semen analysis, in gas monitoring, in solid-in-liquid measurement, in blood diagnostics (e.g. for malaria, parasites), in food and water contamination analysis (e.g. measuring the IR footprint for *E Coli*, in emulsions (e.g. using a in-droplet micro-fluidic system), and the like.

This disclosure provides a cytometry platform for measuring characteristics of particles in a flow using a mid-IR based measurement system and vibrational spectroscopy. The mid-IR based measurement system may be based on a quantum cascade laser (QCL) source delivering mid-IR wavelengths in the range of 3 to 15 microns. The QCL laser has a narrow wavelength emission comprising an easily tailored center wavelength and a low entendue, enabling measurement of a small area and narrow angle and measurements on the order of microseconds. For example, the power of the QCL may be ≤10 mW and a conduction band offset of about 0.1 eV. QCL variations include multiple tunable lasers, broadband, and scanning.

The cytometry platform may include a microfluidic architecture. The cytometry platform enables direct measurement of the chemical content of the cell using vibrational spectroscopy. Two types of vibrational spectroscopy may be used: (a) direct absorption where the particle is exposed to a wavelength in the mid-IR fingerprint region of about 5-12 microns, which corresponds to the frequency of a bond vibration and (b) Raman spectroscopy which is an indirect way of making measurements. Coherent anti-stokes Raman spectroscopy (CARS) may also be used to measure vibrational bond fingerprints in cells.

The cytometry platform enables a stain- and label-free process that is safe to cells and is orientation independent, high throughput, high accuracy, and high yield. The advantages of the cytometry platform include the ability to directly measure an absorption line without labels or dyes/stains. Another advantage is use of light that is 20-25 times less energetic light than UV light that is used in conventional systems and thus much less likely to damage cell. Because of the wavelength being relatively long (six times longer than UV laser), there is less scattering and the scattering is much better behaved compared to other light sources, such as visible light. Another advantage is that as opposed to traditional FTIR that requires cells to be dried, the cytometry platform can measure cells in a liquid medium where refractive index differential is much lower, so scattering index is lower.

In some instances of the cytometry platform, an additional scattering measurement may be made specifically to see how big and dense a cell is. For example, a blood count can be done in this fashion. With mid-IR light and in particular light whose angle can be controlled well (with a very collimated beam), chemical composition and size information may be obtained by measuring scattering off of particles.

In embodiments of the cytometry platform, a conventional fluorescence-activated sorting (FACS) system may be used in parallel in order to obtain a simple binary measurement for a cell then get an accurate numerical measurement for chemical content using the mid-IR based measurement system.

The cytometry platform enables measurement of cellular content, such as protein bonds and nucleic acid bonds. For example, three characteristic DNA peaks, an asymmetric $PO_2-$ stretch (DNA) at 1236 $cm^{-1}$ a symmetric $PO_2^-$ stretch (DNA) at 1087 $cm^{-1}$ and a C—C deoxyribose stretch (DNA) at 968 $cm^{-1}$.

The cytometry platform is engineered to reduce the QCL supply noise, the RIN noise associated with emission of the QCL, shot noise associated with the transmitted mid-IR energy, detector noise, and pre-amp noise. For example, at bandwidths up to 10,000 cells/second, the optoelectronic system noise is 3.7 ppm. Other elements of the cytometry platform were also designed to reduce system noise, such as the selection of the channel height, the input angle, the collection angle, the flow rate, and cell spacing.

One design of the system includes 2 or more fixed wavelength QCLs where at least one is at a "signal" wavelength (corresponding to the resonant absorption for a target analyte) and at least one is at a "reference" wavelength (a nearby wavelength used to cancel out background from other analytes, and from system artifacts). The QCLs may be in a cooling housing and may be driven by a pulsed driver or some other kind of driver. A grating-based QCL tuning system may be included to tune the QCLs. Before reaching the sample, the QCLs may first traverse a pellicle beamsplitter and adjustable aperture. Transmitted mid-IR energy is detected by a signal detector and a reference detector. A detector may measure scattering and compensate for it in the main measurements. For such a system, the predicted collection rate is >4,000/sec and the predicted purity is >99%. The QCLs may have carrier frequencies so that a single detector may be used and the signal is separated by modulation frequencies.

With wide variations in nuclear volume and cell orientation, there is variability in the absorption peak. Selecting a wavelength that is at top of the curve where the strongest absorption exists may not be ideal as strong absorption may make measurements more variable with cell orientation.

The cytometry platform is designed to reduce cell nucleus heating. Heating, due to DNA absorption of mid-IR energy, may be reduced and may have a narrow distribution even with wide nuclear volume/orientation distribution. For example, heating may be kept to under 1K.

In the cytometry platform, a QCL laser source may be configured to emit energy to a single cell in a measurement volume of the platform in order to induce resonant mid-IR vibrational absorption by one or more analytes, leading to local heating that results in thermal expansion and an associated shockwave. The cytometry platform may include an acoustic detector that detects the shockwave transmitted by the single cell, wherein the shockwave is indicative of a cell characteristic.

In the cytometry platform, a cell destruction facility may be included to selectively terminate cells based on a characteristic. In the example of pre-fertilization gender selection, those sperm not exhibiting the desired chromosomal type may be targeted for motility cessation using a laser emitting at 1.5 microns which may be used to immobilize cells without damaging DNA contents. In other cases complete destruction of cells through membrane destruction or other means may be effected, through the use of a laser or other means.

The cytometry platform may take many forms. The cytometry platform may be embodied in a mid-IR cuvette for a standard flow cytometer where cell selection is based on an applied charge. The cytometry platform may be embodied in a 2D manifold/array for immobilizing a plurality of cells and then measuring them individually using the present invention, potentially repeatedly. The cytometry platform may be embodied in a system with laser tweezers that traps cells with a visible laser and moves the cell into position for measurement. The cytometry platform may be embodied in a microfluidic chip with a waveguide to capture IR light that crosses the channel. The microfluidic chip may include fluidic features that pre-filter cells by size. The cytometry platform may be embodied in a circulating cell culture system.

The height of the channel may be optimized so that a resonant optical field is not obtained even if the AR coatings are not robust.

The mid-IR wavelength used in various embodiments herein may be optimized for low scattering.

The mid-IR based inspection and measurement system may further include a facility for a polarization-based measurement of particles in a flow, such as of DNA especially. Even with measurement of phosphate bonds, if left hand or right hand polarized light is emitted, because the DNA is in a helix, an improved separation of a DNA-specific signal may be obtained by using circularly polarized light.

Now that we have described particular embodiments of the present disclosure, we turn to describing a set of figures that will illustrate these and other embodiments.

FIG. 1 illustrates the present invention configured in a flow architecture 100. The flow architecture 100 may be a minimally invasive cytometry system, a microfluidic architecture, a cell inspection system, a label free cytometry system, a dye free cytometry system, a high yield cytometry system, a low energy cytometry system, an aneuploidy measurement system, a growth rate measurement system, an in-droplet microfluidic system, and the like. The flow architecture 100 comprises a laser source 102, a detector 104, a pre-filter 108, a single cell flow 110, a sort facility 112, one or more sort destinations 114, and a handling system 118. The laser source 102 may be a QCL, a QCL array, a QCL array of multiple angles, multiple QCLs with distinct carrier frequencies, a Vernier tuned QCL, a dual QCL/UV array, a QCL with phase scrambling facility, a mid-IR laser, a tunable QCL, a broadband QCL, a scanning QCL, a THz QCL, or any combination thereof. The detector 104, also known as a detection facility, may be one or more of a mid-IR detector, visible/NIR scattered light detector, fluorescence detector, quantum dot label detector, detector with differential numerical aperture, reference detector for calibration, photo-acoustic detector, or a combination thereof, and may be selected in accordance with the laser or light source. The handling system 118 may be a microfluidic handling system, a chip/cassette with or without anti-reflective coating, a 2D manifold/array, a laser tweezers, and the like. The handling system 118 may comprise a facility to enable single particle or cell presentation to the one or more laser sources 102. In an embodiment, handling system 118 may be a fluid handling system in a microfluidic architecture. Various cytometric analyses, characterizations, measurements, diagnoses and identification may be possible using the present disclosure such as pre-fertilization gender selection, cancer detection, reproductive cell/embryo viability detection, high throughput live cell studies (optionally in combination with FACS), stem cell studies, selective cell destruction, measurement of aneuploidy, measurement of growth rate, measurement of DNA, RNA, proteins, sugars, lipids, nutrients, metabolic products, etc, gas monitoring, determining food/water contamination, and the like. A sample fluid may be encased in a sheath fluid that may allow droplets to be charged. The fluid stream may be streamed out of a nozzle. The present invention uses flow architecture 100 of a path length such as 50 microns or less to reduce water absorption of infrared signal. In an embodiment, the stream may be passed through an optical measurement zone, where infrared light emitted by laser source 102 passes through the stream including at least one first cell type 120 and at least one second cell type 122. The optical interrogation may occur either after the fluid exits the nozzle, as shown in FIG. 1, or when it is still within the nozzle. In the in-nozzle case, the nozzle may be made of at least one infrared-transparent material such as Germanium, very pure Silicon, chalcogenide glasses, Calcium Flouride, Zinc Selenide and the like. The beam from QCL 102 passes through the fluid stream and may be detected on the opposite side with one or more mid-infrared detectors 104. When a living cell is detected in the stream, the absorption of analytes within the living cell at one or more mid-IR wavelengths may be measured as the cell moves through the beam by studying the transmitted mid-IR wavelength light. The signal from detector 104 may be processed to yield an estimate of certain biochemical constituents in the cell. The absolute or relative level of these constituents may be used to classify the first cell type 120 and/or the second cell type 122.

According to methods well known in flow cytometry, the stream is actuated in a manner, such as with a piezoelectric actuator that may cause it to break quickly into discrete droplets. These droplets may be given an electrical charge according to the cell classification determined using the QCL system. In an embodiment, the system may apply a single charge for desirable cells, and route all other droplets to a waste bin. However, in other embodiments, various systems may set multiple levels of charge in order to allow sorting in to sort destination 114. Once assigned a charge, the droplet may be attracted/repelled by charged plates in the system. The negatively charged droplets may be attracted by the +Ve plate, and sorted into one output container; the positively charged droplets may be attracted by the −Ve plate. The droplets whose readings may be inconclusive (where the droplet contains no cell, or where the droplet contains more than one cell) may be sorted into a waste container.

In an embodiment, the configuration in FIG. 1 may be applied to pre-fertilization sperm cell sorting for gender, for example. Sperm cells would be interrogated by QCL 102 that may be tuned to the absorption of DNA, possibly QCL 102 tuned to other cellular matter, and possibly a visible laser to measure scatter from the cell. The visible laser and cellular matter QCL wavelengths may be used to determine if a single sperm cell was present, and possibly the orientation of the cell. The absorption of the wavelength tuned to QCL 102, and the associated detector 104, may be integrated and processed together with the other readings to determine the total mass of DNA in the cell. The 2-5% differential in DNA mass between cells carrying the X- and Y-chromosomes would be used to sort cells into X-bearing and Y-bearing samples. Inconclusive measurements, multi-cell droplets, and droplets without cells may be sent to a waste container. In other embodiments, the system may be further simplified for this application by having only "selected cells" and "waste" outputs. In some embodiments, spectral measurements of sperm cells may have been used to measure the extent of any chromosomal/DNA damage in a cell. Cells that may have unusual spectra in their DNA fingerprint may therefore be discarded. Similarly, cells showing unusual ratios of other cellular matter compared to DNA matter may indicate lack of viability or damage to the cell, and these may be used to reject the cell.

Figure 2:
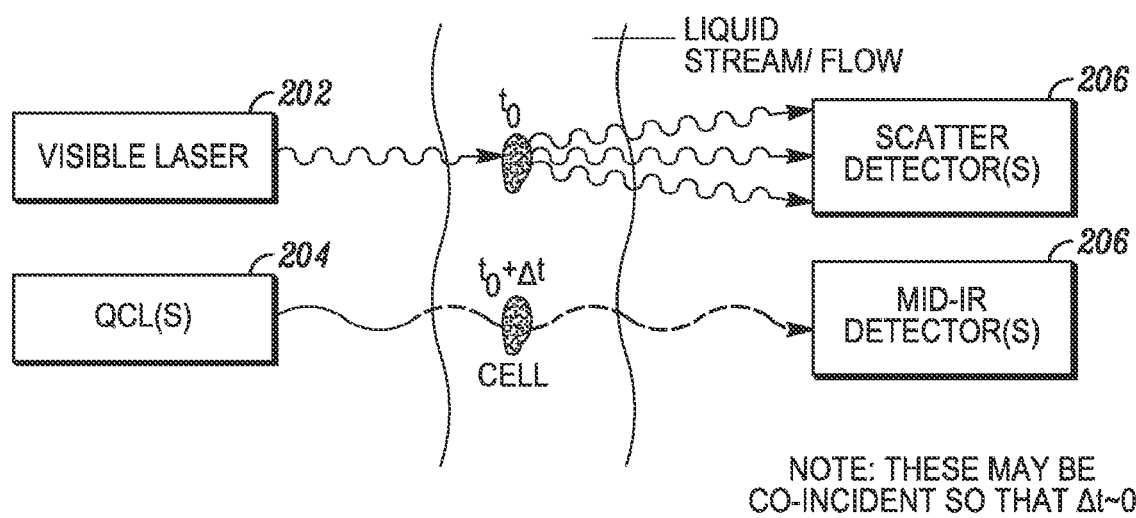
FIG. 2 shows a potential configuration of laser source to interrogate a sample stream, in either flow cytometer configuration as shown in FIG. 1.

FIG. 2 shows a potential configuration of laser source 102 to interrogate a sample stream, in either a flow cytometer 100 configuration as shown in FIG. 1, or in another configuration where cells are presented in a fluid channel such as in a microfluidic chip system. In this embodiment, a visible laser 202 may be used to detect the arrival of a cell in the stream by its scattering signature. The scattering signal may encode other information about the cell including size, features that may help indicate the cell type, or orientation.

The visible scattering signal may then be used to trigger QCL 204 operation where one or more pulsed QCLs are used. The advantage of pulsed QCLs running at a low duty cycle is that they may produce significantly higher power for the short period in which the cell is in the measurement location, allowing for a higher signal-to-noise ratio in the measurement.

The visible laser 202 measurement may be configured such that it detects cells ahead of the QCL 204 volume for a number of reasons as it may allow the QCL 204 to be turned on and stabilize in terms of power and wavelength before the spectral measurement commences, it may also be desirable that the QCL-based measurement begins before the cell arrives, and coincidentally with the visible laser, in the measurement volume, in order to have baseline infrared measurements before and after the cell is measured. However, in other embodiments, a separate detector may be used on the output of the QCL 204 to normalize out laser power. In other configurations, the "visible" and mid-infrared measurement volumes may be the same, and beams may be combined into a single beam. The visible beam may be enlarged along the flow axis to produce a signal that is longer than the QCL-based measurement. The visible measurement may measure scatter to one or more detectors 206, and may even be used to produce an image or pseudo-image of the cell in order to measure size or orientation. Cell orientation may be critical information for the sort based on QCLs 204. For example, sperm cells, which pack DNA very tightly into their body, may be asymmetric. Transmission measurement through the long axis of the cell may result in a significantly different absorption measurement than through the short axis. With the aid of one or more visible beams and their scattered signals, cell orientation may be determined to process the QCL-based measurement more accurately.

Figure 3:
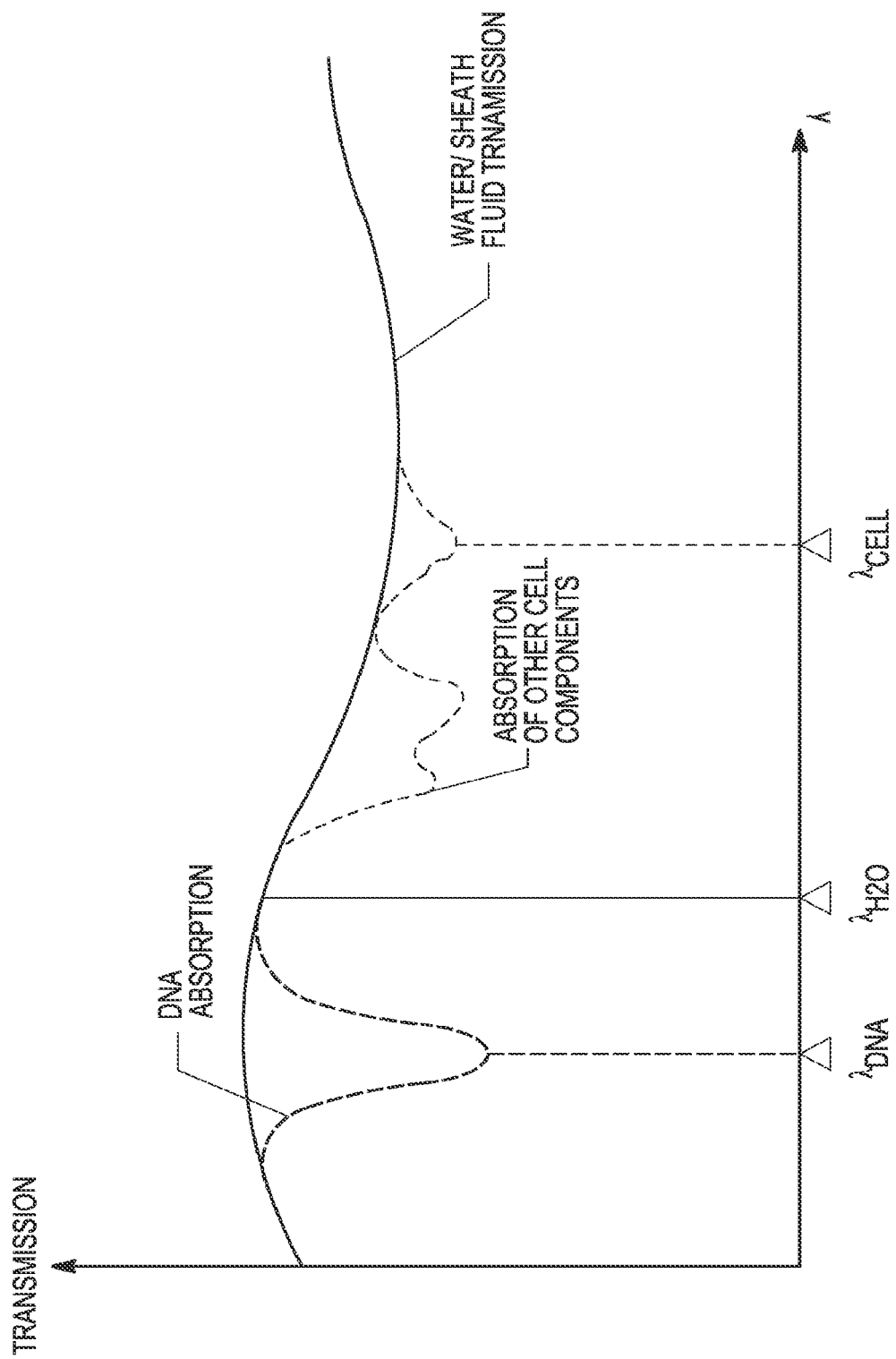
FIG. 3 illustrates a simplified example of mid-infrared spectra for a flow such as those described in FIG. 1 and FIG. 2.

FIG. 3 illustrates a simplified example of mid-infrared spectra for a flow such as those described in FIGS. 1 and 2. The example shows infrared transmission of three constituent materials in the flow of water which may have many absorption features in the mid-infrared, cellular components other than DNA, and DNA.

In an embodiment, three QCL wavelengths may be used: one to measure water absorption through the stream, one to measure cellular components other than DNA, and one to measure the DNA signal. The three absorption spectra may be overlapping, in which case a 3-QCL approach is desirable in order to strip out the DNA signal. In an embodiment, the outputs of the 3 QCLs may be combined into a single beam that is sent through the sample, and then broken into separate wavelengths using thin film filters and the like, and detected by 3 mid-infrared detectors such as cooled Mercury-Cadmium-Telluride (MCT) detectors. The absorption of the water is calculated first, to normalize the measurement of the non-DNA cellular constituents; in the case where the cellular constituent absorption overlaps with the DNA absorption spectrum, this signal is then used to normalize the signal received from the DNA-specific wavelength detector. In an embodiment, the signal corresponding to non-DNA components may be used separately to classify the cell type, orientation, and the like. In other embodiments, a broadband QCL source may be used to produce mid-infrared light covering all the relevant features, and a similar 3-detector configuration may be used. Another configuration may use a scanning tunable QCL that rapidly scans the wavelength range of interest, in addition to a single detector. Another configuration may be the use of a broadband QCL source plus a tunable detector system.

Figure 4:
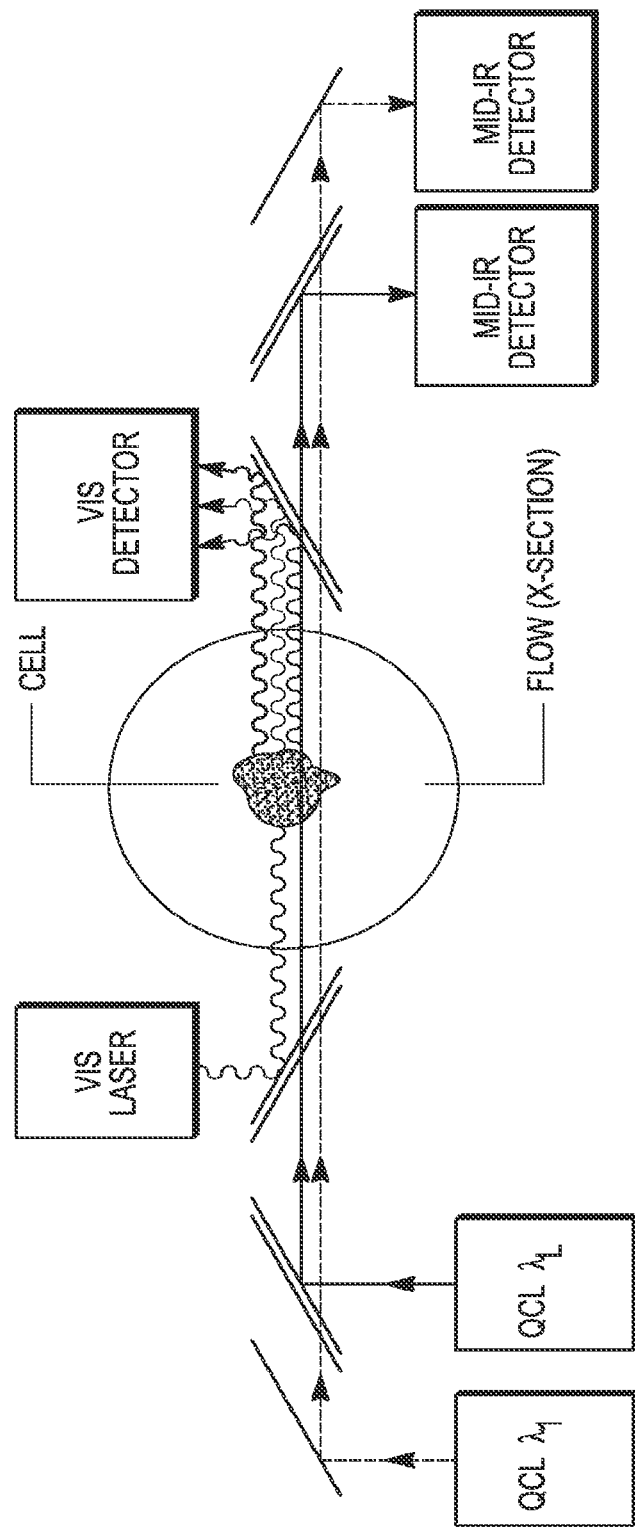
FIG. 4 shows an example configuration of a system interrogating cells in a flow, which is shown in cross-section.

FIG. 4 shows an example configuration of a system interrogating cells in a flow, which is shown in cross-section. In this embodiment, multiple QCL-originated infrared wavelengths may be combined with a visible wavelength to interrogate cells. The wavelengths may be combined, and then separated, using dichroic thin film filters. The QCL wavelengths may be used in this case to normalize for water, or to measure relative constituents within the cell. The visible wavelength may be used to detect the cell, and in other ways described earlier.

Figure 5:
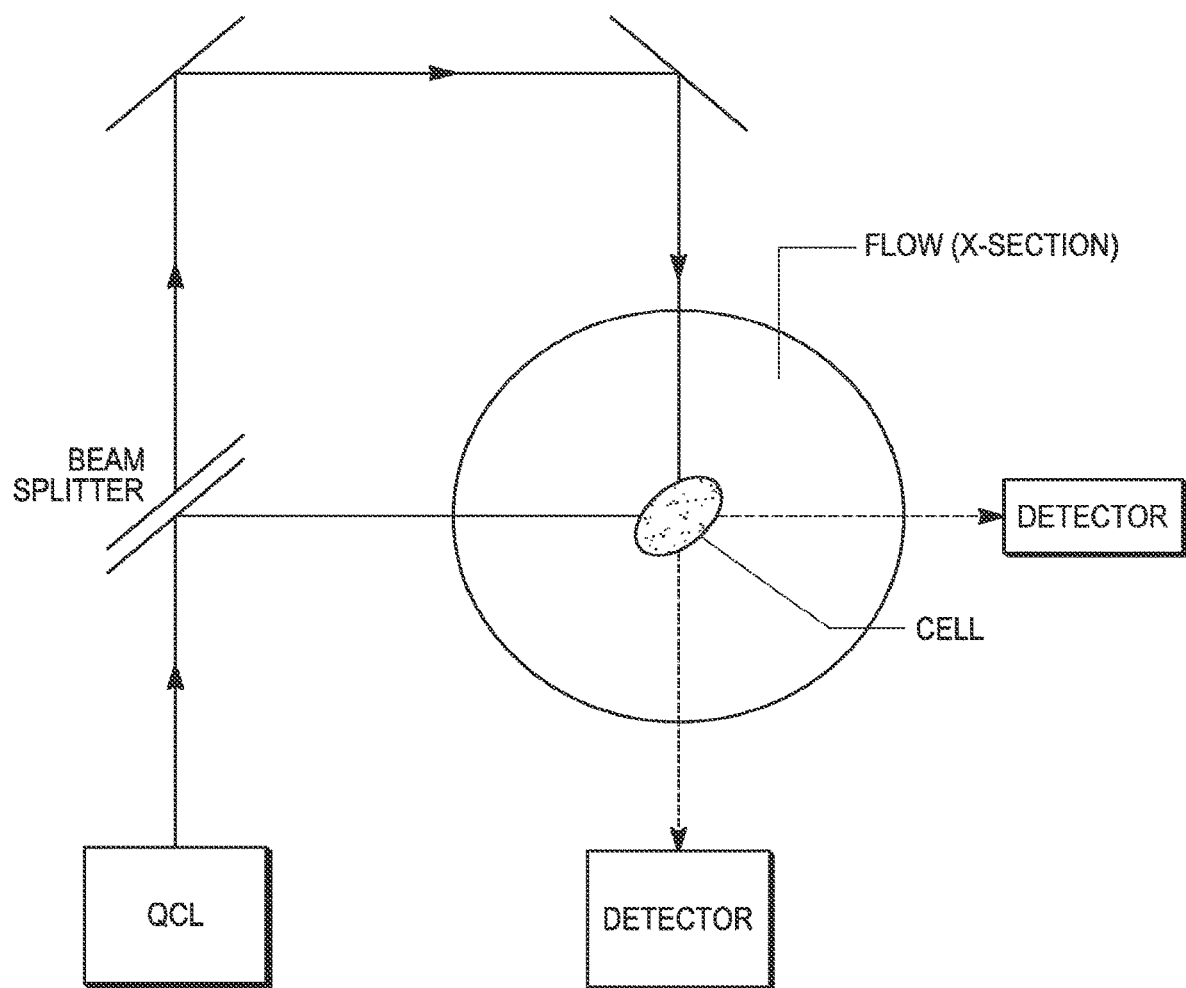
FIG. 5 shows an embodiment of the present invention, in which the flow and cells 120 and 122 are measured from multiple angles.

FIG. 5 shows an embodiment of the present invention, in which the flow and cells 120 and 122 are measured from multiple angles. Again, this system may use one or more QCL wavelengths and visible/near infrared wavelength(s). Measurements using one or more paths through the flow may be used to calculate or normalize for cell orientation or precise position within the fluid flow. Such multi-angle measurements may result in significantly higher precision measurements of cellular components. In other embodiments, visible beams where laser sources and detectors are significantly less expensive may be used from multiple angles to precisely localize the cell in the flow and/or measure its orientation to normalize measurements made using the QCL source(s) and associated mid-infrared detector(s). The embodiment shown in FIG. 5 may be extended to multiple angles through the sample. If additional power is needed to provide high enough (signal-to-noise) SNR, multiple QCL sources may be used. As described above, this may be supplemented with visible/near infrared measurements from multiple orientations, which may use the same beam paths, or a separate set of beam paths.

Figure 6:
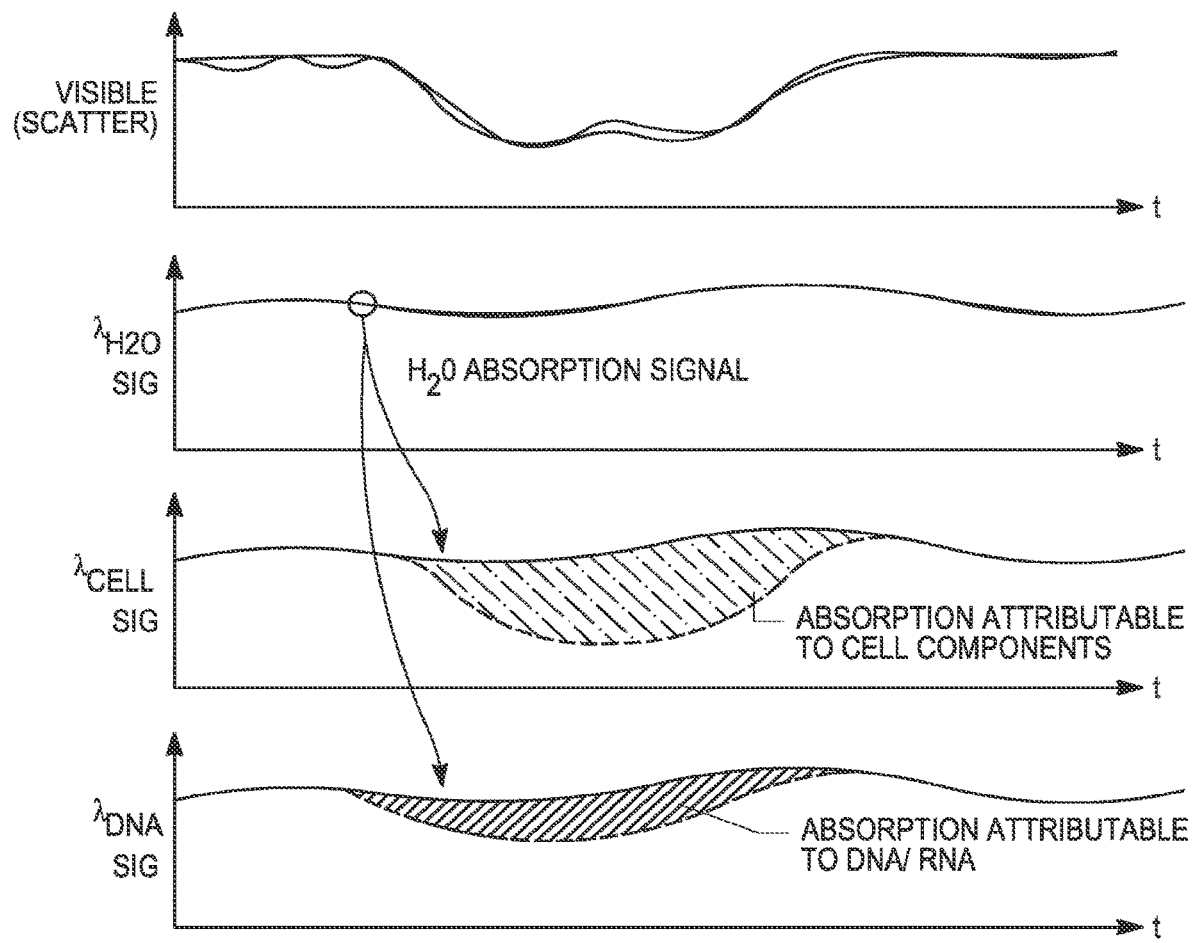
FIG. 6 illustrates simplified detector signal, corresponding to the sample spectra shown in FIG. 3.

FIG. 6 illustrates a simplified detector signal, corresponding to the sample spectra shown in FIG. 3. A visible detector measures scatter from a cell entering the measurement volume, with the dip in signal indicating the presence of a cell. For example, one QCL is used to measure water absorption through the stream (essentially measuring the path length through the stream). Another QCL is used to measure general cellular components. Yet another QCL is tuned specifically to the absorption band for DNA (for example the 0-P—O stretch band at 1095 cm-1 DNA/RNA). In the manner described above, the signals are normalized to isolate the signal of interest (which may be the DNA content of the cell).

Figure 7:
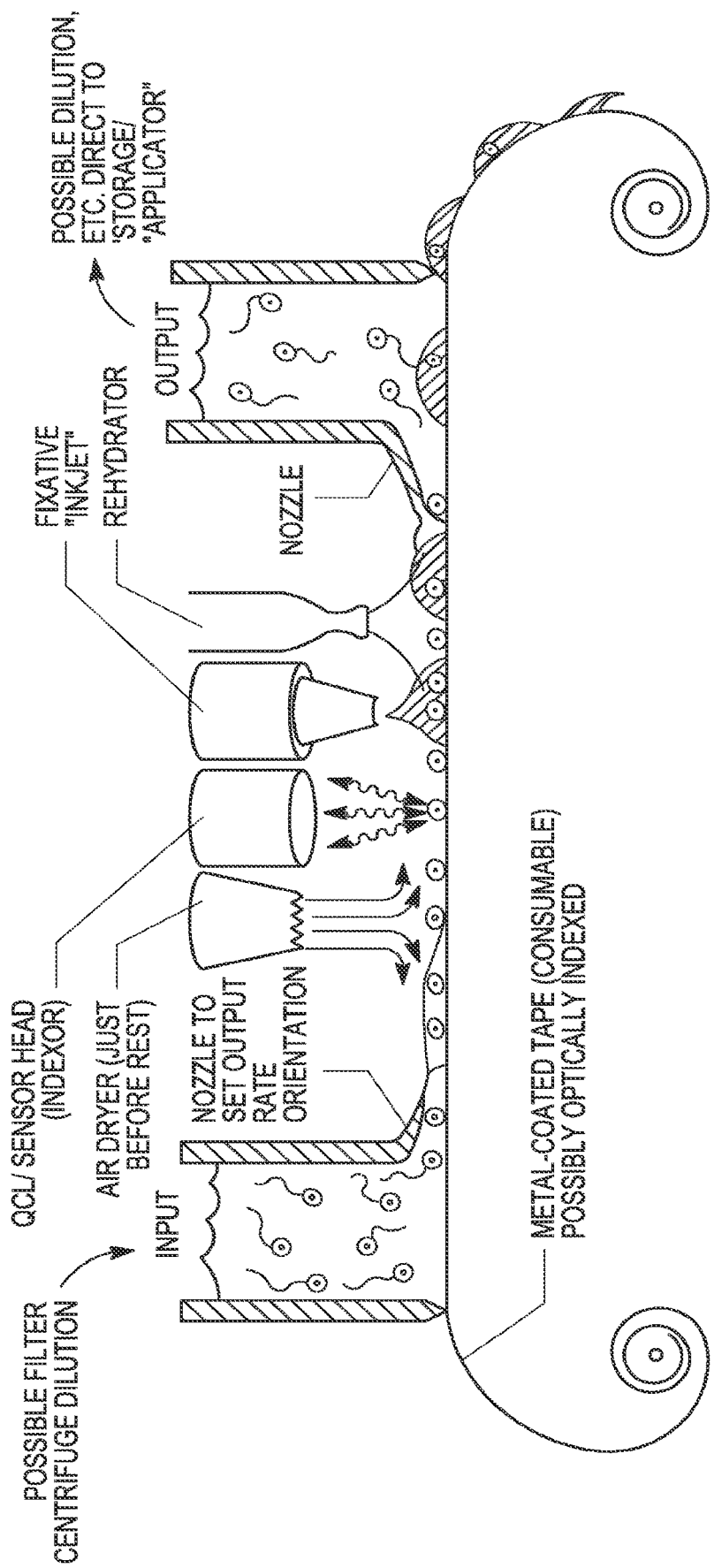
FIG. 7 shows another embodiment of the present invention, where cells are measured in a dry state.

FIG. 7 shows another embodiment of the present disclosure, where cells are measured in a dry state. In this embodiment, a continuous tape is used as a substrate for the cells for measurement and separation. The tape may be metal-coated to provide high reflectivity in the mid-infrared. This example may be shown for sperm cells, which may withstand some level of desiccation. Sperm cells may be spread onto the tape from a liquid reservoir—a "squeegee" type nozzle may be used, potentially with features that may provide the sperm cells with a common orientation on the measurement tape. The sample may be air-dried rapidly but done carefully, so that it does not destroy the cells to a point where very little extraneous fluid is left around the cells. A sensor head containing QCL lasers, detectors, and visible/near infrared lasers/detectors may be then scanned over the tape. Absorption of the QCL wavelengths may be measured to determine, in a manner described above, the absolute amount of DNA contained in the cells and potentially other information regarding the cells.

In an embodiment, cells or regions that may be rejected are then covered, with an ink-jet type device capable of a high output rate, with a substance that fixes the rejected cells to the substrate. Optionally, the tape may be rehydrated to preserve the selected cells. The tape then runs into an output reservoir, where the free (selected) cells may be extracted into a liquid. The tape with the rejected cells fixed to it goes into a waste container. The advantage of this configuration may be that the resulting piece of equipment may be very small, and take advantage of components already developed for low-cost, high-speed scanner and printer systems. As the cost of QCL components may be reduced, this makes possible the use of low-cost, compact systems for clinics or even home use.

In addition, the removal of liquids from the "sample stream" greatly increases the transmission of mid-infrared signal and potentially improves the SNR of the system. The basic system illustrated in FIG. 7 may be configured in alternate manners in line with the present invention. Other embodiments may include use of freezing rather than drying to fix the cells in place and prepare for measurement; use of selective unfreezing and removal in order to accomplish the selection process; and no use of drying or freezing but allowing a thin layer of liquid or gel to remain on the surface of the tape by hardening of the liquid/gel by any means in order to fix certain cells to the tape while others are extracted, including selective drying, exposure to radiation that hardens a gel, and the like. Another embodiment may include use of a laser or other mechanism to destroy or disable cells that may be determined by use of the present invention to be of a type not desired by the sort. Potential subsequent filtering to separate dead from live cells may also be included.

Figure 8:
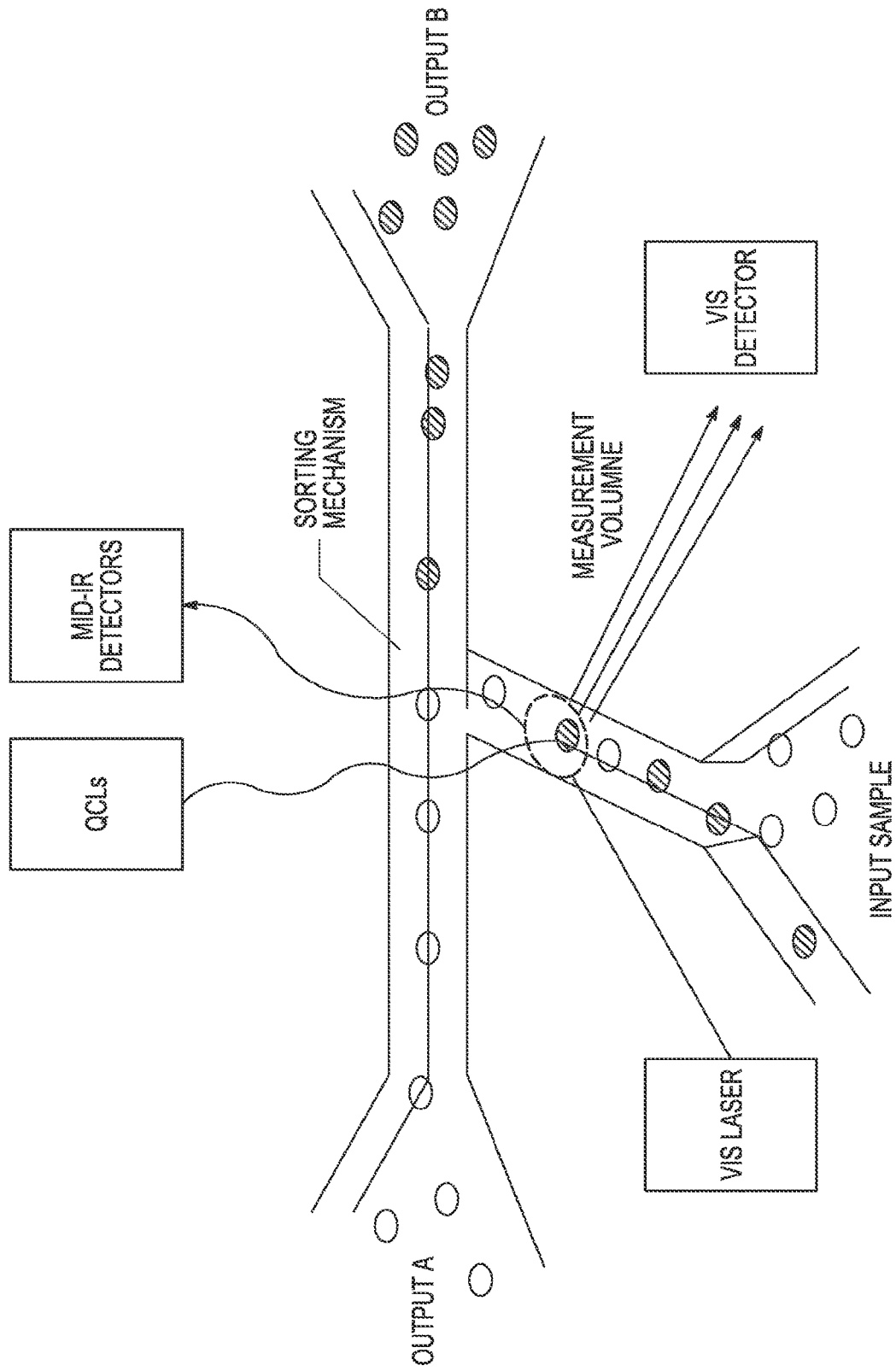
FIG. 8 shows the application of the present invention embodied using a microfluidic-type cell sorting system.

FIG. 8 shows the application of the present invention embodied using a microfluidic-type cell sorting system. Such devices have been demonstrated for cell sorting using conventional dye plus UV-activated fluorescence classification of cells. In an embodiment, the microfluidic device is configured in a basic manner, with an input well and two output wells. Sorting at the junction is accomplished in one of the several ways known to those in the field, including but not limited to electrical fields, lasers, magnetic means (in conjunction with magnetic beads), or fluidic pressure ports. In an embodiment, the system may be configured to allow interrogation using one or more QCLs from the top, and simultaneous interrogation using a visible laser from the bottom. This may be achieved, for example, by using a glass substrate as the lower half of the device (transmissive in the visible) and high-purity silicon as the upper "lid" for the device (transmissive in the mid-infrared). The lids may be coated to improve optical performance; for example, the glass in the channel may be coated with a (visible light) transparent conductive layer that strongly reflects mid-infrared radiation to maximize the mid-IR signal returned to the mid-IR detector(s). As described above, the visible laser may be used to detect a cell in the detection volume, and trigger pulsed QCL operation. The mid-infrared light from one or more QCLs passes through the cell, is reflected by the bottom of the microfluidic channel, and into the mid-infrared detectors. The integrated signal as the cell passes through the detection volume may be used to classify the cell type, and to control the sorting mechanism at the junction.

Figure 9:
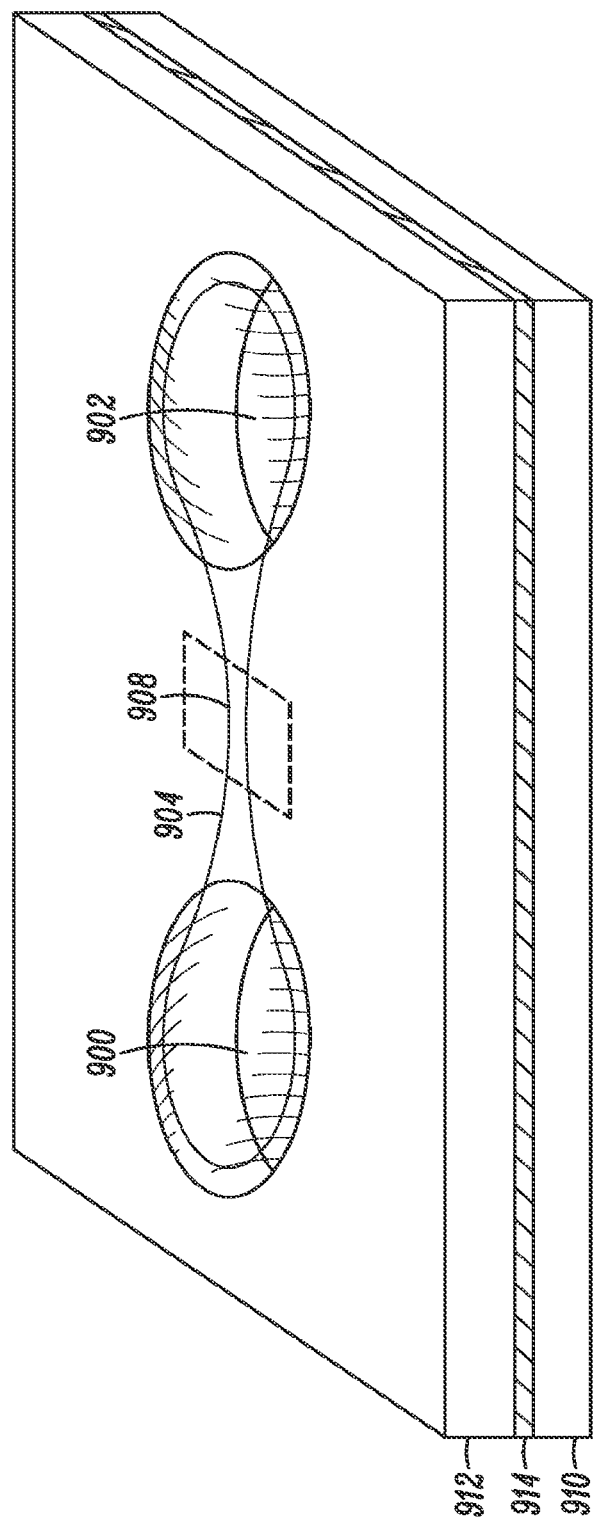
FIG. 9 shows a portion of a very basic embodiment of the present invention which is a microfluidic system for live cell measurements.

FIG. 9 shows a portion of a very basic embodiment of the present invention which is a microfluidic system for live cell measurements. A microfluidic chip with input 900 and output 902 wells may be constructed, in manners well known in the market, here with three layers: a top cap 912 in which the input 900 and output 902 wells are etched, a bottom cap 910, and a patterned layer 914 in which microfluidic features are patterned. This layer may consist of any of a number of materials, for example Polydimethylsiloxane (PDMS), which is readily patternable (by imprinting, for example) and biocompatible. A well may be formed in this material corresponding to those patterned in the top cover. One or more channels 904, which may be tapered to prevent clogging, may be patterned to connect the input 900 and output 902 wells. A portion of the channel constitutes the measurement region 908 where a mid-infrared beam produced by one or more quantum cascade lasers (QCLs) may be focused on the channel 904 and transmitted or reflected to one or more mid-infrared detector(s), such as a mercury cadmium telluride (MCT) photodetector. Cells passing through or positioned in the measurement area 908 may cause absorption of specific wavelengths of mid-infrared light corresponding to molecular vibration modes. The absorption measured by the system at these wavelengths may be used to chemically and therefore biologically characterize the cells.

One or both of the caps 910 and 912 and may be a material that transmits the mid-infrared wavelength(s) of interest. Standard glasses used in microfluidics may absorb these wavelengths. To build this architecture for use with QCLs in the molecular "fingerprint region" (2-20 microns wavelength, where molecules have their fundamental vibration modes), an infrared-transmissive material, for example ZnSe, may be used. Other materials which may be used may include at least one of Ge, Si, $BaF_2$, ZnS, $CaF_2$, and KCl.

Certain materials such as BaF, or ZnSe may be transparent in at least portions of the visible light range, which may be advantageous for systems where visible light guidance, observation, measurements or manipulation may be desired. The visible light may include short wavelength light such as ultra-violet, visible, NIR of upto 2 microns. In certain embodiments of the present invention, 1.5 microns light may be used to ensure compatibility with the infrared-transmissive materials.

If the system may be built for transmission measurements through the channel 904 in the measurement area 908, then both top and bottom caps 910 and 912 must be IR-transparent. An alternative configuration may be reflective, where the mid-IR light from the QCL(s) passes through one cap, passes through the measurement volume, reflects off the opposite cap, passes through the measurement volume a second time, and then exits the cap and is collected by a mid-IR detector. In this case, only mid-IR entry/exit cap may be required to transmit mid-IR light. For example Silicon may be used depending on the precise wavelengths being measured. High-purity Silicon such as float-zone Silicon may be desirable to reduce absorption losses in certain ranges. The opposite cap may use a standard microfluidic material, such as glass. In this architecture, it may be desirable to coat the glass with a mid-IR reflective layer at least in the measurement region 908. For example, even a thin layer of metal may be highly reflective in the mid-IR. Alternatively, a conductive oxide such as indium tin oxide (ITO) may be used in order to reflect mid-IR but be transparent in the visible range, in order to allow visible or near-infrared (NIR) access to the measurement volume from the opposite side. The flow of cells through the channel 904 and measurement area 908 may be controlled in a number of manners well known in microfluidic systems, including pressure differentials between wells and, or an electrical potential over these wells. The system may be configured to provide a continuous throughput of cells through the measurement area 908 for applications such as cell type counting or population statistics, or to allow precise positioning and stationary measurements of cells in this area for high-resolution spectral and other inspection of cells for R&D applications. The structure illustrated may be replicated or multiplexed using multiple fluidic channels, which may be interrogated in parallel or sequentially by QCL-generated mid-IR light. Parallel channels may allow for higher system throughput, and/or redundancy in case of clogging.

In an embodiment, the present invention may be useful to integrate a method for disabling or destroying cells in the system. For example, a laser with sufficient power to destroy key portions of the cell may be used to disable the cell. The disabled cell then flows into the output, where it may be separated using filtering or other means, or left in the sample if it does not disrupt the function of the live cells. An example of such an application may be characterization and selection of sperm cells. Those cells which meet the selection criteria (for gender, for instance) may be allowed to flow through the channel unchanged, those that do not may be irradiated with a pulse of visible or infrared light which damages their cell membrane or propulsion mechanisms. Subsequently, a "swim-up" filtering which selects for motile sperm may be used to extract the live sperm cells. Alternatively, the entire sample may be used and only the live cells are able to fertilize the egg. A system based on the present disclosure would flow a suspension of sperm cells through one or more microfluidic channels. In the measurement volume of a channel, one or more QCL beams would be used to determine the volume of DNA present in the sperm cell, and determine whether the cell is carrying X or Y chromosomes (a 2.5-3% difference in DNA volume may be seen), and optionally whether there are mid-infrared spectral indicators for other problems. The mid-IR measurement may be triggered and/or supplemented by a low-power visible/NIR beam which may measure cell scattering or size, based on the X/Y characterization in the mid-IR and other markers in the mid-IR and/or visible/NIR. Those sperm which are desirable may flow through to the output without further intervention. Those that are not may be illuminated within the measurement area, or immediately after it with a pulse of light which immobilizes it. In an embodiment, the present invention may utilize light in the near or short-wave infrared range to immobilize sperm. In an embodiment, a mechanism for separating motile from non-motile sperm may be built directly into the microfluidic device in this system.

Another example where such a selective-kill mechanism may be employed is in stem cell therapies. For example, when a suspension of differentiated cells grown from pluripotent stem cells may be prepared for delivery into the subject, it is important to remove or disable residual stem cells, which may grow into tumors within the target organ. In this case, a filtering system based on the present invention would inspect a flow of cells in one or more microfluidic channels, and interrogate these cells with mid-IR beams from one or more QCLs. Based on the observed spectral characteristics, and the calculated biochemical makeup of the cells, certain cells that may be identified as stem cells or cells that are not the type of differentiated tissue required, may be destroyed using a laser pulse. In this manner, differentiated cells receive minimal handling and only very low-energy mid-IR radiation exposure, while cells which could cause abnormal growths if delivered intact to the target tissue are rendered non-functional.

A similar system may be used if a closed-circuit culturing, growth and filtering system may be built for stem cell or other applications. Cells may be continuously run through a filtering system that inspects cellular biochemical fingerprints and terminates cells that do not meet the application requirements. Again, applications of such systems may include regenerative medicine based on stem cells. Another potential application of such a system may be in high-throughput "evolutionary" processes where specific cell function is being targeted, and this function or its byproducts may be observed using mid-IR spectroscopic techniques. For example, synthesis of specific chemicals may be the functional target, in this case a system based on the present invention may flow, with high throughput, cells through microfluidic channels where they are interrogated using QCL(s) and mid-IR detectors. Cells showing promise may be recirculated into the system without change, those that do not may be destroyed using a laser or other potential tools such as ultrasound, RF, mechanical punches, liquid jets and the like, so they do not contribute to future populations in the system.

Figure 10A:
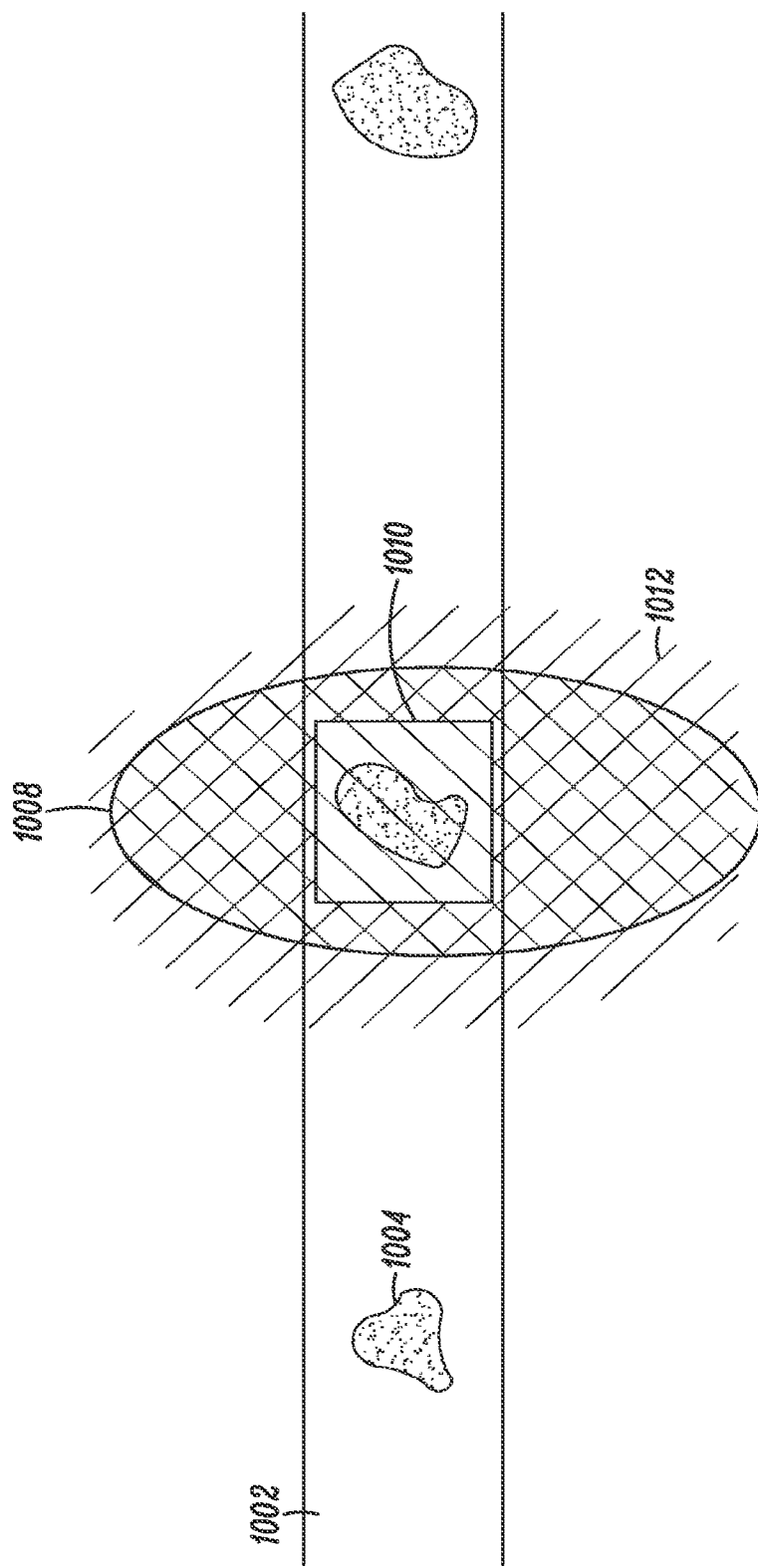
FIG. 10a shows detail of an embodiment of a measurement region in a microfluidic channel.

FIG. 10a shows detail of an embodiment of a measurement region in a microfluidic channel 1002. Cells 1004 flow through the channel 1002 and pass a region illuminated by a mid-IR beam 1008 originating from one or more QCLs. As the cell passes through the beam, mid-IR light is absorbed in a spectrally-dependent manner according to the molecular constituents of the cell. In many cases, the beam area may be larger than the cell itself, and the extracted signal will correspond to an average over the cell and surrounding areas. QCLs, as opposed to traditional mid-IR sources such as hot filaments, may be able to focus significant power into small areas, which provides a strong advantage for this system. In many cases it may be desirable to mask surrounding areas in order to reduce the signal background. In this case a masking layer 1012 may be patterned on to one of the caps in order to create an aperture 1010 through which mid-IR light may pass. This may maximize contrast as the cell passes through the measurement volume, and reduces contributions from other materials such as the PDMS or other material used to create the fluidic channels.

Figure 10B:
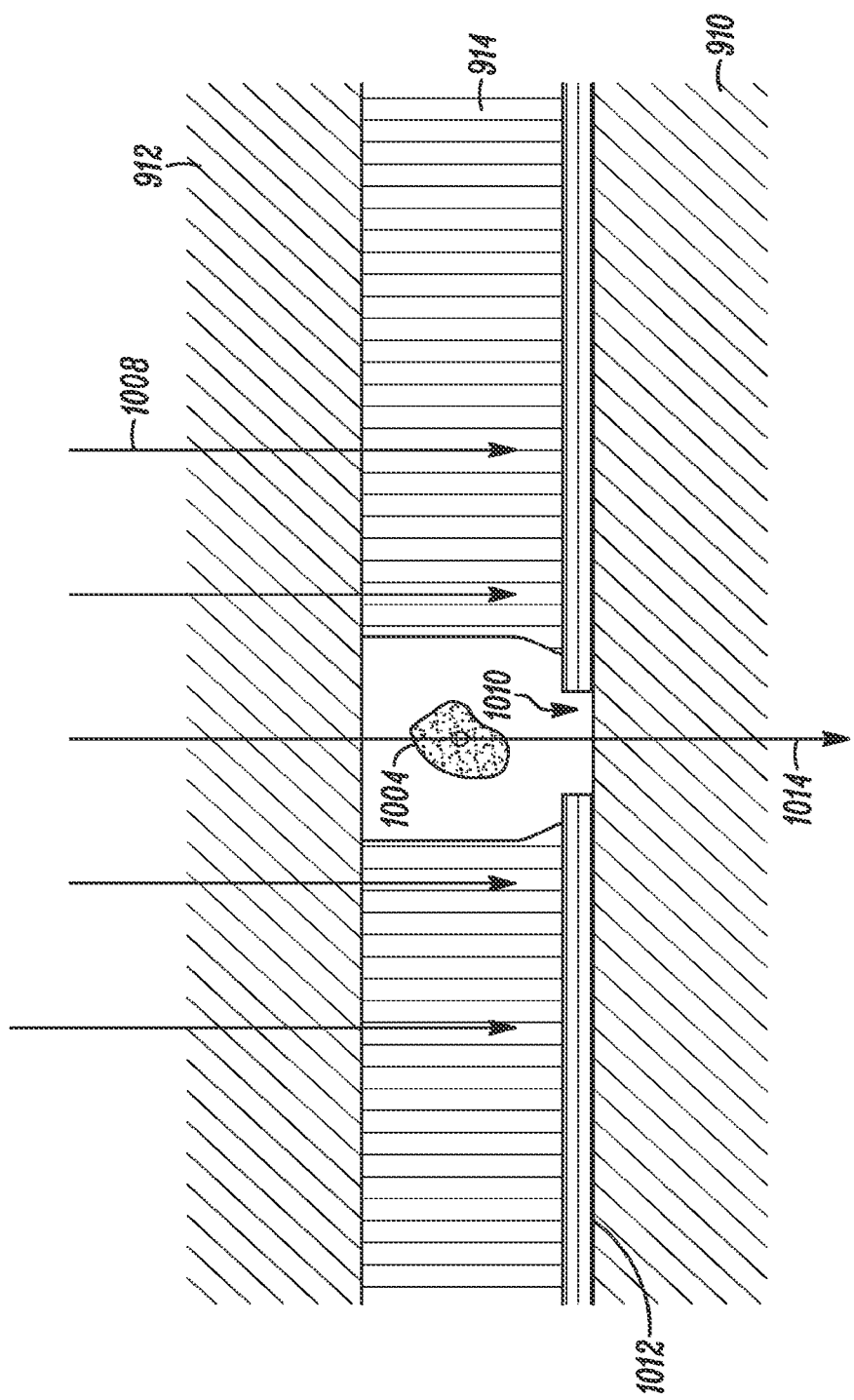
FIG. 10b shows the same example as 10a in cross-section.

FIG. 10b shows the same example as 10a in cross-section. Specifically it shows how a mask is used to ensure only a subset of the incoming mid-IR light from the QCL(s) is transmitted to the mid-IR detectors. In this example, both top and bottom caps 912 and 910 must be made out of a mid-IR transmissive material. If visual-range observation or measurements are also desired, at least one of these must be transmissive in both the mid-IR and visible ranges.

Figure 10C:
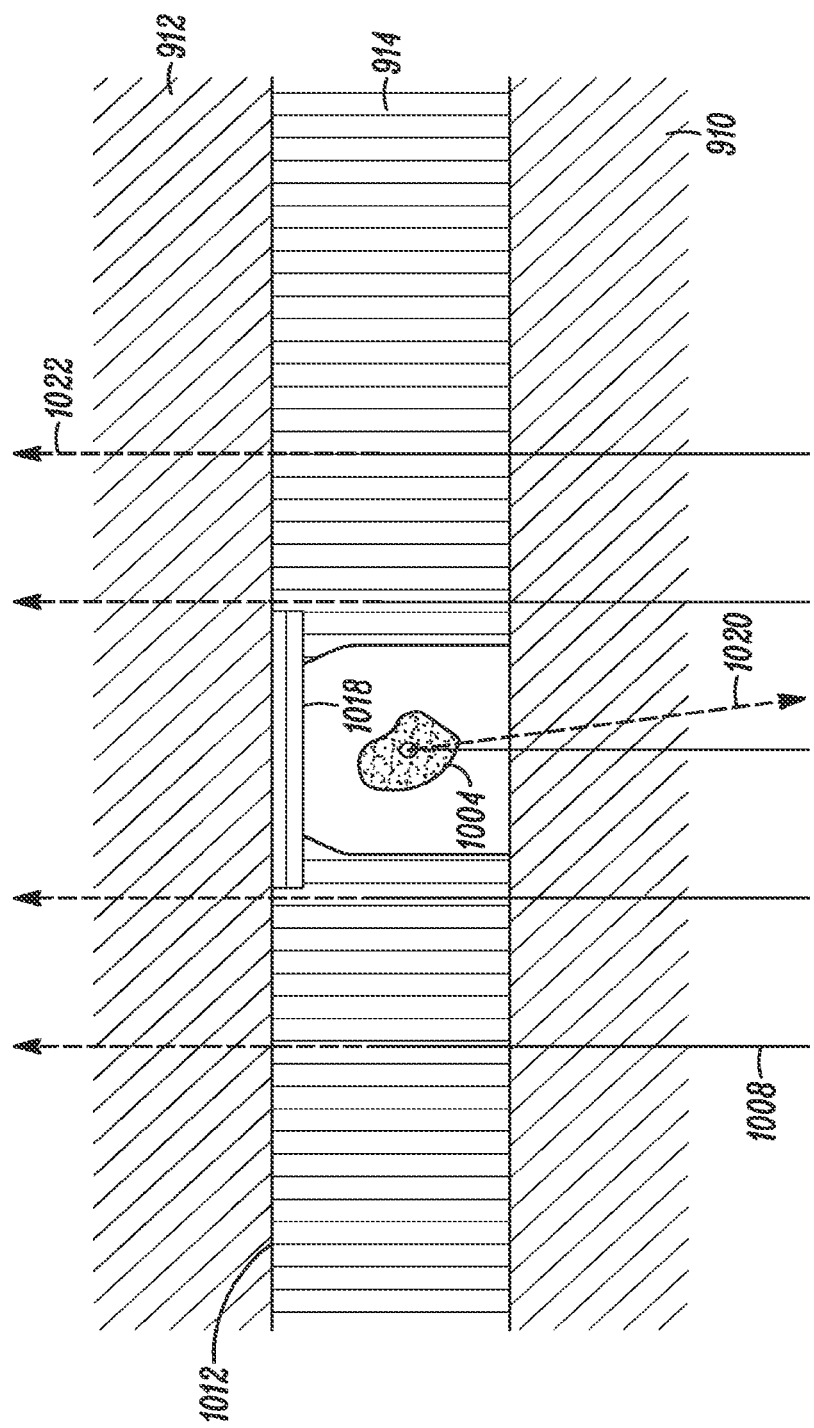
FIG. 10c shows a cross-section of an alternative embodiment that may use a reflective measurement for the mid-IR light.

FIG. 10c shows a cross-section of an alternative embodiment that may use a reflective measurement for the mid-IR light 1008. In this example, the measurement volume is illuminate with mid-IR light 1008 through the bottom cap 910 that is made of IR-transmissive material. A portion of this light passes through the measurement volume, where it may pass through a cell 1002, and is then reflected by a patterned reflective layer. The reflective layer may be a metal layer, or a conductive oxide as described earlier in order to allow visible light access into the volume from the top. Reflected mid-IR makes an additional pass through any cells in the measurement volume, and then passes out through the bottom cap 910 where it may be captured by a mid-IR detector system. The mid-R light 1008 that is not reflected passes into the top cap 912 and is absorbed. The advantage of this architecture may be the ability to use two different wafer materials for the top and bottom caps 912 and 910. For example, the top cap 912 could be made of glass, which is low cost, transparent for visible observation or measurements, and can be readily patterned to form fluid cells/ports. The bottom cap 910 may be made of IR-transmissive material but not necessarily require visible transmission. For example, silicon may be used for certain wavelength ranges.

Figure 11:
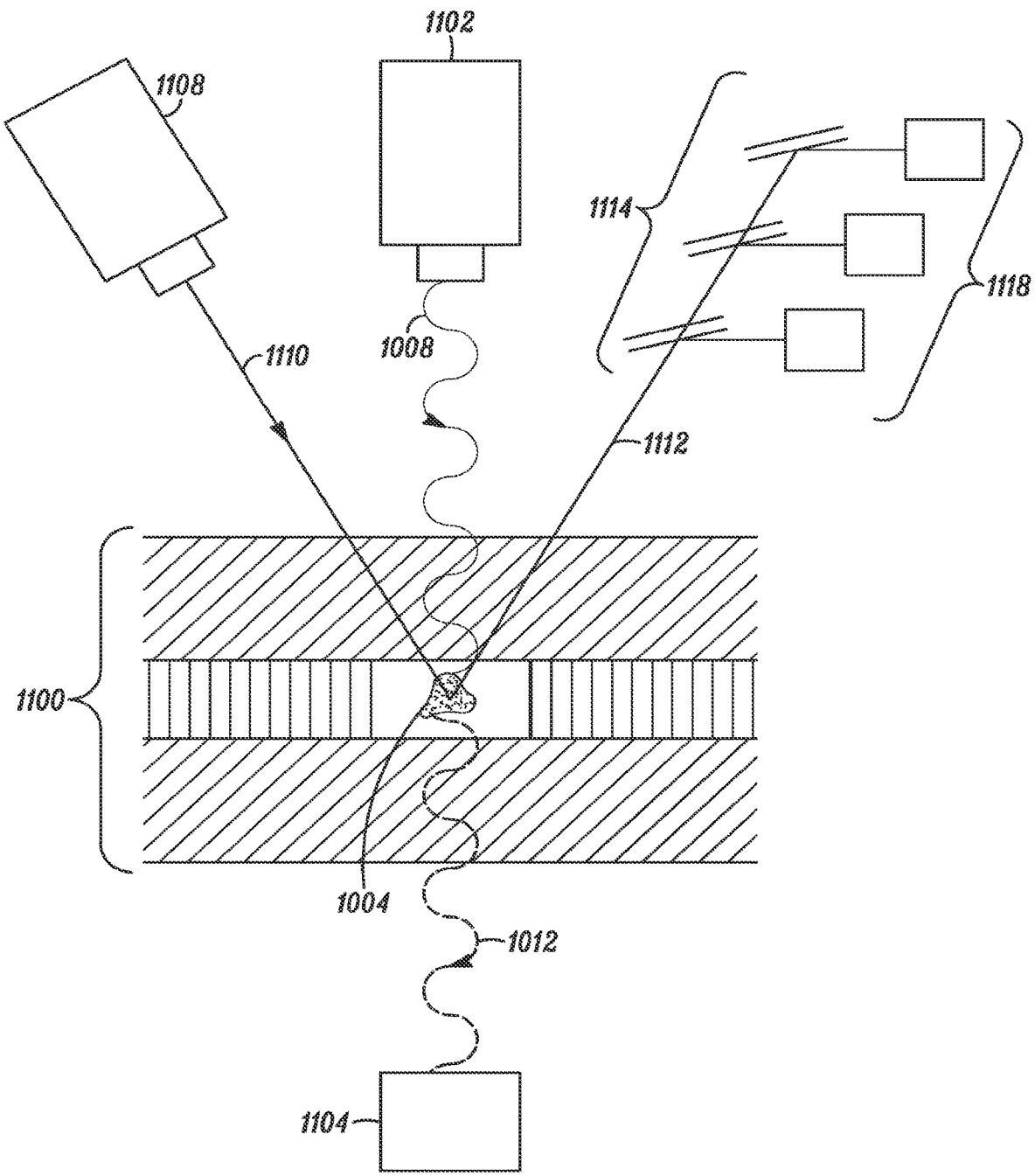
FIG. 11 shows an embodiment of the invention where the microfluidics and QCL-based spectral measurement system may be combined with a more conventional fluorescence-based measurement system.

FIG. 11 shows an embodiment of the invention where the microfluidics and QCL-based spectral measurement system may be combined with a more conventional fluorescence-based measurement system. A microfluidic device 1100 may include channels to hold live cells 1008 as illuminated with one or more QCLs, which may include one or more tunable QCLs 1102. The mid-IR radiation emitted by the QCL passes through the measurement volume and any cells 1008. The transmitted light may be measured by one or more mid-IR detectors 1104. This may be done in either transmission (as illustrated here) or reflection (as described earlier) modes. Here the system may be shown to be complemented by a laser in the UV or visible range 1108 which may emit light 1110 that is also directed at the measurement volume, where it excites fluorescent probes or dyes attached to specific cellular features. The resulting fluorescence may be measured using one or more bandpass filters 1114 and detectors 1118. Such a system configuration may allow correlation of conventional label-based techniques with mid-IR spectroscopic measurements. It may also enable combined-mode systems where labels may be used to identify specific cell types/features, and mid-IR spectral measurements using QCL(s) supplement this information with spectral measurements, such as possibly for biochemical variations not possible to measure with known labels/dyes. Note this system may be configured, as discussed earlier, as a two-sided reflective system where IR and visible systems are positioned on opposite surfaces of the microfluidic system and operate in reflection.

Figure 12:
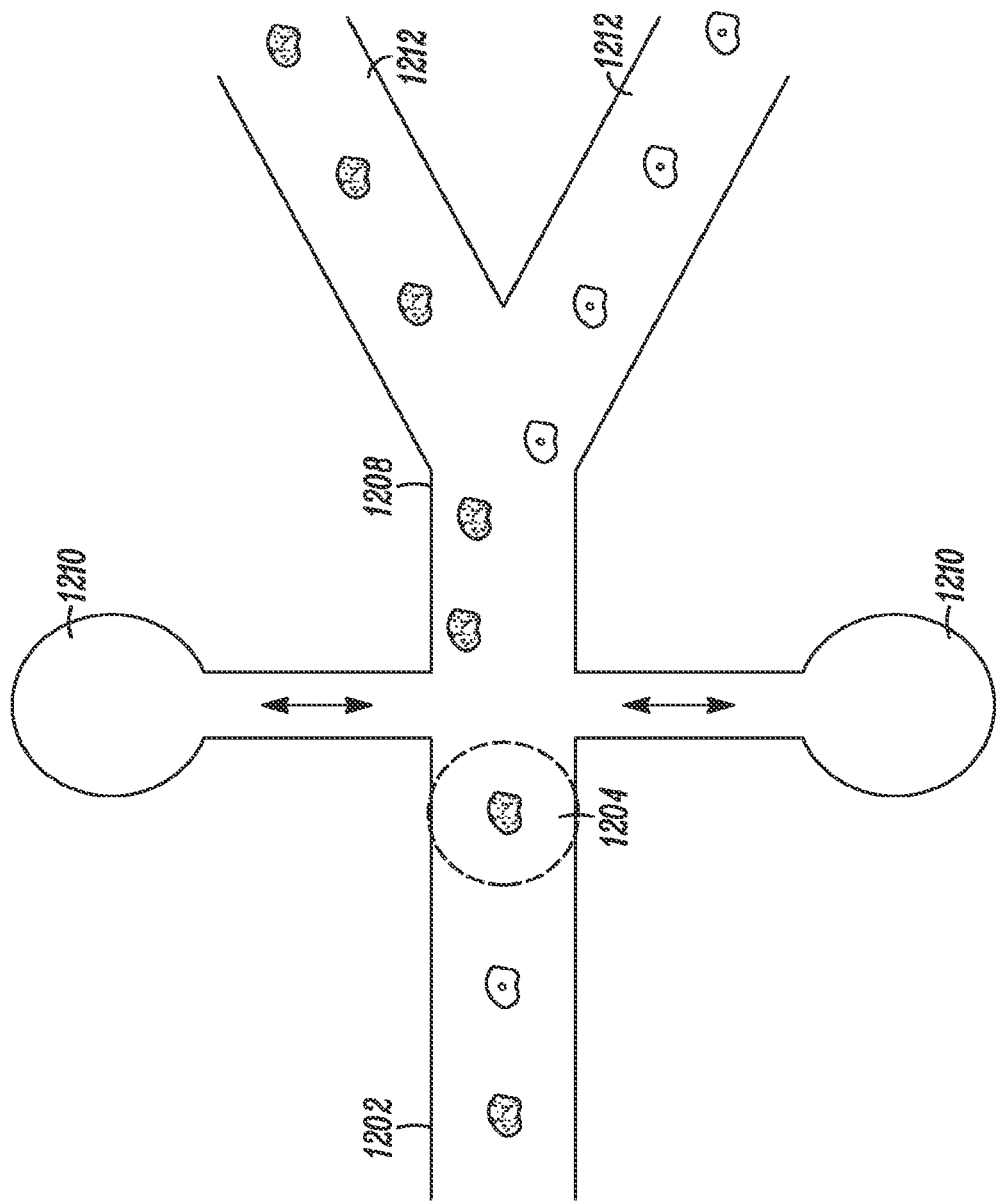
FIG. 12 shows an exemplary embodiment of the present invention where the microfluidic subsystem includes a cell-sorting fluidic switch.

FIG. 12 shows an exemplary embodiment of the present invention where the microfluidic subsystem includes a cell-sorting fluidic switch 1208. An input channel 1202 delivers cells to the measurement volume 1204 where it may pass through a QCL-derived mid-IR beam from one or more QCLs, with one or more wavelengths probing the cell. The microfluidics may have been configured, in manners known in the industry, to center the cells in the flow channel. Based on absorption at these mid-IR wavelengths, the cell may be classified into one of two categories. In some embodiments, two pressure ports 1210 may be used to displace each cell to one side of the microfluidic channel, so as to cause it to flow into one of two output channels 1212. Such a system may be used to accumulate one type of cell out of a general flow of cells, or to forward one or two populations for further inspection and/or processing. An example application of such a configuration may include gender selection, where sperm cells carrying X or Y DNA may be sorted into groups and one type may be retained for fertilization. In an example of a stem cell application, pluripotent stem cells may be separated from differentiated cells during extraction, or before reintroduction to a subject. Other applications include refinement processes where cells are cultured, possibly mutated and repeatedly measured, with certain cells re-introduced to the culture based on their chemical "fingerprint". For example, those cells which produce and therefore contain a specific product may be selected for, on a cell-by-cell basis. The switching function in the microfluidic channel may be performed using any of a number of techniques known to the art, including electrostatic forces, acoustic forces, optical pressure/heating of a portion of the channel, containment of cells in bubbles that may be transported within another medium, and the like.

Figure 13A:
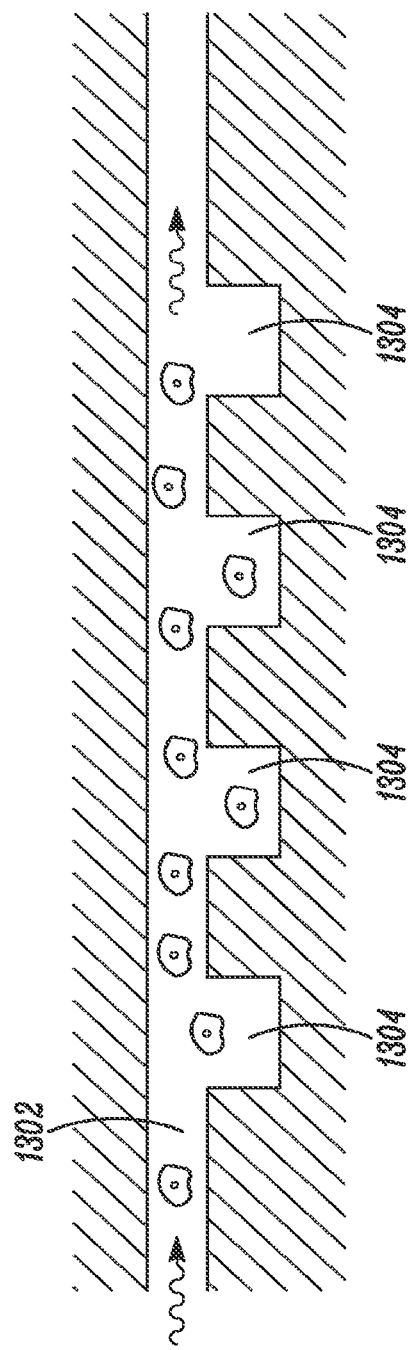
FIG. 13a shows an alternative microfluidic-based embodiment of the present invention, where a series of microwells may be integrated into a microfluidic flow channel/chamber.

FIG. 13a shows an alternative microfluidic-based embodiment of the present invention, where a series of microwells 1304 may be integrated into a microfluidic flow channel/chamber 1302. This structure may be I-dimensional along a single channel or 2-dimensional along an open plane. Multiple parallel channels may be used as well. These wells serve to trap individual live cells in well-defined spaces where they may be measured using mid-IR techniques. For example, a suspension of cells may be flowed through the channel 1302, and stopped momentarily to drop cells into the wells 1304. The suspension and stoppage time must be coordinated such that the majority of wells contain a single cell.

Figure 13B:
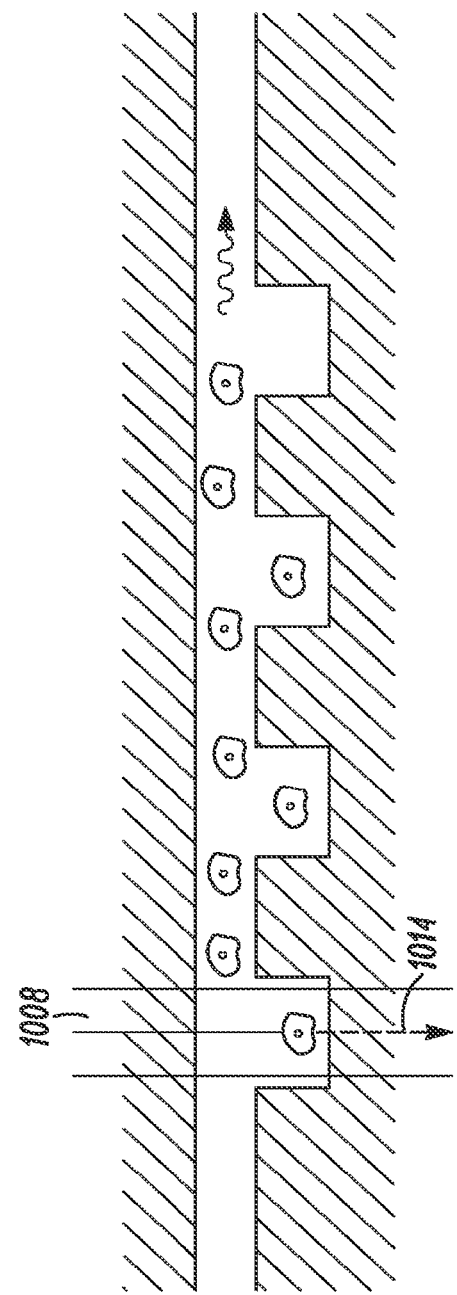
FIG. 13b shows how the wells may be then scanned using mid-IR light from one or more QCLs, the scanning may be accomplished by translating the microfluidic chip, or the laser leading mechanism.

FIG. 13b shows how the wells may be then scanned using mid-IR light from one or more QCLs. Scanning may be accomplished by translating the microfluidic chip, or the laser leading mechanism. As described herein, this may be accomplished in either reflective or transmissive mode. This scan may be repeated multiple times in the case where a time series of measurements is being established to monitor changes in cells, with conditions such as temperature or chemical inputs through the channel possibly being varied. Such time series may be used, for example, to monitor cell differentiation (such as for stem cell applications), cell metabolism for drug studies, and the like.

Using this design, cells may also be separated using optical or electrical or combined techniques. For example, a visible or NIR beam may be used to address a well, and the pressure and heating from this radiation displaces the cell resident in it back into the flow layer, where it may be flowed out of the cell. Electrical heaters in the well may do the same, or electrostatic forces may be used to separate the cell from the well. These operations may be performed in parallel. For example, a projector-type system may be used to project light into multiple selected wells simultaneously, causing the cells contained within them to be pushed up into the flow region, and transported out of the device. This may open the potential for higher throughput processing using large arrays.

Figure 14:
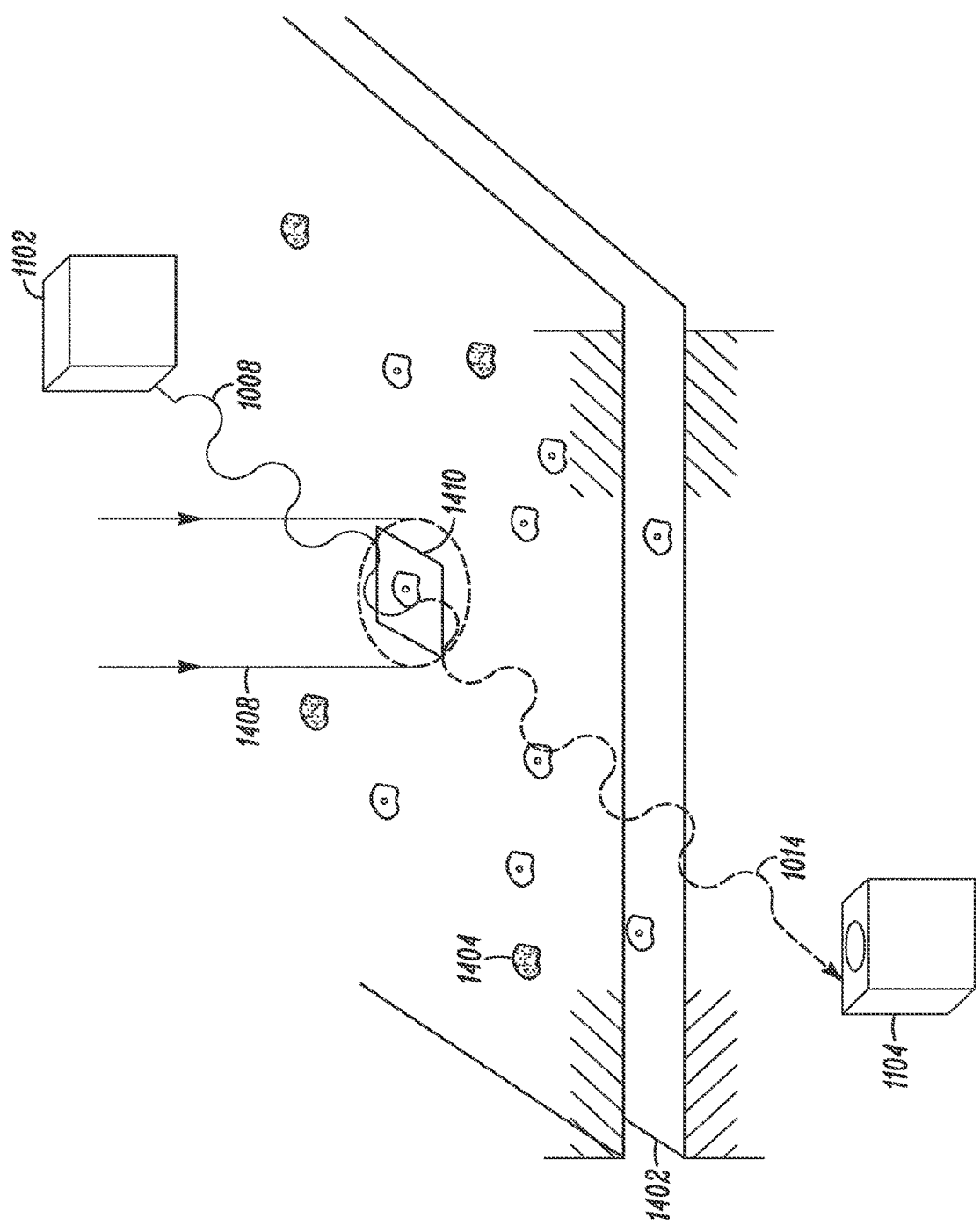
FIG. 14 depicts another embodiment in which the microfluidic chamber may be 2-dimensional.

FIG. 14 depicts another embodiment in which the microfluidic chamber may be 2-dimensional. A 2-dimensional fluid chamber 1402 may be formed between the upper and lower caps. Optionally, if the area is very large, spacers 1404 may be inserted to maintain consistent spacing between the caps. Cells flow into this area where they may be measured using one or more QCL(s) 1102 and mid-IR detector(s) 1104. Measurements may be performed either by translating the microfluidic chamber relative to the beam 1008, or moving the beam itself from cell to cell. This may be controlled by a human operator, or an image processing system may locate cells and steer the QCL-derived beam onto them for spectral interrogation.

Alternatively, an "optical tweezer" beam where a laser spot 1408 (such as visible or near infrared) or annular pattern may be used to trap and move cells within the chamber 1402. This method, which is well documented elsewhere, may be used to immobilize moving cells, such as sperm cells, or mobile microorganisms for interrogation by mid-IR. It may also be used to move cells to a specific measurement volume 1410. In this case, the mid-IR interrogation region may be stationary, and the cells may be translated in and out of the measurement volume using the optical tweezers. The optical tweezers may be used to immobilize the cell temporarily, or at least confine it to the measurement volume for sperm cell inspection, for instance during the mid-IR measurement. In some cases, such a visible or NR beam may also be used to manipulate the cell optically, by heating it, and puncturing its membrane, with the entire process observed by the mid-IR spectral system based on QCLs.

In an embodiment, the optical tweezer may be used to translate a cell in a scanning motion over the measurement region, in order to build up an "Image" of the cell at a sub-cellular level. This method may be used together with special optical features patterned on one of the caps, such as plasmonic or negative index structures that focus mid-IR light to a subwavelength spot for high resolution interrogation of the cell.

Figure 15:
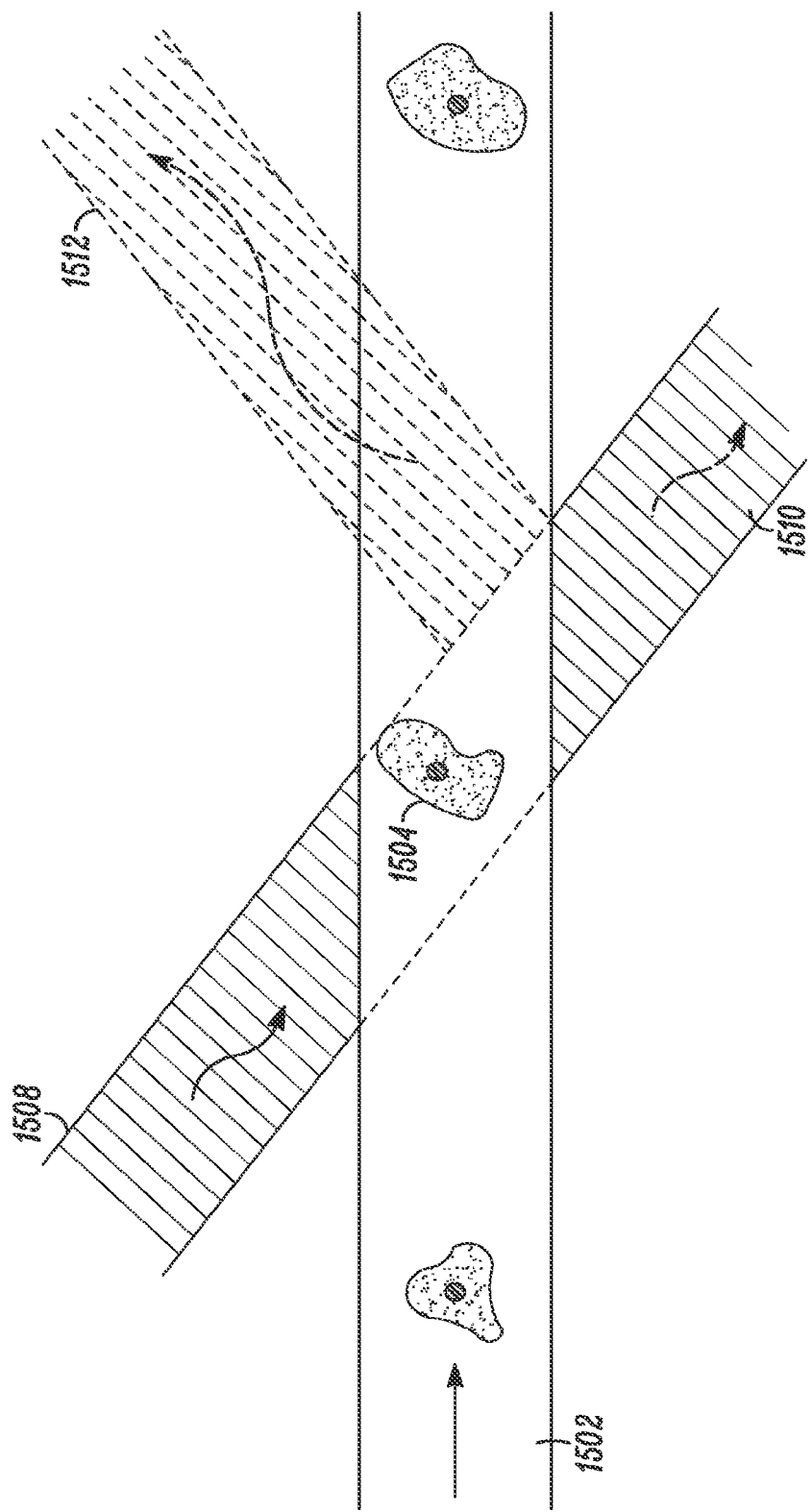
FIG. 15 shows an alternate embodiment of the mid-IR optics combined with a microfluidic channel.

FIG. 15 shows an alternate embodiment of the mid-IR optics combined with a microfluidic channel 1502 in a top view. In this embodiment, optical waveguides capable of carrying mid-IR light without high losses may be used to deliver light from one or more QCLs to the measurement volume within the microchannel. These waveguides may be fabricated from a range of mid-IR transmissive materials. For example, silicon may be bonded to a glass wafer and patterned into waveguides using standard photolithographic techniques. In this example, an input waveguide 1508 delivers the mid-IR light to the measurement volume containing a single cell 1504, where it is absorbed according to its wavelength(s) and the concentration of various chemical constituents in the measurement volume, including the cell. The transmitted light may be collected by the output waveguide 1510 and delivered to a mid-IR detector. Alternatively, a reflective design may be used to get two or more passes through the cell (with output to waveguide 1512)—more than one reflection may also be used.

The potential advantage of a waveguide-based system may be a very consistent alignment of the light source and output relative to the measurement volume, and the beam shape (and therefore illumination) relative to the volume. Changes in beam location and profile relative to measurement volumes in the present invention may be calibrated initially, before use, or periodically, such as through the use of calibrated particles, for example, tiny plastic spheres of known diameter flowed through the microfluidic measurement cell. In addition, the strong absorption of water and other liquids in the mid-IR range may allow the system to be calibrated more easily using a liquid-only approach.

Figure 16:
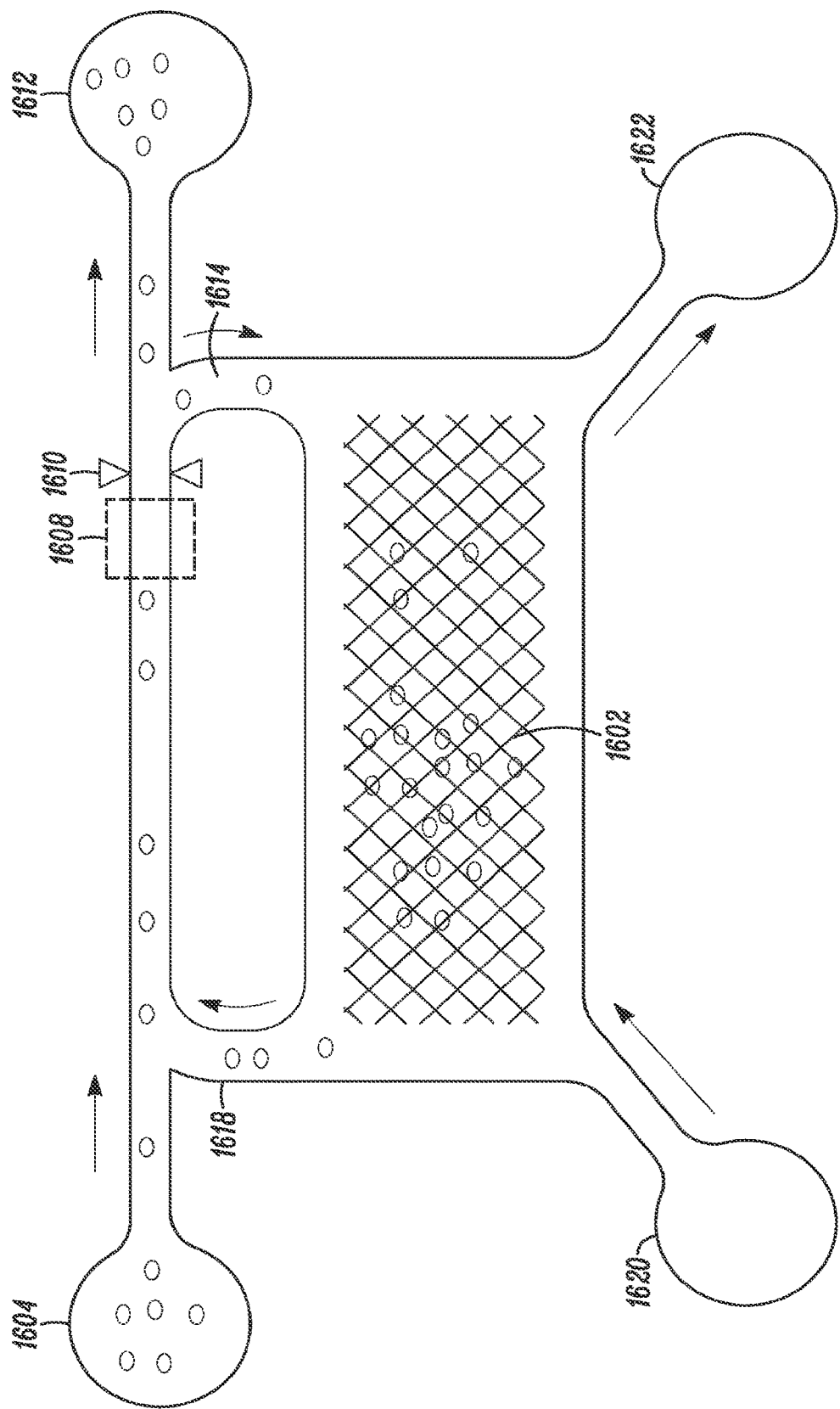
FIG. 16 shows a system for the growth and purification of cells based on the present invention.

FIG. 16 shows a system for the growth and purification of cells based on the present disclosure. A unique aspect of the disclosure may be that it allows repeated interrogation of live cells without labels and UV light or other methods, meaning the preparation steps (such as labeling) may not be required, cell function may not altered, DNA may not be damaged such as that caused by some chemical stains and UV light, and no processing may be required to remove labels. For the aforementioned reason, this makes the disclosed approaches ideal for use in systems where cells or their descendants may be repeatedly interrogated for the purpose of "guiding" growth or purifying a cell culture.

In an embodiment, an integrated bioreactor 1602 may form the center of the system, where cells may be incubated and may multiply, differentiate (such as for stem cell cultures), or produce biochemical compounds of interest. Cells may be introduced to the system through a cell input 1604. On the way into the reactor, the cells may pass through the measurement volume 1608 which may be interrogated by one or more QCLs, and optionally visible/NIR lasers. During input, the cells may undergo purification, time permitting, through the use of a cell sorting switch 1610. Cells that do not meet certain criteria may be sent to the output well 1612 for disposal. Those cells that do meet the criteria may move through the reactor input 1614 into the bioreactor chamber. The reactor chamber may take multiple forms. For example, the bioreactor may either be integrated into the microfluidic chip, or be implemented in macroscopic form. Multiple mid-IR measurement/sorting microfluidic devices may be attached to a single bioreactor in order to achieve higher throughput. The reactor may function in ways well known to those skilled in the art, with cell culture media/growth promoters, etc, and potentially surfaces or structures that may allow temporary attachment of cell structures. Media to feed cells and promote growth, differentiation or mutation or, to stress cells with particular compounds may be introduced to the bioreactor through an input 1620, and waste products may be removed through an output or exhaust 1622. In addition, temperature and other conditions in the chamber may be controlled. In one embodiment, the control is through a feedback loop based on system-integrated sensors.

After a specified interval or operations, cells may be extracted through reactor output 1618 and may be flowed through the measurement volume 1608 and cell sorting switch 1610. This process may eliminate cells not meeting the criteria, such as by ejecting them into output 1612, and flowing the remainder back into the chamber. At the end of the cycle, a final sort outputs 1612 the desired, purified cells into the output 1612 for collection. This final output may be different from the one in which the ejected cells was flowed. An example application is in the use of pluripotent stem cells to grow specific cells for implant into an organ. Initially, the input cells may be sorted to place only pluripotent stem cells into the bioreactor. These cells may then be cultured in order to multiply, with continuous purification to remove any cells which differentiate prematurely. Next, chemicals/media may be introduced into the reactor and conditions changed that may promote differentiation into the target tissue type. At this stage, the QCL-based sorter may serve to continuously remove cells that may have been differentiated into the wrong type of cell. Finally, at the output step, only properly-differentiated cells may be sent to the output 1612, with any pluripotent cells removed to avoid potential tumor growths in the target organ.

Another example where such a system is of interest may be in guiding evolution of cells or even small multicellular organisms with specific chemical properties. For example, there may be used to evolve algae that may be efficient in producing precursors to biofuels. In this example, a system based on the present disclosure, which may be used to characterize and measure intracellular chemical constituents with high throughput, and without damaging the cells, may be of interest in performing high-throughput "guided evolution" of optimized algae cells. In this case, the bioreactor serves to multiply successful cells, to introduce a certain number of mutations, and the QCL-based single-cell chemical measurement system and sorter may serve to measure levels of desirable products being produced by live cells (without puncturing them), and removing those cells which do not meet criteria. Such a system has the potential to eliminate slow, tedious work with macroscopic samples, and significantly accelerate development of optimized cell cultures. Similar methods may be used to "breed" cell cultures for use in other applications, including pharmaceuticals, "green" chemicals, nutritional supplements such as omega-3 fatty acids, and other substances that may be produced by microorganisms.

Figure 17A:
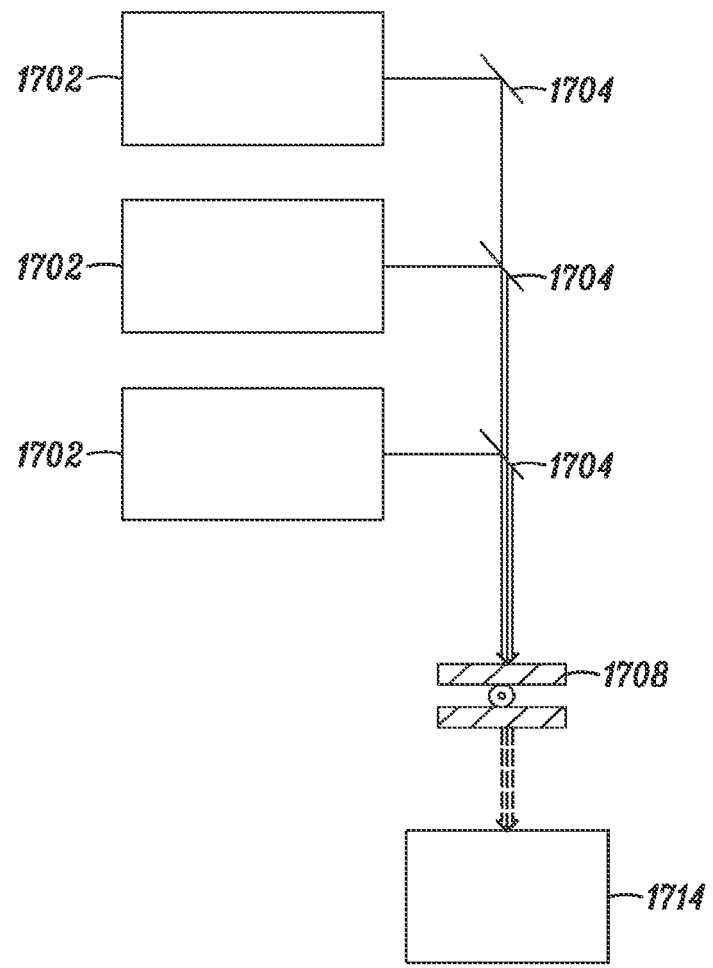
FIGS. 17a and 17b shows two potential configurations for QCLs and mid-IR detectors in the present invention.
Figure 17B:
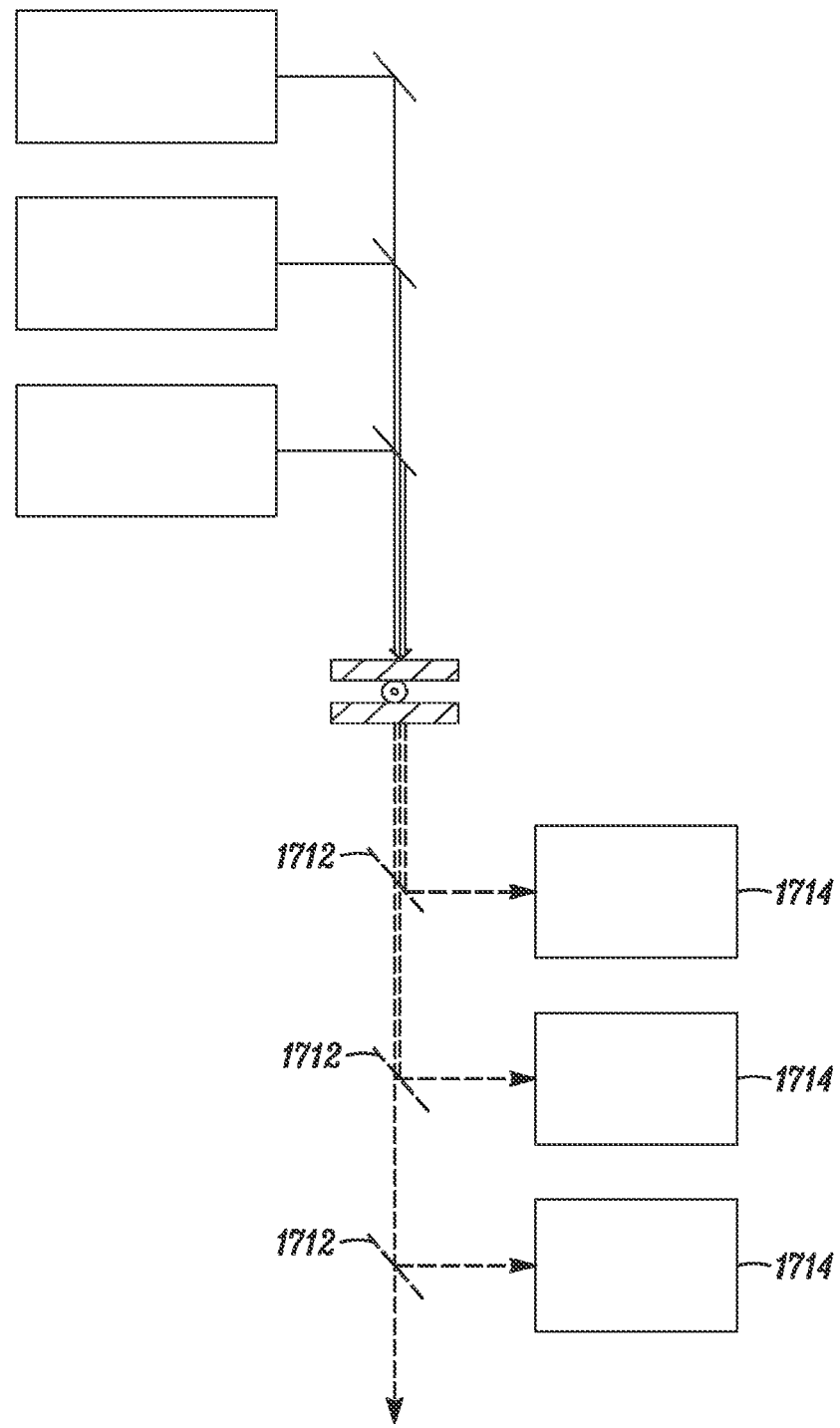

FIGS. 17a and 17b shows two potential configurations for QCLs and mid-IR detectors in the present disclosure. In FIG. 17a, multiple QCLs 1702 may be combined into a single beam by mirrors, such as half mirrors, or thin film interference filters 1704. The use of wavelength-specific filters reduces the losses associated with combining multiple beams, but may reduce the flexibility of the system if multiple tunable QCLs may be used with overlapping wavelength ranges. The beams may pass through the microfluidic measurement volume 1708 and may be collected by a single mid-IR detector 1710. In this configuration, the QCLs may be modulated in a manner that allows their signals minus absorption in the measurement volume to be easily separated by electronic means in the detector output, by methods well known to those skilled in the art. For example, where pulsed QCLs may be used, they may be alternately pulsed such that they result in discrete measurements on the detector. Alternately, they may be modulated at characteristic (and potentially different frequencies), and the signals separated at the output through the use of analog or digital frequency filters.

FIG. 17b shows a configuration where the QCLs are arranged in the same manner, but there may be separate detectors 1714 corresponding to each wavelength, as filtered by filters 1712. The potential advantage of this configuration may be higher system bandwidth, and the use of narrow passbands in filters 1712 to further reduce background signals in the mid-IR.

Figure 18:
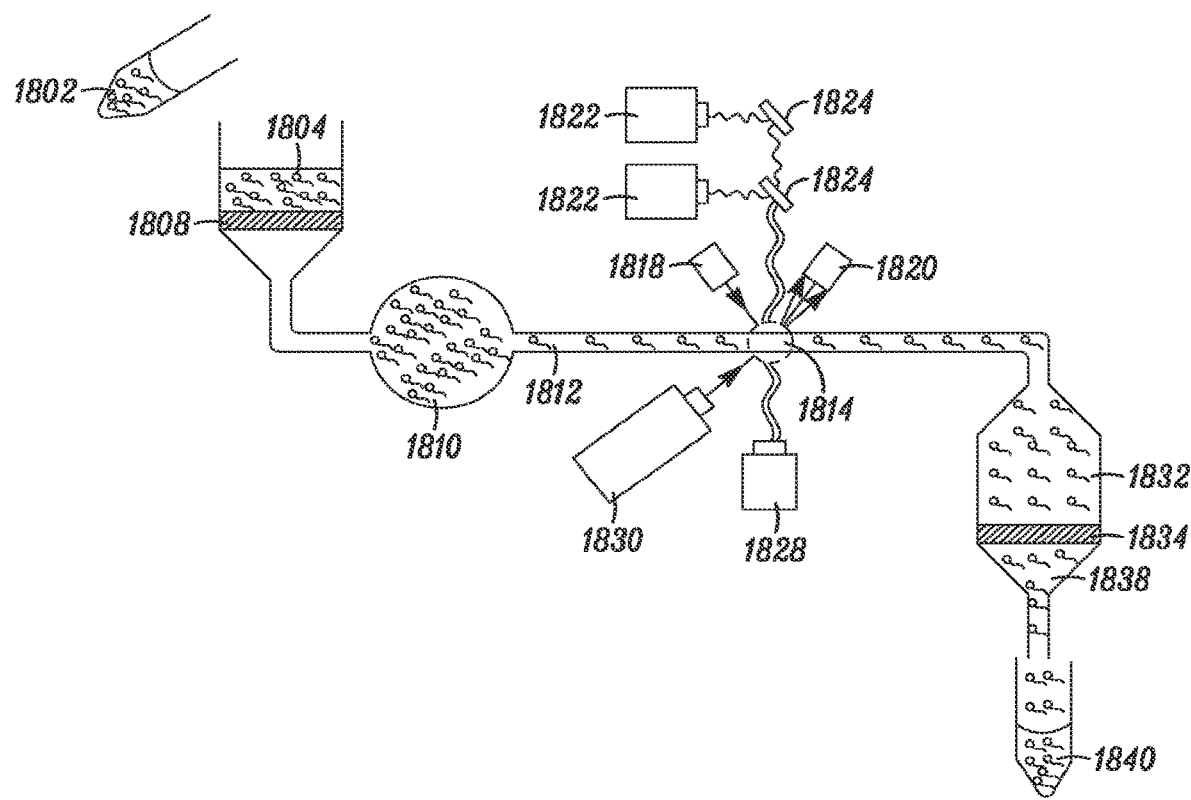
FIG. 18 shows an embodiment of the present invention where it may be used to sort live sperm cells for the purpose of pre-fertilization sex selection.

FIG. 18 shows an embodiment of the present invention where it may be used to sort live sperm cells for the purpose of pre-fertilization sex selection. A sample 1802 may be provided to the system through an input 1804. A filtering mechanism 1808, which may for example be a dense medium through which only sperm cells may travel (possibly including a centrifuge or pressure function, and possibly selecting for motile sperm) is used to separate sperm cells from other constituents of the semen. The filtering mechanism may optionally include a centrifuge or pressure function. The filtering mechanism may optionally select for motile sperm. This step may be done externally from the system through methods well known to those skilled in the art. Such a filter could consist of microfluidic features itself.

The filtered sperm cells possibly with the addition of a medium which promotes flow and viability may be transported to a sorter input chamber 1810. From this chamber, they may flow into the measurement volume of a microfluidic channel 1812, such as through microfluidic features which orient cells and prevent clogging. Multiple microfluidic channels and measurement systems may be used where higher throughput is required. When a sperm cell arrives in the measurement volume 1814, it may be detected through the use of a visible or NIR laser 1818 and a scattering detector 1820. The scattered signal may be used to determine whether the cell entering the measurement volume is indeed a sperm cell, and whether it is oriented correctly, and/or visibly malformed. The signal may also trigger the use of QCLs 1822. In an embodiment, two QCLs may be used. One QCL may be used to measure the asymmetric phosphate bond vibration at approximately 1087 $cm_{-1}$ which is characteristic of the DNA backbone. Another QCL may be used to establish a reference level, which may be done with a wavelength just off the primary QCL, or at a known reference wavelength that establishes a reliable baseline for the measurement. One or both of the primary and reference QCLs may be rapidly scanned in wavelengths over a narrow range in order to facilitate measurement of a second derivative, a common signal used in infrared spectroscopy. The QCLs may be used in pulsed mode to achieve higher peak power, and to allow use of a single mid-IR detector 1828.

The reference wavelength may not be strongly absorbed by DNA or any other target analyte. A subtraction or other analytical procedure may be done, such as by a processor, of the reference signal in relationship to the primary signal. Measurement of the signal itself may involve measuring an amplitude of absorption, standard deviation from the peak of the signal and/or reference curves, AUC/integration of the signal, and the like. In some embodiments, the reference signal may be just the signal measured prior to an absorption curve.

A pre-filter may enable sorting cells by size, a surface property such as an antigen or a cell surface protein, a chemical composition, a characteristic determined by embodiments described herein, and the like.

Mid-IR light from the QCLs passes through the measurement volume 1814 and any cells contained within it, and transmitted light may be measured by mid-IR detector 1828. The calculated absorption in the DNA band, as normalized by the reference QCL wavelength and measurements before and/or after the cell passes through the volume may be used to calculate total DNA contained within the sperm cell. This calculated concentration may be used to determine whether the cell is carrying X, Y or unknown chromosomes. Depending on the desired sex of the offspring, the cell is then either let through unchanged, or disabled/destroyed through the use of an infrared laser 1830. To disable a sperm cell, the infrared source may be pulsed at high power, focused on the cell or preferably, the tail of the sperm cell which may immobilize the sperm cell. The use of a wavelength in the NIR (800 nm or higher) may minimize the possibility of chromosomal damage, should a sperm cell treated in such a manner still result in fertilization. Multiple, lower-power pulses may be used. Subsequently, the sperm cells, both viable and immobilized, may be transported to the microfluidic output 1832, where they may be then filtered using a filter 1834. This filter should ideally select for motile sperm cells through a method such as the "swim-up" method, where sperm swim through a thick cultured medium, thereby enabling collection of only motile cells. As mentioned hereinabove, microfluidic, or well-known macroscopic methods may be used to achieve this filtering. The output 1838 is then placed into a delivery mechanism 1840.

In various embodiments, the sperm cells may be cryogenically preserved before use. In this case it would be desirable to preserve them immediately after sorting, and then run a motility-based filter after unfreezing, since the freezing process itself may render a portion of cells immobile. The present disclosure thereby enables a sperm selection system that does not expose sperm cells to harmful dyes or to UV radiation, that may achieve high specificity in terms of gender selection, and that may be implemented in a closed system, which eventually makes it viable for small clinic or even home or farm use.

FIG. 9a shows a cross-section of a fluid stream 1902 oriented to carry cells through a measurement volume such that flow is into or out of the plane of paper in this case. The flow is illuminated using one or more QCLs, with a hypothetical illumination profile 1908 shown. Note that this may be an unlikely illumination profile and is shown to illustrate the invention only. Various beam shaping optics may be used to shape the beam relative to the flow and to the region where cells are expected to flow through the detection volume. The mid-IR illumination is shown as 1904, illustrated in this example to be wider than the liquid flow. It should be noted that a beam narrower than the flow may be used as well, and may be preferable from an optical power and contrast standpoint. The mid-IR light is strongly absorbed by water in the stream 1902 and therefore, a characteristic absorption pattern 1910 is seen in the transmitted radiation even in the absence of a cell in the measurement volume. The light may be more strongly absorbed in the center since the stream in this case is circular. Ultimately, it will be highly desirable to measure the transmitted mid-IR radiation using a single detector; however, this only resolves the total power transmitted and not the beam profile.

Figure 19A:
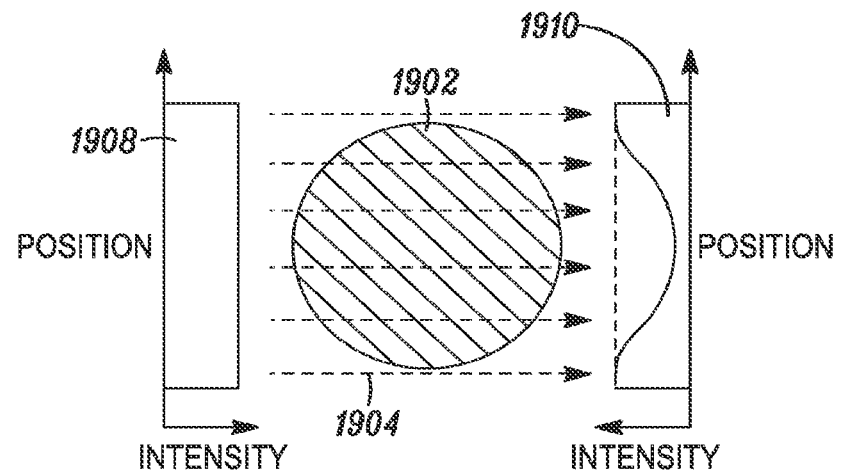
FIG. 19a shows a cross-section of a fluid stream oriented to carry cells through a measurement volume such that flow is into or out of plane of paper in this case.
Figure 19B:
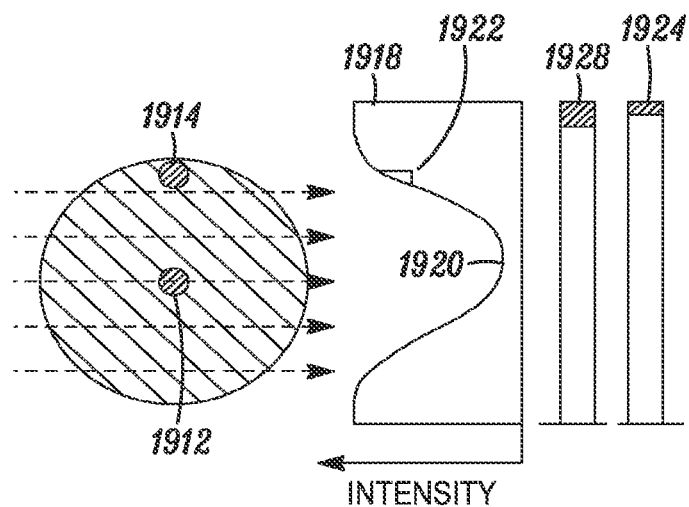
FIG. 19b shows the same configuration with two example cells in the flow.

FIG. 19b shows the same configuration with two example cells in the flow. The positions may be exaggerated for illustration, and two cells may be shown simultaneously only to show positional variation over time. One cell 1912 may be well-centered in the flow, while another 1914 is off-axis. The transmitted intensity profile 1918 shows how this positional variation results in different power levels observed by the detector. Each cell in this example may cause the same incremental fractional absorption of IR light. For the on-center cell 1912, the fractional absorption 1920 may be of a smaller total amount of power reaching the detector and therefore causes a smaller change in total power detected 1924. More mid-IR light arriving at the detector has passed through the off-axis cell 1914 and therefore the fractional absorption 1922 may have a larger effect on total power change 1928.

As a result of this position-dependence, depending on the position variation of cells in the flow, and on the signal ultimately being measured, it may be desirable to either minimize effect of position by design, or compensate effectively for cell position as it flows through the measurement volume.

Figure 20A:
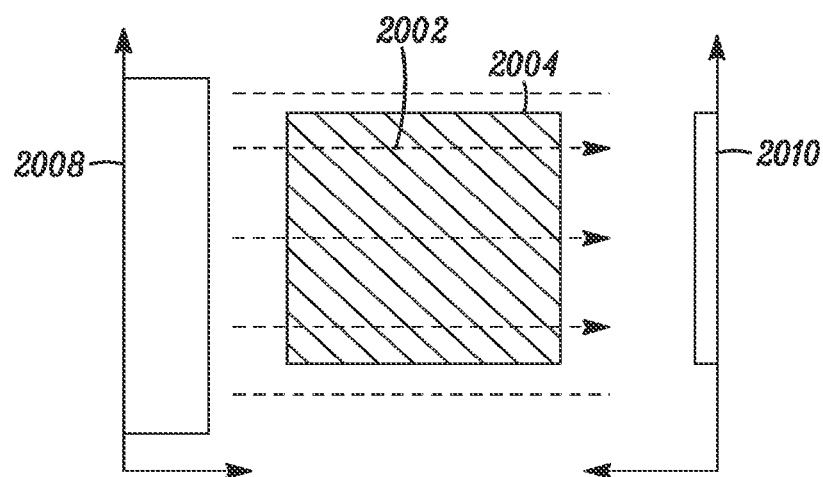
FIG. 20a illustrates one configuration of the present invention that minimizes the effect of cell position in the flow that results from water absorption.

FIG. 20a illustrates one configuration of the present invention that minimizes the effect of cell position in the flow that results from water absorption. In this case, a rectangular or square flow 2002 may be used to force equal path lengths through liquid for all parts of the mid-IR beam.

A rectangular channel 2004 may be formed in material that is transparent to mid-IR at least on the optical input and output sides. These surfaces may be antireflection (AR) coated for water to minimize stray reflections from surfaces and any resonant effects. The input beam profile 2008 may be used to illuminate the channel. In this example, the portions of the beam outside of the sampling volume may be blocked, either by material choice or by making a mask that rejects this light (which would reduce contrast ratio in the measurements). As a result, the transmitted radiation 2010 may have a very consistent power profile spatially (limited by the input beam profile and diffraction effects).

Figure 20B:
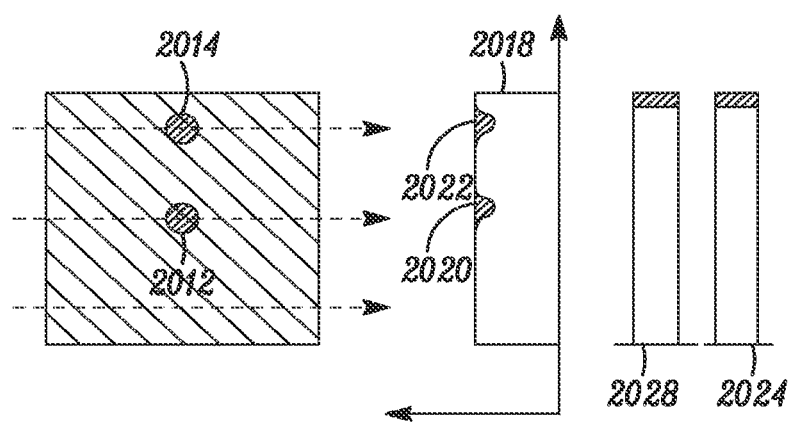
FIG. 20b illustrates the rectangular channel with two hypothetical cell positions in the measurement volume, a well-centered cell and an off-axis cell.

FIG. 20b illustrates the rectangular channel with two hypothetical cell positions in the measurement volume, a well-centered cell 2012 and an off-axis cell 2014. In this configuration, the fractional absorption caused by the cells at different positions may be of the same amount of light (same path length), as is illustrated by these absorptions 2020 and 2022 on the output intensity profile 2018. As a result the power changes 2024 and 2028 that may be detected on the detector may be the same for these positions.

A square or rectangular flow cell may be implemented in a number of ways. Such a nozzle could be drawn using standard glass-forming techniques and made out of IR-transmitting glassy materials such as chalcogenides glasses. However, probably the most proven way to build such a channel may be by building a 2- or 3-layer structure with one layer patterned to form a channel. For example, two wafers of IR-transmitting material could be AR-coated (for AR in water on one side, and air on the other), a material that may be readily patterned deposited on one of them, channels patterned into this material, and then the wafers bonded together and diced to produce multiple measurement channels suitable for the present invention. Multiple methods for forming such microfluidic channels are known in the industry and may be used to implement the present disclosure. Of course, the materials on optical input and output sides must be IR-transmissive. For example, Si, Ge, ZnSe and other materials with good mid-IR transmission may be used to form the channel that acts as the measurement volume. Optionally the material may also be chosen to transmit UV, visible or near-infrared (NIR) light in order to make other measurements of the flow and cells including scattering, such as measurement of cell presence, size, density and the like, and fluorescence, where a combination of traditional fluorescent label-based measurements and Mid-IR measurements are desired.

Figure 21:
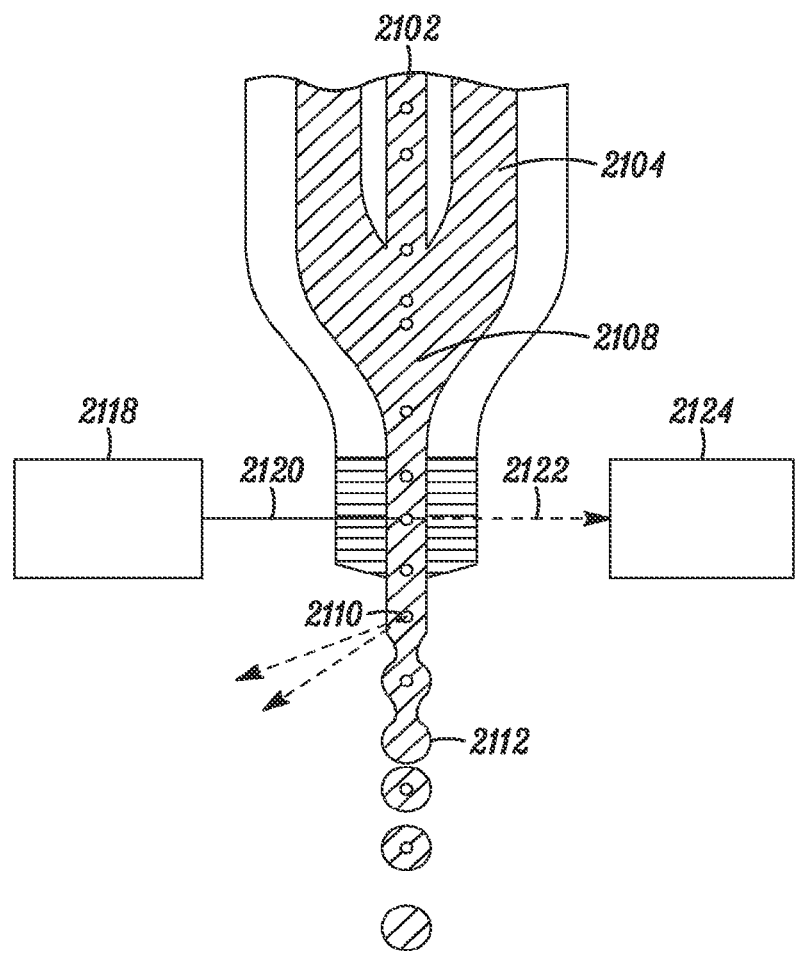
FIG. 21 shows an embodiment of the present invention implemented in a standard flow cytometry system, in this case fitted for mid-IR cell measurements based on QCLs.

FIG. 21 shows an embodiment of the present invention implemented in a standard flow cytometry system, in this case fitted for mid-IR cell measurements based on QCLs. The flow cytometric nozzle uses a sample injector 2102 to provide a steady flow of cells in a "core" flow, which is combined with a sheath flow 2104 that surrounds it and merges with it in a laminar flow, which then narrows 2108 as it reaches the measurement volume and ejection nozzle. An alternative to the core/sheath architecture that is most commonly used may be the use of acoustic focusing of the cells into the center of a single flow. In many traditional flow cytometers, the stream is interrogated using UV and visible lasers while it is a continuous flow in air 2110. In some embodiments, such lasers may also be used to measure cell properties, both through scattering and optionally through standard fluorescent labels. Due to pressure waves applied to the nozzle liquid, the stream then breaks into individual droplets 2112, which may be important for cases where cells are sorted into populations. In an embodiment, a cell sorter case, charge may be applied to the sheath fluid just before each droplet breaks off, based on the measurements that have been done on its volume and any cell it contains. However, in other embodiments, a plurality of cells could be used. Electrostatic fields are then used to guide these droplets into two or more output positions, where they may be collected or discarded. Such systems are in wide use, and well-understood by those familiar with the field of cell sorting.

In an embodiment, the present invention adds use of one or more QCLs 2118 and mid-infrared detectors 2124 to the cell measurements, for direct chemical measurements through vibrational spectroscopy. Rather than measure the flow in air, where it should be circular to facilitate smooth flow and break into droplets, the mid-IR measurement may be done in an enclosed measurement volume using a mid-IR transparent flow cell 2114. This flow cell is made of mid-IR transparent material and AR-coated in order to reduce reflection losses and artifacts (AR coated for water internally, and for air externally). The QCL-generated 2120 light may originate from one or more QCLs, each of which may be tunable at either high or low speed. Low speed tuning would be used for cytometer setup for different tasks, whereas high-speed wavelength scans tuning, for example through the use of drive current, may be used to scan over a particular absorption peak of interest. The light transmitted 2122 through the flow measurement cell and any cells contained within it may be then sent to one or more mid-IR detectors 2124. Multiple detectors may be used to enhance the speed and/or signal-to-noise ratio (SNR) of the system through the use of one detector per wavelength range that is emitted by multiple QCLs. For example, a simple system would employ two QCLs, one for the signal of interest, and one for reference level. The light from the QCLs may be combined using a dichroic thin film filter or other wavelength-dependent component, such as a grating, into a single input beam; the transmitted mid-IR light 2122 may be split using a thin film filter into two mid-IR detectors, such as MCT detectors, one measuring the signal wavelength and the other measuring the reference wavelength. An enhancement to this base system may rapidly scan one or both of these lasers of narrow ranges, allowing a local derivative and second derivative in absorption to be measured, which can greatly enhance measurement accuracy against a varying absorption baseline. The measurement cell 2114 may be fabricated with a square or rectangular cross-section to eliminate optical effects due to varying path lengths, as described hereinabove, as well as lensing and other optical effects that result from light impinging on surfaces non-perpendicularly. Both the external air-facing and internal liquid-facing surfaces may be AR-coated to reduce light loss and stray reflections, and minimize any interference effects. In this architecture and in the other architectures described herein, the present invention may be combined with traditional optical measurements using UV, visible or NIR lasers or other sources to interrogate cells in the flow. For example, fluorescent labels attached to the cells may be read using UV and/or visible lasers. The combination of traditional fluorescent label readout and mid-IR vibrational measurements may open up new possibilities for research and clinical applications. For example, fluorescent antibody labels may establish a "yes/no" measurement for a particular type of cell, and mid-IR measurements may then be used to establish quantitative measurements of biochemical concentrations of materials such as DNA, RNA and the like. Such a combined-mode measurement system may further be used to research and develop mid-IR measurement techniques that offer higher accuracy, lower cell damage and/or easier processes with better applicability to clinical or field devices than their fluorescent label equivalents.

Another example of combined modes may be the use of scattering measurements to determine cell size and shape. Screening cells by size and shape, such as to determine type of cell, may be combined with mid-IR measurements of chemical constituents to provide measurements of a particular cell population, or to provide higher accuracy measurement.

On the output side of the cytometer, there may be various options other than breaking into droplets and sorting as shown in FIG. 21. The cells and fluid may flow directly into a waste container, keeping the system closed, wherever measurement may be the objective. Where sorting may be required, but a closed system is desirable, a number of alternative sorting techniques have been developed, including mechanical sorters where two or more channels are placed into the flow.

Another technique that may be combined with the present invention to produce a closed, "all-optical" cell sorting system is photodamage cell selection. In this architecture, after measurement may have been done using mid-IR absorption measurements possibly in combination with more conventional techniques, those cells that may not be desired in the population are subjected to pulses of light, typically from a laser, sufficient in power to damage or destroy them. One example is the use of pulses of light to immobilize sperm cells with laser pulses in the 1000-2000 nm range and therefore prevent them from fertilizing an egg, without damaging DNA. In other cases, destruction of the cell membrane using a laser pulse may be used to remove the cell from a population. Other non-optical techniques such as acoustic, mechanical, and RF have also been described and may be used in embodiments of the present disclosure.

Figure 22:
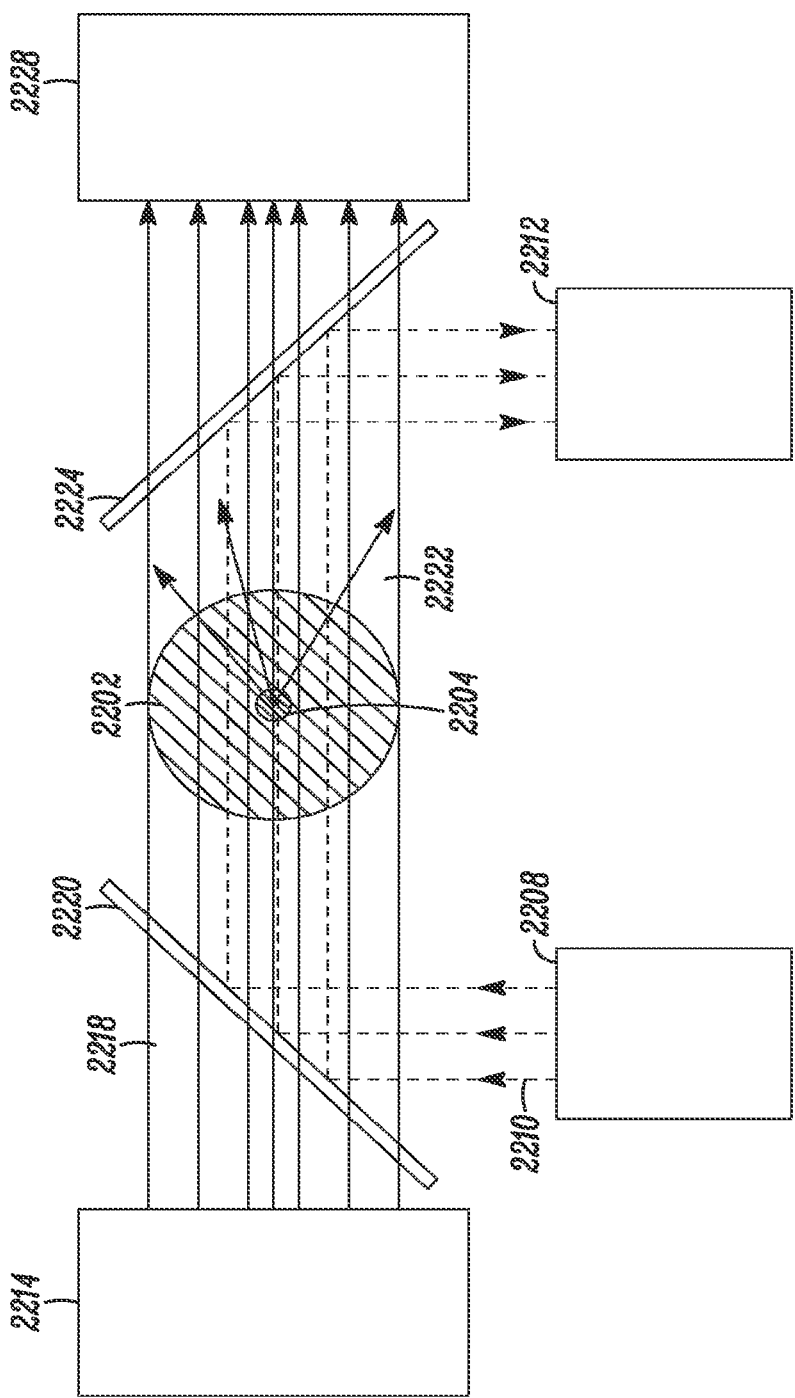
FIG. 22 shows the present invention embodied in an architecture that allows cell position in a flow to be measured accurately, in order to compensate for position-dependent variations in mid-IR absorption signal.

FIG. 22 shows the present disclosure embodied in an architecture that allows cell position in a flow to be measured accurately, in order to compensate for position-dependent variations in mid-IR absorption signal. The flow 2202 directed in or out of the plane of the page contains cells 2204 to be measured using mid-IR light 2210 from one or more QCLs 2208, the transmitted portion of which may be measured by one or more mid-IR detectors 2212. In some embodiments, the mid-IR beam is combined with one or more visible/NIR beams 2218, from light source(s) 2214 which may be used to accurately determine cell position and, potentially, size and shape. Dichroic filters 2220 and 2222 may be used to combine and separate, respectively, the visible/NIR and mid-IR beams. When the visible/NIR light strikes the cell 2204, it may be partially scattered. This scattering is detected by visible/NIR detector(s) 2228. This configuration shows only forward scatter detectors, detectors may be used at other angles to measure wider-angle scattering. If an array of light sources and/or detectors is used, they may be placed in a manner as to enhance the accuracy of the position measurement, for example, they may be placed in a diagonal line across the flow in order to add a time component to the measurement, as cells flow by the light sources/detectors.

The ability to accurately determine cell position in this manner may allow the mid-IR absorption signal to be compensated for cell position. In some embodiments, if the flow 2202 is circular in cross-section and the cell 2204 is displaced from the center, the fact that more mid-IR light signal is originating from the path containing the cell relative to when the cell is centered in the flow may be used to compensate the apparent absorption signal. In addition, visible/NIR sensors may be used to monitor the position and shape of the overall flow relative to the mid-IR laser light path. The flow itself lenses the visible/NIR light based on its position, diameter, and shape.

In all of the embodiments in this invention, it may be useful to compare mid-IR transmission signals before and after cells pass through the measurement volume with measurements during cell residence in the volume. This may give a baseline that may show the water absorption effect that may be very strong in the mid-IR.

Figure 23A:
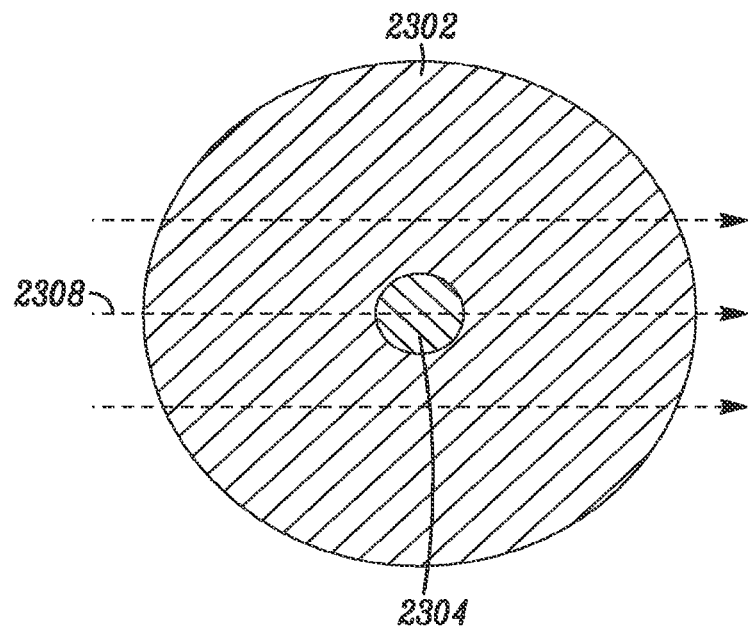
FIG. 23a shows a sheath flow surrounding the core flow being illuminated using mid-IR light from QCL(s).
Figure 23B:
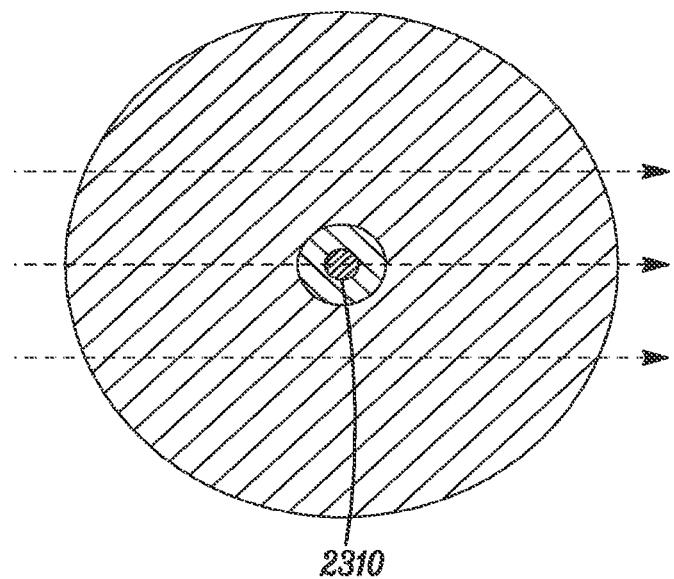
FIG. 23b shows the same flow with a cell in the measurement volume.

FIGS. 23a and 23b show an embodiment of the present invention that may use additives to the core or sheath fluid in a flow to create a "tracer" which may be measured directly by the mid-IR subsystem, and therefore allows accurate real-time calibration/compensation for core flow position, and variations in flow shape and position.

FIG. 23a shows a sheath flow 2302 surrounding the core flow 2304 being illuminated using mid-IR light 2308 from QCL(s). In this example, a tracer may be added to the core flow at a known concentration. The tracer may be selected to absorb at the wavelength of one of the QCL sources in the system. If the core flow diameter may be controlled accurately, such as through accurate core/sheath pressure control, its absorption may then be used to track mid-IR absorption effects, such as water absorption, on the core flow-related signal by using readings before and after cells pass through the measurement volume.

FIG. 23b shows the same flow with a cell 2310 in the measurement volume. In an embodiment, a configuration of this system may employ at least 2 QCLs, or 1 QCL that may rapidly tune over an absorption peak shared by the tracer and the target cell component. The method to determine concentration of the target compound in the cell may be then to measure the absorption at the target mid-IR wavelength relative to water absorption without (FIG. 23a) and with (FIG. 23b) the cell present. This may give a signal relative to a known concentration, with flow-position-related factors removed.

Figure 24:
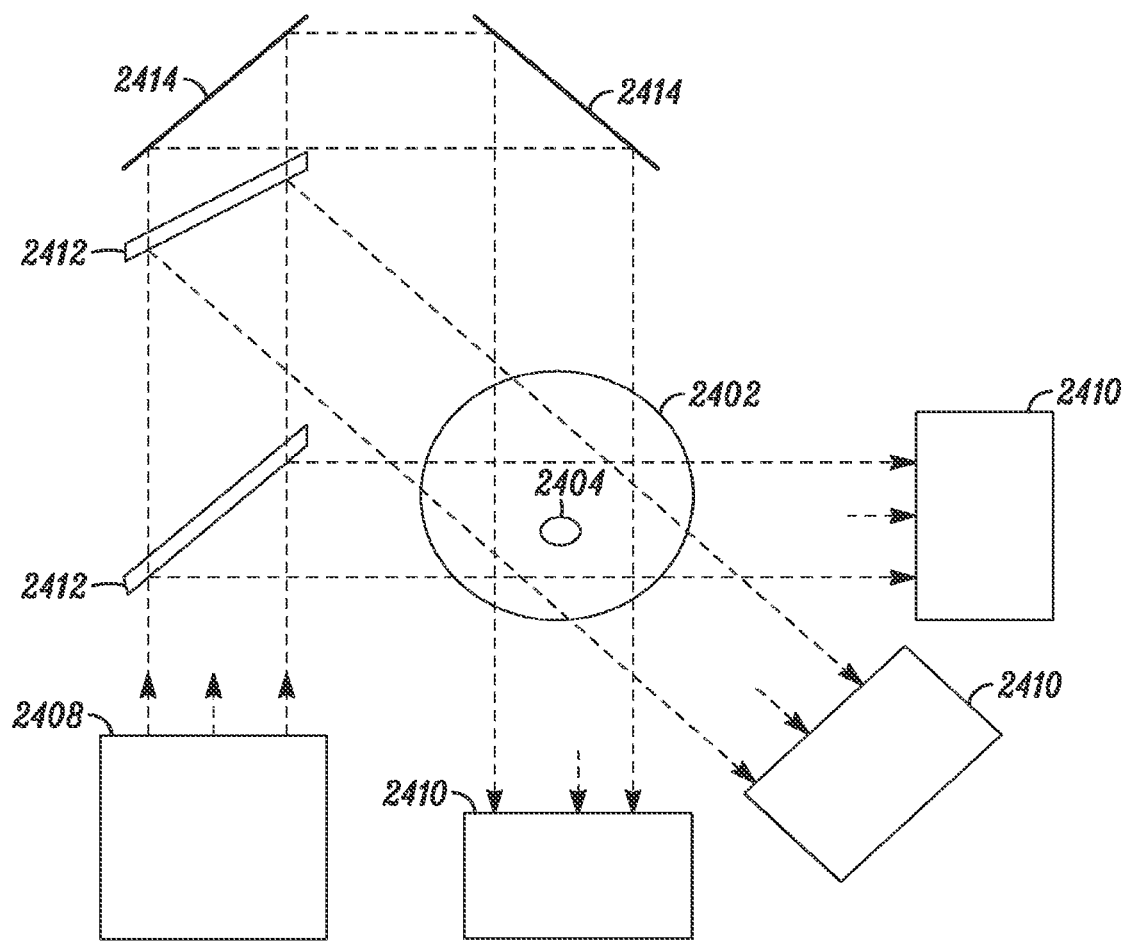
FIG. 24 depicts another embodiment of the present invention in which multiple mid-IR beams may be used to interrogate the measurement volume.

FIG. 24 depicts another embodiment of the present invention in which multiple mid-IR beams may be used to interrogate the measurement volume. The use of multiple beams allows the position as well as the absorption of a cell 2404 to be measured more accurately, akin to computed tomography methods used in medical imaging. One or more QCLs 2408 emit mid-IR light that may then split into three beams by partially-reflecting mirrors 2412. These beams, with the help of fully-reflective mirrors 2414 may be then directed at 3 different angles through the flow 2402, which flows in or out of the plane of the page, and any cells contained within it 2404. The beams may then detect using three mid-IR detectors 2410. Measurements made before or after a cell may pass through the measurement volume in this example may be used to normalize the measurement, as they reflect the position and shape of the water flow. Measurements of the cell made as it passes through the volume may be from three angles. Using three measurements, plus the measurements of the flow without the cell present, it may be possible to determine both position and absorption of the cell within the flow according to algorithms well known in computed tomography.

In an embodiment, the system may be embodied as a microfluidic chip. An example of operation of the chip may include procuring a sample of cells in suspension from patient or culture, with any necessary protocol to individuate cells in the suspension; placing the entire sample into an input port of a one-time-use plastic carrier; and placing the sample carrier into a tool. Then, a cassette of microfluidic measurement/sort chips may be inserted into the tool. Multiple chips may be used for a single sample in the case of clogging or degradation. Chips may be built from materials that are optically compatible with the spectral cell measurement being performed. In the case of mid-infrared (QCL) based measurement, the chip may be made of mid-IR transparent materials including but not limited to Si, Ge, ZnSe, CaF2, BaF2 or salts with protective coatings. Chips may have coatings that protect them from fluid, are hydrophilic (to promote flow of liquid through measurement channel) and provide anti-reflective (AR) functionality. AR coatings may be applied to external surfaces to minimize reflections, and to the top and bottom of microfluidic channels in the measurement zone in order to prevent reflections, maximize signal, and minimize resonant optical effects (in this case the AR coatings are designed to minimize reflection at the interface with water). These internal (channel surface) AR coatings are particularly important where a high-index material is used to construct the chip, in which case a resonant optical field could be created within the channel; this would lead to a situation where optical field intensity, and therefore interaction with biochemical components of a cell being measured, would be dependent on the vertical position of the cell within the channel, introducing variability that may not be acceptable. This may be remedied with appropriate optical coatings that minimize reflections at these interfaces, and therefore minimize these resonance-created variations. Chips may be pre-loaded with liquid in the input and output volumes, as well as the measurement channel, to eliminate issues with starting fluid flow through the measurement volume. Chips may include sealing layers/tapes on the input and output reservoirs to maintain sterility, and prevent evaporation of priming liquid; the fluid in the input volume may be pre-seeded with particles used for calibration of the chip. Chips may be charged with additional liquid which is used to create a "sheath" flow around the core flow containing the cells; this same fluid may be used to apply pressure to the system and maintain flow of cells through the measurement volume.

Known microfluidic configurations for creating 2D or 3D sheath/core flows may be used. Sheath/pump fluid may be sealed in wells on the chip that are opened for the purpose of pumping, or may reside below flexible membranes that can be addressed with an external pressure source, thereby maintaining fluid isolation.

The tool opens the input chamber of a chip, positions the chip onto the sample carrier, and moves a specific volume of sample onto the chip input reservoir; the system may be configured to provide continuous flow from the sample carrier to the chip, or charge the chip in specific increments, either one-time or in multiple batches. One potential architecture opens a tape on input reservoir of the microfluidic chip, loads a small volume of the cell sample, re-seals the tape, and then moves the chip to the optical measurement system, where it remains sealed until the sample has been analyzed/sorted or until the chip clogs; then moves the chip back to the carrier, unseals the output reservoir, and transfers the sorted sample to the output reservoir of the carrier; the chip is then disposed of (in the case where it is a measurement only, the chip may be disposed of directly, without the transfer to carrier step).

At startup on a specific sample, the tool runs a small but statistically significant sample of cells through the measurement channel of the chip, and into the non-selected (disposed) output reservoir. Each cell is measured using the vibrational spectroscopy system described herein. For example, it is probed at three wavelengths corresponding to DNA absorption, absorption of an interfering substance (which also absorbs at the DNA absorption wavelength; as an example certain proteins), and a third reference wavelength (to measure general absorption level due to water and other wide spectral features, for example). From these three measurements, a single DNA content number is calculated. The system also measures average throughput rate of cells.

A histogram of cell counts vs. DNA content is generated and displayed to the user. This gives the user an immediate sense for the distribution of DNA content in cells, and whether there are distinguishable populations. It may give the user an immediate sense, for example, of whether a population of cells is multiplying (at this point some cells have twice the normal amount of DNA). Optionally, the tool may "fit" Gaussian or other distribution curves to the observed population. These curves may be application-specific (where a certain distribution of DNA content is assumed). Such curves serve to calculate expected purity in a sort of the cell population by DNA content.

The user may then select, through the user interface of the tool (which may be either on a built-in control panel, or on an attached devices such as a personal computer, laptop computer, tablet, smartphone, etc) at least two parameters of a sort, in the case where a sort is to be performed The range of DNA contents to select for in the "selected" output sample and the number of cells required in the output sample.

With respect to the range of DNA contents to select for in the "selected" output sample, this could correspond, depending on the application, to significant cell populations including but not limited to: cells with X or Y chromosomes, where gender selection is being performed; cells with an abnormal number of chromosomes, where cancer cells are being separated from a sample; cells that are in the process of dividing, where a cell study is being performed which involves looking at viability or growth rates (the inverse-those that are not dividing, may also be selected for); DNA content-based sorting may also be used in the process of separating differentiated from undifferentiated cells in stem cell related processes. If curves have been fitted to the populations, the tool will indicate the expected purity of the resulting sample as the user moves the selection "window." It will also adjust the expected sort time for a desired number of cells in the output.

With respect to the number of cells required in the output sample, the user may adjust this number, up to a limit set by the expected number of cells in the total sample, or by a maximum sort time.

The user then initiates the sort. In the case of pure measurement, rather than sort, the preceding steps are modified accordingly—the number of cells to be measured are selected; optionally the number of cells sorted may be set by requiring a certain sample size within a specific DNA content window, in order to obtain a statistically significant sample size.

The tool then initiates the sort. Cells are flowed through the measurement channel on the specialized optical chip, at a rate and dilution that allows sufficient measurement time in the optical measurement volume, and allows them to be accurately sorted with the on-chip sorting mechanism. For example the following steps may be performed by the system based on mid-Infrared quantum cascade lasers measuring mid-IR vibrational absorption features in the cells of interest.

Prior to a cell entering the measurement volume, the system continuously measures the absorption of the (for example) three mid-IR wavelengths being used; the signals are generated by three QCLs that are modulated in a manner such that their signals may be separated after detection by a single detector, such as a thermoelectrically (TE)-cooled mercury cadmium telluride (MCT) photodetector. The signals observed at the detector before (and after) the cell passes through the volume are used as a baseline for the measurement, in order to cancel out, in large part, slow-speed variations in the system, including variations in relative laser power, changes in background absorption in the flow channel, and slow-speed changes in optical effects in the system and chip (for example, mechanical changes or index of refraction changes due to temperature). Modulations applied to these lasers may be of various types. Pulsed modes may be used to generate short, distinct peaks, where individual wavelengths are pulsed in rapid succession. In continuous wave (CW) operation, the lasers may be modulated with specific carrier frequencies that may then be separated using analog or digital filters at the detector. Aside from power level modulation, the lasers may be modulated in terms of wavelength. For example, wavelength may "chirp" as lasers are pulsed or modulated, because of current and temperature effects. This may effectively broaden the range of wavelengths at which absorption is measured. This "averaging" effect may be beneficial since absorption features in liquid phase are typically quite broad. External wavelength-modulation components may be used within the QCLs to more broadly sweep wavelength. For example, external cavity Fabry-Perot configurations may be used with wavelength-setting elements such as diffraction gratings or tunable etalons. In one case, very rapid tuning over a broad range could enable measurement of both baseline ("valley" in the absorption spectrum) and signal ("peak" in spectrum) using a single laser for a particular analyte. Center wavelength of the QCLs (or slave lasers, in the case of a CARS system), which may be set using external tuning mechanisms or simply operating temperature (effected by a TE cooler on which the QCL is mounted) may be set to match the absorption peaks (or valleys) observed in the cell sample. This process is performed during the setup of the system, and may be repeated at specific intervals (during which all cells are sent to the "discard" output), or when the system senses recalibration is required. This process may be performed by sweeping the wavelength slowly as cells are measured, accumulating a distribution of signal points vs. wavelength, and then determining where the minimum or maximum signal occurred, and using this as the wavelength set point.

As a cell enters the measurement volume, it is detected using a visible/NR/SWIR beam that is scattered by the cellular material. This beam is separate from the mid-IR beam and is used to detect cell presence, flow speed (along with other sensors, possibly), and unusual scattering signatures that could signal cell agglomerates. The "presence" signal generated by this beam may also be used to trigger integration of the mid-IR signals measured by the system. In the case where the system is built with mid-IR lasers, the material of the chip must primarily be transparent to mid-IR wavelengths. Some materials options such as silicon are transparent in much of the mid-IR, but not transparent in the visible regime. In this case, a SWIR laser (1.5 microns, for example) and detector combination—such as those developed for telecom applications—may be used to measure this cell presence and scattering. Cell presence and scattering may be measured in transmission, reflection, or both.

Within the measurement volume, mid-IR light is transmitted through the cell, where it is absorbed according to its wavelengths and the chemical constituents (chemical bonds) within the cell. For example, where three wavelengths are used to make an accurate DNA measurement: There may be a rise in the signal (i.e. lower absorption of) corresponding to the background, which is dominated by water, because other materials making up the cell, such as proteins, lipids, and DNA displace water; when adjusted for this change in background, a signal corresponding to proteins will show higher absorption; and when adjusted for the change in background, and after subtracting a known interference from protein (calculated by the previous measurement), the DNA absorption signature rises.

The measurements may be integrated over the time that the cell resides within the measurement volume, and the integrated signals may be used to quantify cellular DNA. Other quantities (such as protein content, or cell size based on scattering) may also be measured, and may optionally be presented to characterize the cell sample, or refine sort parameters. Combinations of DNA and protein content, DNA and lipid content, and other 2-axis or multi-axis analyses and sorts may be performed by appropriate extensions of the present invention, using appropriate measurement wavelengths for specific molecular bond vibrations.

Based on the measurement and the setpoint(s) for sorting (when performing a sort), a decision is made either to allow the cell to proceed to the "discard" output reservoir of the chip, or be diverted to the "collection" output reservoir. The microfluidic channels may be configured so as to make the default route to the "discard" reservoir, and only when the switch is actuated will cells be able to reach the "collection" or "select" reservoir.

At a time interval after measurement, determined by the flow velocity in the channel, a microfluidic switch may be actuated in order to push the cell into the appropriate output channel. At the position of this switch, or somewhere along the microfluidic channel preceding it, there may be another measurement point illuminated by visible/NIR/SWIR light where cell presence is measured by scattering. This allows realtime measurement of flow/cell velocity in the channel, and allows the system to recalibrate timing of fluidic switch activation.

The cell, which may have had its position in the flow laterally perturbed, is then routed into one of two or more output channels based on the switch action. There may be additional optical measurement points in these output channels; these serve primarily that the switch actuation is functional and timing is correct, and observe any sorting errors that occur. Should errors occur, the system may adjust timing or magnitude of switch actuation, or simply discard the current chip and use a new chip.

Cells are accumulated in at least two output reservoirs, the "discard" reservoir and the "select" reservoir.

The tool may detect one of a number of problem/failure conditions during the sort, including but not limited to: sample out, or front-end clogging, flow rate variation, switching failure and cell density variation.

With respect to sample out, or front-end clogging, no additional cells appearing in the measurement channel may signal that the input sample on the chip has been exhausted, or that the input of the channel is clogged. The system may: Perform anti-clogging procedures, which could include rapid pressure pulses on the input or back flushing of the system and/or move to unload and discard the current chip, and load a new one to match up to the sample carrier.

With respect to flow rate variation, through the use of optical measurement points, the system may detect that the sample flow rate is out of bounds. In this case, the system regulates the pressure in the system to adjust the speed of cells in the measurement channel. The flow rate may be estimated from a single sensor at the measurement point (by measuring how long the cell is present in the beam) or by 2 or more optical sensors along the measurement channel (by measuring time a cell takes to travel between points). If the cell speed is out of bounds-which may cause DNA measurement SNR problems, or switching inaccuracy problems, the system may send all cells to the default "discard" reservoir until the speed is properly regulated.

With respect to switching failure, through the use of optical measurement points on the output channels, the system may detect that cells are improperly switched to one of the output channels. In such a case, the system may be paused immediately (if a very high purity sort is being performed). Switch timing relative to measurement may be adjusted, as well as magnitude of signal being used on the cell switch mechanism.

With respect to cell density variation, the system may detect that cells are arriving with spacing that is either too dense—not allowing cells to be switched reliably—or too sparse—prolonging the sort operation for a given number of cells. The system may have provisions for adjusting this density (such as dilution or concentration steps), or it may simply update the user as to the change in anticipated purity or sort time. Dilution of cells may be performed during the transfer of sample from the sample carrier to the measurement chip, if this is the case, dilution may be adjusted from chip to chip until an optimum is found. If dilution is far off, a chip may be discarded, and another loaded onto the sample carrier.

When the sample loaded into a particular chip has been sorted completely, the chip's "select" output reservoir is opened by the system, and its contents are transferred to the output reservoir of the sample carrier. This may be done with a liquid purge run through the chip or pipette action.

Once the chip's reservoir has been emptied, it is sealed, removed from the carrier, and discarded, potentially into a sealed compartment attached to the disposable sample carrier.

This process continues until the sort is complete. At this point, the user is signaled, and the sample carrier is prepared for unloading. The sample carrier is removed from the tool, with the sorted sample ready for use in the output reservoir. The sorted sample may subsequently be removed by pipette or other method and used in subsequent lab or clinical procedures.

Figure 25A:
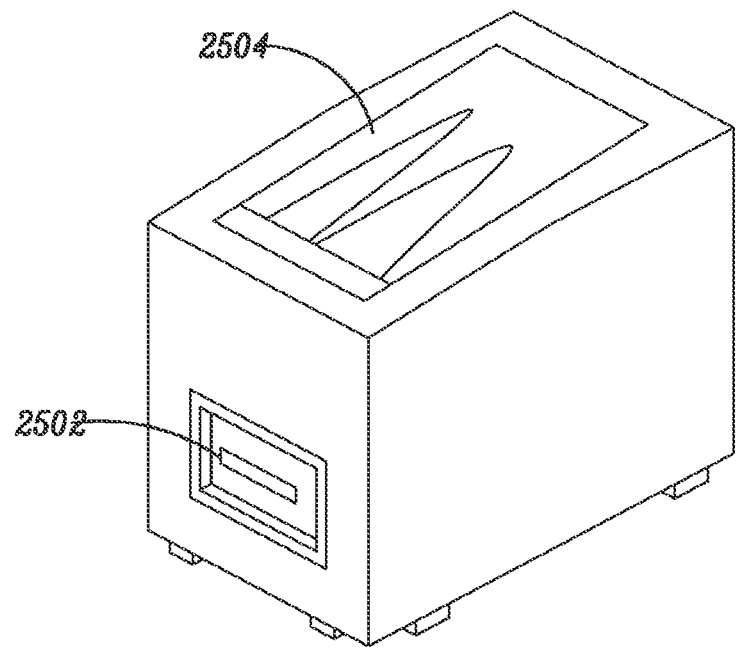
FIG. 25a shows a tool that may accept microfluidic chips that may be pre-loaded by user with the cell sample to be measured and/or sorted.
Figure 25B:
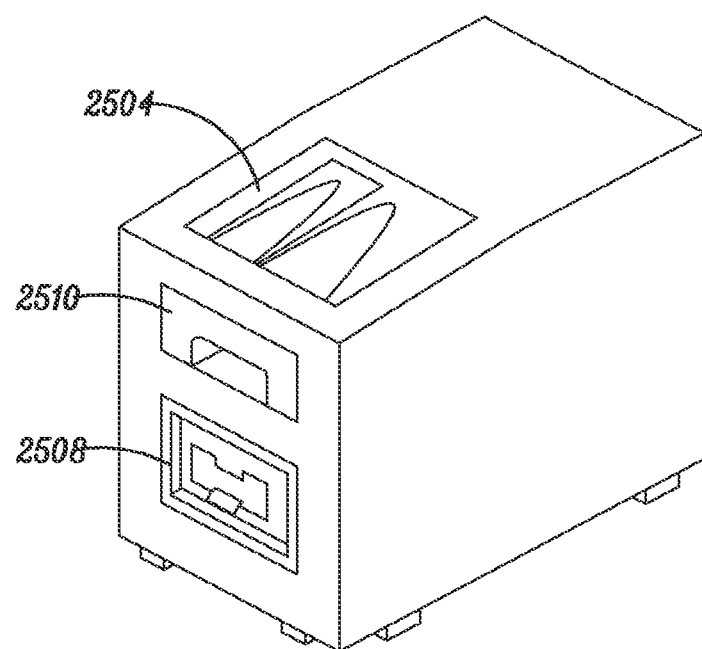
FIG. 25b shows another configuration of the tool described herein.

FIGS. 25a and 25b show two example configurations of the microfluidic chip system. FIG. 25a shows a tool that may accept microfluidic chips that may be pre-loaded by a user with the cell sample to be measured and/or sorted. This may be generally a configuration for relatively small-volume samples that may be contained on and sorted with a single microfluidic chip. A slot 2502 may accept the chip into the measurement/sorting system. A display 2504 shows histograms and other indicators regarding cellular DNA content. The display may be a touchscreen display that may allows the user to make sort set points, set the graphical display of data, and start and stop operation. The tool may include other interfaces, such as a USB interface to allow transfer of data to (or control by) a computer, or transfer or backup of data onto a USB memory stick. Wireless networking interfaces may be included as well.

FIG. 25b shows another configuration of the tool described herein. Again, a display 2504 may allow the user to make setpoints and review data from the cell measurements and/or sort. In this configuration, however, the cell sample may be loaded onto a larger carrier into the sample slot 2508. Separately, a cassette of measurement chips, one or more of which may be used to sort/measure a single sample loaded in a carrier, may be inserted into chip cassette storage 2510. In this manner, multiple chips may be used, if needed, to sort a single larger sample loaded into the machine.

Figure 26A:
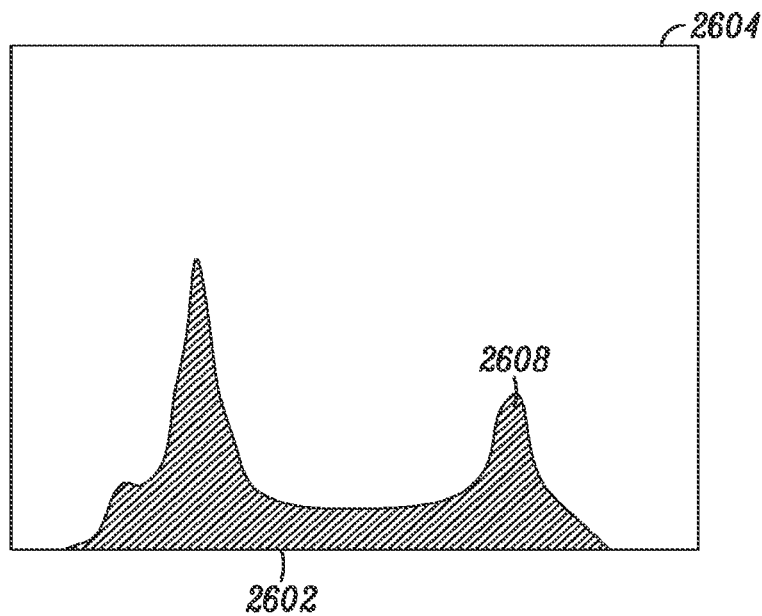
FIGS. 26a and 26b show example displays of DNA content shown to the user of the tool.
Figure 26B:
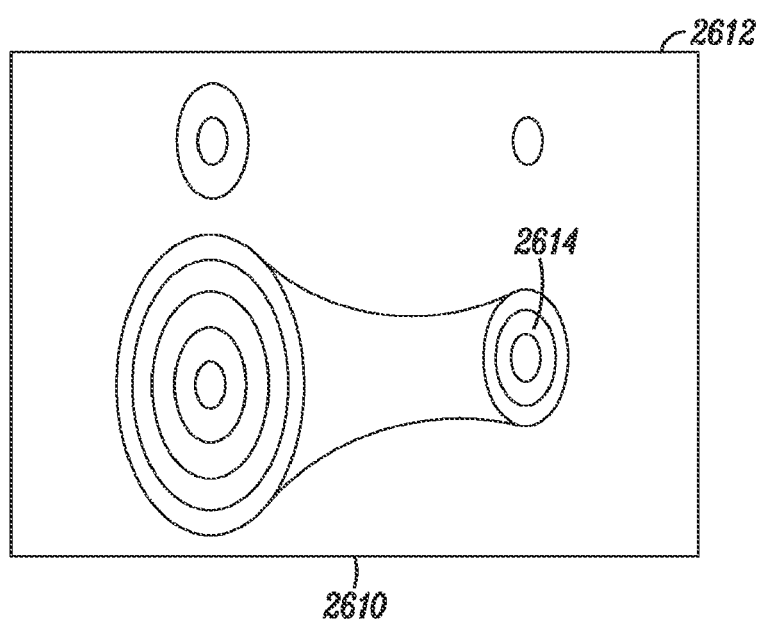

FIGS. 26a and 26b show example displays of DNA content shown to the user of the tool. FIG. 26a shows a configuration where DNA vs. cell count may be displayed in a histogram format. The x-axis 2602 in this example may represent the DNA content of the cell. The y-axis 2604 represents the cumulative cell count in the sample. The distribution of cells measured may be indicated by 2608 (here showing a distribution representative of cells that are actively dividing, and with some number of cells showing an abnormally low DNA count which could indicate aneuploidy indicated by the small peak to the very left). This histogram in itself may be valuable to the user for a rapid assessment of the cell sample. In addition, curve-fitting algorithms may be applied manually or automatically, either in real time or offline after the measurement to estimate the percentage of cells in each state.

FIG. 26b shows a configuration where an additional parameter besides DNA may be used to classify cells. In this case, the x-axis 2610 again represents the cellular DNA content. The y-axis 2612, however, represents another parameter measured by the system. Examples of this parameter may include, but are not limited to, secondary vibrational spectral measurement of the cell using the same technique but different wavelengths to determine for example, protein content, lipid content, sugar content, RNA content. Examples of this parameter may also include visible/NIR/SWIR light scattering from the cell, possibly indicating size and/or morphology. Examples of this parameter may include shape, size and density parameters calculated from imagery of the cell in visible/NIR/SWIR wavelengths. Examples of this parameter may include fluorescence signal from dyes or labels, such labels could include but are not limited to dye for assessing cell viability through membrane integrity, membrane-staining dye to measure overall membrane, antibodies attaching to specific cell types, and the like. Examples of this parameter may include quantum dot and other labels which function in a similar manner to fluorescent labels, though readout method is different. Examples of this parameter may include multiple other cell measurement methods known to those in the field. It should be noted that this is not restricted to one additional parameter. Multi-dimensional cell classification may be supported by the present disclosure.

The density plot 2614 shows the cumulative density of cell counts in the sample. This may be represented by a simple scatter (dot) plot, and supplemented with color or iso density lines to indicate statistical density. In this example, there are two levels of DNA (for example a dividing population of cells), and then two levels along the other parameter. For example, if the other parameter here measured membrane lipids as measured by a secondary vibrational signature, the plot may indicate that there are two sizes of cell or cell agglomerates where two cells are adhered to one another while passing through the measurement volume (and therefore should be rejected from the data, or sorted out of the sample).

Figure 27:
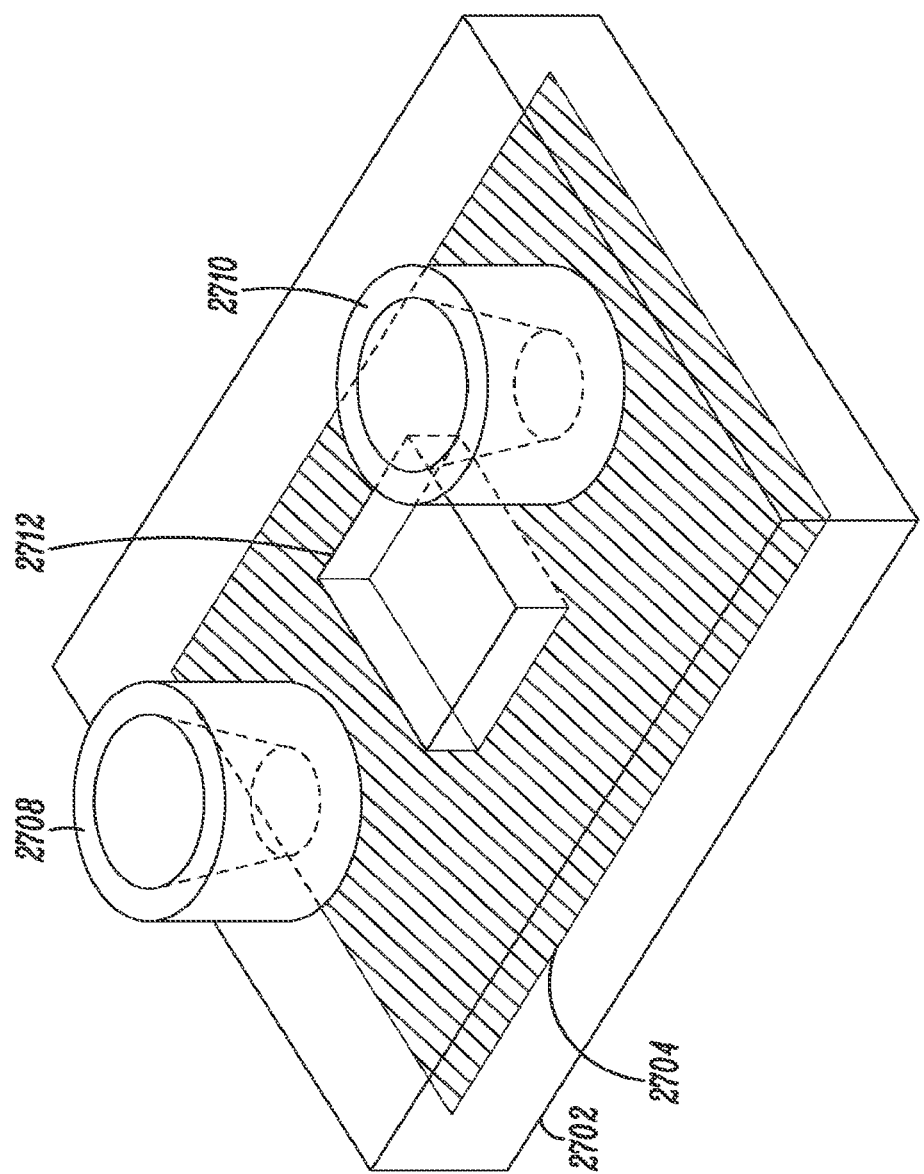
FIG. 27 shows an example of a single-unit disposable measurement unit, consisting of a microfluidic chip with plastic carrier that may be used in a system.

FIG. 27 shows an example of a single-unit disposable measurement unit, consisting of a microfluidic chip 2704 with plastic carrier 2702 that may be used in a system such as the one shown in FIG. 27. The microfluidic chip may be embedded in a plastic carrier, including input port/reservoir 2708 and output port/reservoir 2710. For measurement-only applications, the output port may be optional—the sample in this case would be disposed with the carrier. Likewise, in sort applications, a single output port (the configuration shown here) may be applicable if the rejected cells are disposed of together with the carrier. The input port 2708 may be a well into which a cell sample is pipetted, alternatively it could take the form of a pipette head itself, so that it may be used to draw a sample out of a well.

Where the optical measurement of the cells is made along the microfluidic channel, a window 2712 may be formed in the plastic carrier. This eliminates the effect of the plastic on optical transmission and provides a clear optical port. This is critical in particular in the infrared, where plastic may have very low transmission. For example, the microfluidic chip may be manufactured of Silicon or Germanium, which may be transmissive in portions of the mid-infrared, and antireflection (AR) coated to minimize losses and fringe effects.

The carrier 2702 may be charged with the sample in the input port 2708, and then inserted into the tool. In an embodiment, tubes to control pressure could then be matched to the input port 2708 and output port 2710 in order to control the pressure differential and therefore the sample flow rate through the measurement channel. The plastic carrier may have features to provide rapid rough alignment within the system. Alignment of the chip with the optical readout system may further be refined by passive or active means. For example, the microfluidic chip may have photolithographically-defined mechanical features which allows passive alignment of the chip with the optical readout system, the microfluidic chip may have photolithographically-defined features which may be optically interrogated in order to actively align the chip to the optics or the optics to the chip, or the optical system may perform a "search" in which it uses the inherent absorption signals of the measurement channel, the water in the channel, and any cells flowing through the channel in order to optimize focusing and x-y position of the beam relative to the channel.

After the measurement or sort is performed, the carrier may be ejected from the tool. If this is a measurement-only process and tool, the carrier may be rejected directly into a built-in disposal bin appropriate for biohazardous samples. If the tool is being used for a sort process, the carrier may be ejected or placed in an output bin for the user to remove. The user may then remove the sorted sample from the output port/reservoir 2710 and proceed with the appropriate protocol.

Figure 28:
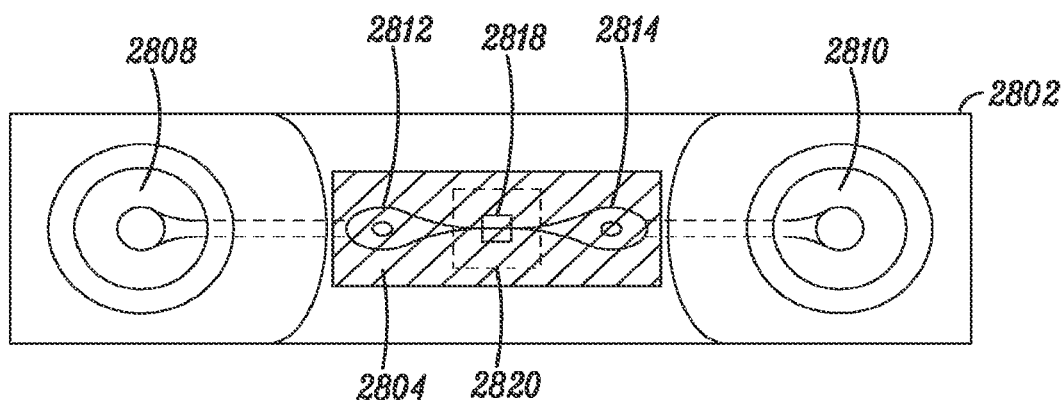
FIG. 28 shows an alternative configuration, where a potentially plastic carrier may be used together with one or more microfluidic chips, where the chip may be a separate piece from the carrier.

FIG. 28 shows an alternative configuration, where a carrier 2802 may be used together with one or more microfluidic chips 2804, where the chip may be a separate piece from the carrier. This enables the use of multiple microfluidic devices for a single larger sample, where clogging or other chip problems are an issue, where precise calibration of dilution is an issue, or where it may be desirable to run multiple measurements on multiple chips in parallel. In this case, multiple chips may be loaded with sample from the carrier, and run in parallel.

The carrier may have an input reservoir 2808 and zero or more output reservoirs 2810. In this case where DNA measurements are done, there may be no accessible output ports, and the sample is discarded with the carrier. One or more output ports may be used in cases where a sort is performed. This example shows a single-output carrier used for measurement applications (the sample is available to the user after measurement).

A microfluidic chip 2804 may be matched up to the carrier, as shown, and a portion of sample may be pushed from the input reservoir of the carrier 2808 to the input port of the chip 2812. The carrier may have compliant gaskets to allow efficient matching with the chip, and a good seal around the transfer locations. In this example, the measurement is then done in place (on top of the carrier). A pressure differential may be applied directly to the carrier ports to transport liquid sample containing cells through the measurement channel on the chip. The sample may flow through the measurement volume 2818 where it is interrogated using the vibrational spectroscopy system. A window 2820 in the plastic carrier may be provided for clear optical access to the chip microfluidic channel. Following measurement, the sample may be pushed/pulled through the chip output port 2814 and into the carrier output reservoir 2810.

If clogging or other problems associated with the microfluidic chip may be detected, the microfluidic chip may be removed and disposed of, and a new chip is matched to the carrier. This disposal may be done at a regular interval to preempt clogging or other issues, and/or to effectively charge a "fee" per incremental sample measured or sorted. In an embodiment, the carrier may include a disposal chamber for the microfluidic chips, so that the system remains as closed as possible, and consumables may be disposed of after each sample run. Similarly, the microfluidic chips may be included in the carrier itself, and removed from an internal magazine in the carrier as needed. In this configuration, all consumables related to the process are delivered in a single carrier or cartridge.

Figure 29A:
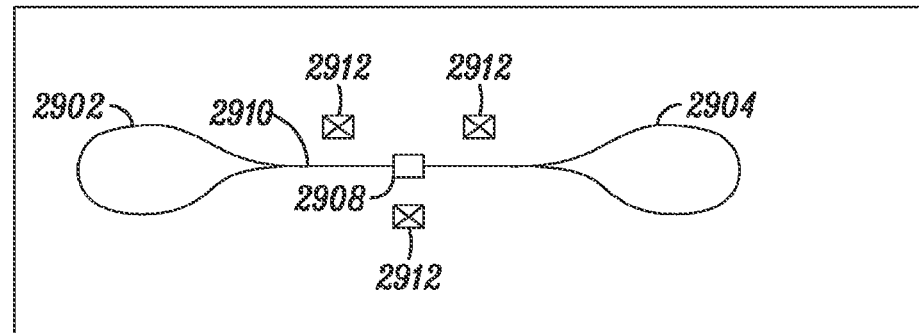
FIGS. 29a and 29b show some example formats for microfluidic chips that may be used in the present invention.
Figure 29B:
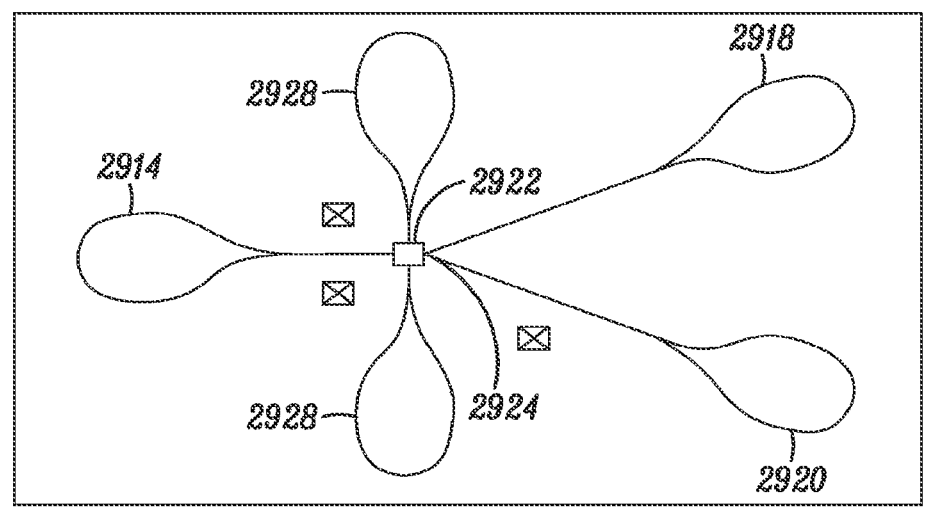

FIGS. 29a and 29b show some example formats for microfluidic chips that may be used in the present invention.

FIG. 29a shows a chip that could be used in a measurement-only application. An input port 2902 may be used to introduce the liquid sample with cells. A microfluidic channel 2910 transports this sample through the measurement volume 2908 to the output port 2904. Features may be built into the chip to prevent clogging at the entrance to the channel from the input port. Features in this region, and within the channel itself, may also be used to orient the cells in a specific manner, such as to prevent clogging, or to promote better measurement. For example, a pattern of posts of specific size and shape may be used to break up agglomerates of cells, or to block large agglomerations of cells or other substances from reaching the channel. Certain configurations of posts may in fact be used to pre-select cells of a certain size for measurement in the channel.

The chip may have photolithographically-defined mechanical or optical features which assist in aligning the chip to the optical interrogation system. For example, an etch process which may be aligned photolithgraphically to the measurement channel (possibly the same etch process step as the one used to create the input and output ports), may be used to create features for passive alignment of the chip to the optical system. Alternatively, these may be optical features (reflective metal, or windows in a metal film) that allow the system to actively align the chip to the optics. Fine alignment may be done with features in the measurement volume itself, using the optical system itself to optimally align for measurement.

FIG. 29b shows a similar chip, this one for use in sorting cells. A sample may be introduced into the input port 2914 and flows through a microfluidic channel through the measurement volume 2922 and microfluidic cell 2924 switch and then into the output ports 2918 and 2920. After measurement in the volume, DNA and other parameters for an individual cell may be calculated. Based on these measurements, and sorting parameters entered into the system, the cell may be routed either to the "discard" port or "select" port. Routing may be performed using a microfluidic switch configuration well known to those working in microfluidics, two pressure ports 2928 may be used to shift the flow in the channel to one side, causing cells to move into one branch or another of the output junction, the mechanism is described in more detail in FIG. 32 below. There may be an asymmetric configuration such as the one shown in FIG. 29b where it is important to maintain purity in the select output 2918. Thereby, in some embodiments, a "default" route is to the discard output 2920, and only when an actuation is performed are cells routed to 2918.

Figure 30A:
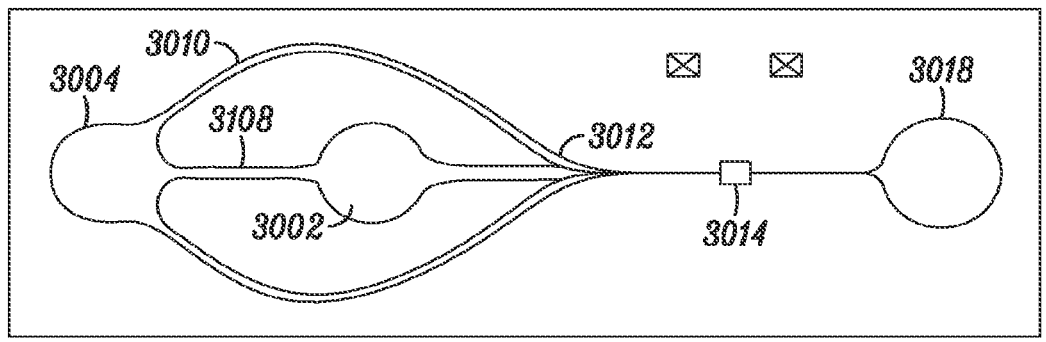
FIGS. 30a and 30b show additional example configurations of microfluidic chips for use in the present invention.
Figure 30B:
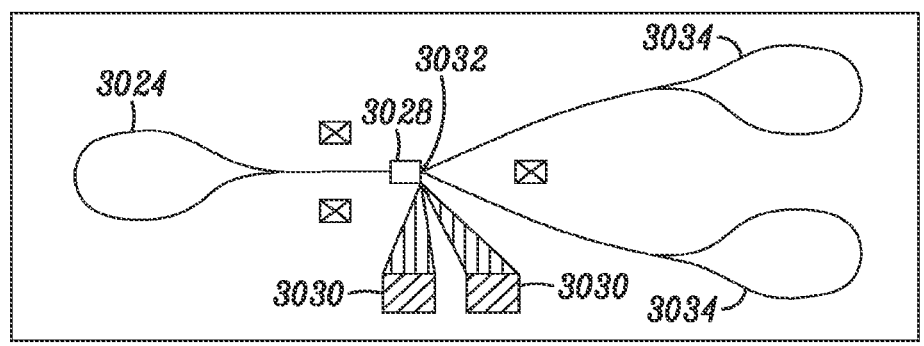

FIGS. 30a and 30b shows additional example configurations of microfluidic chips for use in the present invention.

FIG. 30a shows a configuration where a diluting/sheath fluid may be used together with the sample in order to provide a centered flow in the measurement channels. The sample may be introduced into input port 3002. A diluting fluid may be introduced, or pre-charged, in port/reservoir 3004. This fluid may be used to apply pressure via duct on the input port 3002 to drive sample through the measurement channel. In addition, side channels 3010 may be used to form a sheath fluid around the core/sample flow at junction 3012. This centers the cells in the flow as they pass through measurement volume 3014. The output port 3018 then receives the sample as well as the sheath fluid. This configuration potentially provides a number of advantages, in that cell flow rate and spacing may be better controlled, and cells are centered within a wider channel, where they can be measured with better repeatability. In addition, background signals from the sample fluid are reduced in this configuration, as the core fluid flow may be typically very narrow compared to the sheath flow.

FIG. 30b shows a configuration where cells may be switched, based on the vibrational spectroscopy measurement, using an electric field at the switch point 3032. Cells flow from the input port 3024 through the measurement volume 3028 where they may be measured as previously described. Based on individual cell characteristics, a voltage is applied to contacts 3030 which perturb the path of the cell, and causes it to flow to a selected output reservoir 3034*rec*.

Figure 31:
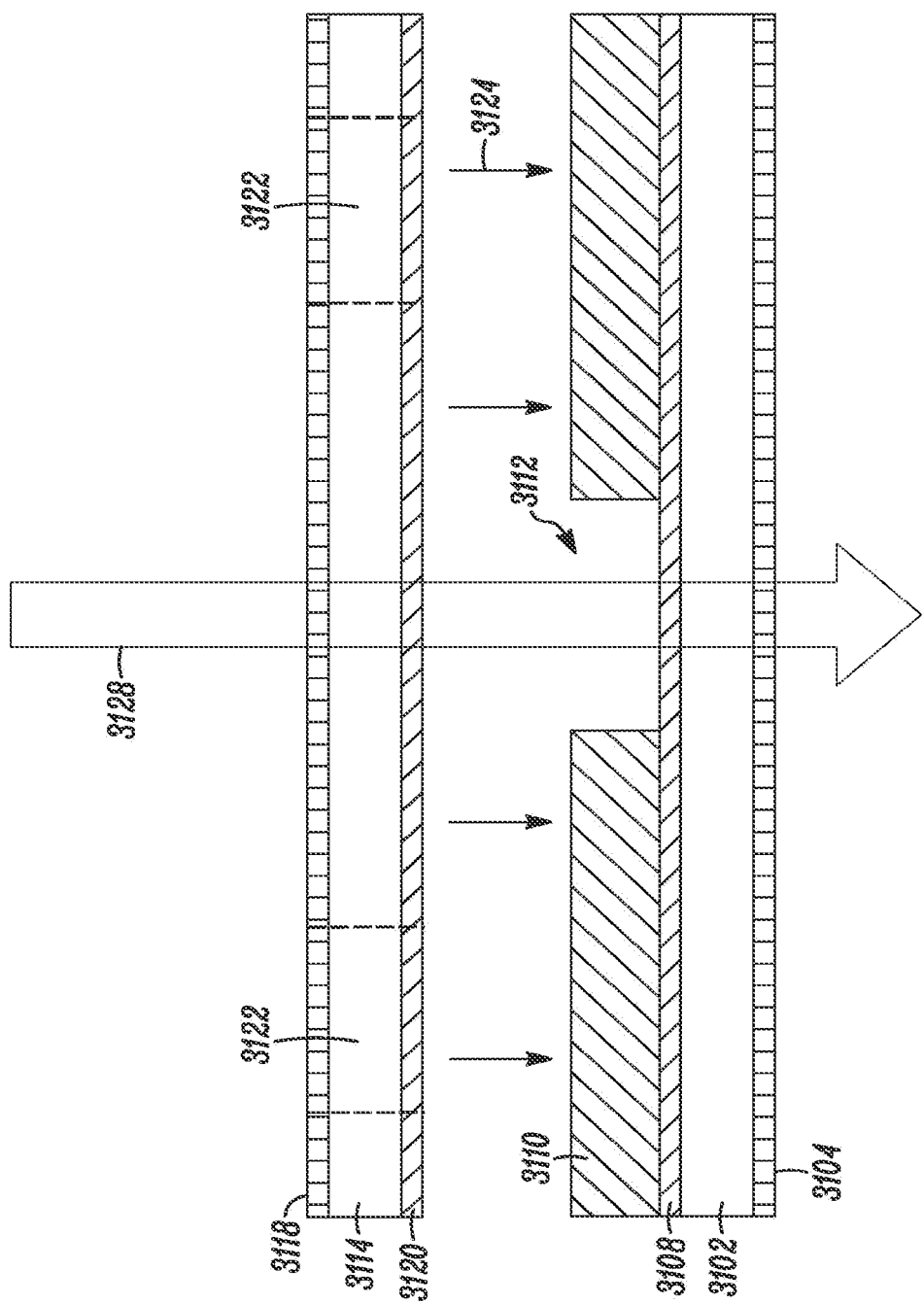
FIG. 31 shows the example construction of a microfluidic chip for use in the present invention.

FIG. 31 shows an example construction of a microfluidic chip. In this example, a chip may be constructed for use in a mid-infrared spectroscopic cellular DNA measurement system utilizing quantum cascade lasers as the optical source (s). A top wafer 3114 and bottom wafer 3102 may be used. These wafers may be made from materials that are transmissive at the QCL wavelengths to be used for cellular interrogation. For example, float-zone Silicon, which has high transmission in the infrared, and which is readily obtained and machined, may be used. Other materials that may be applicable include Germanium, ZnSe, CaF2, BaF2, and other materials well known in infrared optics.

The bottom wafer 3102 may be first antireflection (AR) coated. This is important for a number of reasons, such as to minimize losses of IR light in the system and thereby maximize signal-to-noise ratio, or minimize QCL power required, reduce fringing artifacts from interface reflections which may distort the transmission spectrum of the sample and therefore distort apparent sample absorption and, importantly, minimize any resonant optical cavity effects in the channel 3112. If the channel becomes a resonant optical cavity, the field intensity may vary significantly with vertical position in the channel. In this case, the system may become sensitive to cellular position, because the cell may be in a position to absorb more infrared radiation at field maxima, and less at minima. This may result in higher and lower apparent infrared absorption based on cell position, which should be avoided.

An alternative or complementary solution may be to create a flow in which cells are confined to a specific layer, and therefore are subjected to the same optical field from cell to cell. A good AR coating may be a more robust and simple solution, and design of mid-infrared AR coatings may be well known to those skilled in the art. It may also be important in such a coherent system to reduce coherent optical effects from the source itself, which cause position-dependence within the measurement channel. This may be described in more detail elsewhere in this disclosure.

In an embodiment, internal AR coating 3108 may be designed so as to prevent reflection between the lower substrate material 3102 (usually relatively high index) and the liquid sample in the channel (approximately the index of water, which is relatively low). The external AR coating 3104 should be designed for the atmosphere of the tool, which may be most likely air. The coatings must be designed to withstand subsequent processing and exposure to the sample and associated fluids, without toxicity to the sample. For this purpose, very thin terminal layers may be provided on the internal AR coatings 3108 and 3120.

The microfluidic features such as channel 3112 may be fabricated either by etching the substrate material 3108 to form a channel of specified depth (before AR coating), or, as shown here, formed through addition of another material 3110. For example, SU-8, a UV-crosslinked photoresist that may be etched with high aspect ratio, and is known to be biocompatible, may be spun on the bottom wafer 3102, and then patterned with microfluidic features. The top wafer 3114 is first patterned and etched to provide ports/reservoirs and any mechanical alignment features indicated here by 3122. For this purpose it is desirable to use a wafer material where etch processes are well known, such as silicon. Internal and external AR coatings 3120 and 3118, respectively, may be deposited after this etch step or, if deposited beforehand, removed during the etch process.

The top and bottom wafers may be made from different materials according to processing and operating requirements. For example, the top wafer may be made from silicon, which may be readily etched using well-established processes, and may be a low-cost material in the mid-IR. Silicon, however, suffers from a number of drawbacks for mid-IR spectroscopy. First, it may have some absorption in the mid-IR which may be mitigated by using high-purity float zone Silicon. It may also not allow for visible or NIR light transmission, which may be desirable where visible light measurements may complement the infrared cellular DNA measurement. For example, visible imaging, fluorescent label measurement, or other techniques may require a material with visible-light transmission. In such a case, it may be desirable to use a material such as ZnSe, BaF2, CaF2 or other known visible/mid-IR window as the bottom wafer, and Silicon as a top wafer.

The top wafer 3114 and bottom wafer 3102 may then be aligned and bonded. SU-8 itself may be used to establish a bond between wafers at the appropriate temperature and pressure, usually under vacuum. This may be done with a supplemental layer or pattern of SU-8 on the top wafer, but some groups have been successful with one-sided SU-8 bonding. The wafer may be subsequently diced into multiple microfluidic chip components. These may be individually packed into plastic carriers, or matched with carriers in the tool, as described earlier.

Figure 32:
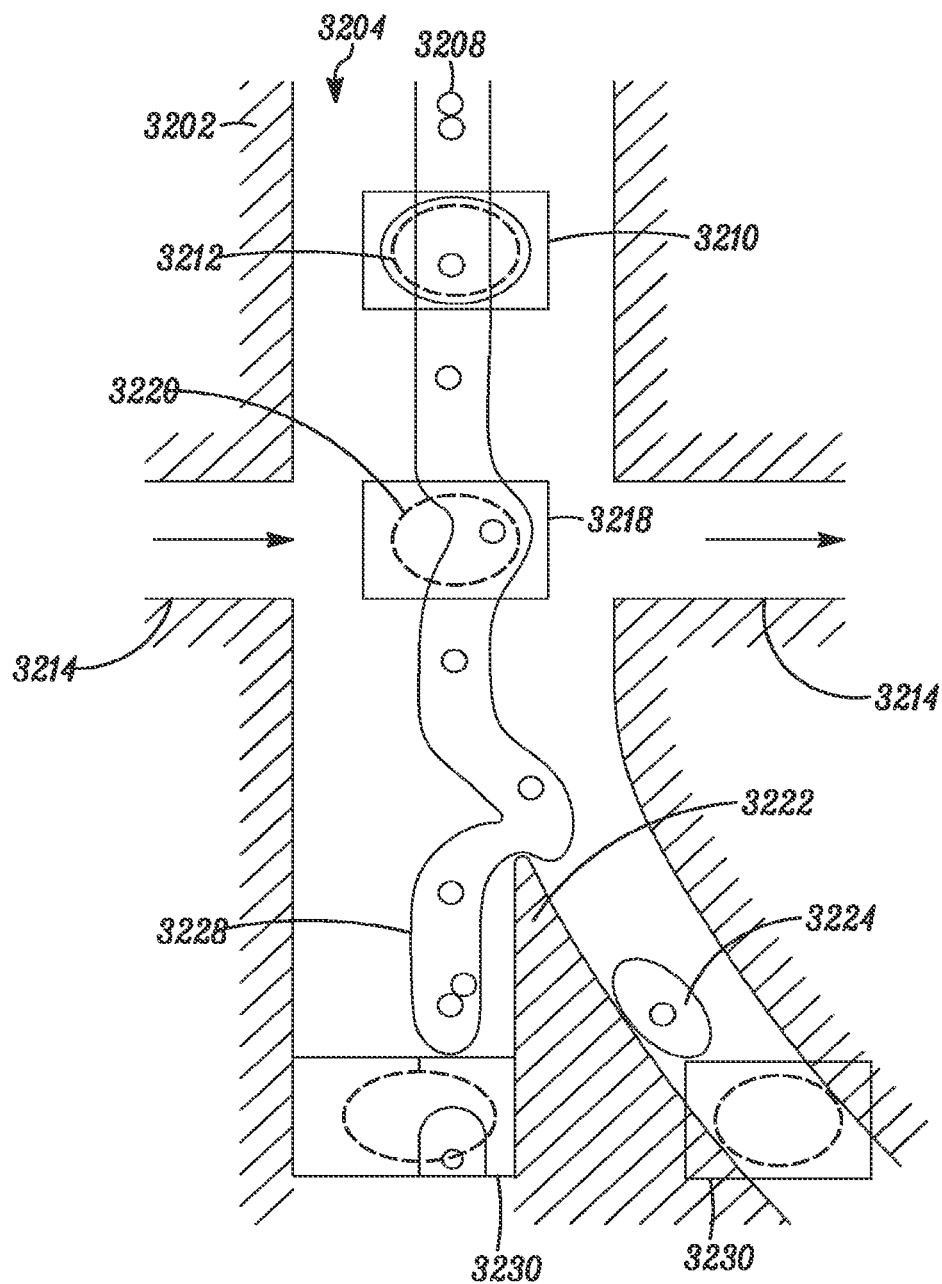
FIG. 32 shows the detail of an example embodiment of a microfluidic channel including a measurement volume and a pressure-actuated cell switch.

FIG. 32 shows the detail of an example embodiment of a microfluidic channel in a top view, including a measurement volume and a pressure-actuated cell switch. The example may be illustrated for the case where a mid-infrared, QCL-based optical system may be used for cell interrogation. An incoming channel 3202 carries a core stream with cells 3208 within a sheath fluid 3204 into the measurement zone 3210. The measurement zone may be delineated using a metal mask that allows the infrared beam (indicated by solid line in 3212) to pass only through the aperture. In this embodiment, the aperture may be larger than the beam, so that mechanical movements do not translate into large optical variations. The aperture, patterned photolithographically onto the microfluidic chip, may serve to allow alignment of the measurement beam with the center of the channel.

As the cell passes through the measurement volume, it breaks the visible/NIR/SWIR beam (dotted within 3212), indicating cell presence, and possibly giving some data on cell size/density. The mid-IR beam (solid line within 3212) may be absorbed by the cell according to its chemical bond constituents. The mid-IR beam may have one, two or more individual wavelengths acting as reference levels, or to measure constituents other than DNA. For DNA measurement, vibrational fingerprint regions such as the 1234 $cm^{-1}$ or 1087 $cm^{-1}$ phosphate bond vibration lines may be used to measure absorption and therefore amount of DNA present.

Based on the calculated DNA quantity, and optionally other parameters, a sort destination for the cell may be determined. By default, the cell continues straight along the channel to the waste output (left branch). If the cell is determined to be of the sought-after type destined to the "selected" output, as it passes through the detection point 3218, the pressure actuating channels 3214 may be used to slightly offset the core flow to the right. A visible/NIR/SWIR beam 3220 may be used in this location to accurately assess cell speed in the channel (from the delay between the measurement point and the switch actuator point). This speed may be used to regulate the overall pressure in the system to maintain flow rates within a window, and may also be used to adjust the timing of switch activation relative to the cell passing through the measurement point.

By default the core flow may go straight 3228 into the "discard" channel. Where the switch has been actuated to select a cell, the core flow may go to the left of the branch point 3222 and selected cells 3224 may go to the "selected" out port/reservoir. Two additional optional detection points 3230 may be used with visible/NIR/SWIR interrogation to monitor cells flowing into channels, so that errors may be detected and corrected. For example, if sort failures are detected, the timing of the switch actuation or the pressure on the system (and therefore cell velocity) may be adjusted to provide accurate switching.

As is illustrated in the FIG. 32, cell agglomerates may be detected either by the visible/NIR/SWIR scattering or imaging patterns, or by the infrared quantification. These may be sent through to the "discard" channel. Likewise, cells that may be spaced too closely within the channel, and as a result where accurate switching may not occur, may be let flow through to the discard, depending on the system parameters. There are of course situations where very rare cells are being collected, in which case it is better to err on the side of switching cells into the collection reservoir.

Through a combination of flow speed monitoring and cell timing measurements provided by the aforementioned optical measurement points, the dilution of the cells may be monitored. If the cells are insufficiently diluted, core vs. sheath pressure may be varied to space cells, or the sample itself may be diluted differently by the tool, sometimes necessitating use of a new microfluidic chip.

Figure 33:
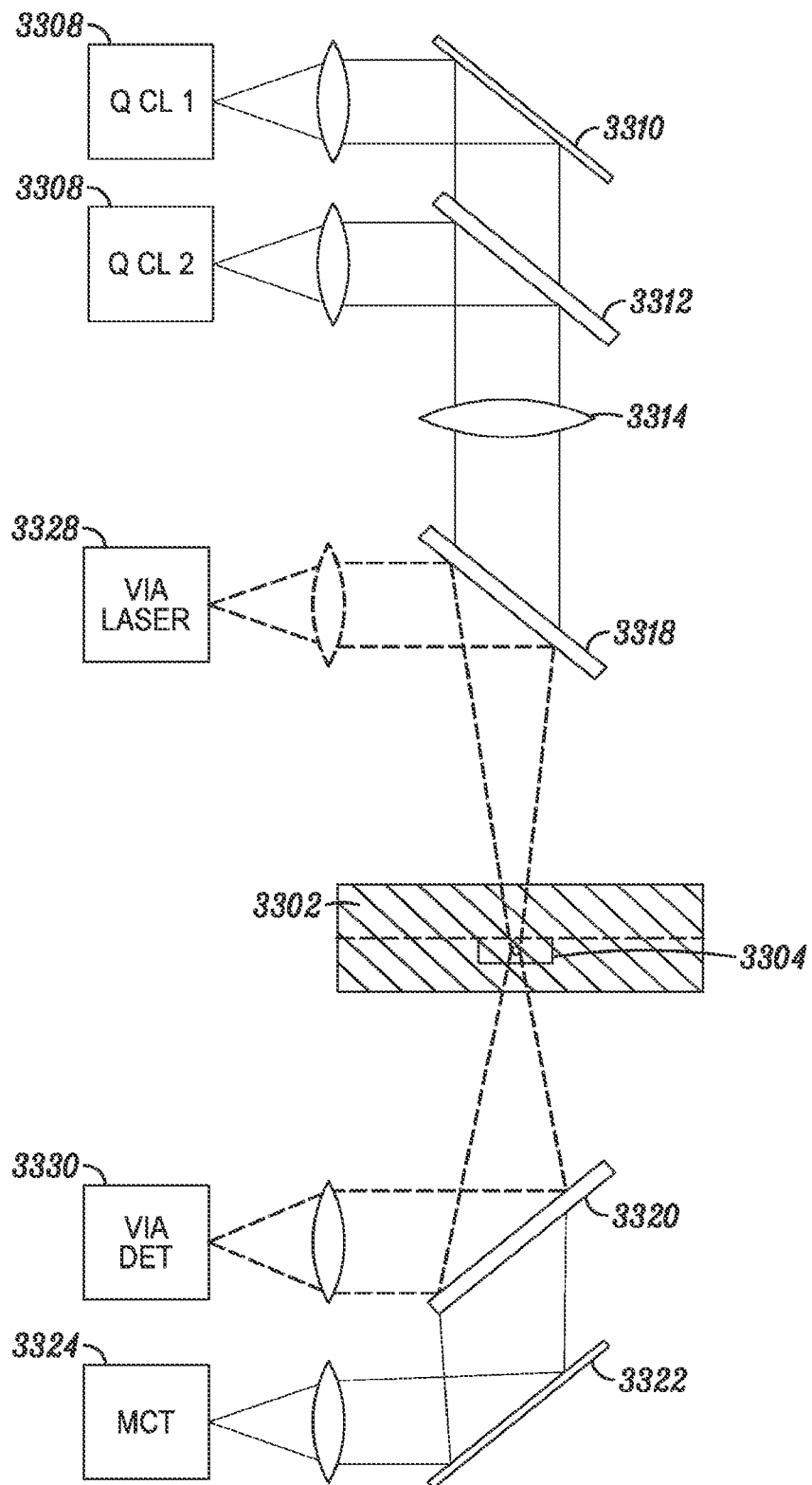
FIG. 33 illustrates an embodiment of the optical interrogation system used in the present invention.

FIG. 33 illustrates an embodiment of the optical interrogation system of the present disclosure. This example may be based on two QCLs 3308 at different wavelengths. For example, one QCL may be centered at the 1234 $cm^{-1}$ symmetric phosphate bond vibration absorption peak typical of the DNA backbone. The other may be at a nearby reference wavelength measuring water absorption within the channel. In this manner, water displacement by the cell may be referenced out of the overall measurement. The mid-IR beam from the first laser here is turned by a plain mirror 3310 and then combined with the beam of the second mirror by a dichroic filter 3312. A lens 3314, which may be a reflective or refractive element, focuses the infrared beams onto the measurement volume 3304 on the microfluidic chip 3302. The transmitted infrared radiation (the input beam minus the absorption of the sample in the channel) may be transmitted via a fold mirror 3322 to a mercury cadmium telluride (MCT) detector 3324 that measures intensity.

The different wavelength QCLs are modulated/pulsed so their signals may be separated in the electrical output of the MCT detector. Optionally, an additional dichroic filter and MCT may be used to separately measure a particular IR wavelength. The MCT detector may be uncooled, TE-cooled, or even liquid nitrogen cooled to achieve maximum signal-to-noise ratio. Optionally, thermal infrared detectors such as pyroelectric or bolometric detectors may be used, generally with inferior signal-to-noise characteristics.

In an embodiment, a reference detector, placed on the laser side of the sample, may be used to measure laser output powers in the case where there are significant fluctuations in laser power. In this case, a small fraction of the beam may be sampled with a partially-reflective mirror, and a MCT or other detector used to measure power before the sample and chip absorption. This signal may be then used as a baseline for measurements.

As described earlier, multiple signal processing techniques may be used to establish baselines in this system and accurately measure DNA content in cells. Most of these may be well known in the fields of cytometry and time-series infrared absorption measurements.

A visible, NIR, or SWIR laser 3328 may be integrated into the system for the purpose of detecting cell presence, and possibly size and density. The visible beam may be combined with the infrared beam using a dichroic filter 3318, focused through the measurement volume, and then sent via another dichroic filter 3320 to a visible detector. Additional optics, such as masks, may be added into the system ahead of the detector in order to remove the unscattered light from the measurement (achieved by blocking the zero-order light).

The chip may be constructed in a method described above so as to maximally transmit infrared light, and reduce any optical cavity effects.

The infrared light may also be pre-treated by devices to reduce coherence length, and further minimize coherent optical effects that could introduce spatial dependence in the measurement channel. One such device may be described in more detail below.

Figure 34:
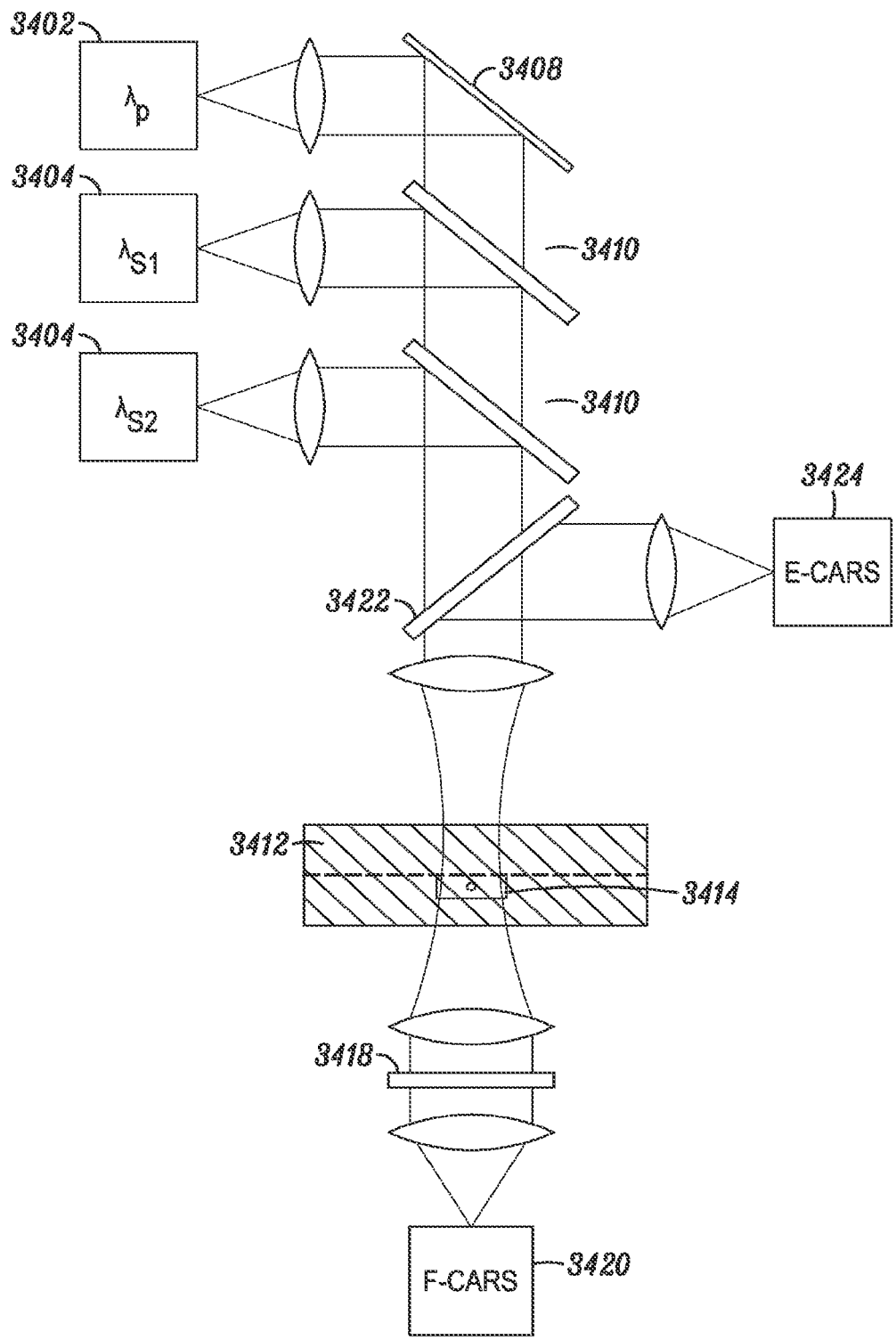
FIG. 34 shows an example of the present invention using coherent anti-stokes Raman spectroscopy (CARS) to measure vibrational bond fingerprints in cells at high speed.

FIG. 34 shows an example of the present invention using coherent anti-stokes Raman spectroscopy (CARS) to measure vibrational bond fingerprints in cells at high speed. The system consists of a pump laser 3402 that may be combined with one or more slave lasers 3404 to excite one or more bond vibrations in the cells being measured. The combination of pump wavelength and specific slave wavelengths may serve to resonantly excite specific molecules so as to emit coherent light at an anti-Stokes frequency.

In the example shown in FIG. 34, the pump 3402 may be folded by mirror 3408 and combined with two slave wavelengths from lasers 3404 using dichroic filters 3410. The pump may be typically pulsed in synch with the slave (one slave at a time) to maximize signal. The pump and slave wavelengths may be focused on the measurement volume 3414 and any cells contained within it. The forward coherent Raman signal ("F-CARS") may be separated using a wavelength-selective filter 3418 and focused on the detection system 3420 that may typically consist of a photomultiplier tube (PMT) and associated electronics.

In addition, an epi-detected CARS ("E-CARS") signal may be measured by separating backward emission from the sample with a dichroic filter 3422 and focusing it on a detection system 3424. Additional optical detectors may be used to detect the pump beam as a direct measurement of scattering by the cells in the volume. In one example, pump beam may be pulsed alternately with each of the two slave wavelength lasers, each corresponding to a different vibration band or, one to a vibration band corresponding to DNA, and another to a reference band. Coherent Raman signal generated by these pulses from the sample may be read out by the detectors, and processed by the system to calculate cellular DNA as described previously.

Although the laser wavelengths differ, and the readout mechanism may be different, the fundamental "molecular bond fingerprint" being measured may be the same as when QCLs may be used to interrogate the cells. Similarly, many of the same issues come to bear in the system. For example, good AR coatings on the microfluidic channels may be required to minimize variation as a result of mechanical or temperature variations, and to minimize the position-dependence of the laser intensity received by the cell (and the emitted signal intensity).

Figure 35:
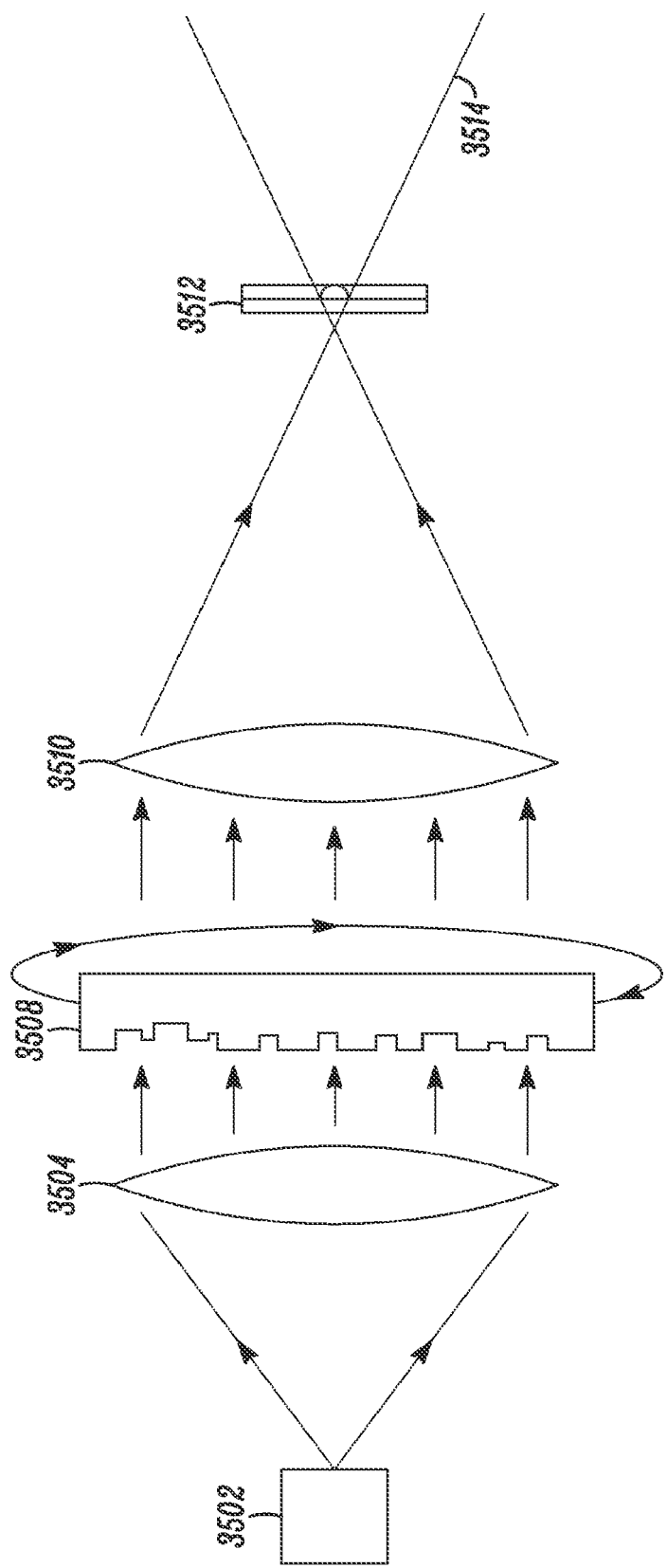
FIG. 35 shows a configuration of a QCL with components to reduce coherence length, so as to minimize spatial dependence in the readout of cell spectral measurements.

FIG. 35 shows a configuration of a QCL with components to reduce coherence length, so as to minimize spatial dependence in the readout of cell spectral measurements. The QCL 3502 may be collimated by optics 3504 and then passed through a diversity of phase shifts introduced by phase plate 3508. This plate may be spun or translated mechanically so as to provide rapid changes in phase to each part of the beam, with a time constant shorter than the integration time of the system. Additional optics 3510 then focus the beam onto the chip 3512 with the measurement volume, and the transmitted beam 3514 is relayed to detector systems. The "decoherence" device may be applied to multiple overlapping beams from multiple QCLs (at different wavelengths) simultaneously. Such a device reduces coherence length, and reduces coherent effects near the focus of the system.

Figure 36:
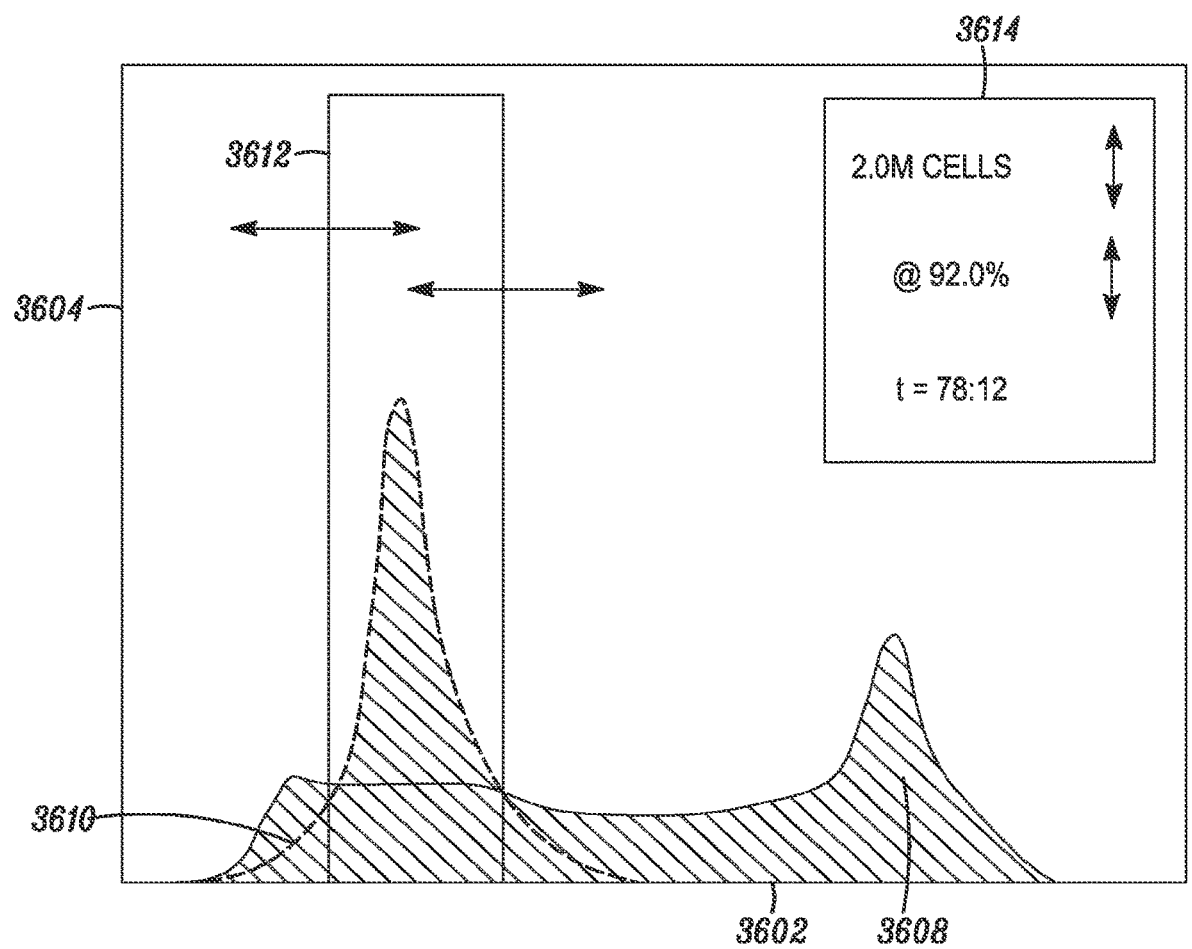
FIG. 36 shows an example of the display/user interface when the tool may be used for cell sorting.

FIG. 36 shows an example of the display/user interface when the tool may be used for cell sorting. The x-axis 3602 of the graph displayed indicates cellular DNA content. The y-axis 3604 may indicate cumulative cell count. The histogram 3608 may then generate from multiple cellular measurements. The tool may run a small sample of cells in order to build up a distribution for display to the user or for fitting curves to the distribution automatically.

In this example, a fitted distribution curve 3610 may be superimposed onto the histogram in order to indicate the spread of a particular population of cells. For single-purpose tools, or for repeated protocols performed with a general-purpose tool, these curves may be generated and applied automatically. For example, in a tool based on the present invention meant to enrich sperm cells to either X-carrying or Y-carrying populations, two such curves may be fit automatically onto the data, and the user then simply selects enrichment fraction and number of cells. A selection range 3612 indicates which range of measured DNA content may be selected using the sorting function of the tool. This window may be manipulated directly by the user for some applications.

Alternatively, the user may use the panel 3614 to simply specify the number of cells required, and the enrichment percentage desired. The tool may then automatically calculate the optimal position for the selection window 3612 and calculate the estimated run time for the sort.

In an embodiment, where the present invention may be used for gender selection purposes, the user interface may be simplified further: a) select X- or Y-enrichment, b) select desired enrichment level, and c) select number of cells desired. The system then displays estimated run time, and if this is within an acceptable range, the user may initiate sorting. As the sort proceeds, the projected sort time may be updated based on how many cells are being selected. In addition, the system may automatically alter the sort window 3612 in order to achieve the targeted enrichment.

Other examples of single-purpose tools or protocols enabled by the present invention may include but are not limited to tools to separate out dividing cells those with double, or at least excess DNA which may indicate cell division is in progress only or only non-dividing cells, tools to separate out cells exhibiting aneuploidy (abnormal DNA content) or only cells with "normal" DNA content.

A system may include one or more of a liquid flow cell which is specifically designed for high-speed measurements using a mid-IR QCL, an element for creating phase diversity in the mid-IR laser light, an optical subsystem that ensures a narrow, focused spot is sampled in the liquid sample, an element minimizing the scattered or reflected light that reaches the detector, and a QCL with a rapid, low-cost, coarse tuning mechanism specifically suited to liquid- or solid-phase measurements. Rather than making a surface measurement of a liquid such as that performed by existing mid-IR sampling architectures, this system makes a transmission measurement through the entire sample, in which mid-IR light is transmitted directly through the sample. The system minimizes reflections of any type, and methods may be used with the system to reduce contributions from scattered or reflected light.

Depending on the speed at which the absorption spectrum of the liquid must be measured, and the QCL power available, the path through the flow channel must likely be designed to be short because mid-IR absorption of liquids (water, in particular) is often very high. Typically, a path length on the order of microns is required—for very high-speed measurements, 25 microns or less. A limiting factor, even in the case where laser power is not, is the total power absorbed by the liquid, and any temperature constraints (for example, it could complicate matters significantly if the liquid starts boiling in the channel).

Such a flow channel may be fabricated in one of a number of ways known to those skilled in the art. For example, channels may be fabricated by bonding together two wafers which are transparent in the mid-IR, at least one of which has been patterned with flow channels, either by etching into the wafer, or by adding and then patterning another material on top of the wafer. For example, SU-8, a photopatternable polymer, may be used to pattern flow channel walls on one of the wafers, and then may be used as an adhesive to bond another wafer on top of it, finally, these wafers are diced into individual devices. Wafers may additionally be patterned and etched to form inlets and outlets for liquids. Channels may be narrow, or may in fact be large areas.

In some cases, the "channel" may in fact be a large liquid volume between two windows, and rather than the liquid flowing past the detection point, the sample holder may be translated past a measurement system—with the sample holder (windows and interposing liquid space) designed as described below.

For the purpose of consistent measurements of the liquid and any contents therein, it is important to take into account coherent and resonant optical effects that may occur in such a measurement system. Such effects may include: laser (QCL) coherence effects which cause a varied field strength and therefore absorption over the sample volume, causing position dependence within the measurement, either along the axis of the laser (depth dependence) or laterally (x-y dependence or "speckle"); reflective or semi-reflective surfaces adjacent to the sample, which result in a spatial variation in EM field strength near the surface (physically, a mirror will have a field minimum at its surface); and reflective or semi-reflective surfaces which interact to form a resonant cavity, resulting in: wavelength-dependence in absorption due only to resonance or lack or resonance (effectively, some wavelengths will have more average passes through the liquid sample than others); and again, at fixed wavelength, result in a static distribution of field strength within the sample, making it unevenly sampled and position-dependent.

The present disclosure includes a number of specific design parameters for the liquid channel/sample holder and the optical delivery system to minimize these issues and assure higher accuracy in absolute measurements of the sample. These may be applied singly, or in combination, to minimize position-dependent absorption within the flow channel of the mid-IR beam(s).

One specific design parameter may be fabricating the sample holder with well-designed antireflection (AR) coatings on both external (air-facing) and internal (liquid-facing) surfaces. These coatings prevent reflections at the interfaces, which is important both for eliminating local field minima/maxima near the interfaces (which may cause non-uniform "sampling" of the liquid), and reducing resonant optical effects within the system. AR coatings for air interfaces are well known for mid-IR wavelengths. If the index of the liquid sample is close to that of air, these may be sufficient for internal (liquid-facing) surfaces as well. However, they may require special design, including: matching of the AR coating to minimize reflection between the window (which is a material transparent to mid-IR radiation, for example Zinc Selenide, Silicon, Germanium, Barium Fluoride, Calcium Fluoride, and certain plastics with high IR transmission) and the liquid analyte (water, for example); designing the AR coating for the specific wavelength, or range of wavelengths, to be used in the spectral analysis system; designing the AR coating for the (range of) angles of incidence of light that will be seen by the surface, wherein the angle is a combination of the beam cone angle (most systems will be focused down to the channel) and the angle at which the sample holder is placed relative to the beam (see discussion below); designing the AR coating for compatibility with the liquid analyte—since many mid-IR coatings are comprised of materials that absorb water—either alternate materials must be used, or capping layers that resist water penetration must be used; and/or terminating the AR coating with layers, or post-treating the AR coatings in order to make the surface with the appropriate hydrophilic properties required to move fluid into the channel or cavity;

possibly coating or treating the surface in order to minimize (or, in rare cases, maximize) adherence of biological or other particles to the surface; for example, in a flow cytometry application, ensuring that cells do not adhere to the channel walls in the measurement volume (or elsewhere); these terminal layers or treatments must of course not significantly reduce the effectiveness of the AR coating itself.

Another specific design parameter may be angling the surfaces of the sample holder such that any reflections are rejected from the system and not delivered to the detector, or reflected back to the laser source. The cone angle of the light focused onto the sample holder should be taken into account in this case. In addition, AR coating designs may be modified to take into account this angle of incidence. Angling the entire channel may effectively increase the path length through the analyte. This may be beneficial in some cases but needs to be constrained in others where the liquid analyte (or liquid carrying particles of interest) is highly absorptive at the target wavelength(s). The beam may be asymmetric in order to achieve higher uniformity in measurements—for example, in a flow application it may be desirable to have a short axis parallel to the flow, and long axis across it in order to have the most uniform illumination across the center of the flow—the resulting cone angles should be taken into account. In this case it would usually be desirable to tilt around the short axis, since the cone angle along the long axis will be narrower, and therefore less tilt will be required to ensure no reflected light is sent to the detector or laser subsystem.

Another specific design parameter may be using nonparallel surfaces in order to minimize resonant effects. However, the optical path through the liquid should be consistent in cases where particles in the liquid are to be measured, so that the attenuation due to liquid absorption is identical regardless of particle position within the sample volume.

Another specific design parameter may be employing specific gap distances through the channel, tuned to the interrogating wavelength(s) and the average index of the liquid analyte or liquid carrier plus sample particles. A channel thickness (or gap) may be specifically non-resonant at the wavelength of interest, meaning that the gap times the index of the liquid contained in it are a non-quarter wave multiple of the interrogating wavelength. This prevents constructive or destructive interference effects to the maximum extent possible, reducing buildup of resonances in the cavity, and in this manner minimizing spatially dependent absorption in the system.

The system is focused on enabling high-speed liquid-phase (or solid particles/cells within a liquid medium) spectral measurements. Liquid- and solid-phase absorption lines in the mid-IR are far broader (several wavenumbers at a minimum) than gas-phase absorption features. As a result, it is acceptable to have broad linewidth, but at the same time, it is necessary, to effectively have a wide tuning range in order to reach one or more absorption peaks of interest, as well as reference points in the spectrum which are used to establish a baseline. For the sake of speed, this tuning must be performed very rapidly over this broad range. So the requirements on the QCL subsystem are very different than for gas-phase spectroscopy. The system is described as separated elements in a system, as some applications will benefit from the simplicity of having a separate microfluidic element—that may be disposed of after use in some applications, or at least swapped out periodically.

One of several designs for the QCL subsystem may be used in the present disclosure. One design is discrete fixed-wavelength QCLs that are optically multiplexed. In this design, individually packaged QCLs are used. They may be either distributed feedback (DFB) or external cavity Fabry-Perot (FP) type (where wavelength is set in the external cavity). The outputs of the lasers are collimated, and are combined with one another, typically using either dichroic or bandpass filters (which, for example, reflect one wavelength and transmit others). If power is not an issue, semi-transmissive mirrors may be used to multiplex the beams. These lasers may then be pulsed in rapid succession to measure absorption at different peak and reference wavelengths of the liquid in the microchannel. Alternatively, if the QCLs are operated in continuous wave (CW) mode, they may be modulated with different frequencies and their signals demultiplexed electronically after detection by a mid-IR detector (after passing through the liquid sample). Optical demultiplexing to multiple detectors is also a possibility, where the highest signal-to-noise ratio is absolutely necessary. The advantage of multiple discrete QCLs in the present invention is that they are more readily available from suppliers today, and that they may be changed relatively easily (for example, if systems with different chemical targets are being built). In addition, they may span very broad wavelength ranges, whereas the tunable solutions described hereafter will cover a relatively narrow range of wavelengths (and therefore may require the use of several tunable QCL subsystems within the present invention).

Another design is the QCL array-on-chip. This design consists of an array of DFB lasers fabricated on a single chip. This means a single growth design is used, but gratings that set laser wavelength are individually patterned to result in different center wavelengths. The potential advantage of this architecture is the lower cost of packaging, cooling elements, and associated elements. It also opens the potential for a very compact system that may be rapidly switched from one wavelength to another simply by electronically switching between lasers in the array. The array may be produced with regular-spaced wavelength over the interval of interest (which covers one or more absorption peaks in the liquid sample, and perhaps one or more reference absorption measurements). Wavelengths may be spaced apart at wider intervals, and even at irregular intervals. For example, the array could contain 4 discrete and unevenly-space wavelengths over a frequency interval of 200 cm-1, corresponding to peaks and references. For example, if cellular DNA in live cells flowing through the liquid channel is to be quantified, and therefore the characteristic symmetric phosphate bond peak at 1087 cm-1 is to be measured (phosphate is an element of the DNA backbone), three closely-spaced wavelengths at 1075 cm-1, 1087 cm-1 and 1099 cm-1 could be employed to measure absorption peak absolute height and "shape," and another wavelength at 1055 cm-1, corresponding to a nearby absorption minimum (and therefore potentially good reference level) could be added. In this manner, a single chip containing all relevant wavelengths may be fabricated and packaged with minimum size and cost. The beams from the lasers on the common chip may be delivered in at least two ways to the microfluidic channel: 1) A grating may be used to redirect individual wavelengths in a manner such that a single, overlapping collimated beam is formed. The coincident beams may then be focused onto the microfluidic channel where they are absorbed by the analyte, and then relayed to a detector. Note that for irregularly spaced wavelengths, laser diodes may have to be spaced accordingly on the chip in order to have a diffraction grating accurately redirect the beams into a single overlapping beam. Or 2) The plurality of lasers may be imaged directly onto the microfluidic channel using appropriate optics. In this case, an array of points corresponding to the array of lasers will be projected onto the microfluidic channel. In a 1:1 imaging setup, for example, if the DFBs are patterned 20 microns apart on the chip, a series of spots 20 microns apart will be sampled in the liquid channel. For example, these could be oriented along the direction of flow of a microchannel, and the liquid and anything being carried by the liquid would be sampled sequentially by the beams emanating from the series of lasers on the chip. The wavelengths of the lasers could in this case be in any pattern; for example they could simply be an alternating array of two wavelengths (signal and reference wavelengths). In other configurations a larger number of wavelengths could be used to build up a rough spectrum. If configured in this way in a system where particles such as cells are run through the liquid channel, appropriately spaced, the lasers could in theory be run in CW mode, and signal processing could be used to extract the absorption levels. In most cases, however, individual lasers will still be pulsed in rapid succession, or modulated at different frequencies to provide for easy electronic separation after detection by a mid-IR detector. The spots from the array may be imaged such that they are not entirely parallel to the microfluidic channel. They could be oriented in a diagonal manner in order to give some lateral resolution to the system. Such lateral resolution within the flow channel could be used for example to measure position of cells within the channel as they flow by (to compensate for any known I calibrated spatially-dependent detection nonuniformities), or, for example, to measure concentrations across a flow with non-uniformities, from either differential velocities (center vs. edge), or because two liquids are mixed upstream in a largely laminar flow.

Another design may a QCL that rapidly tunes to discrete wavelengths. As discussed earlier, continuous or fine-stepped tuning is not required for the liquid spectroscopy application. High speed is a requirement. A rapid tuning mechanism that samples sparse wavelengths would be ideal. One tuning mechanism that lends itself to potentially rapid, discrete, controllable, low-cost tuning is a Vernier tuning arrangement in the external cavity of a FP QCL. In such an architecture, thermal tuning (for example) can be used to achieve much faster, broader tuning than would otherwise be possible. Such architectures are well known and have been used to build telecommunications lasers in the 1.5 micron range. We propose that such an external cavity architecture for a mid-IR (or eventually THz) QCL, integrated into a system with a fluid microchannel in which absorption is measured, would be a potentially ideal solution for high-speed liquid spectroscopy. In the Vernier filter configuration, two Fabry-Perot resonant elements are used in the external cavity, designed with free spectral ranges (FSR) that are close but not equal. By slightly tuning one or both of these elements, different transmission peaks will coincide. In this manner, the portion of the gain spectrum of the QCL that is amplified is selected. The advantage is that with relatively little input signal to the Fabry-Perot cavities (in the form of temperature in thermo-optically tuned systems, or voltage in electrostatically-tuned systems), large hops in wavelength may be achieved. Furthermore, the wavelength settings themselves are relatively well controlled since the modes of the Fabry-Perot cavities are known. The spacing and centers of these wavelengths may in fact be optimized within the present invention to provide the most efficient measurement of the liquid or liquid-suspended analyte. For example, the spacing of emission peaks could be configured to fall on the absorption peak of interest and on a reference point only for maximum efficiency. With the addition of a third filter to the external cavity of the QCL, one could sample a few wavelengths around the absorption peak, then a few wavelengths at one or two reference points.

More conventional tunable QCLs (such as those tuned by piezo-actuated external gratings) may also be used in the context of the present invention, in conjunction with other elements described herein, so long as they provide the required tuning speed.

Unlike with hot filament blackbody ("globar") sources used in FTIR instruments, QCLs are inherently coherent optical devices, and a number of potential complexities arise as a result. Coherent effects in imaging systems are well known ("laser speckle") and arise from constructive or destructive interference of the laser light returning from various points in the sample. We wish to avoid such effects, to the extent possible. A few elements described below may be employed to ensure that coherent effects—particularly spatially-dependent effects—are minimized. One element involves optical apertures—optical apertures through which the interrogating beam is focused may serve to reduce optical effects from the laser, and provide higher consistency in measurements. An aperture on the QCL side of the system (before the sample) may be used to "clean up" the beam from the QCL, and therefore deliver the minimum spot size onto the sample in the microfluidic channel or cavity. In this configuration, lenses are used at the output of the QCL to focus mid-IR light through an aperture of roughly 20 microns or less (approximately the desired spot size on the sample). This aperture will be imaged onto the sample, and ensure that a "clean," small spot is sampling the liquid. An aperture on the detector side of the system (after the beam passes through the sample) may be used again to "clean up" the beam—this time also removing any scattered light from the measurement. Combinations of scattered and directly transmitted light in a coherent system could cause unwanted effects. In addition, elimination of scattered light from the measurement ensures that only light that has passed more or less directly though the sample (and therefore reflective of Beers law absorption) will be measured in the system.

Another element involves phase scramblers. Phase scramblers may be used on the input (QCL) side of the system in order to de-cohere the light impinging on the sample. Scramblers typically rapidly change optical phase across a beam, on a time scale some multiple shorter than the measurement time (for a single event). In this manner, coherent effects such as those described above are effectively "averaged out" over a number of states. One example of a phase scrambler is a transmissive disc that has been etched with a pseudo-random pattern of fields with differing phase delays (by virtue of material index and thickness differences). This disc is the spun at an angular rate sufficient to "scramble" phases over a single measurement, and the beam from the laser is sent through the disc before it is focused onto the sample. We propose such a phase scrambler, designed for the mid-IR, combined with a mid-IR QCL, for microscopic spectroscopy applications in the mid-IR such as the ones described herein.

The present disclosure may be applied to, and form the core of, multiple types of systems that rely on rapid liquid-phase spectral measurements.

One such system is a fast reaction monitoring system. In such systems, very small volumes of reagent are used in a microchannel or microcavity, and the ensuing reaction is measured. The advantage of the present system is its capability to measure chemical concentrations, or even changes in chemical configuration (shape, folding, etc.) at high speed in liquid phase, and producing accurate results on an absolute scale (rather than just a time series of relative measurements). Such capability could be used for medical diagnostics, environmental tests, or combinatorial chemistry done at large scale on a chip.

Another such system is a high-throughput screening system. Many technologies have been devised to measure changes in cellular behavior in response to potential drugs. Most of these sample the cell superficially (for example, with surface-oriented optical techniques), and/or do not have the ability to directly measure key biochemical concentrations within the cell. The present invention enables such measurements to be made, consistently, in the native liquid environment, and at high speed. High speed may enable either very rapid successive measurements in a single cell, or will allow the system to step rapidly over a large number of wells in which cells have been placed with compounds. The ability to sample small volumes of liquid, containing cells, in a manner not dependent on cell position within the volume—and to do so accurately and quickly—is an advantage of the present disclosure.

Another such system is for high-speed cell classification. Emerging technologies that trap cells in a microfluidic cavity using structured and/or coated surfaces often require follow-up measurement and screening of cells to classify them. Often extremely rare cell events are of interest. For example, circulating tumor cells, or embryonic cells within the mother's bloodstream are typically 1 in a billion or less in frequency. Microfluidic structures may serve to enrich these to 1 in 1,000 or 1 in 10,000 in frequency. Subsequently, the trapped cells (which include many white blood cells, for example), must be screened in order to find true occurrences of the rare cells. The cells identified may then be extracted for further analysis. The present invention may be used to build a system for performing these screens rapidly on a population of cells that are trapped within a microfluidic cavity. Known biochemical markers established with FTIR or Raman spectroscopy in research studies may be interrogated using the present invention to accurately and rapidly screen and classify cells. Stem cell cultures may be measured in a similar manner to determine state of differentiation, while in a microfluidic cavity.

Another such system may be rapid cell counting/classification in a flow system. The present disclosure may be embodied in a format where a suspension of cells, or bodily fluid containing cells, flows through a microfluidic channel, and cells are interrogated as they pass through the mid-IR beam. The absorption of one or more wavelengths is measured by the system, and the cell is classified, or measurements are directly displayed to the user as a histogram. For example, cellular DNA measurement for cell cycle characterization may be done. Distribution of DNA quantity in a cell sample is indicative of how quickly cells in the sample are dividing and therefore multiplying. Cells with twice the "normal" DNA are in the process of dividing. In another example, cellular DNA measurement for aneuploidy detection may be done. Unusual levels of DNA are often an indicator for cancer. Detection of an unusual distribution of DNA within a sample can be a strong indicator that a sample is cancerous. In another example, blood cell counts may be measured. A complete blood count, including counts of all white blood cell types, may be possible using embodiments of the present disclosure, without the use of fluorescent labeling or other preparation. Cells would be classified using a combination of mid-IR wavelengths, potentially in combination with visible-light detection schemes. Besides individual cell measurements and counts, the liquid content of the blood plasma itself could be analyzed using the same system. In another example, an analysis of semen could be performed using embodiments of the present disclosure. Sperm cells could be counted and potentially characterized (for proper DNA packaging and chromosome count, gender); other cell counts could be determined (white blood cells); seminal fluid characteristics measured.

Another such system may be a cell sorting system. Well-known sorting mechanisms may be added to the cell measurement systems above in order to sort cells into distinct populations based on the measurements described. For example, sperm cells may be sorted for gender, cells exhibiting abnormal DNA count (potential marker for cancer) may be selected for analysis, cells that are actively dividing may be selected to create a sample with high viability, and cells may be sorted based on other biochemical markers; for instance in development of biofuels, cells that are determined to be producing a large amount of the target chemical may be identified spectroscopically without destroying the cell, and cycled back into the cell culture, while "less successful" cells are disposed.

Another such system may be for embryo scoring. In in-vitro fertilization procedures, it is strongly desirable to implant the minimum number of embryos required for a successful pregnancy. To this end, there is significant research ongoing into "scoring" embryos for viability, based on biochemical and/or morphological changes in early development. There is research that indicates biochemical concentrations could be a key indicator for viability. Embodiments of the present disclosure could be used to interrogate and score embryos, in a liquid environment, without the use of dyes or labels, and using only very low photon energy light. The ability to rapidly measure spectra, and potentially track spectra over early development, could be a significant advance in the ability to score and select embryos for implantation.

Another such system includes a gas monitoring system. In some cases, monitoring gas flows directly (sometimes done using mid-I.R spectroscopy) is not practical. In such cases, it may be possible to flow gas over or through a liquid stream that reacts with the target compound in the gas. The liquid stream flows through a microfluidic channel where it is in turn interrogated using the present invention. We propose this system as a whole as an effective, compact, rapid manner of monitoring some gas compositions—for example, detecting trace impurities in gases, or detecting biological or chemical agents in air. Similarly, a liquid surface may be exposed to air or another gas flow for a specified duration, and then the liquid, together with any particles trapped over that duration, analyzed using the present invention.

Another such system may be a solid sampling system. Sampling of solids by infrared spectroscopy is a long-standing challenge. There is very little optical penetration into most solids by mid-IR. As a result, surface techniques such as ATR must be used, which are often limited by surface layers or texture. The liquid spectroscopy system described herein may be used in an embodiment where a solid is sampled by mechanically fracturing/grinding it into very small particles, filtering these particles to ensure a reasonable range of diameters/shapes, and then suspending them in liquid for subsequent measurement. Measurement could be performed in a cavity where the solid particles are dispersed across an area (or a line), or with liquid that flows through a channel through a small measurement volume. According to the designs laid out above, the liquid and suspended solids are the measured using mid-IR transmission. In one embodiment, one mid-IR wavelength may be used to measure water absorption, in a range where the solid of interest does not absorb strongly in the mid-IR. As a particle moves through the optical detection area, its volume may be estimated by the decrease in water-line absorption. At the same time (or in rapid succession), the absorption of the solid particle at the target wavelength is measured. It may then be normalized for particle volume in order to calculate the chemical composition of the particle. An example embodiment is an environmental sampling tool. A tool with a small drill is constructed to drill into a layer suspected of being asbestos. A small amount of liquid is injected, and then a capillary-type tube is used to sample this liquid with any suspended solid. This liquid is then interrogated at the appropriate wavelengths to determined chemical composition and structure to signal whether the substance is asbestos. Pharmaceutical purity inspection is another example.

Another such system may be an emulsion measurement system (oil in water; water in oil).

Figure 37:
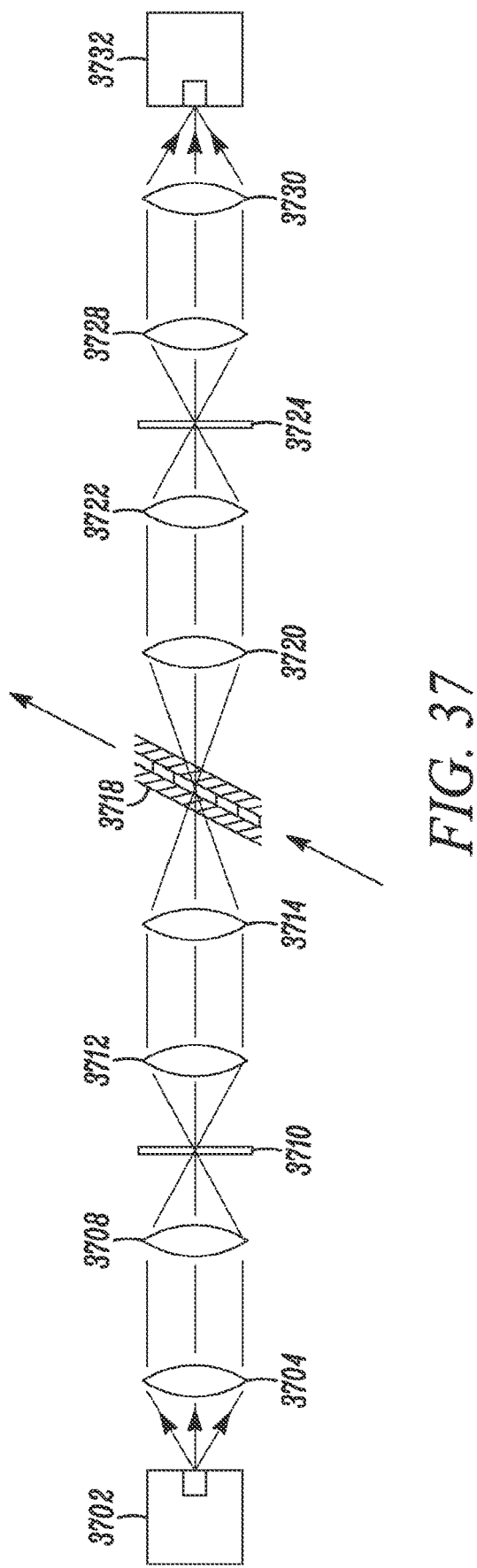
FIG. 37 shows a sample embodiment of the present invention that may include elements to minimize spot size on the sample, and to reject scattered light from the sample.

FIG. 37 shows a sample embodiment of the present invention that may include elements to minimize spot size on the sample, and to reject scattered light from the sample. A QCL subsystem 3702 which may consist of one or more mixed or tunable QCLs in the mid-IR or THz range may be collimated and then refocused by lenses 3704 and 3708 into an aperture 3710 that serves to "clean" the beam from the QCL and ensure a minimum-size, Gaussian beam profile at the sample. Lenses 3712 and 3714 and may be then used to refocus the beam with minimum spot size onto the fluid microchannel in the sample holder 3718. The sample chamber may be shown here at an angle to ensure any stray reflections are not propagated to the detector, and to reduce any resonant optical effects. The flow of the liquid shown here by arrows may be a sample that may be transported through a channel, through the measurement volume onto which the QCL-originated beam is focused. Lenses 3720 and 3722 collect the light that may be transmitted through the liquid in the sample holder, and refocus it onto another aperture 3724 which may serve to block scattered light from the sample or sample holder, and restrict, to the extent possible, light reaching the detector to directly-transmitted radiation, thereby giving the best possible absorption measurement for the liquid sample and any suspended particles/cells. Lenses 3728 and 3730 deliver the light to a detector 3732, for example a mercury cadmium telluride (MCT) detector for the mid-IR (which may be cooled by thermoelectric elements or liquid nitrogen).

Figure 38C:
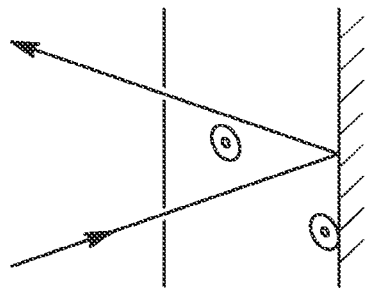
FIGS. 38a-38c show several sample configurations used by others that may suffer from surface effects that the present invention is specifically designed to avoid.
Figure 38B:
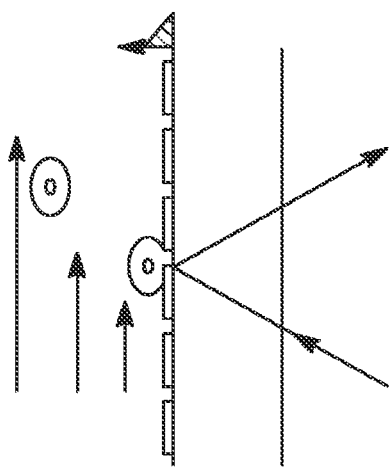
Figure 38A:
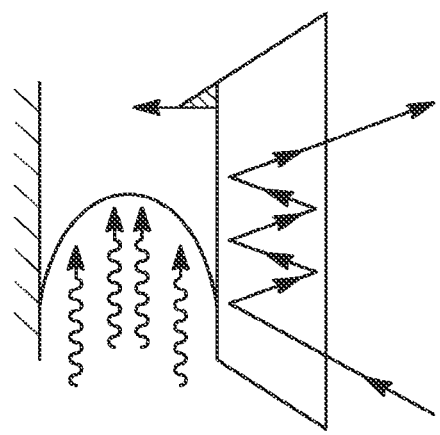

FIGS. 38a-38c show several sample configurations used by others that may suffer from surface effects that the present invention is specifically designed to avoid. FIG. 38a shows an attenuated total reflectance ATR configuration often used to measure liquids or solids using Fourier Transform Infrared (FTIR) spectroscopy in the mid-IR. Here it is shown in contact with a liquid micro channel showing flow velocity in the cross-section. As is usually the case in such systems, velocity near the interface may be very low. Also shown is the limited penetration of the evanescent field from the ATR prism into the liquid flow. The advantage of using ATR in conventional FTIR systems is that even when liquid absorption is very high, very little light may be absorbed in this configuration. The strong disadvantage obvious from this figure may be the limited depth of penetration into the core of the flow. FIG. 38b shows a more recent configuration used by a number of groups, which may be similar but uses plasmonic layers (patterned metal conductive layers) to enhance absorption. This may strongly enhance absorption signatures of samples in direct contact with the plasmonic filter. Again, however, the mid-IR field may have very limited penetration into the liquid. For measurements of stationary cells adhered to the substrate as shown by one of the biological cells in this example, this may allow time series measurements. However, for high-speed interrogation of cells passing through a liquid microchannel, this may not be an appropriate architecture, because of the strong depth dependence and limited depth of the absorption. FIG. 38c shows a true transmission architecture that may have been used for mid-IR measurements by several groups. In this "transflection" architecture, mid-IR light passes through the sample, may be reflected by a mid-IR reflective substrate (which may be transmissive in the visible), and then makes a second pass through the sample before proceeding to the detector. Holman et al described an "open channel" measurement based on this architecture, where there is no top window rather it is open and liquid flows for a limited distance over the reflective substrate. The advantage of this may be improved transmission and more simple construction. The strong disadvantage may be that any variability in liquid layer thickness may result in large apparent changes in sample absorption. A more substantial problem with the transflection architecture, however, derives from interference effects resulting from the reflective substrate. For example, a cell very close to the reflective surface, where the electric field must necessarily fall to a low level, may absorb relatively little mid-IR light. Conversely, a cell at a certain distance from the substrate will absorb a maximum amount of light. This dependence on depth will cause variations in signal that will be difficult to compensate. In addition, in this architecture it may be difficult to distinguish which light may be reflected by the sample, scattered by the sample, or transmitted through the sample. The present invention may seek to remove most of the issues with these architectures.

Figure 39:
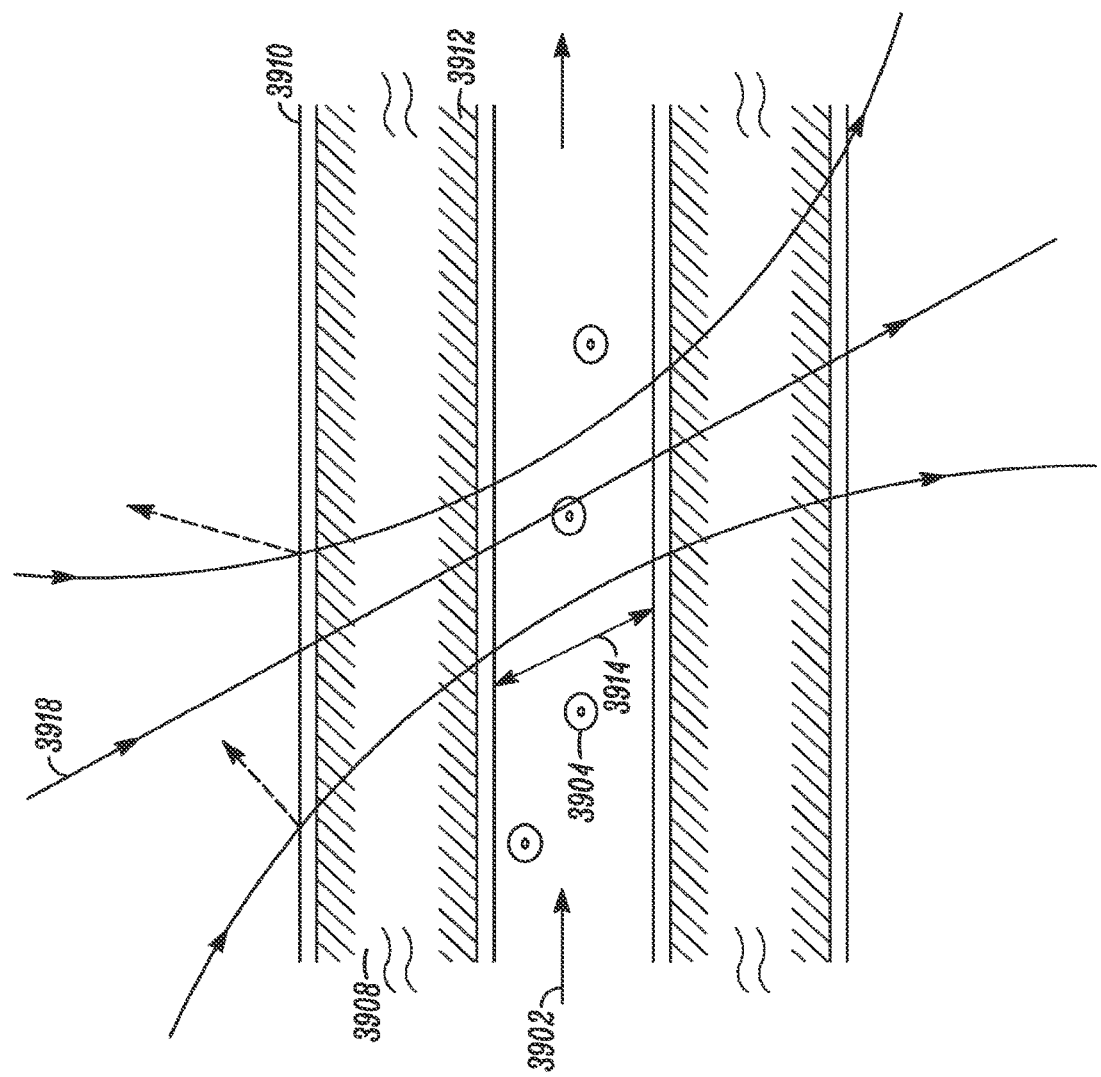
FIG. 39 shows an example embodiment of a microfluidic channel described in the present invention.

FIG. 39 shows an example embodiment of a microfluidic channel described in the present invention. A fluidic channel 3902 may carry fluid and, in this example, biological cells 3904. The channel may be fabricated between two mid-IR transparent windows 3908, whose thickness may not shown to scale (typically, the channel will have a thickness on the order of IO's of microns, and the windows will have thickness on the order of IOO's of microns). The windows may be fabricated from mid-IR compatible materials such as Germanium, Silicon, ZnSe, CaF2, and the like. The windows may be antireflection coated, with a coating to prevent reflection at the air interface 3910, and another coating on the internal surface 3912 tuned to prevent reflection at the liquid interface. A mid-IR beam carrying one or more mid-IR wavelengths 3918 may be then focused onto a sample volume in the fluidic channel. Indicated here may be the average path length 3914 which may also be tuned to minimize any resonant effects in the fluidic cavity. In this example, the beam may be brought in at an angle to guide any stray reflections away from the detector, and to minimize any resonant effects in the fluidic channel. As cells pass through the measurement volume, absorption changes at one or more mid-IR wavelength (which may be used serially). The system may detect the signals corresponding to the absorption levels, remove background levels, and calculate the chemical concentration of one or more cellular constituents. For example, DNA levels may be interrogated using the present system. The microfluidic channel may be fabricated on a disposable microfluidic chip and carrier so as to prevent contamination. An alternative configuration does not use a flowing channel, but rather a 2-dimensional planar cavity in which many cells are immobilized. The chip may then be translated in x- and y-directions, possibly guided by a visible-light system that identifies candidate cell locations, and mid-IR is used to interrogate cells. For example, in circulating tumor cell (CTC) applications, a 2D microfluidic pattern may be used to trap rare CTCs in blood. The present invention may be used to scan the trapped cells, and detect actual CTCs among white blood cells and other particles trapped in the array.

Figure 40A:
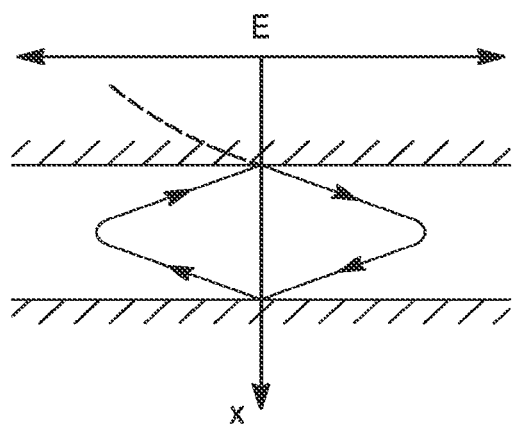
FIGS. 40a-40c shows how a microfluidic cavity may be optimized to reduce resonant optical effects, such that as much position dependence as possible is taken out of the QCL-based fluidic measurement system.
Figure 40B:
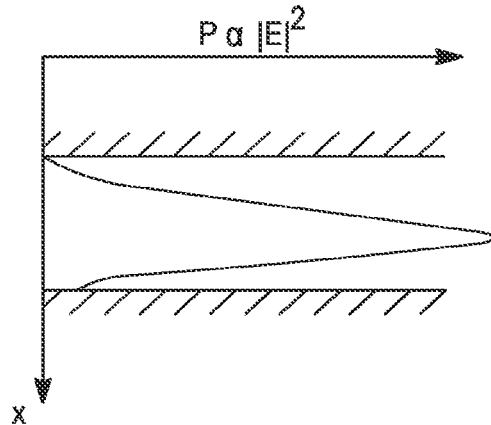
Figure 40C:
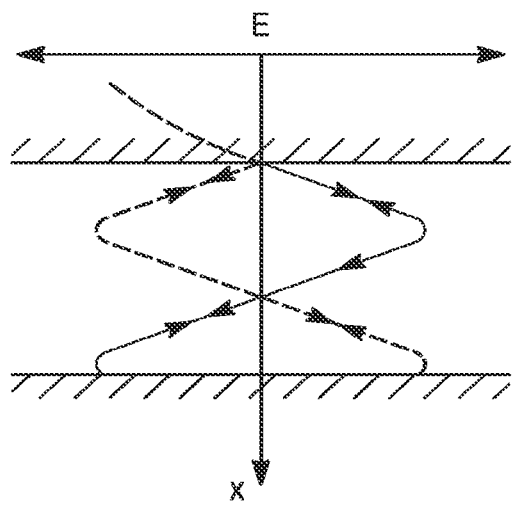

FIGS. 40a and 40b show how a microfluidic cavity may be optimized to reduce resonant optical effects, such that as much position dependence as possible is taken out of the QCL-based fluidic measurement system. FIG. 40a shows a microfluidic gap which may be an even quarter wave multiple of the interrogating wavelength, which may be a peak resonance. The diagram on the left shows electric field, the optical intensity may be shown to the right. As may be seen, there may be a strong peak near the center of the fluidic gap. In general it may be desired to avoid such strong spatial dependence, and have more uniform sampling of the absorption in the liquid (this may be particularly important when a suspension is being measured, where particles may be positioned at various heights within the channel). FIG. 40b shows the preferred configuration, where a gap may be used that may not be resonant at the interrogating wavelength(s), and ensures more uniform sampling of the contents of the fluidic channel. This configuration may of course be used in conjunction with AR coatings and angling as described.

Figure 41:
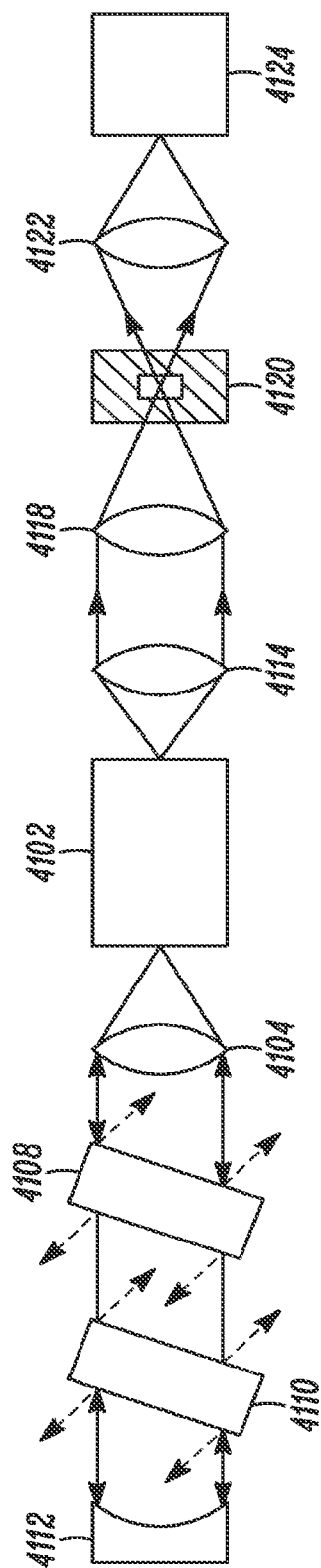
FIG. 41 shows an embodiment of the present invention based on a Vernier-tuned external cavity quantum cascade laser.

FIG. 41 shows an embodiment of the present invention based on a Vernier-tuned external cavity quantum cascade laser. This type of laser, which may be a well known architecture, may be ideal for certain liquid spectroscopy applications, because these applications require only rough but fast tuning to a relatively small number of emission peaks within a particular wavelength range. Several of these lasers may be used to interrogate a liquid and/or suspended solids within a particular system. A gain medium 4102 emits mid-IR light on its rear (low-reflectivity) facet, which may be collimated by lens 4104, and then passes through two etalons 4108 and 4110. The free spectral ranges of these etalons may be slightly different, so that only one set of transmission peaks coincides over the gain range of the gain block. The etalon wavelengths may be tuned by thermal or mechanical means. Importantly, only slight tuning may be required to tune rapidly over a wide range, in large steps particularly compatible with liquid measurements where absorption peaks may be broad. A rear mirror 4112 returns the beam back through the etalons to the gain medium. Light emitted through the high-reflective front facet may be collimated and refocused by lenses 4114 and 4118. Note a subsystem for "cleanup" of the beam employing additional lenses and a small aperture may be used to achieve minimal spot size. The beam may be then focused onto the liquid sample holder 4120 including a microchannel or microcavity. The transmitted light may be then focused onto a mid-IR detector 4124 using lens(es) 4122.

Figure 42:
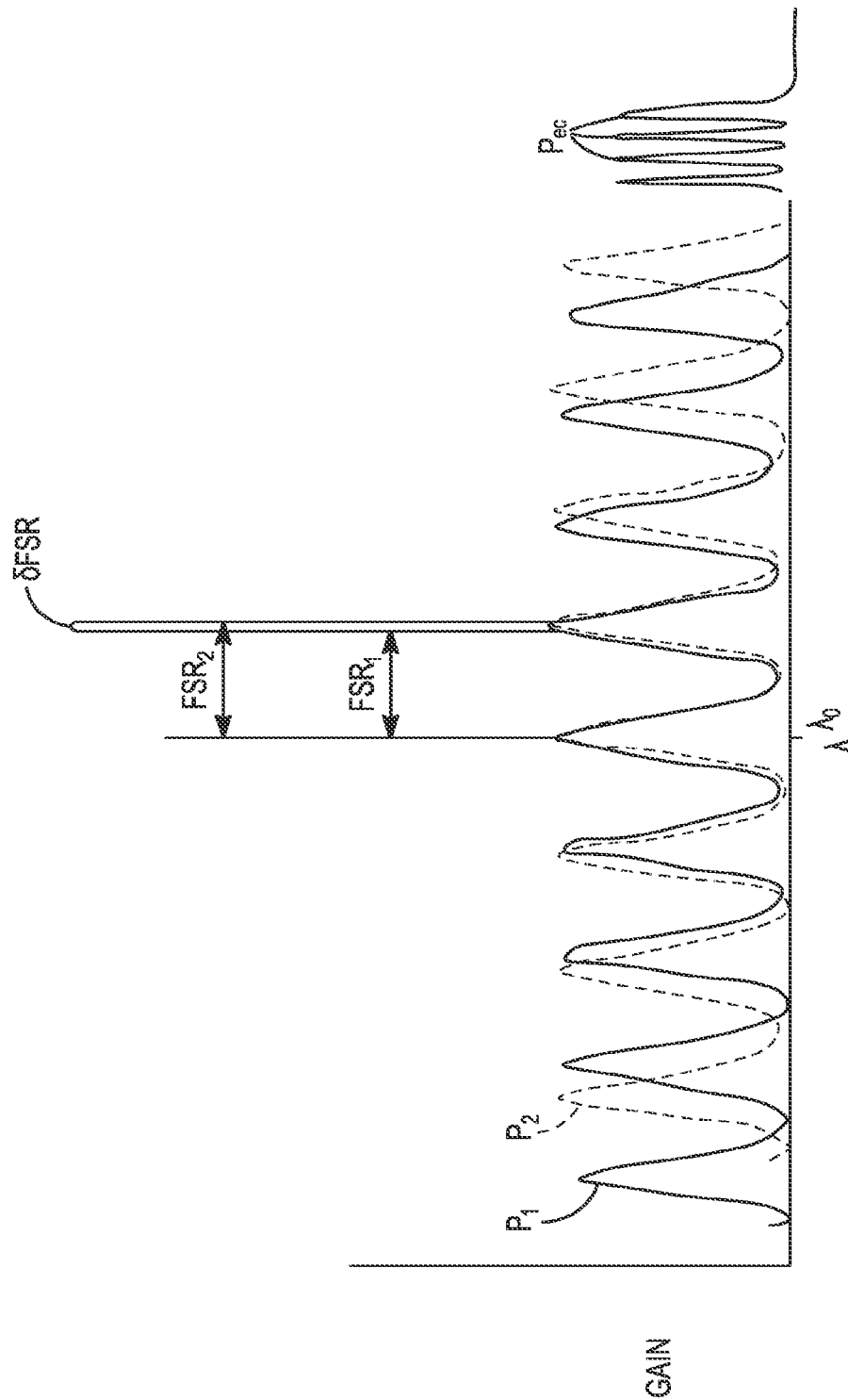
FIG. 42 further illustrates the Vernier tuning mechanism proposed for high-speed mid-IR liquid spectroscopy as part of the present invention.

FIG. 42, taken from U.S. Pat. No. 6,853,654, further illustrates the Vernier tuning mechanism proposed for high-speed mid-IR liquid spectroscopy as part of the present invention. It shows the transmission spectra of two etalons used to tune the laser, their different FSRs, and how they coincide on a single peak.

Figure 43A:
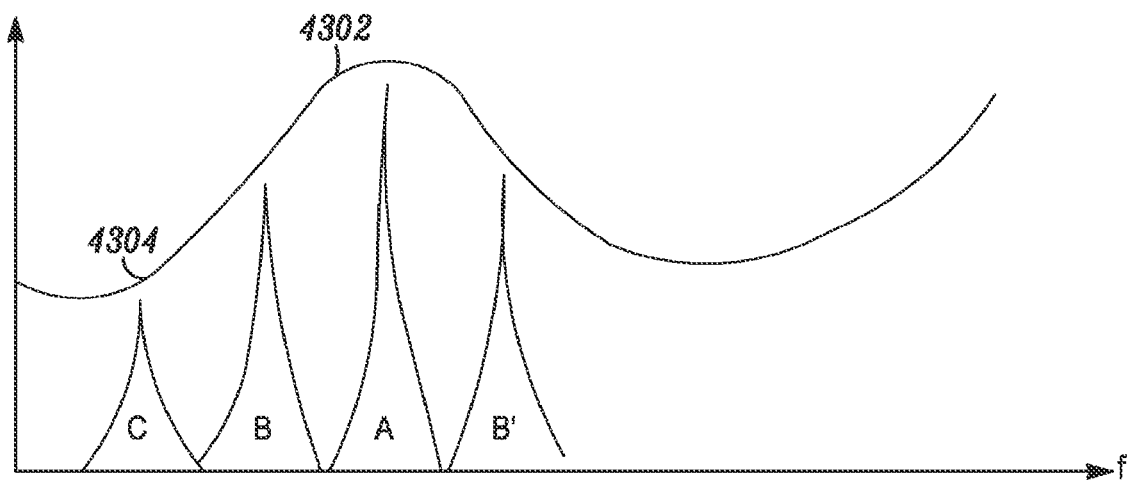
FIGS. 43a and 43b show the examples of multiple wavelengths used in the present invention.
Figure 43B:
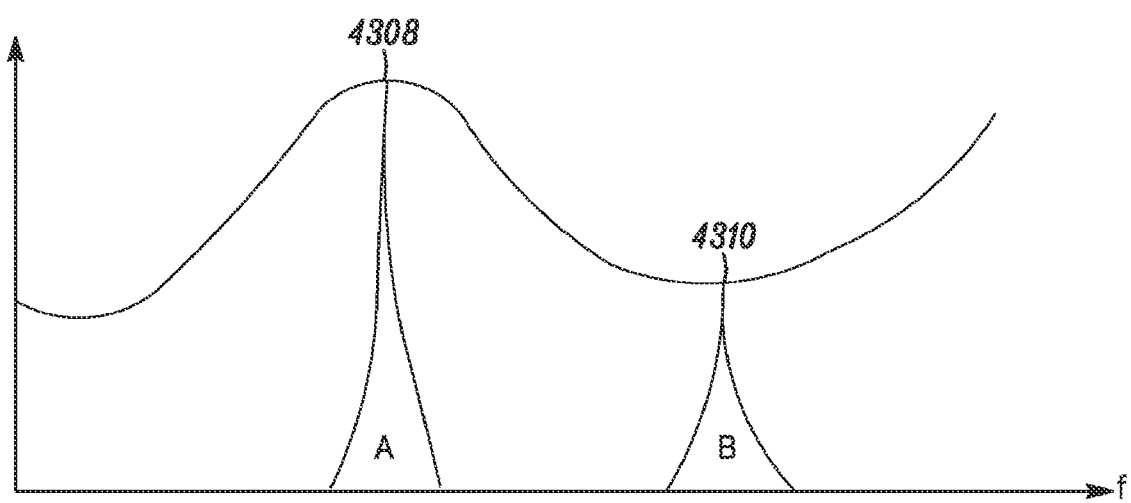

FIGS. 43a and 43b show the examples of multiple wavelengths used in the present invention. The individual wavelengths may be produced by a tunable QCL (for example, the Vernier configuration specifically described herein), individually-packaged fixed-wavelength QCLs, or a monolithic QCL array on a chip, delivered either as individual beams, or combined into a single spot. For the purposes of this figure, the horizontal axis represents mid-IR frequency, and vertical axis represents absorbance. FIG. 43a shows a configuration where an absorption spectrum may be measured at an absorption peak of interest 4302, with three points being measured on the peak. This allows the shape derivative, or second derivative to be measured as well as absolute absorption. Second derivative may be often used to measure an absorption peak in the presence of broad background signals. In addition, a local absorption minima 4304 may be interrogated by one of the system wavelengths. This may allow a measurement of the background absorption level, for instance, of the liquid medium delivering cells or particulates into the measurement volume. FIG. 43b shows a more minimal configuration, wherein only a peak absorption wavelength 4308 and a reference wavelength 4310 may be sampled.

Figure 44:
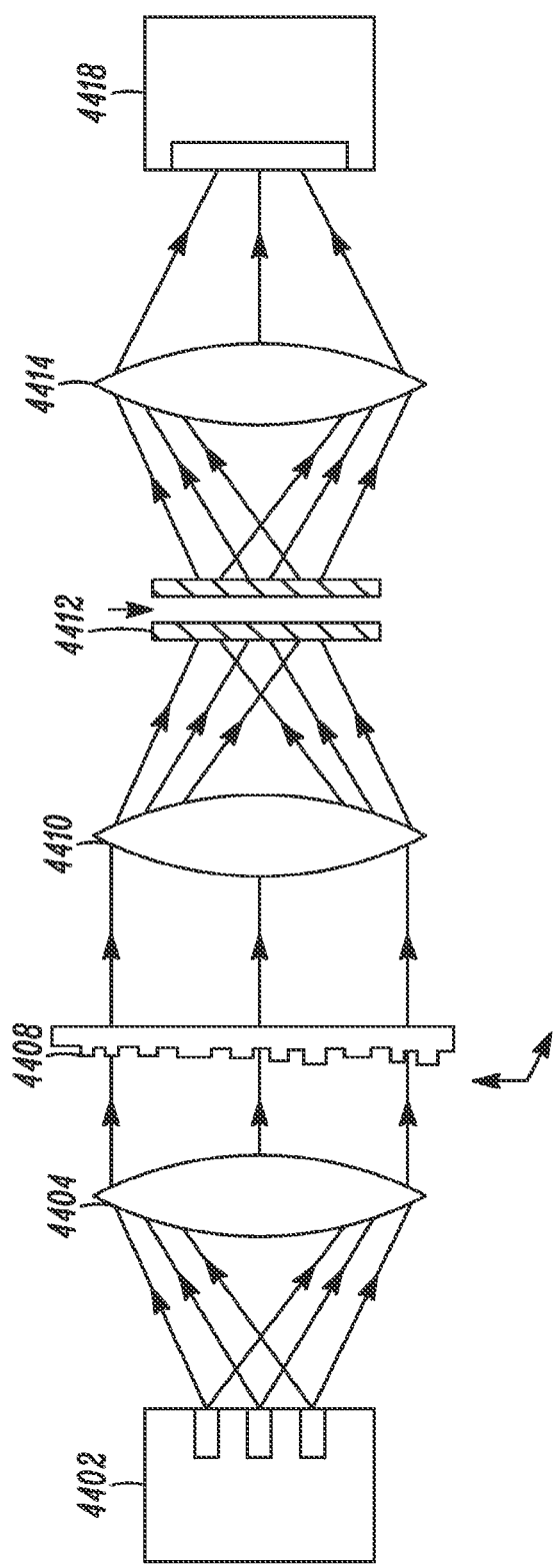
FIG. 44 shows another example embodiment of the present invention.

FIG. 44 shows another example embodiment of the present invention. A single-chip QCL array 4402 may contain multiple QCLs at multiple wavelengths. These may be collimated by lens 4404 and then treated using a rapidly-moving phase delay element 4408 in order to reduce coherence in the system, as described earlier. Another lens 4410 may focus the beams onto the microfluidic channel 4412. In this example, the laser array may be imaged onto the microchannel such that a series of volumes may be illuminated along the axis of flow. The transmitted portions of the beams may be then delivered to a mid-IR detector 4418 via one or more lenses 4414. In this configuration, different points along the channel may be sampled by each wavelength/laser. For example, in a cytometry system for measuring biological cells, a cell will pass through one beam after the next, causing different signals on the mid-IR detector. The changes in signal as the cell passes may then be processed, and chemical concentrations calculated. The individual lasers may be pulsed sequentially such that individual signals are easily resolved, they may be modulated with different frequencies or they may be used in continuous mode, and location of the cell inferred from the pattern of signals experienced as it may move through the channel. In a system using CW lasers, analog or digital differentiation may be used to isolate signals corresponding to absorption by a cell moving through the volume. The potential advantage of CW lasers, besides total optical power, is stability. CW lasers may be sufficiently stable to make a series of fast, referenced measurements as one cell passes through the measurement volume with reference power levels read out before and after the cell is in the volume whereas pulsed lasers may vary from pulse to pulse and require an additional detector in the system to reference QCL power.

One of the problems raised in mid-IR microspectroscopy is that of scattering. Mie scattering is dominant when the particles in the path are on the order of the interrogating wavelength. The magnitude and angle of scattering is determined by size of particles and index of particles relative to the medium. Described is a high speed particle measurement system for measuring the chemical composition/content of particles in the mid-IR using QCLs emitting at a few discrete wavelengths and optical system architectures to mitigate or harness scattering effects for the purpose of making these measurements.

Scattering is generally quite large in the visible regime, as the probe wavelengths used are small relative to the cellular dimensions. In addition, measurements made in this regime are generally dependent on wavelength only insofar as scattering is dependent on wavelengths vs. feature size; refractive indices are relatively constant over wide ranges within the visible.

In the mid-IR, refractive indices of cellular components may vary quite rapidly: in the "fingerprint region" for compounds, molecular bonds vibrate at frequencies corresponding to the mid-IR. At these frequencies, molecules absorb light, resulting in absorption bands. In gases, these absorption lines are generally extremely narrow. In liquid and solid substances, these bands are broadened.

Because there are localized absorption bands, corresponding to raised imaginary components in the complex refractive index, there is necessarily a local fluctuation in the real refractive index of the compound, as may be demonstrated or calculated from the Kramers-Kronig relation between the real and imaginary components of refractive index.

As a result, when designing systems for measuring particle spectroscopic properties in the mid-IR, these local refractive index fluctuations should be considered, and their effect on scattering as a function of wavelength. In some cases, system design may be optimized to minimize effects of this scattering. In others, references may be used to characterize the scattering intensity and compensate for it in an absorption measurement. Finally, in certain instances, scattering and its strong wavelength dependence near absorption peaks may be harnessed to perform a measurement.

Figure 45A:
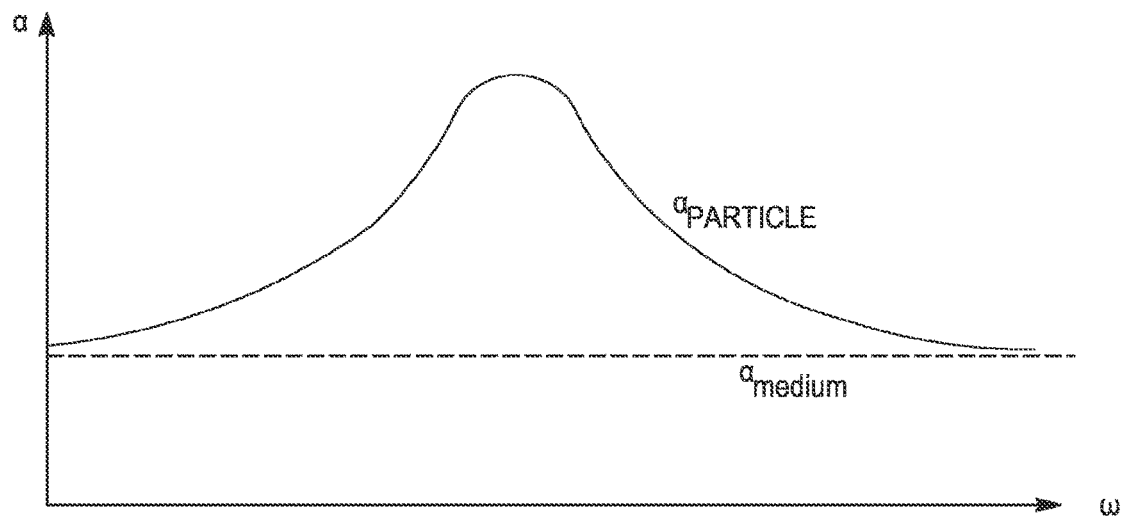
FIGS. 45a and 45b show a schematic example of a molecular absorption peak in the mid-IR.
Figure 45B:
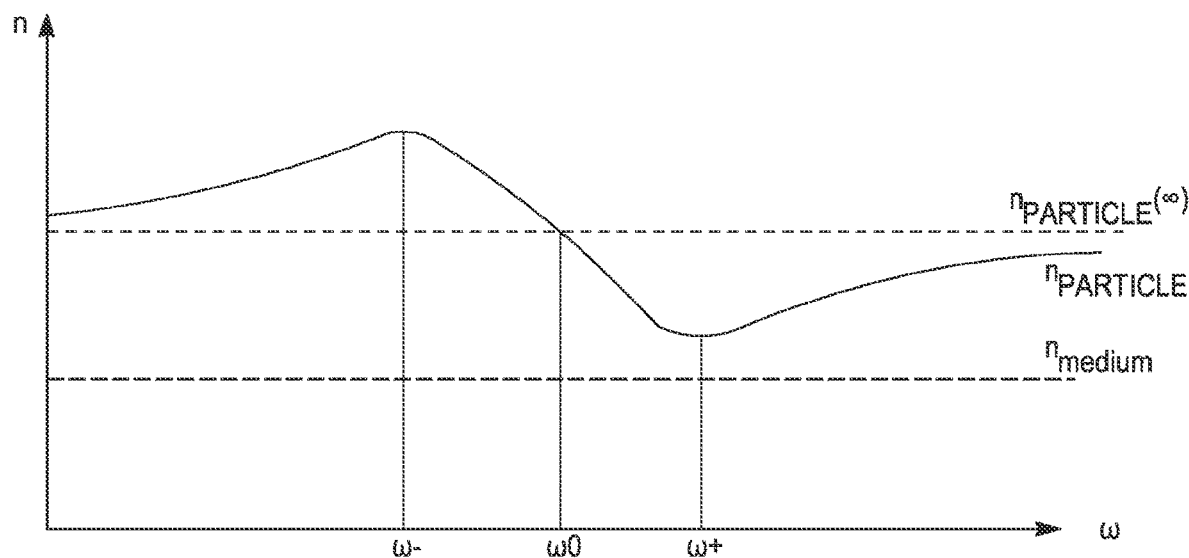

FIGS. 45a and 45b show a schematic example of a molecular absorption peak in the mid-IR. FIG. 45a shows the absorption of the particle (composed in part of the target molecule) and the medium in which it is measured, both as a function of optical frequency. FIG. 45b shows the derived real refractive index of the particle and the medium. As shown in FIG. 45b, there is a fluctuation in particle refractive index around the center of the absorption peak. The particle has a baseline refractive index ("index at infinity") that may be different than that of the medium. For certain applications it may be desirable to change the medium to have a refractive index closer (less scatter) or further (more scatter) from the particle. If a straight absorption measurement is desired, it is desirable to reduce index mismatch so as to minimize the effect of scatter. On the other hand, if a scattering-based measurement of particle size, for example, is desired, then it may be helpful to lower the medium index relative to the particle index.

FIG. 45b also indicates three frequencies, the center frequency for the absorption band wO, a high index point w−, and low index point w+. The maximum and minimum scattering may occur roughly around these points (scattering will generally rise with frequency). In building a discrete-wavelength measurement system for particles or cells, it may be crucial to select signal and reference wavelengths while taking into account wavelength-related scattering. Further, in order to minimize scattering losses, it may be desirable to shift these measurements towards low-scatter (low index differential) regions of the spectrum.

Another factor to optimize in wavelength selection is complex index (absorption) of the target. In an embodiment where absorption is very weak, local resonant scattering is also weak. Therefore, it may be optimal to probe the particle at the absorption peak. Even if there are changes in shape or orientation of the particle, the effects on measurement may be weak, as there is minimal self-shading. However, if absorption is very strong, not only will there be strong resonant scattering effects as a function of wavelength; there is also the potential for strong orientation dependence in the measurement. This is partly as a result of scattering dependence on orientation (not accounted for in Mie scattering models, which assume spherical particles) a short path through a large cross-section may be different than long path through small cross-section. However, ignoring scattering, the pure absorption signal of a non-spherical particle becomes orientation-dependent when absorption is high. This is a result of the exponential decay of light intensity on the path through the particle vs. the linear change with cross-sectional area. For large exponent factors (absorptivities) there may be a stronger mismatch as the particle rotates relative to the interrogating beam. Therefore, it may be desirable in many cases to select off-peak wavelengths for absorption measurements.

Figure 46:
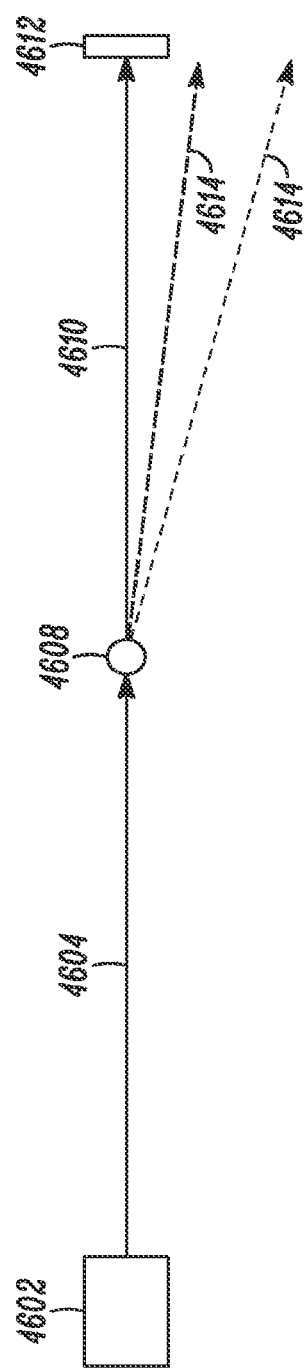
FIG. 46 shows a generalized system diagram for measurement of mid-IR absorption of a particle of cell, including but not limited to living cells.

FIG. 46 shows a generalized system diagram for measurement of mid-IR absorption of a particle of cell, including but not limited to living cells. A QCL 4602 is the optical source for the system. In the context of the present invention, QCL may be mid-IR or THz-emitting quantum cascade laser, or multiplicity of lasers. The QCLs may be fixed in wavelength or tunable with one of a number of known tuning mechanisms. In the case where a multiplicity of QCLs are used, they may be focused onto the same measurement volume, or different volumes, and then the particle may translate across volumes (or vice versa, with the system translating across particles) and absorption/scattering from different QCL sources measured sequentially.

As shown in FIG. 46, light emitted from the QCL 4604 is delivered to the particle being measured 4608. Light passing directly through the particle 4610, with some fraction absorbed according to the wavelength and the molecular composition of the particle, may be relayed to an appropriate detector 4612. In this embodiment of absorption measurement, where gas or uniform mixtures are being measured, it may sufficient. However, in other embodiments where particles are measured (such as cells in a suspension, an emulsion, solid particles in a liquid stream, or indeed liquid droplets in air), it may be insufficient. In such embodiments, particularly where the particles size approaches the wavelength, significant scattering may occur in an angle-dependent manner, depicted here by scattered rays 4614. Unless the system is designed to capture or compensate for this scattered light, it may obtain misleading absorption measurements for the particle or particles.

Figure 47:
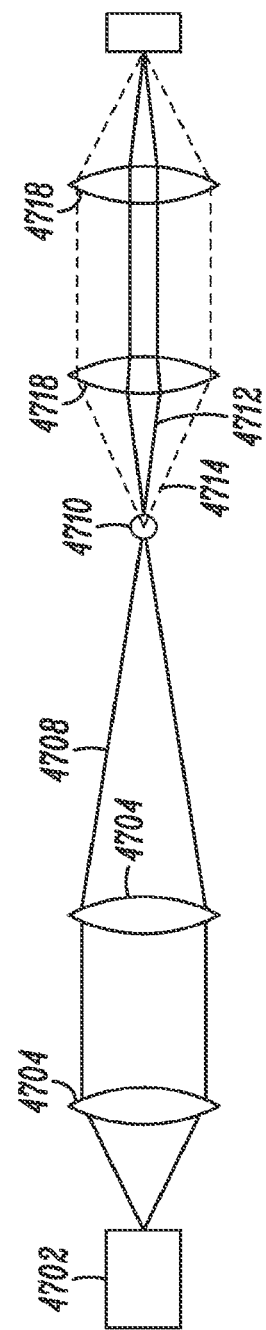
FIG. 47 shows one approach to remedying the scattering problem.

FIG. 47 shows one approach to remedying the scattering problem. QCL(s) 4702 are focused using optics 4704 to form an input beam 4708 with a specific angle, focused onto a measurement volume containing particle(s) 4710. On the output side, both directly-transmitted (and shallow scatter) light 4712 as well as scattered light within a certain angle 4714 are collected using a high NA lens as part of the collection optics 4718. With a sufficiently large differential between the input beam maximum angle and the output collection angle, scattering losses may be reduced. For a system with a small enough refractive index differential and particle volumes vs. wavelength, this may be sufficient to remove most scattering effects from the absorption measurement. As described earlier, probe wavelengths may be optimized as well to ensure no excess scattering losses (at least to the level required by the accuracy required in the system).

Figure 48:
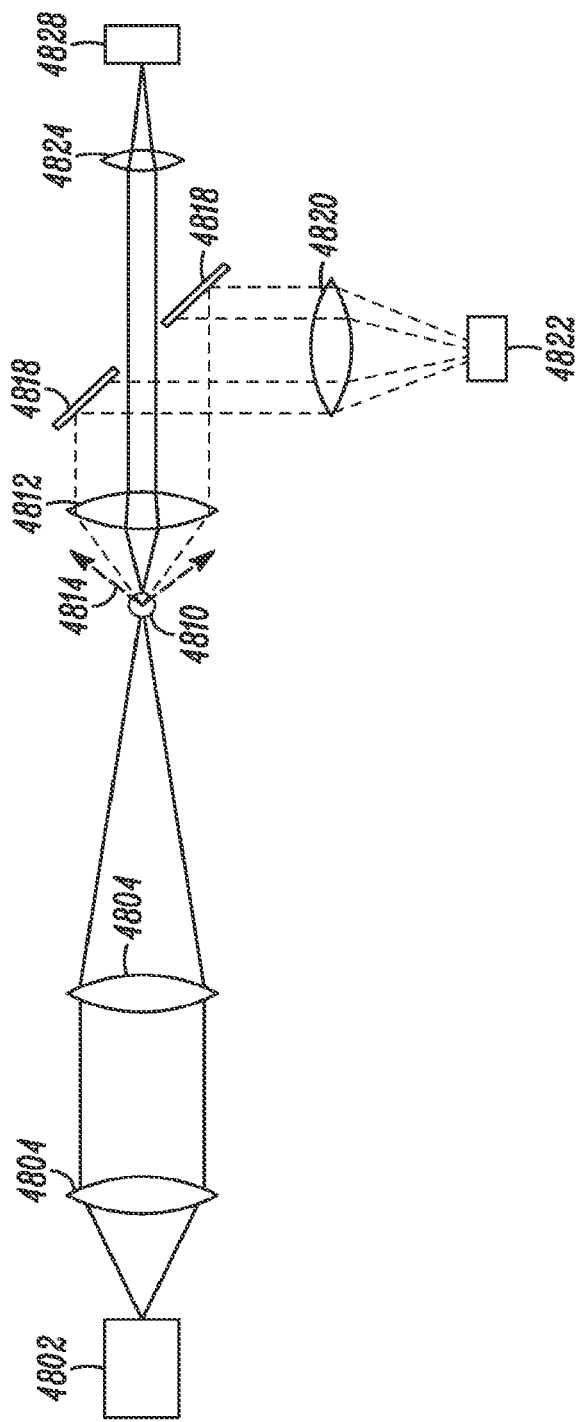
FIG. 48 shows an alternative architecture where scattered light is measured directly.

FIG. 48 shows an alternative architecture where scattered light is measured directly. Scattered light measurement may then be used in a number of ways. First, it may be used to estimate the total amount of scattered light in the system, including lost light, to correct for this loss in the output of the system. Second, it may be used to estimate particle parameters including index and volume, together with the direct absorption measurement(s). Third, it may provide a gating signal for absorption measurements, because it provides a positive signal on a zero background, while the absorption measurement may be a small delta on a bright background.

The components of this embodiment include: QCL(s) 4802 are focused using input optics 4804 into an input beam 4808 with a smaller angle than the output collection angle, onto particle(s) 4810 in the measurement volume. A high NA collection lens 4812 is used to collect both the transmitted light, as well as scattered light within a given angle. Some scattered light at high angles 4814 will be lost in the system. After the collection lens, an annular mirror 4818 is used to divert the scattered light portion through a focusing lens 4820 onto one detector 4822. This "scattered light" detector 4822 measures primarily scattering from the particle(s). The signal from this detector may be used as described above. The directly-transmitted or small angle scattered light is focused by a focusing lens 4824 onto the direct transmission detector 4828 which may be the primary absorption detector.

In this embodiment, the system may operate with a multiplicity of wavelengths to determine chemical concentrations and other particle attributes (size). With multiple QCL wavelengths in this architecture, both absorption and scattering may be measured at multiple points on the curves shown in example form in FIGS. 45a and 45b. By measuring scattering at a known angle at multiple wavelengths, when refractive index varies locally with wavelength as it does in resonant mid-IR measurements, it may be possible to accurately determine particle properties from known-angle, multi-wavelength measurements—while determining specific chemical concentration as well. This is a novel capability that is not present in visible or near-visible light conventional flow cytometers, and has not been explored in mid-IR or THz systems because of the lack of powerful, wavelength-matched, brilliant sources. QCLs fill this gap for measurement of cells and other particles in liquid streams.

Furthermore, the present invention may be used in a system that is differentiating populations of particles, such as cells, the outputs of the scattered light detector 4822 and direct-transmission detector 4828 at multiple wavelengths may be used with existing algorithms that optimize separation between populations. In a sorting-type system, the parameters may be refined continuously to maximize separability of populations. The QCL-based, absorption resonance-tuned infrared forward transmission and scattering system offers multiple capabilities in a variety of applications, and may be tuned accordingly.

Figure 49:
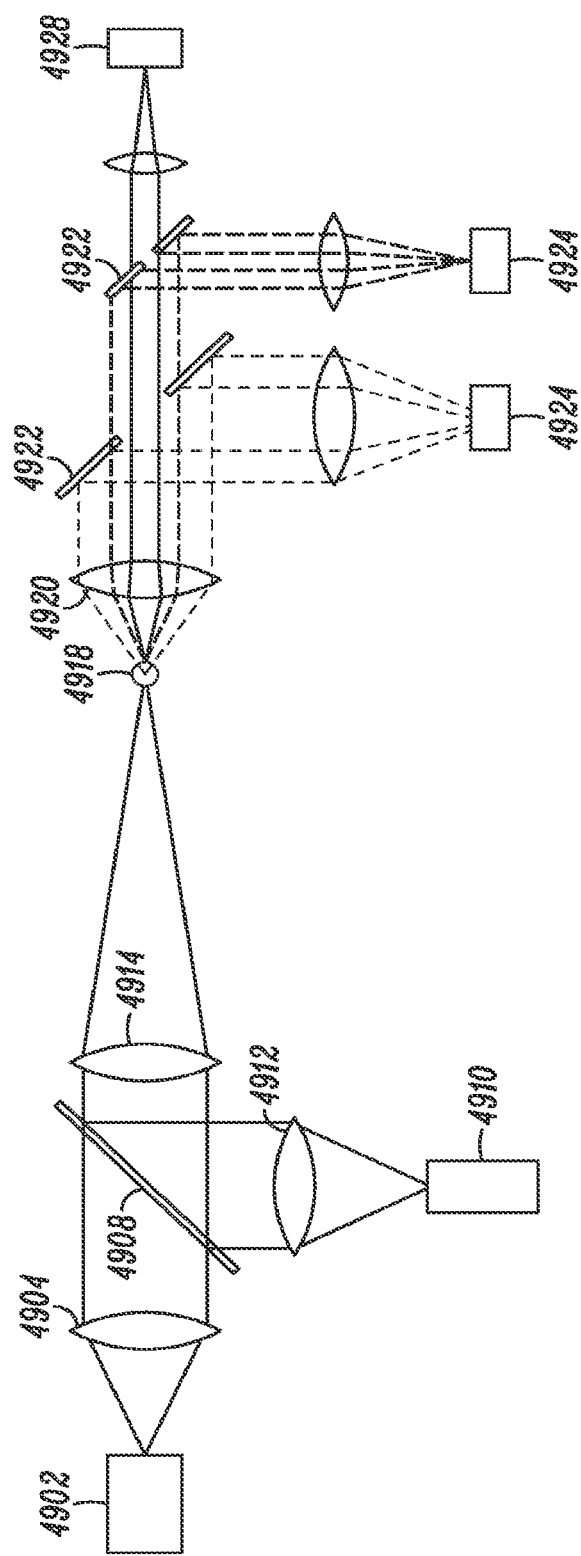
FIG. 49 shows an embodiment that has the potential to use QCLs to measure particle size and chemical concentration through scattered light only.

FIG. 49 shows an embodiment that has the potential to use QCLs to measure particle size and chemical concentration through scattered light only. In this embodiment, the system works even when particles are strongly absorbing at certain resonant wavelengths (for example, when DNA is very densely packed in the nucleus of a cell). It may also have the potential advantage that all signals are zero-based; in other words, when no particle is based, sensor readings are close to zero (even with the QCL sources powered up); particles entering the volume cause positive readings on the scatter detectors. The absolute and relative readings on scattered light detectors 4924 at one or more wavelengths may be used to determine both particle size and chemical composition (or at least concentration of one target compound within the particle).

In FIG. 49, the components of the embodiment include two QCL sources 4902 and 4910 to illustrate schematically how their signals are combined using collimating optics 4904 and 4912, and a beam combiner 4908 which is optimally a dichroic thin film interference filter. The combined beams are focused using lens 4914 onto the particle(s) 4918 in the measurement volume. Light is scattered in a wavelength- and angle-dependent manner, some of which is captured by collection lens 4920. A series of spatial filters 4922 (in this case annular mirrors) are then used to select ranges of scattering angles for detection by detectors 4924. There are a number of ways to achieve this configuration, including detectors that are segmented, blocking or reflecting filters, etc. Optionally, direct transmission is measured with another detector 4928.

While this example is shown to have symmetry around the output beam (all 360 degrees around an annular section is diverted into a single scatter detector), the system may be further refined to have horizontal and vertical scatter detectors, or more detectors arranged in a circular manner around the beam. This would allow more complex cell shapes to be accounted for and measured, if desired. Using the scattered light detectors to measure scattered light at two angle ranges, and at one or more wavelengths near absorption resonance for the target compound, one may estimate both particle size and concentration. This may be done either through Mie scattering models which iteratively calculate these quantities by achieving best fits to the data (lookup tables may be generated in advance in high-throughput systems), or particles may be classified empirically, either using independent measurements, or by tweaking parameters until known statistical populations are well separated in the output of the system. For example, in a system where sperm cells are being separated by DNA content in order to select X- or Y-carrying populations, it is known that roughly 50% of the sample carries each. Consequently, the outputs of the detectors in the system (at different angles, wavelengths) may be weighted to achieve separation between two populations, without reference to a quantitative model to describe scattering.

In a system where QCL sources are tunable, the measurement wavelengths may be optimized empirically as well. In the case of application-specific tools, this may be done in the product development stage. In the case of more flexible instruments, or where the analyte (particles, and medium) may vary substantially, the sources may be tunable in operation, and may either sweep through the course of a measurement, or find an optimal measurement wavelength with a subset of particles and then perform the main measurement or sorting operation. The generalized function of the scattering-based system is described here: one or more frequencies at resonant and optionally non-resonant bands are used, and one or more angle ranges of scattered light are measured. The resulting signals may be used to calculate particle volume and one or more chemical concentrations (or, in some cases, molecular conformations/configurations, which also cause changes in absorption/refractive index profiles in the mid-IR).

The present invention may be applied to a wide range of applications where infrared vibrational absorption resonances are an indicator of interest. One application may be in measurements of biological cells. The label-free measurement of biochemical content in cells is of strong interest. The present invention has the potential to significantly improve accuracy of systems previously described by the inventor. In addition, it has the potential to simultaneously measure cellular or cellular component (i.e. nuclear) dimensions and chemical contents. With embodiments of this disclosure, effective volume and concentration for multiple cellular components could be measured simultaneously using multiple wavelengths. For each cellular constituent (protein, DNA, lipid, etc.) a concentration and a spatial distribution figure could be calculated using resonant absorption and/or scattering signals at resonant peaks for each. For example, the invention may be applied to diagnostic applications, such as applications where a large number of cells are measured in a high-throughput cytometry tool. Cellular dimensions are measured using scattering, and contents such as DNA, RNA, proteins, and/or metabolic products are measured using resonant IR absorption. Cell population statistics are accumulated and outliers identified in order to detect abnormalities to diseases. For example, a tool which detects malaria from a raw blood sample could isolate DNA measurements from red blood cells, where DNA readings over a threshold could indicate presence of parasites (sizing capability of the system used to separate readings from red blood cells from other blood components). In another example, a system based on the present disclosure could refine samples from circulating tumor cell (CTC) capture devices; cells may be characterized by DNA and other content as well as size.

In another example, embodiments of the disclosure may be applied to assisted reproductive applications. A system based on the present invention could accurately determine the DNA content of sperm cells for human or animal applications, even as the nuclear volume of the cells varies within a patient sample. The ability to measure DNA level allows separation of X- and Y-bearing sperm cell for gender selection applications. Similar systems could screen out cells with chromosomal abnormalities, or abnormal DNA packing configurations for in vitro fertilization applications. The invention could also be applied to scoring of embryos, where chemical content and byproducts is known to correlate with viability, and label-free, non-ionizing radiation-based techniques would be highly preferable. The present invention could characterize chemical content of an embryo while compensating for scattering effects, or indeed harnessing resonant scattering to product a more accurate score.

In another example, embodiments of the disclosure may be applied to regenerative medicine. The present invention may be used to refine cell populations by both size/shape and chemical content in order to separate pluripotent stem cells from mixtures of cells, without attaching labels or interrogating the cells with potentially damaging radiation. For differentiated cells generated from stem cells, the system may be applied to remove any residual pluripotent stem cells before insertion into patient tissues, in order to prevent tumor formation by non-differentiated cells.

In another example, embodiments of the disclosure may be applied to industrial biology. The present invention may be used to characterize and/or sort cells for industrial processes at high speed. For example, it may be used to refine a culture of cells that produces a high number of lipids or other products under certain conditions. Such measurements of cellular products could be done by isolating cells in droplets which are in turn manipulated in an oil medium as an emulsion.

In another example, embodiments of the disclosure may be applied to contamination monitoring. Water and other substances may be monitored for infectious diseases without pre-processing using the present invention. Some filtering for particle/cell size may be performed on the input, and then particles flowed through a measurement system. The present invention's ability to characterize cell size, general refractive index, and resonant absorption/scattering for particular compounds may allow it to identify specific pathogens. Where pathogens are airborne, the system may capture a sample on an open liquid surface, then flow the liquid through an analysis system. For solid samples such as food, well-known processes for blending the sample, then filtering them, may be used to separate potential pathogens before flowing them through a system based on the present invention.

Another application may be measurement of emulsions. In many cases it is useful to measure droplets within an emulsion. This can facilitate handling in some cases. In other cases the sample being measured is inherently an emulsion. In a droplet-based measurement system, water droplets suspended in oil are used to manipulate cells and discrete volumes of chemicals in a microfluidic system. The present invention could be used in conjunction with such systems in order to measure chemical concentrations within droplets optically, and at the same time potentially adjust for the size of droplet. In some cases, the droplet size measurement may be done at shorter wavelengths. In other cases, a combined measurement around mid-IR resonances is helpful to measure overall chemical content. In some cases the analyte of interest is an emulsion of chemicals. The present invention can serve to characterize such mixtures both by chemical content and by particle size. This may be useful in a number of industrial and food processes.

Another application is in the measurement of solid particles in suspension. With the present invention, it may in some cases be desirable to build a system that places solid particles into a liquid suspension in order to characterize them. For example a system may include a capability that collects a solid sample from a surface through scraping, milling or vacuuming, then introduces these samples into a liquid medium, then runs these samples through one or more size filters to select particles that are appropriate for measurement and exclude unwanted substances (including, potentially, size-sorting microfluidic devices such as those demonstrated by Robert Austin at Princeton University), then runs the particles through the an optical measurement system based on the present invention. The liquid medium may be tuned to have specific refractive index relationship to the particles of interest, so that it in effect becomes a "reference" in the system. Even if the particles are very dense and have high optical absorption at resonant wavelengths, the present scattering-compensated/enhanced measurements system may provide volumetrically-compensated chemical composition information, or both volume and chemical composition information. Such systems may be of interest in applications where diffuse reflective or ATR-type spectroscopy are currently used, but signals are insufficiently accurate or sensitive. This may include cases where there is a very thin layer of interest on an object (the described system serves to consolidate the layer into a flow), or where the underlying substances interfere with measurement.

Emulsion-based microsystems for handling of small volumes of analyte or biological materials, including cells, are an area with growing activity. One common challenge in such systems is measurement of droplet or flow contents, where individual volumes are tiny. It would be highly desirable to be able to measure the contents of such an emulsion non-invasively, without adding additional chemicals that may disturb the chemical reaction or cellular metabolism, and without radiation that could disturb or harm the contents of the droplets, cells, emulsions, etc.

The unique properties that a QCL-based system brings to an emulsion or droplet-based fluidic system include the ability to provide high spectral power density at specific wavelengths in the mid-IR and THz regime corresponding to molecular bond vibrations; and the ability to focus this light very tightly and efficiently onto a small spot for the purpose of interrogating individual particles, droplets, biological cells, etc. with micron resolution, thereby creating the ability to measure these at a high rate while resolving them individually. Correspondingly, the low etendue of QCL light sources allows light to be very well and efficiently collimated in the case where it is desirable to have the angle distribution of the illuminating source to be very narrow.

Unlike most Raman spectroscopy systems that probe the same molecular vibrations, mid-IR systems have very strong interaction with the target molecules. In addition, mid-IR light, including light from QCLs, has the advantage that it is very low energy (per photon), minimizing the chance of photon damage. Finally, mid-IR light has the advantage of long wavelength vs. UV/Visible/NIR and Raman measurements; this long wavelength reduces scattering effects and makes them more easily manageable in a measurement system.

The fluidics may be fabricated using materials appropriate for mid-IR light transmission and designed optically to avoid fringing and resonances at the wavelengths employed.

A number of configurations are described below. Any of the configurations, techniques, architectures previously described using QCLs to interrogate particles, cells, droplets and sub-flows in fluids are applicable to these.

One additional optical method that may be applied to the previous configurations disclosed herein adds polarization as a sensing modality to the QCL-based interrogation of these particles in a flow. If molecules being interrogated by mid-IR vibrational spectroscopy are arranged in specific manners within the particle being measured—for example, DNA in helical configuration—the measured absorption at the absorption band of the molecules will depend on the polarization of the mid-IR light. One may alternately polarize the light in left and right circular polarization and measure the differential. The observed differential, so called vibrational circular dichroism (VCD) may provide a particularly sensitive measurement of chiral or helical molecules, and/or provide information about the folding or configuration of a particular molecule within the analyzed particle/cell/droplet.

QCL-VCD interrogation of particles in a fluid may be combined with other techniques described herein, such as scattering, or use of mid-IR active labels/dyes, to measure certain types of target molecules.

One example of a target molecule measurement is DNA measurement. DNA is a helical molecule and therefore exhibits polarization-dependent absorption at resonant absorption bands of its constituents (phosphate and deoxyribose components on its backbone). This property may be used to separate a DNA absorption signature from other analytes when measuring using one or more QCL wavelengths. It may also be used to determine, with high accuracy, the folding or packing state of DNA within a cell nucleus.

Figure 50A:
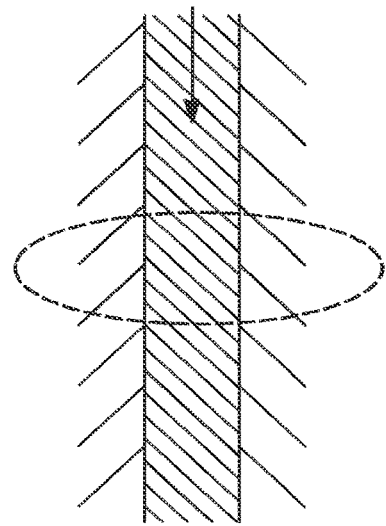
FIG. 50a depicts shows a simple flow architecture where the fluid to be measured flows through a channel.

FIG. 50a shows a simple flow architecture where the fluid to be measured flows through a channel, where it is interrogated using a mid-IR or THz QCL-derived beam (shown as dotted ellipse). The transmission at one or more wavelengths through the channel is measured to determine chemical concentrations within the flow.

Figure 50B:
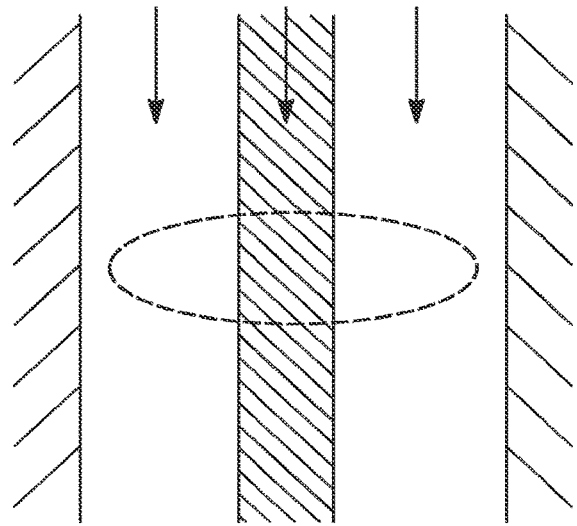
FIG. 50b depicts a fluid-within-fluid flow.

FIG. 50b shows a fluid-within-fluid flow, also within a channel structure or manifold. At small scales, as is well known, fluids tend to remain in a laminar (non-turbulent/non-mixing). This enables a "core" flow of analyte to remain centered and unmixed with a "sheath" flow, as is shown here. This method of presenting an analyte (which may be a liquid, liquid with solid particles and/or biological matter, liquid with dissolved gases, emulsion, or suspension) gives some additional possibilities for QCL-based measurements. First, it eliminates potential artifacts arising from the laser beam (dotted ellipse) crossing the edge of the fluid channel. Second, in this configuration it is more straightforward to make scattering-based measurements that accentuate differences between the core and sheath fluids. Refractive index (both real and imaginary) differences between the sheath and core flows will result in optical interference effects (often described as Mie scattering for particles), effectively changing the angle of some of the light transmitted through the flow. As discussed earlier, in the mid-IR regime addressable by QCLs, there are relatively narrow, resonant refractive index variations (dispersion) around absorption peaks characteristic of molecular bond vibrations. These may be exploited, with QCL-derived illumination whose angle is well controlled, to get very sensitive concentration measurements within the fluid flow. Depending on the concentration of a particular molecule within the core flow, there will be characteristic variations in refractive index—and therefore in observed scattering/diffraction intensity and angle—as a function of mid-IR wavelength.

The flow shown in FIG. 50b may simply be two fluids (core and sheath) flowing laminarly, but not otherwise separated. Alternatively, the flow may be an emulsion, where the two fluids naturally remain separated. For example, the sheath fluid could be oil, whereas the core flow could be an aqueous solution. Several measurements could then be performed using the QCL-based architectures previously disclosed: the characteristics of the core flow (dimension, base index) could be measured at one wavelength where the molecule of interest is not resonant; then other wavelengths could be used to measure specific chemical concentrations of interest, using either direct transmission/absorption measurements, or scattering-based measurements. Knowledge of the core flow diameter derived from the initial measurement may then be used to compensate the target-specific signal, for example accurately calculating concentration of the chemical within the core flow. Multiple angles (direct transmission, and multiple scatter angles) may be used to calculate dimensions and concentrations.

With this as well as other architectures disclosed herein, multiple configurations for measuring scattering over multiples angles may be used. Discrete detectors capturing light scattered at different angles may be used, for example. In another configuration, a mid-IR focal plane array may be used to simultaneously measure light emerging at different angles from the measured fluid/cell/particle. Alternatively, mirror systems may be used to sample portions of the output beam. Mirror arrays such as the Texas Instruments digital micromirrors may be used to sample portions of the emerging beam and relay them to a single detector (such as a high-speed MCT). Rotating mirrors may be used to scan the emerging beam over a detector with an aperture, either along 1 or 2 axes (useful where potentially asymmetric particles/droplets are being measured).

These architectures, with two or more QCL wavelengths, one or more of which corresponds to wavelengths where a substance of interest has a resonant dispersion feature, may be used with multiple architectures that present particles, cells, fluids, droplets and the like to the mid-IR beams. For example, this QCL-based resonant Mie scattering architecture may be used with cells that have been mounted on a mid-IR transparent substrate (or mid-IR reflective substrate).

Figure 50C:
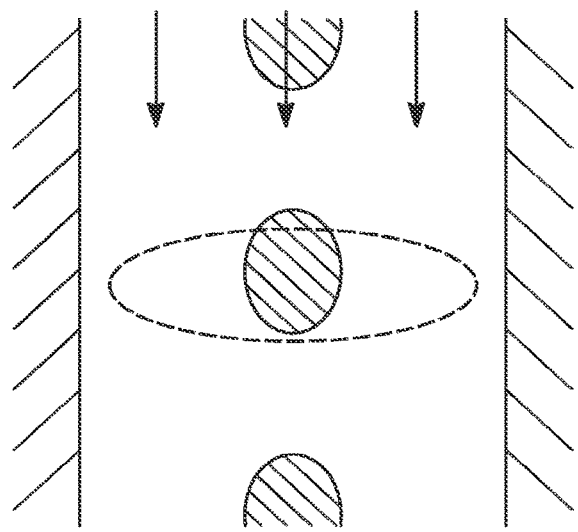
FIG. 50c depicts an example of a flow where the core has been broken into droplets.

FIG. 50c shows an example of a flow where the core has been broken into droplets. These droplets may be emulsed in the sheath flow. The droplets pass through the QCL measurement beam (dotted line) and are measured using direct transmission and/or scattered light detection.

All of these architectures based on mid-IR QCL light may be combined with other measurement techniques, including optical. These include but are not limited to scattering measurements, fluorescence measurements, and others previously disclosed.

Figure 51A:
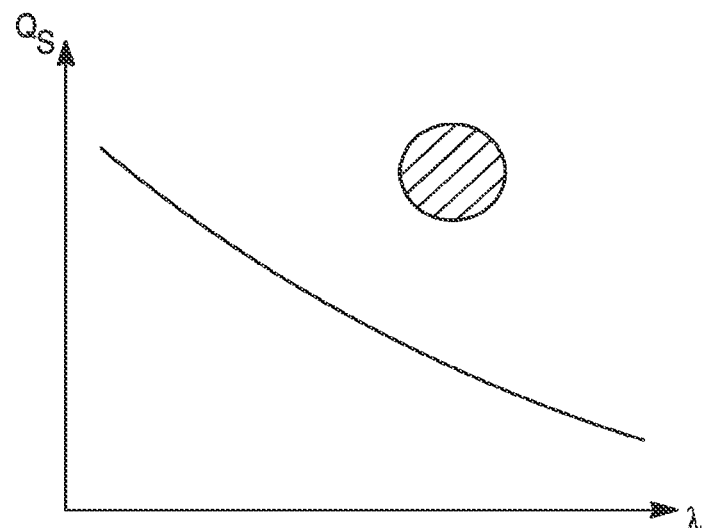
FIG. 51a shows an example of scattering efficiency (Qs) of a volume such as a droplet, as a function of wavelength (lambda).

FIG. 51a shows an example of scattering efficiency (Qs) of a volume such as a droplet, as a function of wavelength (lambda). Assuming relatively constant refractive index for the volume as well as the surrounding medium, scattering drops as a function of wavelength.

Figure 51B:
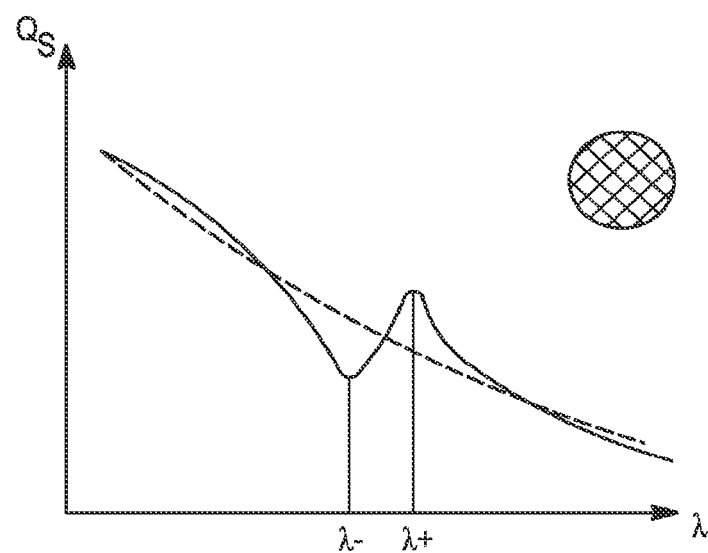
FIG. 51b shows scattering efficiency as a function of wavelength

FIG. 51b shows scattering efficiency as a function of wavelength where a chemical within the droplet has a vibrational absorption band in the wavelength range being displayed. A local increase in absorption necessarily corresponds (as can be determined from the Kramers-Kronig relation) to a local resonant variation in real refractive index. This variation in real index results in a local (wavelength) perturbation of the optical interference pattern (scattering) arising as the mid-IR beam passes through the droplet and surrounding medium. The term "droplet" here is used to mean droplet, cell, particle within another liquid, including cases where the droplet is in an emulsion.

It should be noted that several mid-IR (or other) wavelengths may be used to accurately determine chemical concentration within such a system. The resonant dispersion (local index variation around the absorption band) measurements are done using mid-IR QCLs. Other wavelengths in non-resonant regimes may be used to measure the overall droplet (size, shape, orientation) by scattering. For this, visible, NIR, or mid-IR wavelengths may be used. Visible wavelengths are already used to assess size and shape in systems such as blood count tools today. They, however, do not have the capability of doing chemistry-specific measurements enabled by the mid-IR resonant scattering architecture disclosed herein.

Figure 52A:
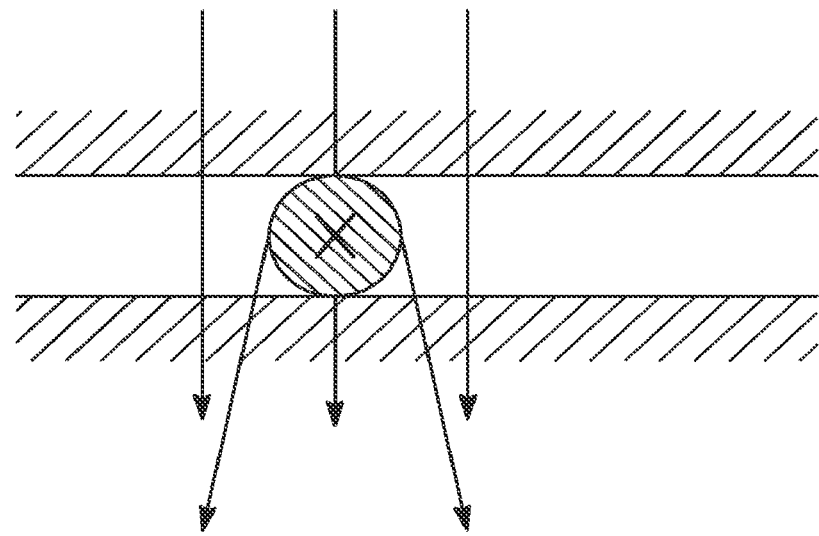
FIG. 52a shows a fluidic configuration where a droplet or flow is confined within a 2D channel or manifold.

FIG. 52a shows a fluidic configuration where a droplet or flow is confined within a 2D channel or manifold, such as those found in many microfluidic chip architectures. Mid-IR light from one or more QCLs passes through the droplet and the surrounding medium. Depending on the wavelength and chemical concentrations within the droplet and surrounding medium, light is absorbed and/or scattered.

Figure 52B:
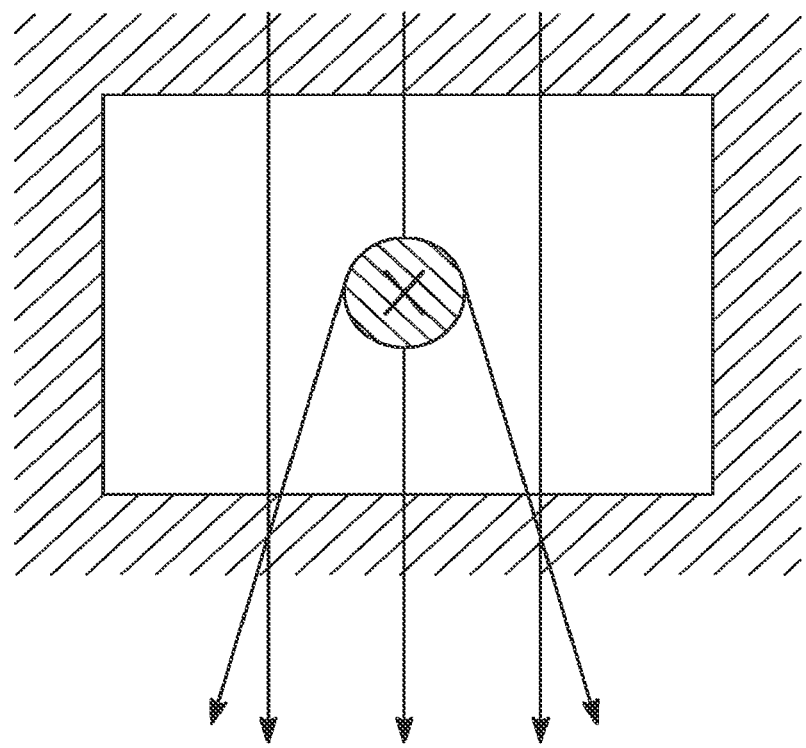
FIG. 52b shows a fluidic system where droplets or a core flow is centered within a larger, 3D core flow.

FIG. 52b shows a fluidic system where droplets or a core flow is centered within a larger, 3D core flow. This is more typical of conventional flow cytometer cuvettes, for instance. The QCL-based measurements described previously are then made of the droplet or flow, based on directly transmitted or scattered mid-IR light.

The fluidic architectures shown in cross section in FIGS. 52a-52b may be used in cases where the "droplets" or "flows" are in emulsion; in other words, where the droplets shown here do not mix with the surrounding flow, even when stationary.

Figure 53A:
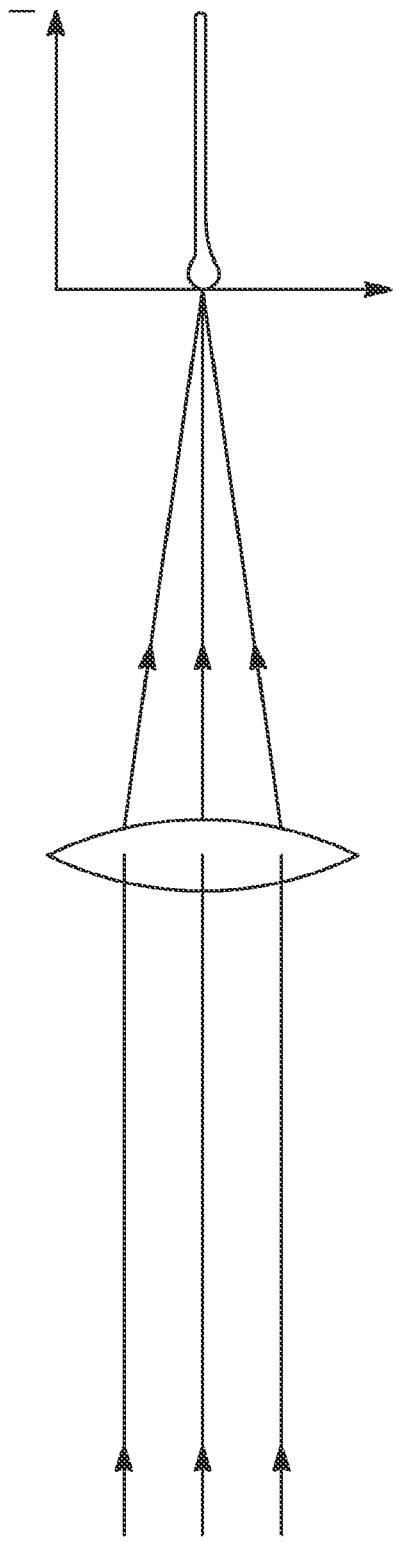
FIGS. 53a-53c show a representative example of a system measuring droplets or flows using QCL-originated mid-IR beams.
Figure 53B:
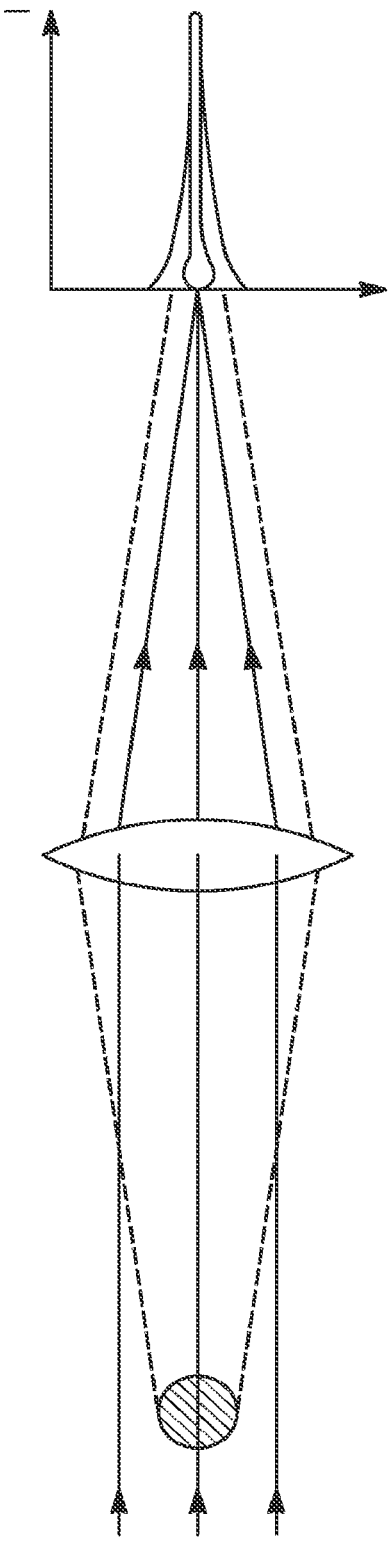
Figure 53C:
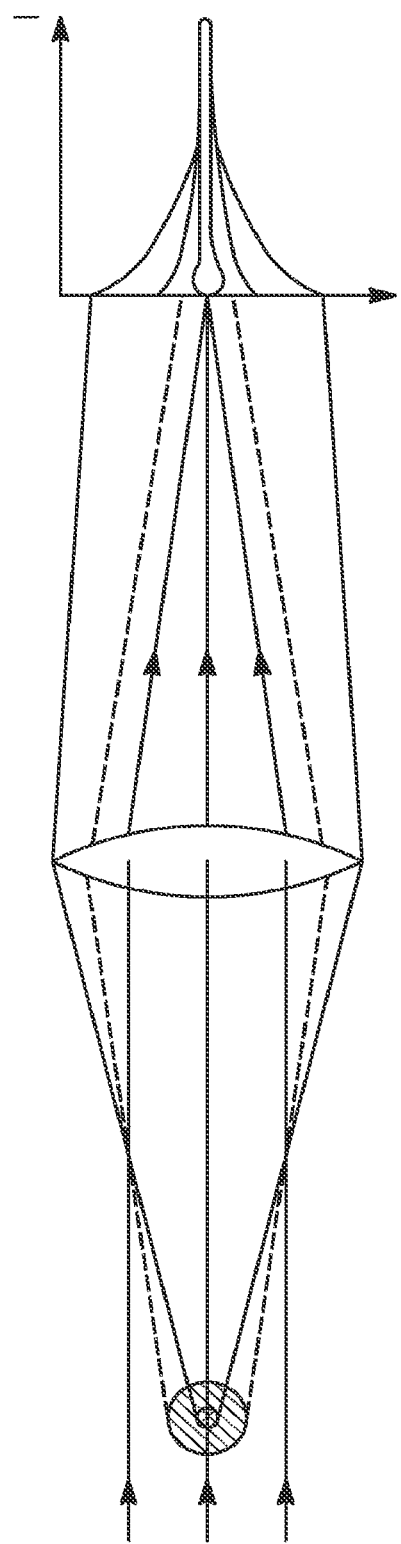

FIGS. 53a-53c show a representative example of a system measuring droplets or flows (within a sheath flow, which is not shown) using QCL-originated mid-IR beams. They are used to illustrate scattering as a function of the flow/droplet content, and mid-IR wavelength, as described under FIGS. 53a-53c.

FIG. 53a shows the system with the sheath flow only, or a baseline state. All mid-IR light is focused onto a single point, corresponding to traversal of the sheath fluid without angular perturbation resulting from refractive index differences.

FIG. 53b shows the system as a droplet or core flow are introduced. The droplet will cause some differential absorption of the directly-transmitted mid-IR light (this could be in some cases be negative, where the droplet absorbs less than the sheath flow). As a function of refractive index and wavelength, the droplet will also diffract some of the mid-IR light so it exits the flow off-axis. When imaged onto a plane, this light will appear away from the central spot. As described earlier, this pattern will be wavelength-dependent, and around certain resonant absorption wavelengths, will have stronger wavelength dependence. A combination of the directly-transmitted (central) signal and scattered signal as a function of mid-IR wavelength and scattering angle (position on the plane) may then be used to estimate both droplet dimensions and specific chemical concentrations within the droplet. The droplet, here, could be a continuous flow of liquid (viewed in cross-section), either in laminar flow or emulsed in a sheath fluid; it could be a single droplet; it could be a biological cell; a solid particle; or other form of spectrally-measurable object in a liquid flow, as described earlier.

FIG. 53c shows the same droplet or flow, now with another object inside of it. For example, this could be a cell, a dense nucleus or other organelle. It could be a droplet in an emulsion containing a single cell (or multiple cells). The system may be used again, as described above, to characterize the droplet, and then to characterize the particle within the droplet using the same techniques, often using different mid-IR wavelengths that correspond to molecular bond vibrations of interest within the contained particle. Again, this will result in absorption of the QCL-originated light passing through the contained particle, and scattering of the light based on refractive index at those wavelengths, which may show resonant dispersion around characteristic absorption lines.

In this architecture, a tunable QCL could be used to interrogate a series of wavelengths corresponding to non-resonant (reference) wavelengths, then resonant wavelengths corresponding to the droplet fluid and particle fluid, respectively.

In some cases, the droplets may accumulate chemical species as a result of chemical reactions that have occurred inside of them, or biological processes occurring in a cell contained within them (possibly stimulated/inhibited with additives to the droplet).

Figure 54B:
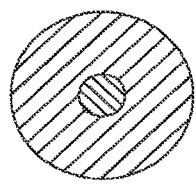
FIG. 54b shows a different technique, illustrate here through the use of a droplet in an emulsion.
Figure 54B:
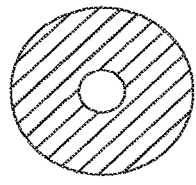
Figure 54A:
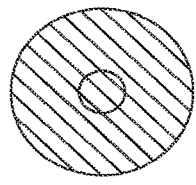
FIG. 54a shows a case where a biological cell (inner circle) is contained within a droplet, which is contained within an emulsion.
Figure 54A:
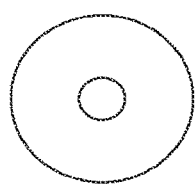

FIG. 54a shows a case where a biological cell (inner circle) is contained within a droplet, which is contained within an emulsion. An advantage of such a system, described in detail in Boehm et al, is that the droplet acts as an independent volume, not mixing with the surrounding (transport/sheath) liquid. As a result, chemical reactions can be performed at a tiny scale, and their results measured (assuming an appropriate measurement technique, such as ours). Alternatively, as is shown in this representative example, a cell may be incubated in the droplet with nutrients, drugs, toxins and/or other substances, in parallel with thousands or millions of other cells in a microfluidic system. At a fixed time, the present invention may be used to interrogate the droplet using QCL-derived light. At this point, the contents of the cell may be measured directly using vibrational spectroscopy techniques described herein. However, it may also be of interest to measure the contents of the droplets, which will contain the metabolic byproducts of the cell, accumulated in the course of incubation. The byproducts and their concentration may be a powerful indicator of cell function. The droplet contents may be measured using the QCL-based techniques described herein.

In some cases, only the contents of the emulsed droplet itself will be of interest, and the techniques described above may be used to "substract out" the optical signature of the cell from the transmitted and/or scattered mid-IR light.

FIG. 54b shows a different technique, illustrated here through the use of a droplet in an emulsion. Here the droplet is formed, containing a cell, but also containing a dye or label with a known and preferably distinct mid-IR vibrational signature. As with fluorescent dyes/labels, and emerging quantum dot based tags, it is functionalized in order to bind to or localize in particular portions of the cell, possibly depending on the cell phenotype, surface antibodies, etc.

The advantage of using a mid-IR dye/label, with readout using QCL-based mid-IR interrogation (absorption and scattering) are multiple: (1) a high degree of chemical flexibility, since virtually all molecules have mid-IR fingerprints; (2) the potential for a large number of labels simultaneously present and measured, because of the complex fingerprints achievable; (3) well-behaved scattering at mid-IR wavelengths, at the scale of cells and organelles. Moreover, scattering, as has been described, can be measured in a very chemical- and size-specific manner. As a result, it is possible to measure chemical concentration and associated structural information using resonant Mie scattering and QCL-originated beams with well-controlled angular incidence.

In this example, the droplet is filled with a mid-IR label, which over the course of incubation, binds to specific structures on the contained cell. By interrogating the droplet using QCL beam(s) after this incubation, one may determine how much of the label has been concentrated on the surface of, in the nucleus of, or within another organelle of the cell.

This technique of labeling using mid-IR active dyes/labels/particles may be applied with QCL-based vibrational absorption/scattering architectures previously disclosed by the inventor. It is potentially a strong complement to the label-free techniques previously disclosed, and to UV/visible/NIR techniques in broad industry use today.

Figure 55:
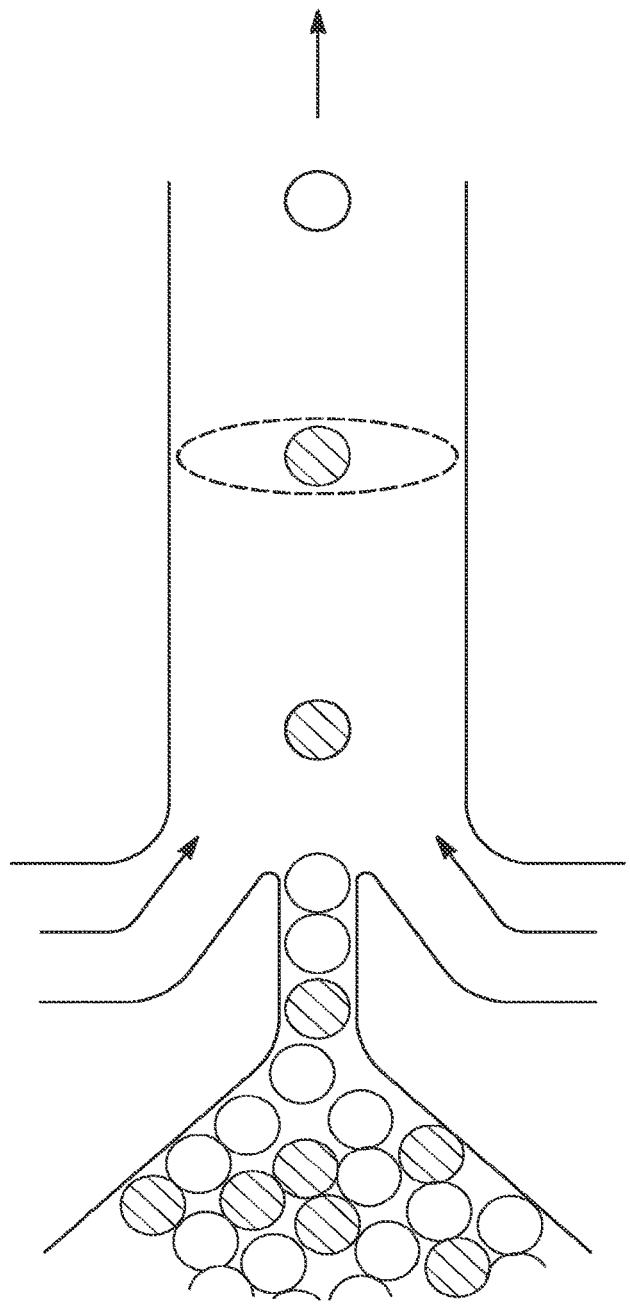
FIG. 55 shows an example of a droplet-based system where droplets contain biological cells.

FIG. 55 shows an example of the present invention used in a droplet-based system where droplets contain biological cells. The droplets may also be seeded with growth media, nutrients, drugs, etc. In general it may be desirable to have a set number of cells (often one) per droplet; generally the number of cells will follow a Poisson distribution as described by Boehm et al. The cells may be incubated for a fixed period at specific conditions, and then run into a measurement volume as shown here, where microfluidic channels guide individual droplets into a flow channel with a sheath flow that centers the droplets.

Alternatively, various focusing techniques, including acoustic, optical, and mechanical may be used to center the flow of droplets and space them appropriately for measurement, and in some cases, subsequent sorting.

In this configuration, multiple wavelengths of QCL (or, tunable QCL(s)) may be used in conjunction with direct transmission and/or scattering detectors in order to determine any one or combination of the following: (1) how many cells are present within a particular droplet, potentially eliminating from consideration those with the wrong number of cells, or compensating remaining measurements appropriately; (2) gathering spectral/scattering information regarding the cells to ascertain their contents or phenotype: (3) determine droplet volume; and (4) measure chemical contents of the droplets to measure, for example, the metabolic products of the cell(s) contained within. The resulting measurements could include anything from simple characterization of what type of cell(s) are contained within droplets, of the purpose of sorting, diagnostics or statistical measurements; what the contents of the cells are, including contents such as DNA, RNA, protein, sugars, lipids, metabolic byproducts, etc.; what chemicals are produced by the cell. The measurements may be recorded, or used to sort droplets in real time.

In other configurations, the droplets may be immobilized in "pots" where they may be observed over time. In this manner, time series (or at least before/after) measurements may be made of droplets maintained or processed under specific conditions. The array of pots may either be translated across the QCL beam for one-by-one measurement, or the pots may be unloaded sequentially past a QCL measurement point.

Figure 56:
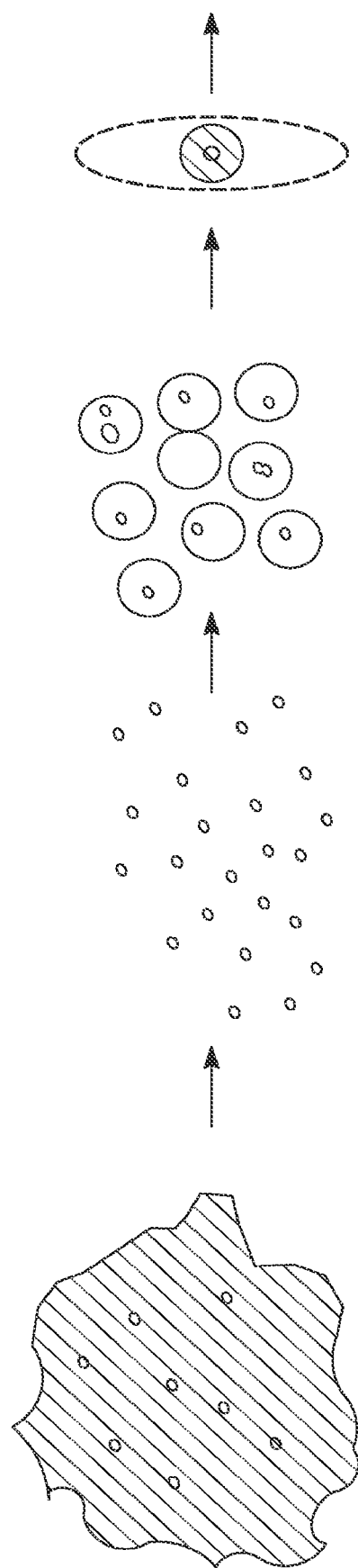
FIG. 56 shows a configuration where a solid sample with very sparse particles of interest.

FIG. 56 shows another configuration where a solid sample with very sparse (potential) particles of interest is to be analyzed. The process of analyzing a bulk sample for trace chemical or biological components is often difficult because signal is low when the entire sample is measured, or highly variable if small points are measured (for example, by ATR prism using FTIR).

According to the present invention, the solid may be milled into a fine powder (if it is not already in powder form), and then introduced into an appropriate liquid. Depending on the material being analyzed, this could be water, alcohol, oils or other liquids. The particles may then be sorted or filtered to achieve uniform size, potentially through the use of microfluidic structures. The particles are then incorporated into droplets in an emulsion. These droplets may, in some cases, contain not only the particles but also additive chemicals or tags that attach to I react with the molecules of interest in the solid, and may produce byproducts detectable by mid-IR vibration spectroscopy.

The droplets are then interrogated, possibly after some reaction time, using one or more QCL beams, in order to determine the content of the solid particle, by direct measurement of the particle, by measurement of complexes formed between additives and the particle, or byproducts of reactions between the particle and additives.

Particles here could include minerals of interest, trace pollutants or contaminants, explosives or chemical/biological weapons traces, or microbes including food contaminants.

Figure 57A:
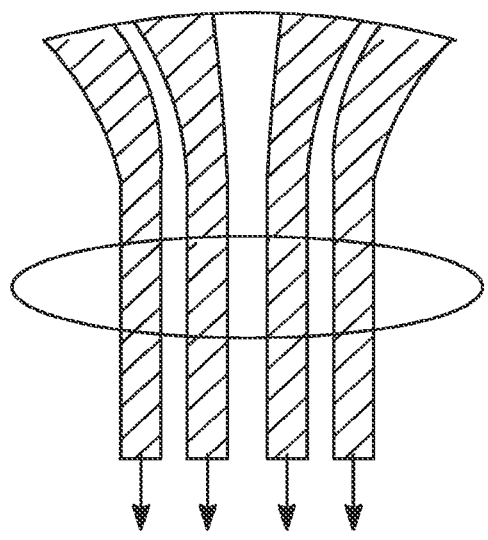
FIGS. 57a-57c show flow and particle configurations that could be used to enhance resonant optical interference measurements in the mid-R.
Figure 57B:
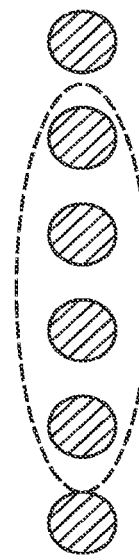
Figure 57C:
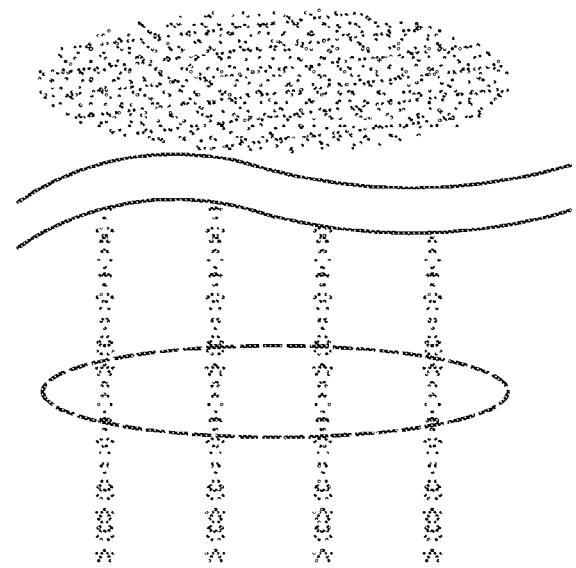

FIGS. 57a-57c show flow and particle configurations that could be used in the present invention to enhance resonant optical interference measurements in the mid-IR. Here, rather than a single particle, droplet or stream producing an interference (scattering) pattern when QCL-originated mid-IR beams hits it, multiple parallel particles or streams are used to produce a periodic "grating" in order to enhance scattering effects and increase signal-to-noise for specific chemical bond detection.

FIG. 57a shows parallel laminar flows which may be formed initially by relatively large microfluidic nozzles, and then narrowed to the appropriate dimensions, to form a liquid diffraction grating which may serve to measure the liquid content with very high specificity and accuracy in the mid-IR. In such a configuration, the diffraction angles of light imparted by the grating as light passes through it (perpendicular to the page) depends on the phase difference imparted by the alternating fingers, and therefore on the relative refractive index between the flows. As noted, where there are chemicals present in one set of flows that have resonant absorption bands in the mid-IR, there are associated refractive index fluctuations (resonant dispersion) near the same wavelengths, and two or more QCL-based measurements at wavelengths in or around these resonant features made with detectors measuring off-angle transmission can result in precise chemical measurements. Both resonant and non-resonant measurements may be made to accurately determine concentration and compensate for size and operating environment effects.

FIG. 57b shows a series of droplets passing through an asymmetric beam at regular intervals to similarly form a liquid diffraction grating.

FIG. 57c shows an architecture where particles, cells or bubbles are focused using acoustic, fluidic or optical means into parallel streams for interrogation by QCL beam(s) according to the present invention.

Figure 58:
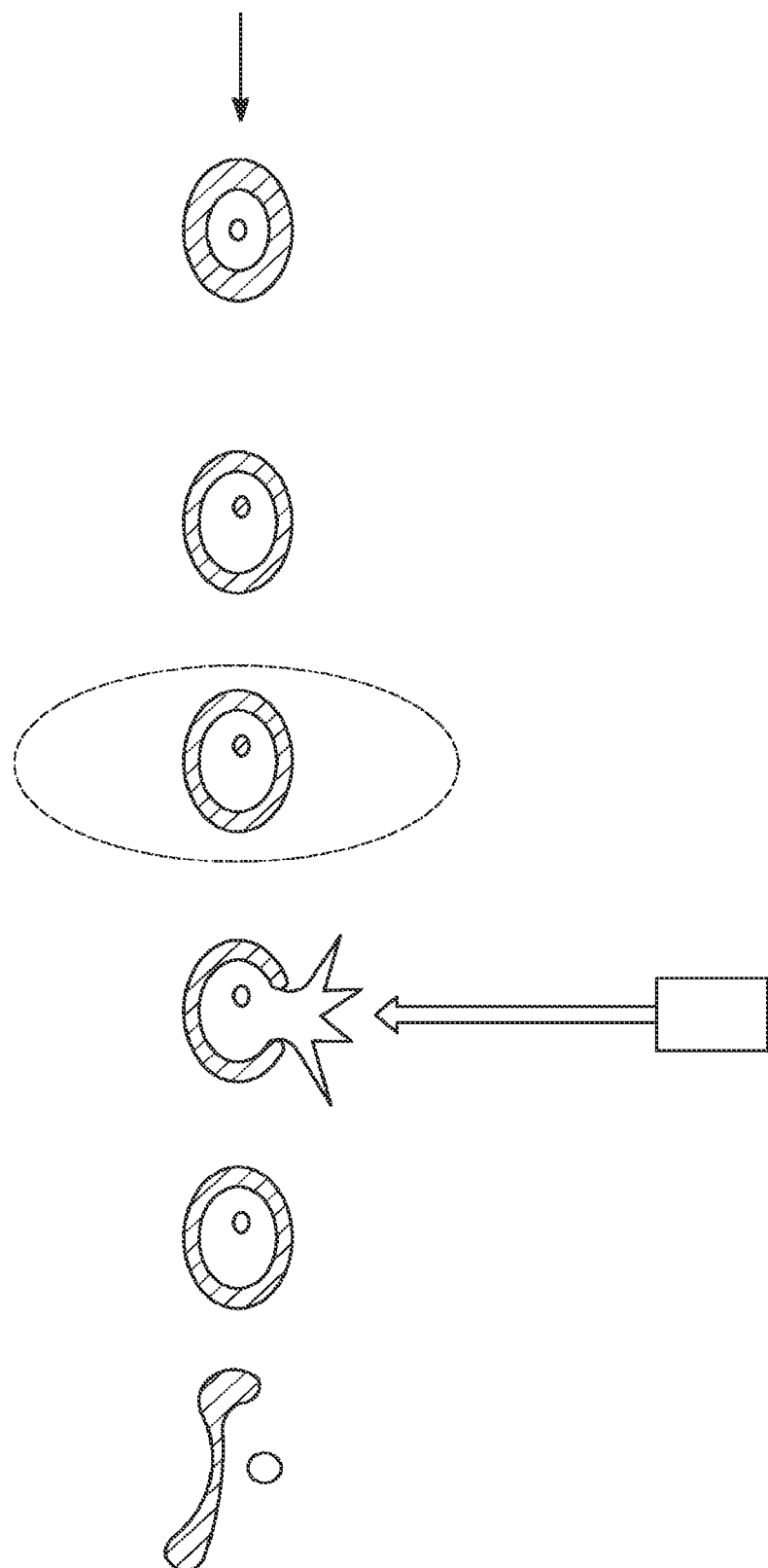
FIG. 58 shows one method by which cells or particles could be measured and sorted.

FIG. 58 shows one method by which cells or particles could be measured and sorted using QCL-based vibration spectroscopic techniques described herein, and droplet emulsions described by Boehm et al. In this example, a double emulsion is used, where cells are contained in a water-based droplet, which is encased in an oil "shell" (a double, or triple emulsion), which itself is suspended in a water-based medium. According to methods described above in the invention, QCL based beam(s) are used to interrogate the cell and/or surrounding liquid that (for example) contains metabolic byproducts from the cell. Depending on the outcome of the measurement, the system may break open the oil shell and release the contained cell. This release step may be performed using one of a number of means, including but not limited to: acoustic forces that break up the droplet, optical pulses which force a hole into the shell (including but not limited to mid-IR radiation which may target specific absorption lines for the oil), or mechanical. After release, cells still in oil cases may be separated passively by appropriate microfluidic structures from cells which have been released from their shells.

The methods and systems described herein may be deployed in part or in whole through a machine that executes computer software, program codes, and/or instructions on a processor. The processor may be part of a server, cloud server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, cloud servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, cloud servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. An apparatus for determining a characteristic of a sample, comprising:
    a light source configured to provide a light;
    a measurement volume, wherein the sample passes through the measurement volume in order to be measured;
    an optic device configured to direct the light through the measurement volume, wherein the sample passing through the measurement volume interacts with the light directed through the measurement volume, thereby resulting in a detectable change in the light;
    only one detector configured to detect the detectable change in the light in two modes; and
    a processor operably coupled to the detector, wherein the processor executes computer-readable instructions to determine a characteristic of the sample based on the detectable change in the light detected by the detector.

2. The apparatus of claim 1, wherein the detectable change in light is due to Raman scattering.

3. The apparatus of claim 1, wherein the detectable change in the light is a change in transmitted light, a change in scattered light, a change in diffracted light, a change in fluorescence, a change in refracted light, a change in circular dichroism, or a combination thereof.

4. The apparatus of claim 1, wherein the sample is in a form of a droplet or a stream as it passes through the measurement volume.

5. The apparatus of claim 1, wherein the light directed through the measurement volume results in an illumination pattern in the measurement volume, wherein the sample interacts with the illumination pattern, resulting in the detectable change in the light.

6. The apparatus of claim 5, wherein the illumination pattern comprises distinct spots or distinct lines in the measurement volume.

7. The apparatus of claim 1, wherein the detectable change in light is a fluorescence emission from a fluorescent label that is coupled to the sample.

8. The apparatus of claim 1, further comprising one or more pressure ports or channels configured to sort the sample based on the determined characteristic and direct the sorted sample into an output channel of a plurality of output channels.

9. An apparatus for providing spectroscopic measurements of samples with favorable signal to noise ratio comprising:
    a light source configured to provide a light;
    a measurement volume configured to contain a sample to be measured;
    an optic device that is configured to direct the light through the measurement volume, wherein the light directed through the measurement volume results in an illumination pattern in the measurement volume, wherein the sample interacts with the illumination pattern resulting in a detectable change in the light as the sample passes through the measurement volume, wherein the detectable change is due to Raman scattering;
    only one detector that is configured to detect the detectable change in the light in two modes; and
    a processor operably coupled to the detector for determining a characteristic of the sample based on the detectable change in the light and the temporal pattern.

10. The apparatus of claim 9, wherein the Raman scattering is coherent Raman scattering or anti-stokes Raman scattering.

11. The apparatus of claim 9, wherein the Raman scattering is a forward coherent Raman signal or an epi-detected coherent Raman signal.

12. The apparatus of claim 9, wherein the Raman scattering enables measurement of a vibrational bond fingerprint in a cell in the sample.

13. The apparatus of claim 9, wherein the light source comprises a pump laser and one or more slave lasers, and wherein a combination of the pump and slave lasers allows for excitation of one or more specific molecules so as to emit coherent light at an anti-Stokes frequency.

14. The apparatus of claim 9, wherein the measurement volume is fabricated.

15. The apparatus of claim 9, wherein the sample is a droplet or a stream as it passes through the measurement volume.

16. The apparatus of claim 9, wherein the illumination pattern comprises distinct spots or distinct lines in the measurement volume.

17. The apparatus of claim 9, wherein the detectable change in the light is a change in transmitted light, a change in scattered light, a change in diffracted light, a change in fluorescence, a change in refracted light, a change in circular dichroism, or a combination thereof.

18. An apparatus for sorting a plurality of sperm cells, the apparatus comprising:
    a light source configured to provide a light, wherein the light source comprises a UV or visible laser configured to cause an emission by a fluorescent label attached to each sperm cell in the plurality of sperm cells;
    a measurement volume configured to contain a sample to be measured;
    a first optic device configured to direct the light through the measurement volume, wherein the apparatus is configured to flow the plurality of sperm cells through the measurement volume one by one such that as each sperm cell flows through the measurement volume, it interacts with the light from the light source, thereby resulting in a change in light originating from the measurement volume, wherein the change in light is the emission due to fluorescence;

a second optic device configured to direct a portion of the light originating from the measurement volume to only one detector;

the detector configured to detect the portion of light directed by the second optic device in two modes;

a signal processor operably coupled to the detector, and configured to execute computer-readable instructions to perform operations comprising:

generating an estimate of DNA quantity in each sperm cell in the plurality of sperm cells based on the change in light originating from the measurement volume; and determining a characteristic of each sperm cell based on the estimate of the DNA quantity in said sperm cell, wherein the characteristic is whether the sperm cell is x-bearing or y-bearing; and one or more pressure ports or channels configured to sort each sperm cell in the plurality of sperm cells to one side or the other of a microfluidic channel, based on the determined characteristic of the sperm cell so as to cause it to flow into one of a plurality of output channels.

19. The apparatus of claim 18, wherein the plurality of sperm cells are bovine sperm cells, ovine sperm cells, porcine sperm cells, or equine sperm cells.

20. The apparatus of claim 18, wherein the light directed through the measurement volume results in an illumination pattern in the measurement volume, wherein each sperm cell that flows through the measurement volume interacts with the illumination pattern, thereby resulting in a fluorescent signal from the measurement volume, wherein the detector detects the fluorescent signal and the second optic device directs a portion of the fluorescent signal from the measurement volume to the detector, wherein the signal processor generates an estimate of the DNA quantity in each sperm cell in the plurality of sperm cells based on the fluorescent signal.

* * * * *